(12) United States Patent
DiMarchi et al.

(10) Patent No.: US 8,940,860 B2
(45) Date of Patent: Jan. 27, 2015

(54) SINGLE-CHAIN INSULIN AGONISTS EXHIBITING HIGH ACTIVITY AT THE INSULIN RECEPTOR

(75) Inventors: Richard D. DiMarchi, Carmel, IN (US); Julia Azriel, Indianapolis, IN (US); Zach Kaur, Bloomington, IN (US); Jonathan Meyers, Bloomington, IN (US); Todd Parody, Bloomington, IN (US); Yan Zhao, Bloomington, IN (US)

(73) Assignee: Indiana University Research and Technology Corporation, Indianapolis, IN (US)

( * ) Notice: Subject to any disclaimer, the term of this patent is extended or adjusted under 35 U.S.C. 154(b) by 24 days.

(21) Appl. No.: 13/701,146

(22) PCT Filed: Jun. 16, 2011

(86) PCT No.: PCT/US2011/040699
§ 371 (c)(1),
(2), (4) Date: Nov. 30, 2012

(87) PCT Pub. No.: WO2011/159895
PCT Pub. Date: Dec. 22, 2011

(65) Prior Publication Data
US 2013/0203665 A1    Aug. 8, 2013

Related U.S. Application Data

(60) Provisional application No. 61/355,366, filed on Jun. 16, 2010, provisional application No. 61/433,500, filed on Jan. 17, 2011.

(51) Int. Cl.
*C07K 14/62* (2006.01)
*A61K 47/48* (2006.01)
(Continued)

(52) U.S. Cl.
CPC .......... *A61K 47/48338* (2013.01); *C07K 14/62* (2013.01); *A61K 38/28* (2013.01); *A61K 38/00* (2013.01)
USPC .............. 530/303; 514/5.9; 514/6.1; 514/6.2; 514/6.3

(58) Field of Classification Search
CPC . C07K 14/62; A61K 38/00; A61K 47/48338; A61K 38/28
See application file for complete search history.

(56) References Cited

U.S. PATENT DOCUMENTS 3,740,385 A    6/1973   Ondetti
4,275,152 A    6/1981   Esders et al.
(Continued)

FOREIGN PATENT DOCUMENTS

EP    0220958    5/1987
EP    741188 A2 *    11/1996  ............. C12N 15/17
(Continued)

OTHER PUBLICATIONS

Peavy et al (Receptor Binding and Biological Potency of Several Split Forms (Conversion Intermediates) of Human Proinsulin, Journal of Biological Chemistry, vol. 260(26):13989-13994 (1985).*
(Continued)

*Primary Examiner* — Christina Bradley
*Assistant Examiner* — Randall L Beane
(74) *Attorney, Agent, or Firm* — Barnes & Thornburg LLP

(57) ABSTRACT

Single chain insulin analogs are provided having high potency and specificity for the insulin receptor. As disclosed herein optimally sized linking moieties can be used to link human insulin A and B chains, or analogs or derivatives thereof, wherein the carboxy terminus of the B25 amino acid of the B chain is linked to the amino terminus of the A1 amino acid of the A chain via the intervening linking moiety. In on embodiment the linking moiety comprises a polyethylene glycol of 6-16 monomer units and in an alternative embodiment the linking moiety comprises a non-native amino acid sequence derived form the IGF-1 C-peptide and comprising at least 8 amino acids and no more than 12 amino acid in length. Also disclosed are prodrug and conjugate derivatives of the single chain insulin analogs.

4 Claims, 51 Drawing Sheets

```
A-Chain                                    D-Chain
             1                    21          1      8
Insulin    GIVEQCCTSICSLYQLENYCN           ********
IGF I      ---DE--FRS-D-RR--M--A           PLKPAKSA
IGF II     ----E--FRS-D-AL--T--A           *T*PAKSE B-Chain
             1                              30
Insulin    FVNQHLCGSHLVEALYLVCGERGFFYTPKT
IGF I      *GPET---AE--D--QF---D---YFNKP-
IGF II     AYRPSET---GE--DT-QF---D---YFSRPA C-Chain
             1                                  35
Proinsulin RREAEDLQVGQVELGGGPGAGSLQPLALEGSLQKR
IGF I      GYGSSSRRAPQT
IGF II     SRVSRRSR
```

(51) Int. Cl.
*A61K 38/28* (2006.01)
*A61K 38/00* (2006.01)

(56) References Cited

U.S. PATENT DOCUMENTS

| | | | |
|---|---|---|---|
| 4,741,897 | A | 5/1988 | Andrews et al. |
| 4,876,242 | A | 10/1989 | Applebaum et al. |
| 4,985,407 | A | 1/1991 | Foxton et al. |
| 5,359,030 | A | 10/1994 | Ekwuribe |
| 5,514,646 | A | 5/1996 | Chance et al. |
| 6,180,767 | B1 | 1/2001 | Wickstrom et al. |
| 6,197,926 | B1 | 3/2001 | Gaur et al. |
| 6,476,290 | B1 | 11/2002 | Wright et al. |
| 6,630,348 | B1 | 10/2003 | Lee et al. |
| 6,746,853 | B1 | 6/2004 | Dahiyat et al. |
| 7,045,337 | B2 | 5/2006 | Schultz et al. |
| 7,326,688 | B2 | 2/2008 | O'Harte |
| 7,521,422 | B2 | 4/2009 | Bernard |
| 2002/0038026 | A1 | 3/2002 | Rao et al. |
| 2002/0160938 | A1 | 10/2002 | Brandenburg et al. |
| 2003/0195147 | A1 | 10/2003 | Pillutla et al. |
| 2003/0204063 | A1 | 10/2003 | Gravel et al. |
| 2004/0054130 | A1 | 3/2004 | Ng et al. |
| 2004/0121940 | A1 | 6/2004 | DeGroot et al. |
| 2005/0014679 | A1 | 1/2005 | Beals et al. |
| 2005/0187147 | A1 | 8/2005 | Newman et al. |
| 2006/0171920 | A1 | 8/2006 | Shechter et al. |
| 2006/0210534 | A1 | 9/2006 | Lee et al. |
| 2006/0223753 | A1 | 10/2006 | Glass |
| 2007/0173452 | A1 | 7/2007 | DiMarchi et al. |
| 2007/0203058 | A1 | 8/2007 | Lau et al. |
| 2007/0224119 | A1 | 9/2007 | McTavish |
| 2008/0113411 | A1 | 5/2008 | Sheffer |
| 2008/0113905 | A1 | 5/2008 | DiMarchi et al. |
| 2008/0125574 | A1 | 5/2008 | Sheffer et al. |
| 2009/0054305 | A1 | 2/2009 | Schlein et al. |
| 2009/0176964 | A1 | 7/2009 | Walensky et al. |
| 2009/0192072 | A1 | 7/2009 | Pillutla et al. |
| 2011/0065633 | A1 | 3/2011 | DiMarchi et al. |
| 2011/0288003 | A1 | 11/2011 | DiMarchi et al. |

FOREIGN PATENT DOCUMENTS

| | | |
|---|---|---|
| EP | 1161452 | 2/2000 |
| EP | 1193272 B1 * | 6/2004 |
| EP | 2036539 A1 | 3/2009 |
| EP | 2036923 A1 | 3/2009 |
| WO | 90/12814 | 11/1990 |
| WO | 93/03174 | 2/1993 |
| WO | 96/34882 | 11/1996 |
| WO | 98/11126 | 3/1998 |
| WO | 99/46283 | 9/1999 |
| WO | 02/10195 | 2/2002 |
| WO | 2004/067548 | 8/2004 |
| WO | 2004/078777 | 9/2004 |
| WO | 2005/054291 | 6/2005 |
| WO | 2006/047214 | 5/2006 |
| WO | 2006/097521 | 9/2006 |
| WO | 2008/019368 | 2/2008 |
| WO | 2008/021560 | 2/2008 |
| WO | 2008/025528 | 3/2008 |
| WO | 2009/034118 A1 | 3/2009 |
| WO | 2009/034119 A1 | 3/2009 |
| WO | 2009067636 A2 | 5/2009 |
| WO | 2009/095479 | 8/2009 |
| WO | 2009099763 A1 | 8/2009 |
| WO | 2010/011313 | 1/2010 |
| WO | 2010/071807 | 6/2010 |
| WO | 2010/080605 | 7/2010 |
| WO | 2011/163012 | 12/2011 |
| WO | 2011/163460 | 12/2011 |
| WO | 2011/163462 | 12/2011 |

OTHER PUBLICATIONS

"Peptides: Frontiers of Peptide Science," Proceedings of the Fifteenth American Peptide Symposium, Jun. 14-19, 1997, Nashville, Tennessee, USA; ed. James P. Tam and Praven T.P. Kaumaya.
Battersby et al., "Diketopiperazine Formation and N-Terminal Degradation in Recombinant Human Growth Hormone", *International Journal of Peptide & Protein Research* 44: 215-222, (1994).
Breiner, M., et al., Heterogeneity of Insulin-Receptors in Rat-Tissues as Detected with the Partial Agonist B29,B29'-Suberoyl-Insulin. Molecular Pharmacology, 1993. 44(2): p. 271-276.
Coffman et al., "Insulin-metal ion interactions: the binding of divalent cations to insulin hexamers and tetramers and the assembly of insulin-hexamers," Biochemistry, Aug. 9, 1988, vol. 27, No. 16, pp. 6179-6187.
Coy et al, J of Medicinal Chemistry, 1973, vol. 16, No. 7, 827-829.
De, Design of peptide-based prodrug chemistry and its application to glucagon-like peptide 1. Masters Thesis Aug 2007. [Retrieved from the Internet on Jun 16, 2009: <https://scholarworksiu.edu/dspace/browse?value=De%2C+ArnabBtype=author>]; p. 8, para 2; p. 16, para 3; p. 40, para 1; p. 66, para 2; p. 77, para 1-2; p. 79, para 1.
De, et al., "Investigation of the feasibily of an amide-based prodrug under physiological conditions," Int. J. Pept. Res. Ther., 14, pp. 255-262 (2008).
Deppe, C., et al., Structure-Activity Relationship of Covalently Dimerized Insulin Derivatives—Correlation of Partial Agonist Efficacy with Cross-Linkage at Lysine B29. Naunyn-Schmiedebergs Archives of Pharmacology, 1994. 350(2): p. 213-217.
Du et al., "Biochemistry and Molecular Biology International," vol. 45, No. 2, Jun. 1, 1998, pp. 255-260 XP008147747.
Du X et al, Hydroxyl group of insulin A19Tyris essential for receptor binding: studies on (A9Phe) insulin, BioChem and Mol Biology International, Academic Press, Lindon, GB vol. 45, No. 2, Jun. 1, 1998, pp. 255-260. found in extended EP search report 09837982.9.
Eriksson et al., "hPEPT1 Affinity and Translocation of Selected Gln-Sar and Glu-Sar Dipeptide Derivatives", *Molecular Pharmaceutics* vol. 2, No. 3: 242-249 (May 10, 2005).
European supplemental search report for EP 09837983.7 completed by the EPO on Mar. 15, 2012.
Evans et al., "Effect of β-Endorphin C-Terminal Peptides on Glucose Uptake in Isolated Skeletal Muscles of the Mouse", Peptides, vol. 18, No. 1, pp. 165-167, (1997).
Garcia-Aparicio et al., "Design and Discovery of a Novel Dipeptidyl-peptidase IV (CD26)-Based Prodrug Approach", *J. Med. Chem.* 49: 5339-5351 (2006).
GenBank entry AAH05278, Jul. 15, 2006 [http:www/ncbi.nim.nih.gov/protein/13528972>].
Gershonov et al, A Novel Approach for a Water-Soluble long Acting Insulin Prodrug . . . , J. Med. Chem (2000) vol. 43, pp. 2530-2537.
Goolcharran et al., "Comparison of the Rates of Deamidation, Diketopiperazine Formation, and Oxidation in Recombinant Human Vascular Endothelial Growth Factor and Model Peptides", *AAPS Pharmsci 2000* 2(1) article 5: 1-6 (Mar. 17, 2000).
Hamel et al "Cyclosporin a prodrugs: Design, synthesis and biophysical properties", J. Peptide Research, vol. 63 No. 2 pp. 147-154 (Feb. 2004).
Harris, J. Milton, Final Word: PEGylation—A "Sunset" Technology? <http://licence.icopyright.net/user/viewFreeUse.act?fuid=OTU1NjY3OA%3D%3D>, BioPharm International, Jun. 1, 2004.
Hinds et al, Advanced Drug Delivery Reviews 2002, (54) 505-530.
Hua et al, J of Biological Chemistry, Mar. 2008, vol. 283, No. 21, 14703-14716.
Joost, H.G., et al., Quantitative Dissociation of Glucose-Transport Stimulation and Insulin-Receptor Tyrosine Kinase Activation in Isolated Adipocytes with a Covalent Insulin Dimer (B29,B29'—Sunberoyl-Insulin). Biochemical Pharmacology, 1989. 38(14): p. 2269-2277.
Kaur et al., "Novel Single Chain Insulin Analogs Consisting of a Non-Peptide Based Connection," APS poster presentation, May 12, 2011.
Kristensen et al., "Alanine Scanning Mutagenesis of Insulin," The Journal of Biological Chemistry, 1997, 272(20):12978-12983.

(56) References Cited

OTHER PUBLICATIONS

Kurapkat et al "Inactive conformation of an insulin despite its wild-type sequence", Protein Science, vol. 6, No. 3, pp. 580-587 (Mar. 1997).

M.J. Roberts et al., "Chemistry for Peptide and Protein PEGylation," Advance Drug Delivery Reviews, Elsevier BV, Amsterdam, NL, vol. 54, No. 4, Jun. 17, 2002, pp. 459-476.

Madsen et al., "Structure—Activity and Protraction Relationship of Long-Acting Glucagon-like Peptide-1 Derivatives: Importance of Fatty acid Length, Polarity, and Bulkiness," J. Med. Chem. 2007, 50, pp. 6126-6132.

Mayer et al., Insulin Structure and Function, Peptide Science 2007, 88(5):687-713.

O'Brien, Assay for DPPIV Activity using a Homogenous, Luminescent Method, Cell Notes, 2005, 11:8-11 (http://www.promega.com/resources/articles/pubhub/cellnotes/assay-for-dppiv-activity-using-a-homogeneous-luminescent-method/).

PCT International Search Report for PCT/US2009/031593 completed by the US Searching Authority on Jul. 16, 2009.

PCT International Search Report for PCT/US2009/068711 completed by the US Searching Authority on Feb. 4, 2010.

PCT International Search Report for PCT/USS2009/068712 completed by the US Searching Authority on Mar. 24, 2010.

PCT International Search Report for PCT/US2009/068716 completed by the US Searching Authority on May 3, 2010.

PCT International Search Report for PCT/US2009/068745 completed by the US Searching Authority on Feb. 1, 2010.

PCT International Search Report for PCT/US2011/041601 completed by the US Searching Authority on Nov. 10, 2011.

Phillips et al., "Supramolecular protein engineering: design of zinc-stapled insulin hexamers as a long acting depot," J. Biol. Chem., Apr. 16, 2010, vol. 285, No. 16, pp. 11755-11759.

Roth, R.A., et al., Effects of Covalently Linked Insulin Dimers on Receptor Kinase-Activity and Receptor down Regulation. Febs Letters, 1984. 170(2): p. 360-364.

Santos et al., Cyclization-Activated Prodrugs. Synthesis, Reactivity and Toxicity of Dipeptide Esters of Paracetamol, *Bioorganic & Medicinal Chemistry Letters* 15: 1595-1598 (2005).

Sato, H., "Enzymatic procedure for site-specific pegylation of proteins," Advanced Drug Delivery Reviews 54, pp. 487-504 (2002).

Schilling et al., "Degradation of Insulin by Trypsin and Alphachymotrypsin," Pharmaceutical Research 1991, 8(6):721-727 (abstract).

Schuttler, A. and D. Brandenburg, Preparation and Properties of Covalently Linked Insulin Dimers. Hoppe-Seylers Zeitschrift Fur Physiologische Chemie, 1982. 363(3): p. 317-330.

Shojaee-Moradie, F., et al., Demonstration of a Relatively Hepatoselective Effect of Covalent Insulin Dimers on Glucose-Metabolism in Dogs. Diabetologia, 1995. 38(9): p. 1007-1013.

Tatnell, M.A., et al., Evidence Concerning the Mechanism of Insulin-Receptor Interaction and the Structure of the Insulin-Receptor from Biological Properties of Covalently Linked Insulin Dimers. Biochemical Journal, 1983. 216(3): p. 687-694.

Tatnell, M.A., R.H. Jones, and P.H. Sonksen, Covalently-Linked Insulin Dimers—Their Metabolism and Biological Effects In vivo as Partial Competitive Antagonists of Insulin-Clearance. Diabetologia, 1984. 27(1): p. 27-31.

Wang et al., "Identification of Site(s) of Insulin Nitration by Peroxynitrite and Characterization of its Structural Change," Protein & Peptide Letters 2008, 15:1063-1067.

Ward, "Fatty Acid Acylation of Peptides: Developing strategies to enhance medicines for treating metabolic disorders," Jan. 14, 2009.

Weiland et al, "Antagonistic effects of a covalently dimerized insulin derivatized insulin derivative on insulin receptors in 3T3-L1 adipocytes", PNAS, vol. 87, pp. 1154-1158, Feb. 1990.

Yang et al, World J. of Gastroentero, 2000: 6(3): 371-373.

Yang et al., "A Novel Approach to Resin-Based Cysteine Alkylation," American Peptide Society, 2005.

PCT International Search Report and Written Opinion completed by the U.S. Searching Authority on Feb. 12, 2012 and issued in connection with PCT/US2011/040699.

Suaifan et al., "Effects of steric bulk and stereochemistry on the rates of diketopiperazine formation from $N$-aminoacyl-2,2-dimethylthiasolidine-4-carboxamides (Dmt dipeptide amides)—a model for a new prodrug linker system," Tetrahedron, vol. 62 (2006), pp. 11245-11266.

Hua Qing-Xin et al., "Design of an active ultrastable single-chain insulin analog-Synthesis, structure and therapeutic implications", J. Biol Chem, Amer Society for Biochemistry and Molecular Biology, vol. 283, No. 21 (May 2008), pp. 14703-14716.

Rajpal et al., "Single-Chain Insulins as Receptor Agonists", Molecular Endocrinology, vol. 23, No. 5 (Feb. 2009) pp. 679-688.

Kristensen et al, A single-chain insulin-like growth factor I/insulin hybrid binds with high affinity to the insulin receptor, Biochemical Journal, the Biochem Society, London, GB vol. 305 (Pt 3) (Feb. 1995) pp. 981-986.

* cited by examiner

Synthetic "A⁷-B⁷"-derived Insulin Receptor Binding

Fig. 5

A-Chain

```
           1                       21
Insulin    GIVEQCCTSICSLYQLENYCN
IGF I      ---DE--FRS-D-RR--M--A
IGF II     ----E--FRS-D-AL--T--A
```

B-Chain

```
           1                              30
Insulin    FVNQHLCGSHLVEALYLVCGERGFFYTPKT
IGF I      *GPET---AE--D--QF--D---YFNKP-
IGF II     AYRPSET---GE--DT-QF----D---YFSRPA
```

C-Chain

```
            1                                      35
Proinsulin  RREAEDLQVGQVELGGGPGAGSLQPLALEGSLQKR
IGF I       GYGSSSRRAPQT
IGF II      SRVSRRSR
```

D-Chain

```
        1        8
IGF I   ********
IGF II  PLKPAKSA
        *T*PAKSE
```

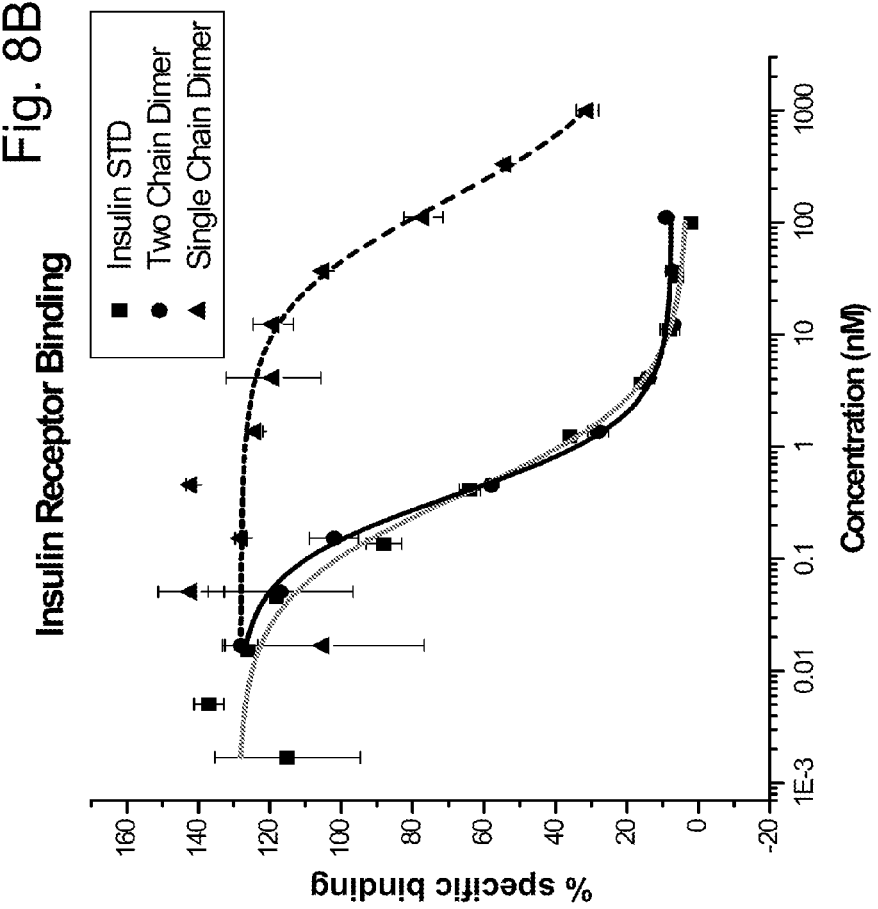

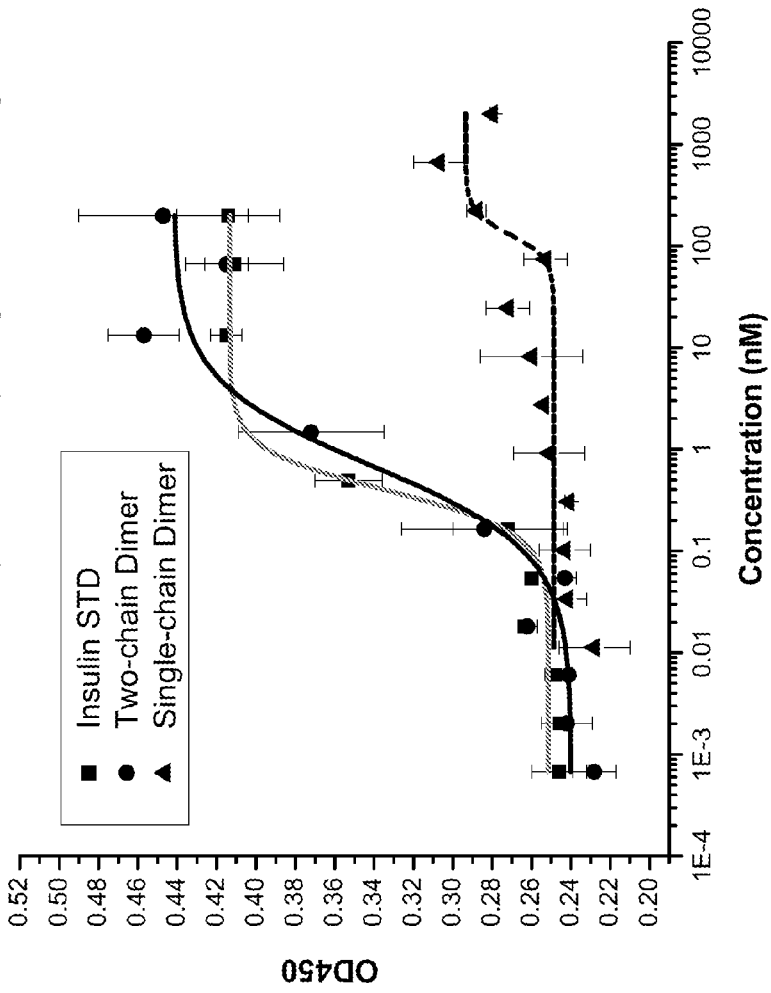

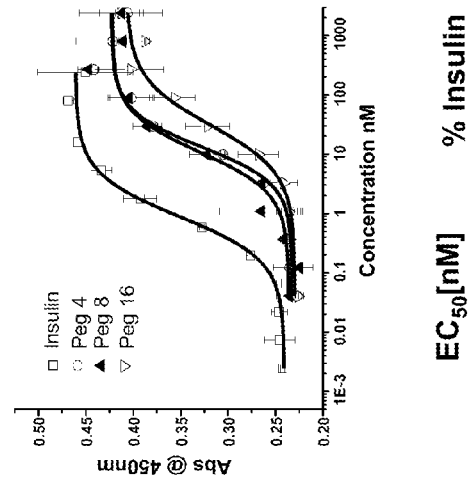
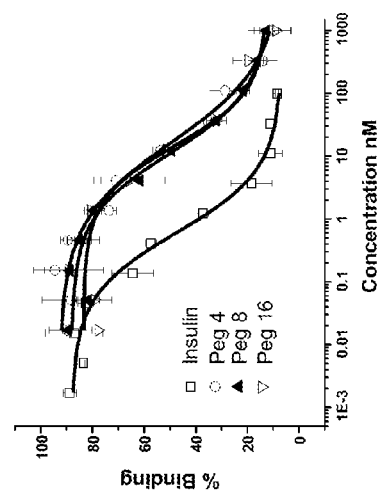
FIG. 20 A
FIG. 20 B

Addition of His$^{B10}$ in PEG$_{12}$ Des V
Phosphorylation Data

|  | %Insulin | n | %I

| | %Insulin | n | %IGF-1 | n | | %Insulin | n | %IGF-1 | n |
|---|---|---|---|---|---|---|---|---|---|
| 1. Insulin | 100 | 6 | 0.92 | 16 | Peg$_4$ | 5.69 | 3 | 0.44 | 2 |
| 2. Peg$_8$DesV | 91.2 | 5 | 2.43 | 8 | Peg$_8$ | 7.44 | 5 | 1.21 | 4 |
| 3. Peg$_{12(4-8)}$DesV | 342 | 4 | 8.35 | 6 | Peg$_{16}$ | 5.17 | 3 | 0.16 | 2 |
| 4. Peg$_{16}$DesV | 83.3 | 3 | 1.39 | 8 | Peg$_8$ PK | 11.57 | 2 | 1.27 | 2 |
| 5. Peg$_{12}$DesV | 179 | 3 | 5.31 | 3 | Peg$_8$ PK 2C | 10.04 | 2 | 0.24 | 2 |
| 6. Peg$_{12}$A$^{H8}$DesV | 241 | 4 | 9.06 | 5 | Peg$_4$ HHDesV | 8.34 | 2 | 0.13 | 2 |
| 7. Peg$_{12}$HHHDesV | 83.1 | 3 | 1.31 | 3 | 8. Peg$_4$HHDesV 2C | 451 | 2 | 50.4 | 2 |
| Peg$_{12}$B$^{H5H10}$DesV | 36.3 | 2 | 0.81 | 2 | Peg$_4$HHHDesV | 0.90 | 2 | 0.04 | 2 |
| IGF-1 DesV Blunt | 0.04 | 1 | 0 | 1 | 9. PEG4HHHDesV2C | 295 | 2 | 6.49 | 2 |
| K Peg4 DesV | 2.37 | 2 | 0.16 | 2 | | | | | |

Added Lysine to A-chain
| Analog | | IR Binding (%Ins) | IR Phosphor. (%Ins) | IGF-1 Binding (% IGF-1) | IGF-1 Phosphor. (%IGF-1) |
|---|---|---|---|---|---|
| Insulin | | 100 | 100 | 1.00 ± 0.00 | 0.67± 0.35 |
| $Peg_{12}$DesV | | 172± 21 | 216 ± 51 | 2.50 ± 0.14 | 5.31 ± 2.83 |
| $Peg_{12}$DesV KK | | 136 ± 27 | 194 ± 16 | 1.93 ± 0.51 | NA |
| $Peg_{16}$DesV | | 167 ± 2 | 83.3± 8.5 | 0.75 ± 0.35 | 1.39 ± 1.18 |
FIG. 28B

Analogs Tested in Mice

| Analog | IR Phosphor (%Ins) | IR Binding (Ins %) |
|---|---|---|
| Insulin | 100 | 100 |
| InsPeg$_{12}$DesV | 92 | 98 |
| Peg$_{12}$DesV | 216 (5x) | 172 (9x) |
| Peg$_{12}$DesVH$^{B10}$ | 39 | 18 |
| Peg$_{12}$DesVH$^{B10}$A$^{10}$ | 83 | 25 |
| Peg$_{12}$DesVH$^{B10}$ T$^{A8}$ I$^{A10}$ | 59 | 30 |
| Peg$_{12}$DesV KK | 194 | 136 |

FIG. 29A

Comparative Insulin Tolerance Tests Acylated Analogs

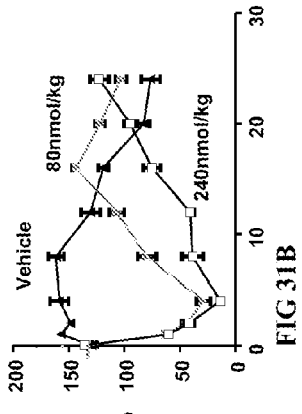
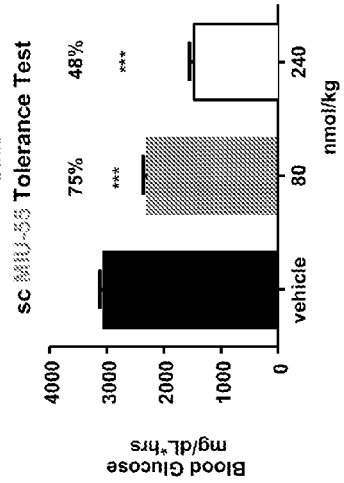
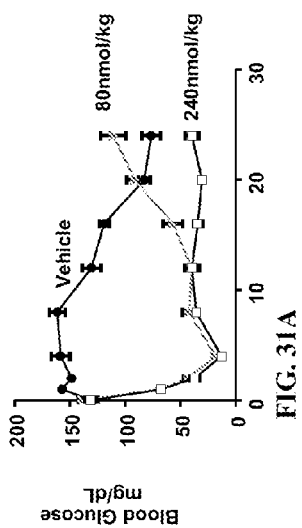
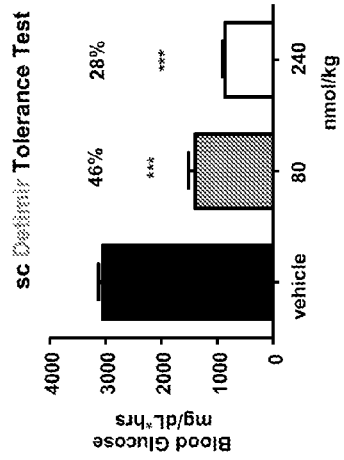

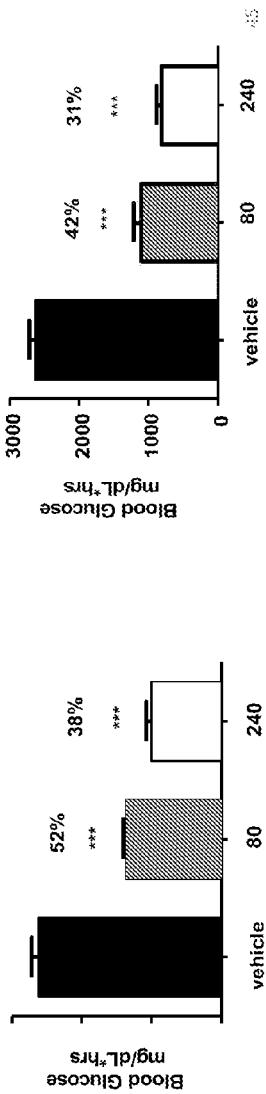
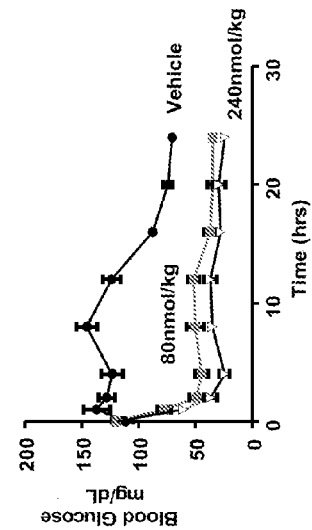
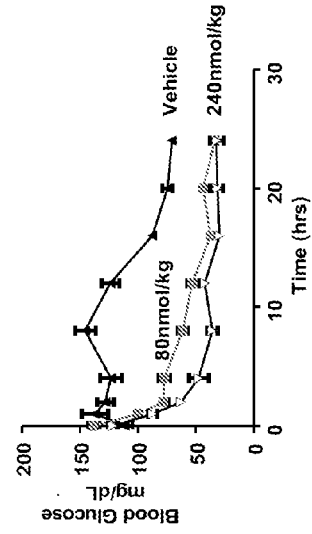

Comparative Insulin Tolerance Test for MIU-56 & MIU-57

Comparative Insulin Dose Titration MIU 67-69
40 nmol/kg

Glucose in 12 & 24 in db/db mice

SINGLE-CHAIN INSULIN AGONISTS EXHIBITING HIGH ACTIVITY AT THE INSULIN RECEPTOR

CROSS REFERENCE TO RELATED APPLICATIONS

This application is a U.S. national counterpart application of International Application No. PCT/US2011/040699 filed Jun. 16, 2011, which claims priority to U.S. Provisional Patent Application Nos. 61/355,366 and 61/433,500, filed Jun. 16, 2010 and Jan. 17, 2011, respectively. The entire disclosures of PCT/US2011/040699, USSN 61/355,366 and USSN 61/433,500 are hereby incorporated by reference.

INCORPORATION BY REFERENCE OF MATERIAL SUBMITTED ELECTRONICALLY

Incorporated by reference in its entirety is a computer-readable nucleotide/amino acid sequence listing submitted concurrently herein and identified as follows: One 90KB ACII (Text) file named "SeqlistsingleST252" created on Mar. 19, 2013.

BACKGROUND

Insulin is a proven therapy for the treatment of juvenile-onset diabetes and later stage adult-onset diabetes. The peptide is biosynthesized as a larger linear precursor of low potency (approximately 2% to 9% of native insulin), named proinsulin. Proinsulin is proteolytically converted to insulin by the selective removal of a 35-residue connecting peptide (C peptide). The resultant heteroduplex formed by disulfide links between the insulin "A chain" (SEQ ID NO: 1) and "B chain" (SEQ ID NO: 2) chain, representing a total of 51 amino acids, has high potency for the insulin receptor (nM range). Native insulin has approximately one hundredfold selective affinity for the insulin receptor relative to the related insulin-like growth factor 1 receptor, but demonstrates little selectively for the two different insulin receptor isoforms, named A & B.

The insulin-like growth factors 1 and 2 are single chain liner peptide hormones that are highly homologous in their A and B chain sequences, sharing approximately fifty percent homology with native insulin. The IGF A and B chains are linked by a "C-peptide", wherein the C-peptides of the two IGFs differ in size and amino acid sequence, the first being twelve and the second being eight amino acids in length. Human IGF-1 is a 70 aa basic peptide having the protein sequence shown in SEQ ID NO: 3, and has a 43% homology with proinsulin (Rinderknecht et al. (1978) J. Biol. Chem. 253:2769-2776). Human IGF-2 is a 67 amino acid basic peptide having the protein sequence shown in SEQ ID NO: 4. The IGFs demonstrate considerably less activity at the insulin B receptor isoform than the A-receptor isoform.

Applicants have previously identified IGF-1 based insulin peptides analogs, (wherein the native Gln-Phe dipeptide of the B-chain is replaced by Tyr-Leu) that display high activity at the insulin receptor (see PCT/US2009/068713, the disclosure of which is incorporated herein). Such analogs (referred to herein as IGF YL analog peptides) are more readily synthesized than insulin and enable the development of co-agonist analogs for insulin and IGF-1 receptors, and selective insulin receptor specific analogs. Furthermore, these insulin analogs can also be formulated as single chain insulin agonists in accordance with the present disclosure.

Single chain insulin analogs comprising the insulin A and B chains have been previously prepared (see EP 1,193,272 and US 2007/0129284). However, previously disclosed single chain insulin analogs suffer the disadvantage of either exhibiting low potency at the insulin receptor and/or relatively high potency at the IGF-1 receptor. The compounds of the present invention are prepared based on the discovery that single chain high potency insulin agonists can be prepared by insertion of the IGF-1 C-peptide, or analogs thereof, as a connecting peptide linking the insulin B and A peptides. The selective mutation of individual amino acids in the C-peptide sequence yields peptides that are highly selective for insulin relative to IGF-1 receptor.

In addition, the preparation of single chain insulin agonists are likely to enhance the secondary structure of insulin and insulin analogs, yielding improvements in biophysical stability, therapeutic index and in vivo pharmacology. The pharmacology of insulin is not glucose sensitive, and as such, the administration of insulin can result in excessive action that can lead to life-threatening hypoglycemia. Inconsistent pharmacology is a hallmark of insulin therapy such that it is extremely difficult to normalize blood glucose without occurrence of hypoglycemia. Furthermore, native insulin is of short duration of action and requires modification to render it suitable for use in control of basal glucose. Single chain insulin analog peptides are suitable for further structural enhancements that are envisioned to yield improved therapeutic index, through the use of prodrug chemistry; extended duration of action, by linkage of plasma proteins such as albumin, or other modifications, including pegylation and acylation; enhanced physical stability, by glycosylation; and preferred tissue targeting through the use of chemical modification with cholesterol or vitamin-like substituents. The preparation of single chain insulin analogs using a C-peptide linker also provides a novel structural location for where many of these chemical modifications can be successfully deployed. The primary use of such optimized insulin-agonists would be in the treatment of insulin-dependent diabetes.

SUMMARY

As disclosed herein applicants have discovered high potency single chain insulin analogs. More particularly, in one embodiment a high potency single chain insulin agonist polypeptide is provided that is highly selective for the insulin receptor relative to the IGF-1 receptor. In accordance with one embodiment the single chain insulin analog agonist comprises a B chain and A chain of human insulin, or analogs or derivatives thereof, wherein the carboxy terminus of the B chain is linked to the amino terminus of the A chain via a linking moiety. In one embodiment the B chain is a C-terminal truncated B chain having amino acids B26-B30 removed (positions relative to the native insulin B chain). In this embodiment the carboxy terminus of the B25 amino acid of the B chain is directly linked to a first end of the linking moiety and the second end of the linking moiety is directly linked to the amino terminus of the A1 amino acid of the A chain. In one embodiment, wherein the linear single chain insulin analog comprises a C-terminal truncated B chain, and the linking moiety is a peptide, the linking moiety is at least 8 amino acids in length but not greater than 17 amino acids in length. In embodiments where the linear single chain insulin analog comprises a full length B chain, and the linking moiety is a peptide, the linking moiety is at least 8 amino acids in length but not greater than 12 amino acids in length.

In accordance with one embodiment the linking moiety comprises
a) a polyethylene glycol of 6-16 monomer units;
b) a non-native insulin or IGF amino acid sequence of at least 8 amino acids and no more than 17 amino acid in length, or a peptidomimetic thereof, and comprising the sequence $X_{51}X_{52}X_{53}X_{54}X_{55}X_{56}X_{57}X_{58}$ (SEQ ID NO: 9); or
c) a combination of said polyethylene glycol and a shortened amino acid sequence of 1 to 4 amino acids, wherein $X_{51}$ is selected from the group consisting of glycine, alanine, valine, leucine, isoleucine, proline, phenylalanine and methionine;

$X_{52}$ is any amino acid other than tyrosine;

$X_{53}$ through $X_{56}$ are each independently any amino acid; and $X_{57}$ and $X_{58}$ are independently selected from the group consisting of arginine, ornithine and lysine. The linking moiety may comprise non-naturally occurring amino acids as well as a retroinverso fragment, or incorporation of non-peptide bonds such as an azapeptide bond (CO substituted by NH) or pseudo-peptide bond (e.g. NH substituted with $CH_2$) or an ester bond (e.g., a depsipeptide, wherein one or more of the amide (—CONHR—) bonds are replaced by ester (COOR) bonds). When the linking moiety comprises an amino acid sequence it is also intended that any of the designated amino acids also encompasses derivatives of the indicated amino acid including chemical modifications to the amino acid, e.g. a nitro group in a tyrosine residue, or iodine in a tyrosine residue, or by conversion of a free carboxylic group to an ester group or to an amide group, or by converting an amino group to an amide by acylation, or by acylating a hydroxy group rendering an ester, or by alkylation of a primary amine rendering a secondary amine or linkage of a hydrophilic moiety to an amino acid side chain. Other derivatives are obtained by oxidation or reduction of the side-chains of the amino acid.

In one embodiment the a single chain insulin analog comprises a hydrophilic moiety linked to the N-terminus of the B chain or to a side chain of an amino acid of the linking moiety. More particularly, in one embodiment the single chain insulin agonist analog comprises the general structure B-LM-A wherein B represents an insulin B chain, A represents an insulin A chain and LM represents a linking moiety linking the carboxy terminus of the B chain to the amino terminus of the A chain, wherein the linking moiety further comprises a hydrophilic moiety linked to the side chain of an amino acid of the linking moiety and/or to the N-terminal alpha amine of the B chain (position B1 for insulin based B chains and position B2 for IGF-1 based B chains) or the side chain of an amino acid at a position selected from the group consisting of A9, A14 and A15 of the A chain or positions B1, B2, B10, B22, B28 or B29 of the B chain. In one embodiment the hydrophilic moiety is linked to the N-terminal alpha amine of the B chain (i.e. positions B1 for insulin or position B2 for IGF insulin agonist using the insulin-based number scheme). In one embodiment the hydrophilic moiety is a polyethylene chain and in a further embodiment the polyethylene chain is covalently bound to the side chain of an amino acid of the linking moiety. In one embodiment the linking moiety (LM) comprises an amino acid sequence of no more than 17 amino acids in length and comprising the sequence $X_{51}X_{52}X_{53}X_{54}X_{55}X_{56}X_{57}X_{58}$ (SEQ ID NO: 9), wherein $X_{51}$ is selected from the group consisting of glycine, alanine, valine, leucine, isoleucine, proline, phenylalanine and methionine;

$X_{52}$ is any amino acid other than tyrosine;

$X_{53}$ through $X_{56}$ are each independently any amino acid; and $X_{57}$ and $X_{58}$ are independently arginine, lysine, cysteine, homocysteine, acetyl-phenylalanine or ornithine. In one embodiment the linking moiety (LM) comprises the sequence $X_{51}X_{52}GSSSX_{57}X_{58}$ (SEQ ID NO: 29) or $X_{51}X_{52}GSSSX_{57}X_{58}APQT$ (SEQ ID NO: 46) wherein the amino acid designated by $X_{57}$ or $X_{58}$ further comprises a hydrophilic moiety linked to the side chain of the amino acid at that position. In one embodiment the hydrophilic moiety is a polyethylene glycol chain.

In one embodiment the linking moiety comprises an 8-17 amino acid sequence comprising the sequence $GYGSSSX_{57}X_{58}$ (SEQ ID NO: 85) or $GYGSSSX_{57}X_{58}APQT$; (SEQ ID NO: 37), or a peptidomimetic thereof;

wherein $X_{57}$ and $X_{58}$ are independently arginine, lysine or ornithine. In one embodiment the hydrophilic moiety is linked to the side chain of an amino acid located at position 8 of a linking moiety comprising SEQ ID NO: 37 or 85.

In one embodiment the linking moiety comprises
1) a linear polyethylene glycol chain of 6-16 monomer units,
2) an amino acid sequence at least 8 amino acids and no more than 12 amino acid in length and comprising the sequence $X_{51}X_{52}X_{53}X_{54}X_{55}X_{56}RR$ (SEQ ID NO: 10), or
3) a combination of said polyethylene glycol chain and an amino acid sequence. In a further embodiment the linking moiety is selected from the group consisting of $(Y_1)_k$-$X_{51}AX_{53}X_{54}X_{55}X_{56}RR(Y_2)_n$ (SEQ ID NO: 23), $(Y_2)_k$-$GYGSSSX_{57}R$ (SEQ ID NO: 51) and

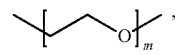

wherein $Y_1$ is selected from the group $X_{46}$, $X_{46}X_{47}$, $X_{46}X_{47}X_{48}$, $X_{46}X_{47}X_{48}X_{49}$ (SEQ ID NO: 24) and $X_{46}X_{47}X_{48}X_{49}X_{50}$ (SEQ ID NO: 13); and $Y_2$ is selected from the group $X_{70}$, $X_{70}X_{71}$, $X_{70}X_{71}X_{72}$ and $X_{70}X_{71}X_{72}X_{73}$ (SEQ ID NO: 15);

n is 0 or 1;

k is 0 or 1;

m is an integer ranging from 7 to 16; and $X_{46}$ through $X_{50}$ and $X_{70}$ through $X_{73}$ are each independently any amino acid;

$X_{51}$ is selected from the group consisting of glycine, alanine, valine, leucine, isoleucine, proline, phenylalanine and methionine;

$X_{52}$ is any amino acid other than tyrosine;

$X_{53}$ through $X_{56}$ are each independently any amino acid; and $X_{57}$ is arginine, lysine or ornithine.

In another embodiment the linking moiety is a relatively short bifunctional non-peptide polymer linker that approximates the length of an 8-16 amino acid sequence. In accordance with one embodiment the non-peptide linking moiety is a polyethylene glycol linker of approximately 4 to 20, 8 to 18, 8 to 16, 8 to 14, 8 to 12, 10 to 14, 10 to 12 or 11 to 13 monomers. In one embodiment a single chain insulin agonist is provided wherein the last five carboxy amino acids of the B chain are deleted, and amino acid B25 is linked to amino acid A1 of the A chain via a polyethylene glycol linking moiety (LM) of at least 6 but no more than 20 monomer units, or at least 8 but no more than 14 monomer units, or at least 10 but no more than 14 monomer units. In one embodiment the linking moiety is a polyethylene glycol having a total of 12 monomers.

In one embodiment the linking moiety of the single chain insulin analog is a bifunctional complex of the formula X-Y, wherein X is a non-peptide linker (e.g., polyethylene glycol) and Y is an amino acid or a 2-4 amino acid peptide. In one embodiment the last five amino acids of the native B chain carboxy terminus are deleted, and the carboxy terminus of amino acid B25 is linked directly to X, and Y is directly linked to the amino terminus of an insulin A chain. In another embodiment a single chain insulin agonist is provided wherein the last five carboxy amino acids of the native B chain carboxy terminus are deleted, and amino acid B25 is linked to amino acid A1 of the A chain via a linking moiety comprising a polyethylene glycol of at least 8 but less than 14 monomer units in length and a 2-5 amino acid sequence. The 2-5 amino acid sequence can be located between the B chain and the polyethylene glycol chain or between the A chain and the polyethylene glycol chain. However, when the 2-5 amino acid sequence is located between the B chain and the polyethylene glycol chain, the amino acid sequence is not YTPKT (SEQ ID NO: 16) or FNKPT (SEQ ID NO: 76). In one embodiment the linking moiety comprises two polyethylene chains separated by 1 or 2 amino acids. In one embodiment the 1 or 2 amino acids are independently lysine or cysteine. In one embodiment the linking moiety comprises a two polyethylene chains representing a total of 8-12 or 10-14 or 12 monomeric units of ethylene glycol separated by a single amino acid. In one embodiment the single amino acid is lysine or cysteine.

The single chain insulin agonists of the present invention may comprise the native B and A chain sequences or any of the known analogs or derivatives thereof that exhibit insulin agonist activity when linked to one another in a heteroduplex. As disclosed herein such A chain and B chain peptides can be linked to one another by the linking moieties described herein to form a single chain insulin agonist. In accordance with one embodiment the B chain comprises the sequence $R_{22}$-$X_{25}LCGX_{29}X_{30}LVX_{33}X_{34}LX_{36}LVCGX_{41}X_{42}GFX_{45}$ (SEQ ID NO: 20), and the A chain comprises the sequence $GIVX_4X_5CCX_8X_9X_{10}CX_{12}LX_{14}X_{15}LX_{17}X_{18}X_{19}CX_{21}$-$R_{13}$ (SEQ ID NO: 22), wherein $X_4$ is glutamic acid or aspartic acid;
$X_5$ is glutamine or glutamic acid
$X_8$ is histidine or phenylalanine;
$X_9$ is serine, arginine, lysine, ornithine or alanine;
$X_{10}$ is isoleucine or serine;
$X_{12}$ is serine or aspartic acid;
$X_{14}$ is tyrosine, arginine, lysine, ornithine or alanine;
$X_{15}$ is glutamine, glutamic acid, arginine, alanine, lysine, ornithine or leucine;
$X_{17}$ is glutamic acid, aspartic acid, asparagine, lysine, ornithine or glutamine;
$X_{18}$ is methionine, asparagine, glutamine, aspartic acid, glutamic acid or threonine;
$X_{19}$ is tyrosine, 4-methoxy-phenylalanine or 4-amino phenylalanine;
$X_{21}$ is selected from the group consisting of alanine, glycine, serine, valine, threonine, isoleucine, leucine, glutamine, glutamic acid, asparagine, aspartic acid, histidine, tryptophan, tyrosine, and methionine;
$X_{25}$ is histidine or threonine;
$X_{29}$ is selected from the group consisting of alanine, glycine and serine;

$X_{30}$ is selected from the group consisting of histidine, aspartic acid, glutamic acid, homocysteic acid and cysteic acid;
$X_{33}$ is selected from the group consisting of aspartic acid and glutamic acid;
$X_{34}$ is selected from the group consisting of alanine and threonine;
$X_{36}$ is tyrosine;
$X_{41}$ is selected from the group consisting of glutamic acid, aspartic acid or asparagine;
$X_{42}$ is selected from the group consisting of alanine, ornithine, lysine and arginine;
$X_{45}$ is tyrosine;
$R_{22}$ is selected from the group consisting of AYRPSE (SEQ ID NO: 14), FVNQ (SEQ ID NO: 12), PGPE (SEQ ID NO: 11), a tripeptide glycine-proline-glutamic acid, a tripeptide valine-asparagine-glutamine, a dipeptide proline-glutamic acid, a dipeptide asparagine-glutamine, glutamine, glutamic acid and an N-terminal amine; and
$R_{13}$ is COOH or $CONH_2$. In one embodiment $X_8$, $X_{25}$ and $X_{30}$ are each histidine.

In one embodiment, prodrug derivatives of single chain insulin analogs are provided wherein the prodrug comprises a dipeptide prodrug element (U-B) covalently linked to an active site of the single chain insulin analog via an amide or ester linkage (see International applications WO 2009/099763 and PCT/US2009/068713 the disclosures of which are incorporated herein). Subsequent removal of the dipeptide under physiological conditions and in the absence of enzymatic activity restores full activity to the single chain insulin analog. In one embodiment the prodrug element comprises a dipeptide of the structure U-B, wherein U is an amino acid or a hydroxy acid, B is an N-alkylated amino acid linked to said single chain insulin agonist through an amide bond between a carboxyl moiety of B and an amine of the single chain insulin agonist, wherein U, B, or the amino acid of the single chain insulin agonist to which U-B is linked is a non-coded amino acid. In one embodiment the chemical cleavage half-life ($t_{1/2}$) of U-B from the single chain insulin agonist is at least about 1 hour to about 1 week in PBS under physiological conditions. In one embodiment the single chain agonist comprises a 4-amino phenylalanine at position A19, and dipeptide prodrug element U-B is linked to a single chain insulin agonist through an amide bond between a carboxyl moiety of B and the para amine of 4-amino phenylalanine.

Additional derivatives of the single chain insulin agonists are encompassed by the present disclosure including modifications that improve the solubility of the underlying single chain insulin agonist. In one embodiment the solubility of the single chain insulin agonist peptide is enhanced by the covalent linkage of a hydrophilic moiety to the peptide. In one embodiment the hydrophilic moiety is linked to either the N-terminal amino acid of the B chain or to the side chain of an amino acid located at the terminal end of the B chain (e.g. a lysine present at any of positions B26-30) or to the linking moiety binding the B chain to the A chain. In one embodiment the hydrophilic moiety is albumin, including for example, albumins such as human serum albumin (HSA) and recombinant human albumin (rHA). In one embodiment the hydrophilic moiety is a polyethylene glycol (PEG) chain, having a molecular weight selected from the range of about 500 to about 40,000 Daltons. In one embodiment the polyethylene glycol chain has a molecular weight selected from the range of about 500 to about 5,000 Daltons. In another embodiment the polyethylene glycol chain has a molecular weight of about 10,000 to about 20,000 Daltons.

Acylation or alkylation can increase the half-life of the single chain insulin analog peptides, and prodrug derivatives thereof, in circulation. Acylation or alkylation can advantageously delay the onset of action and/or extend the duration of action at the insulin receptors. The insulin analogs may be acylated or alkylated at the same amino acid position where a hydrophilic moiety is linked (including, for example at position 8 of the linking moiety), or at a different amino acid position.

Also encompassed by the present disclosure are pharmaceutical compositions comprising the single chain insulin analog agonist, and derivatives thereof, and a pharmaceutically acceptable carrier. In accordance with one embodiment a pharmaceutical composition is provided comprising any of the single chain insulin analogs disclosed herein, or derivative thereof, preferably at a purity level of at least 90%, 91%, 92%, 93%, 94%, 95%, 96%, 97%, 98% or 99%, and a pharmaceutically acceptable diluent, carrier or excipient. Such compositions may contain a single chain insulin agonist peptide as disclosed herein at a concentration of at least 0.5 mg/ml, 1 mg/ml, 2 mg/ml, 3 mg/ml, 4 mg/ml, 5 mg/ml, 6 mg/ml, 7 mg/ml, 8 mg/ml, 9 mg/ml, 10 mg/ml, 11 mg/ml, 12 mg/ml, 13 mg/ml, 14 mg/ml, 15 mg/ml, 16 mg/ml, 17 mg/ml, 18 mg/ml, 19 mg/ml, 20 mg/ml, 21 mg/ml, 22 mg/ml, 23 mg/ml, 24 mg/ml, 25 mg/ml or higher. In one embodiment the pharmaceutical compositions comprise aqueous solutions that are sterilized and optionally stored within various package containers. In other embodiments the pharmaceutical compositions comprise a lyophilized powder. The pharmaceutical compositions can be further packaged as part of a kit that includes a disposable device for administering the composition to a patient. The containers or kits may be labeled for storage at ambient room temperature or at refrigerated temperature.

In accordance with one embodiment an improved method of regulating blood glucose levels in insulin dependent patients is provided. The method comprises the steps of administering to a patient a single chain insulin agonist peptide, or derivative thereof, in an amount therapeutically effective for the control of diabetes.

BRIEF DESCRIPTION OF THE DRAWINGS

FIG. 5 is an alignment of the human proinsulin (A chain, SEQ ID NO: 1; B chain, SEQ ID NO: 2 and the C chain, SEQ ID NO: 92) and insulin-like growth factors I and II (IGF I; SEQ ID NO: 3 and IGF II; SEQ ID NO: 4) amino acid sequences. The alignment demonstrates that these three peptides share a high level of sequence identity (* indicates a space with no corresponding amino acid and a dash (-) indicates the identical amino acid as present in insulin).

FIG. 8A-8C provides the activity of a dimer prepared in accordance with the present disclosure. FIG. 8A shows the structure of an IGF-1 single chain dimer that comprises two single chain IGF$^{B16B17}$ analog peptides (IGF 1B chain [$C^0H^5Y^{16}L^{17}O^{22}$]-A chain[$O^{9,14,15}N^{18,21}$]; SEQ ID NO: 93) linked together by a disulfide bond between the side chains of the amino terminus of the B chains. The native insulin disulfides ($A^6$-$A^{11}$, $A^7$-$B^7$, $A^{20}B^{19}$) are not shown but are resident in the dimer form. The single chain form of the disulfide dimer can be converted to a two-chain form by selective proteolytic digestion of the two Arg-Gly bonds as denoted by the arrows. FIG. 8B is a graph demonstrating the relative insulin receptor binding of insulin, a single chain IGF$^{B16B17}$ analog peptide dimer and a two chain IGF$^{B16B17}$ analog peptide dimer. FIG. 8C is a graph demonstrating the relative activity of insulin, and a two chain IGF$^{B16B17}$ analog peptide dimer to induce insulin receptor phosphorylation.

FIG. 10A is a graph comparing relative insulin receptor binding of native insulin (measured at 1 hour at 4° C.) and the A19 IGF prodrug derivative (Aib, dPro-IGF1YL) over time (0 hours, 2.5 hours and 10.6 hours) incubated in PBS. FIG. 10B is a graph comparing relative insulin receptor binding of native insulin and the A19 IGF prodrug derivative (Aib, dPro-IGF1YL) over time (0 hours, 1.5 hours and 24.8 hours) incubated in 20% plasma/PBS at 37° C. As indicated by the data presented in the graph, increased activity is recovered from the A19 IGF prodrug derivative sample as the prodrug form is converted to the active IGF1YL peptide.

FIG. 11A is a graph comparing relative insulin receptor binding of native insulin and the A19 IGF prodrug derivative (IGF1YL: dK, (N-isobutylG) over time (0 hours, 5 hours and 52 hours) incubated in PBS. FIG. 11B is a graph comparing relative insulin receptor binding of native insulin and the A19 IGF prodrug derivative (IGF1YL: dK, (N-isobutylG) over time (0 hours, 3.6 hours and 24.8 hours) incubated in 20% plasma/PBS at 37° C. As indicated by the data presented in the graph, increased activity is recovered from the A19 IGF prodrug derivative sample as the prodrug form is converted to the active IGF1YL peptide.

FIG. 12A is a graph comparing relative insulin receptor binding of native insulin (measured at 1 hour at 4° C.) and the A19 IGF prodrug derivative (IGF1YL: dK(e-acetyl), Sar) over time (0 hours, 7.2 hours and 91.6 hours) incubated in PBS. FIG. 12B is a graph comparing relative insulin receptor binding of native insulin and the A19 IGF prodrug derivative (IGF1YL: dK(e-acetyl), Sar) over time (0 hours, 9 hours and 95 hours) incubated in 20% plasma/PBS at 37° C. As indicated by the data presented in the graph, increased activity is recovered from the A19 IGF prodrug derivative sample as the prodrug form is converted to the active IGF1YL peptide.

FIGS. 20A & B are graphs depicting the relative in vitro binding activity (FIG. 20 A) and phosphorylation activity (FIG. 20 B) of single chain insulin analogs linked via a 4, 8 or 16 monomeric PEG linking moiety relative to the native insulin heteroduplex.

FIG. 22A provides data comparing single chain insulin analogs comprising either the native insulin sequences or the IGF-1 A and IGF-1 YL B chains wherein the last 5 carboxy amino acids of the B chain are the deleted (DesV) and the B chain is linked to its corresponding insulin or IGF-1 A chain by a 12 monomeric PEG linking moiety. FIGS. 22B & C are graphs showing the results of comparative insulin tolerance tests conducted on mice comparing the ability of MIU-38 [a single chain insulin analog wherein the B and A chains are linked via PEG: [B¹(H5, H10,Y16, L17)25(Peg12)A¹(H8, N18, N21)], see FIG. 22B and MIU-35 [a single chain insulin analog wherein the B and A chains are linked via a peptide linker: B¹(H5, H10, Y16, L17)25-C¹-A¹(H8, N18, N21), see FIG. 22C, relative to a vehicle control, to reduce and sustain low blood glucose concentration. Two experiments were conducted wherein MIU-38 and MIU-35 were administered at 27 and 90 nmol/kg.

FIGS. 28A and 28B is a comparative analysis of single chain peg/amino acid-linked analogs in vitro activities at the insulin and IGF-1 receptors as measured by receptor binding and receptor signaling through phosphorylation. FIG. 28A shows the in vitro activity of a single chain analog comprising a $PEG_{12}$ chain with an inserted single amino acid (glycine or lysine) as the linking moiety linking a DesV B chain to the native insulin A chain. FIG. 28B shows in vitro activity of a single chain analog comprising a linking moiety comprising a $PEG_{12}$ chain with two lysine residues inserted (single chain peg/(lysine)$_2$-linked analog).

FIG. 29A-E provides in vivo data of mice administered various single chain insulin analogs. FIG. 29A provides in vitro comparative analysis of single chain peg-linked analogs activities at the insulin receptor as measured by receptor binding and receptor signaling through phosphorylation; FIGS. 29B and 29C provide data on blood glucose concentrations over 8 hours after administration of the listed analogs. FIGS. 29D and 29E provide data on blood glucose AUC values after administration of the listed analogs at two different concentrations (27 nmol/kg and 90 nmol/kg).

FIGS. 31A-31D show the results of comparative insulin tolerance tests conducted on mice comparing the activity of the commercially available acylated insulin analog (Detemir) relative to the acylated two chain insulin analog MIU-55. MIU-55 [$B^1$(H5, 10, Y16, L17, C16rE-K22)25a:$A^1$(N18, N21)] has the C-terminal 5 amino acids of the B chain deleted and terminates as a B chain amide. It is acylated with a C16 fatty acid through a gamma Glu linker at the e-amino group of Lys B22. The results indicate that MIU-55 is about one third as potent as Detemir (see FIGS. 31A and 31B). The data also indicate that the acylated forms of insulin are longer acting than the non-acylated forms and that MIU-55 while less potent than Detemir, exhibits a similar profile as Detemir. FIGS. 31C and 31D provide data on blood glucose AUC values after administration of the listed analogs.

FIGS. 32C and 32D provide data on blood glucose AUC values after administration of the listed analogs.

FIGS. 33A and 33B are graphs showing the results of insulin tolerance tests comparing the ability of the acylated insulin analog Detemir relative to the pegylated single chain insulin analog MIU-56 to reduce and maintain low blood glucose levels. FIGS. 33C and 33D show the blood glucose $AUC_{24\ hrs}$ in mice administered Detemir and MIU-56, respectively.

FIGS. 34A-34F represents the results obtained from a comparative insulin tolerance test for MIU-56 and MIU-57 using C57/Blk mice. MIU-57 is an insulin single chain analog ($B^1$(H5, Y16, L17)25-$C^1$-$A^1$(N18, 21) comprising a 20 kDa PEG linked to the N-terminus of the B chain. FIGS. 34A and 34B are graphs showing the results of insulin tolerance tests comparing MIU-56 and MIU-57. FIGS. 34C and 34D show the blood glucose $AUC_{24\ hrs}$ in mice administered MIU-56 and MIU-57, respectively. Results from comparative insulin dose titrations of MIU-56 and MIU-57 reveal that a similar profile is obtained in mice for dosages ranging from 20 nmol/kg through 80 nmol/kg (see FIGS. 34E and 34F). A dimer (MIU 58) was prepared comprising two insulin single chain analogs ($B^1$(H5, Y16, L17)25-$C^1$-$A^1$(N18, 21) linked head to head via a 20 kDa PEG chain. FIGS. 34G and 34H are graphs showing the results of insulin tolerance tests comparing MIU-57 (monomer) and MIU-58 (dimer). FIGS. 34I and 34J show the blood glucose $AUC_{24\ hrs}$ in mice administered MIU-57 and MIU-58, respectively.

As shown in FIG. 38 the two compounds performed almost identically.

DETAILED DESCRIPTION

Definitions

Figure 1:
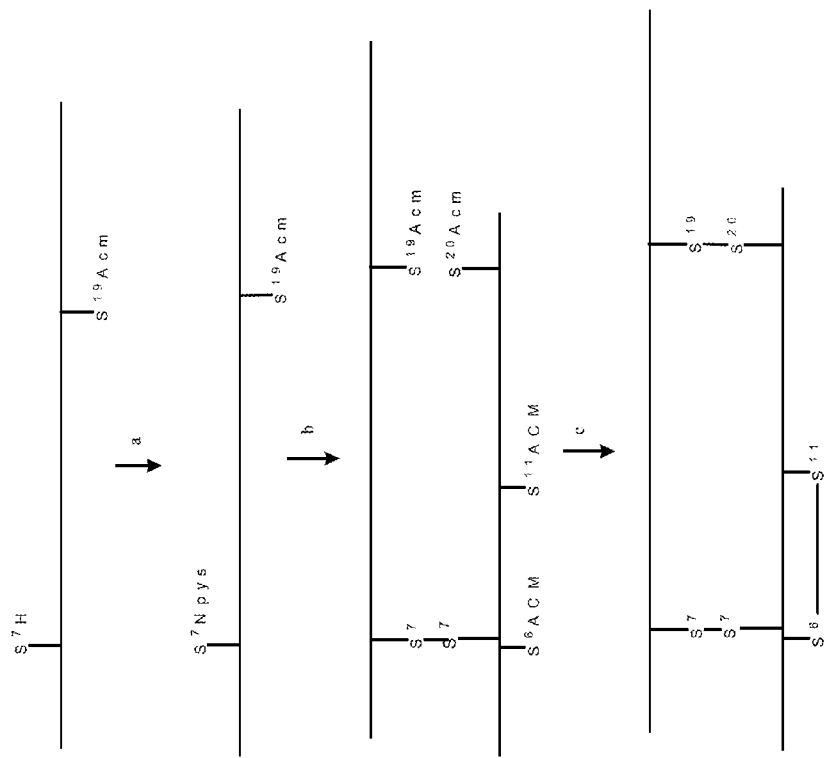
FIG. 1. is a schematic overview of the two step synthetic strategy for preparing human insulin. Details of the procedure are provided in Example 1.

In describing and claiming the invention, the following terminology will be used in accordance with the definitions set forth below.

The term "about" as used herein means greater or lesser than the value or range of values stated by 10 percent, but is not intended to designate any value or range of values to only this broader definition. Each value or range of values preceded by the term "about" is also intended to encompass the embodiment of the stated absolute value or range of values.

As used herein, the term "prodrug" is defined as any compound that undergoes chemical modification before exhibiting its pharmacological effects.

As used herein the term "amino acid" encompasses any molecule containing both amino and carboxyl functional groups, wherein the amino and carboxylate groups are attached to the same carbon (the alpha carbon). The alpha carbon optionally may have one or two further organic substituents. For the purposes of the present disclosure designation of an amino acid without specifying its stereochemistry is intended to encompass either the L or D form of the amino acid, or a racemic mixture. However, in the instance where an amino acid is designated by its three letter code and includes a superscript number, the D form of the amino acid is specified by inclusion of a lower case d before the three letter code and superscript number (e.g., dLys$^{-1}$), wherein the designation lacking the lower case d (e.g., Lys$^{-1}$) is intended to specify the native L form of the amino acid. In this nomenclature, the inclusion of the superscript number designates the position of the amino acid in the insulin analog sequence, wherein amino acids that are located within the insulin analog sequence are designated by positive superscript numbers numbered consecutively from the N-terminus. Additional amino acids linked to the insulin analog peptide either at the N-terminus or through a side chain are numbered starting with 0 and increasing in negative integer value as they are further removed from the insulin analog sequence. For example, the position of an amino acid within a dipeptide prodrug linked to the N-terminus of an insulin analog is designated aa$^{-1}$-aa$^0$-insulin analog, wherein aa$^0$ represents the carboxy terminal amino acid of the dipeptide and aa$^{-1}$ designates the amino terminal amino acid of the dipeptide.

As used herein the term "hydroxyl acid" refers to amino acids that have been modified to replace the alpha carbon amino group with a hydroxyl group.

As used herein the term "non-coded amino acid" encompasses any amino acid that is not an L-isomer of any of the following 20 amino acids: Ala, Cys, Asp, Glu, Phe, Gly, His, Ile, Lys, Leu, Met, Asn, Pro, Gln, Arg, Ser, Thr, Val, Trp, Tyr.

A "dipeptide" is a compound formed by linkage of an alpha amino acid or an alpha hydroxyl acid to another amino acid, through a peptide bond.

As used herein the term "chemical cleavage" absent any further designation encompasses a non-enzymatic reaction that results in the breakage of a covalent chemical bond.

A "bioactive polypeptide" refers to polypeptides which are capable of exerting a biological effect in vitro and/or in vivo.

As used herein a general reference to a peptide is intended to encompass peptides that have modified amino and carboxy termini. For example, an amino acid sequence designating the standard amino acids is intended to encompass standard amino acids at the N- and C-terminus as well as a corresponding hydroxyl acid at the N-terminus and/or a corresponding C-terminal amino acid modified to comprise an amide group in place of the terminal carboxylic acid.

As used herein an "acylated" amino acid is an amino acid comprising an acyl group which is non-native to a naturally-occurring amino acid, regardless by the means by which it is produced. Exemplary methods of producing acylated amino acids and acylated peptides are known in the art and include acylating an amino acid before inclusion in the peptide or peptide synthesis followed by chemical acylation of the peptide. In some embodiments, the acyl group causes the peptide to have one or more of (i) a prolonged half-life in circulation, (ii) a delayed onset of action, (iii) an extended duration of action, (iv) an improved resistance to proteases, such as DPP-IV, and (v) increased potency at the IGF and/or insulin peptide receptors.

As used herein, an "alkylated" amino acid is an amino acid comprising an alkyl group which is non-native to a naturally-occurring amino acid, regardless of the means by which it is produced. Exemplary methods of producing alkylated amino acids and alkylated peptides are known in the art and including alkylating an amino acid before inclusion in the peptide or peptide synthesis followed by chemical alkylation of the peptide. Without being held to any particular theory, it is believed that alkylation of peptides will achieve similar, if not the same, effects as acylation of the peptides, e.g., a prolonged half-life in circulation, a delayed onset of action, an extended duration of action, an improved resistance to proteases, such as DPP-IV, and increased potency at the IGF and/or insulin receptors.

As used herein, the term "pharmaceutically acceptable carrier" includes any of the standard pharmaceutical carriers, such as a phosphate buffered saline solution, water, emulsions such as an oil/water or water/oil emulsion, and various types of wetting agents. The term also encompasses any of the agents approved by a regulatory agency of the US Federal government or listed in the US Pharmacopeia for use in animals, including humans.

As used herein the term "pharmaceutically acceptable salt" refers to salts of compounds that retain the biological activity of the parent compound, and which are not biologically or otherwise undesirable. Many of the compounds disclosed herein are capable of forming acid and/or base salts by virtue of the presence of amino and/or carboxyl groups or groups similar thereto.

Pharmaceutically acceptable base addition salts can be prepared from inorganic and organic bases. Salts derived from inorganic bases, include by way of example only, sodium, potassium, lithium, ammonium, calcium and magnesium salts. Salts derived from organic bases include, but are not limited to, salts of primary, secondary and tertiary amines.

Pharmaceutically acceptable acid addition salts may be prepared from inorganic and organic acids. Salts derived from inorganic acids include hydrochloric acid, hydrobromic acid, sulfuric acid, nitric acid, phosphoric acid, and the like. Salts derived from organic acids include acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluene-sulfonic acid, salicylic acid, and the like.

As used herein, the term "hydrophilic moiety" refers to any compound that is readily water-soluble or readily absorbs water, and which are tolerated in vivo by mammalian species without toxic effects (i.e. are biocompatible). Examples of hydrophilic moieties include polyethylene glycol (PEG), polylactic acid, polyglycolic acid, a polylactic-polyglycolic acid copolymer, polyvinyl alcohol, polyvinylpyrrolidone, polymethoxazoline, polyethyloxazoline, polyhydroxyethyl methacrylate, polyhydroxypropyl methacrylamide, polymethacrylamide, polydimethylacrylamide, and derivatised celluloses such as hydroxymethylcellulose or hydroxyethylcellulose and co-polymers thereof, as well as natural polymers including, for example, albumin, heparin and dextran.

As used herein, the term "treating" includes prophylaxis of the specific disorder or condition, or alleviation of the symptoms associated with a specific disorder or condition and/or preventing or eliminating said symptoms. For example, as used herein the term "treating diabetes" will refer in general to maintaining glucose blood levels near normal levels and may include increasing or decreasing blood glucose levels depending on a given situation.

As used herein an "effective" amount or a "therapeutically effective amount" of an insulin analog refers to a nontoxic but sufficient amount of an insulin analog to provide the desired effect. For example one desired effect would be the prevention or treatment of hyperglycemia. The amount that is "effective" will vary from subject to subject, depending on the age and general condition of the individual, mode of administration, and the like. Thus, it is not always possible to specify an exact "effective amount." However, an appropriate "effective" amount in any individual case may be determined by one of ordinary skill in the art using routine experimentation.

The term, "parenteral" means not through the alimentary canal but by some other route such as intranasal, inhalation, subcutaneous, intramuscular, intraspinal, or intravenous.

Throughout the application, all references to a particular amino acid position by letter and number (e.g. position A5) refer to the amino acid at that position of either the A chain (e.g. position A5) or the B chain (e.g. position B5) in the respective native human insulin A chain (SEQ ID NO: 1) or B chain (SEQ ID NO: 2), or the corresponding amino acid position in any analogs thereof. For example, a reference herein to "position B28" absent any further elaboration would mean the corresponding position B27 of the B chain of an insulin analog in which the first amino acid of SEQ ID NO: 2 has been deleted. Similarly, amino acids added to the N-terminus of the native B chain are numbered starting with B0, followed by numbers of increasing negative value (e.g., B-1, B-2 . . . ) as amino acids are added to the N-terminus. Alternatively, any reference to an amino acid position in the linking moiety of a single chain analog, is made in reference to the native C chain of IGF 1 (SEQ ID NO: 17). For example, position 9 of the native C chain (or the "position C9") has an alanine residue.

As used herein the term "native insulin peptide" is intended to designate the 51 amino acid heteroduplex comprising the A chain of SEQ ID NO: 1 and the B chain of SEQ ID NO: 2, as well as single-chain insulin analogs that comprise SEQ ID NOS: 1 and 2. The term "insulin peptide" as used herein, absent further descriptive language is intended to encompass the 51 amino acid heteroduplex comprising the A chain of SEQ ID NO: 1 and the B chain of SEQ ID NO: 2, as well as single-chain insulin analogs thereof (including for example those disclosed in published international application WO96/34882 and U.S. Pat. No. 6,630,348, the disclosures of which are incorporated herein by reference), including heteroduplexes and single-chain analogs that comprise modified analogs of the native A chain and/or B chain and derivatives thereof. Such modified analogs include modification of the amino acid at position A19, B16 or B25 to a 4-amino phenylalanine or one or more amino acid substitutions at positions selected from A5, A8, A9, A10, A12, A14, A15, A17, A18, A21, B1, B2, B3, B4, B5, B9, B10, B13, B14, B17, B20, B21, B22, B23, B26, B27, B28, B29 and B30 or deletions of any or all of positions B1-4 and B26-30. Insulin peptides as defined herein can also be analogs derived from a naturally occurring insulin by insertion or substitution of a non-peptide moiety, e.g. a retroinverso fragment, or incorporation of non-peptide bonds such as an azapeptide bond (CO substituted by NH) or pseudo-peptide bond (e.g. NH substituted with $CH_2$) or an ester bond (e.g., a depsipeptide, wherein one or more of the amide (—CONHR—) bonds are replaced by ester (COOR) bonds).

An "A19 insulin analog" is an insulin peptide that has a substitution of 4-amino phenylalanine or 4-methoxy phenylalanine for the native tyrosine residue at position 19 of the A chain of native insulin.

As used herein an "$IGF^{B16B17}$ analog peptide" is a generic term that comprising an A chain and B chain heteroduplex, as well as single-chain insulin analogs thereof, wherein the A chain comprises the peptide sequence of SEQ ID NO: 19 and the B chain comprises the sequence of SEQ ID NO: 21 as well as analogs of those sequences wherein the analog of the A chain and/or B chain comprise 1-3 further amino acid substitutions, with the proviso that the B chain does not comprise the sequence of SEQ ID NO: 2 and comprises a tyrosine at position B16 and a leucine at position B17.

An "IGF YL analog" is a peptide comprising an IGF A chain of SEQ ID NO: 19 and an IGF B chain of SEQ ID NO: 58.

As used herein, the term "single-chain insulin analog" encompasses a group of structurally-related proteins wherein insulin or IGF A and B chains, or analogs or derivatives thereof, are covalently linked to one another to form a linear polypeptide chain. As disclosed herein the single-chain insulin analog comprises the covalent linkage of the carboxy terminus of the B chain to the amino terminus of the A chain via a linking moiety.

As used herein the term "insulin A chain", absent further descriptive language is intended to encompass the 21 amino acid sequence of SEQ ID NO: 1 as well as functional analogs and derivatives thereof, including the A chain of A19 insulin analogs and other analogs known to those skilled in the art, including modification of the sequence of SEQ ID NO: 1 by one or more amino acid insertions, deletions or substitutions at positions selected from A4, A5, A8, A9, A10, A12, A14, A15, A17, A18, A21.

As used herein the term "insulin B chain", absent further descriptive language is intended to encompass the 30 amino acid sequence of SEQ ID NO: 2, as well as modified functional analogs of the native B chain, including modification of the amino acid at position B16 or B25 to a 4-amino phenylalanine or one or more amino acid insertions, deletions or substitutions at positions selected from B1, B2, B3, B4, B5, B9, B10, B13, B14, B17, B20, B21, B22, B23, B25, B26, B27, B28, B29 and B30 or deletions of any or all of positions B1-4 and B26-30.

As used herein the term "derivative" is intended to encompass chemical modification to a compound (e.g., an amino acid), including chemical modification in vitro, e.g. by introducing a group in a side chain in one or more positions of a polypeptide, e.g. a nitro group in a tyrosine residue, or iodine in a tyrosine residue, or by conversion of a free carboxylic group to an ester group or to an amide group, or by converting an amino group to an amide by acylation, or by acylating a hydroxy group rendering an ester, or by alkylation of a primary amine rendering a secondary amine or linkage of a hydrophilic moiety to an amino acid side chain. Other derivatives are obtained by oxidation or reduction of the side-chains of the amino acid residues in the polypeptide.

As used herein the term IGF A chain, absent further descriptive language is intended to encompass the 21 amino acid sequence of native IGF 1 or IGF 2 (SEQ ID NOs: 5 and 7 respectively), as well as functional analogs thereof known to those skilled in the art, including modification of the sequence of SEQ ID NO: 5 and 7 by one or more amino acid substitutions at positions selected from A5, A8, A9, A10, A12, A14, A15, A17, A18, A21.

As used herein the term "IGF YL B chain", absent further descriptive language is intended to encompass an amino acid sequence comprising SEQ ID NO: 21, including for example the sequence of SEQ ID NO: 168, as well as analogs of the IGF YL B chain and derivatives thereof, including modification of the amino acid at position B16 or B25 to a 4-amino phenylalanine or one or more amino acid substitutions at positions selected from B1, B2, B3, B4, B5, B9, B10, B13, B14, B17, B20, B21, B22, B23, B26, B27, B28, B29 and B30 or deletions of any or all of positions B1-4 and B26-30.

The term "identity" as used herein relates to the similarity between two or more sequences. Identity is measured by dividing the number of identical residues by the total number of residues and multiplying the product by 100 to achieve a percentage. Thus, two copies of exactly the same sequence have 100% identity, whereas two sequences that have amino acid deletions, additions, or substitutions relative to one another have a lower degree of identity. Those skilled in the art will recognize that several computer programs, such as those that employ algorithms such as BLAST (Basic Local Alignment Search Tool, Altschul et al. (1993) J. Mol. Biol. 215:403-410) are available for determining sequence identity.

As used herein, the term "selectivity" of a molecule for a first receptor relative to a second receptor refers to the following ratio: $EC_{50}$ of the molecule at the second receptor divided by the $EC_{50}$ of the molecule at the first receptor. For example, a molecule that has an $EC_{50}$ of 1 nM at a first receptor and an $EC_{50}$ of 100 nM at a second receptor has 100-fold selectivity for the first receptor relative to the second receptor.

As used herein an amino acid "modification" refers to a substitution of an amino acid, or the derivation of an amino acid by the addition and/or removal of chemical groups to/from the amino acid, and includes substitution with any of the 20 amino acids commonly found in human proteins, as well as atypical or non-naturally occurring amino acids. Commercial sources of atypical amino acids include Sigma-Aldrich (Milwaukee, Wis.), ChemPep Inc. (Miami, Fla.), and Genzyme Pharmaceuticals (Cambridge, Mass.). Atypical amino acids may be purchased from commercial suppliers, synthesized de novo, or chemically modified or derivatized from naturally occurring amino acids.

As used herein an amino acid "substitution" refers to the replacement of one amino acid residue by a different amino acid residue.

As used herein, the term "conservative amino acid substitution" is defined herein as exchanges within one of the following five groups:

I. Small aliphatic, nonpolar or slightly polar residues:
   Ala, Ser, Thr, Pro, Gly;
II. Polar, negatively charged residues and their amides:
   Asp, Asn, Glu, Gln, cysteic acid and homocysteic acid;
III. Polar, positively charged residues:
   His, Arg, Lys; Ornithine (Orn)
IV. Large, aliphatic, nonpolar residues:
   Met, Leu, Ile, Val, Cys, Norleucine (Nle), homocysteine
V. Large, aromatic residues:
   Phe, Tyr, Trp, acetyl phenylalanine As used herein the general term "polyethylene glycol chain" or "PEG chain", refers to mixtures of condensation polymers of ethylene oxide and water, in a branched or straight chain, represented by the general formula $H(OCH_2CH_2)_nOH$, wherein n is at least 2. "Polyethylene glycol chain" or "PEG chain" is used in combination with a numeric suffix to indicate the approximate average molecular weight thereof. For example, PEG-5,000 refers to polyethylene glycol chain having a total molecular weight average of about 5,000 Daltons.

As used herein the term "pegylated" and like terms refers to a compound that has been modified from its native state by linking a polyethylene glycol chain to the compound. A "pegylated polypeptide" is a polypeptide that has a PEG chain covalently bound to the polypeptide.

As used herein an "acylated" amino acid is an amino acid comprising an acyl group which is non-native to a naturally-occurring amino acid, regardless by the means by which it is produced. Exemplary methods of producing acylated amino acids and acylated peptides are known in the art and include acylating an amino acid before inclusion in the peptide or peptide synthesis followed by chemical acylation of the peptide. In some embodiments, the acyl group causes the peptide to have one or more of (i) a prolonged half-life in circulation, (ii) a delayed onset of action, (iii) an extended duration of action, (iv) an improved resistance to proteases, and (v) increased potency at the insulin receptor.

As used herein, an "alkylated" amino acid is an amino acid comprising an alkyl group which is non-native to a naturally-occurring amino acid, regardless of the means by which it is produced. Exemplary methods of producing alkylated amino acids and alkylated peptides are known in the art and including alkylating an amino acid before inclusion in the peptide or peptide synthesis followed by chemical alkylation of the peptide. Without being held to any particular theory, it is believed that alkylation of peptides will achieve similar, if not the same, effects as acylation of the peptides, e.g., a prolonged half-life in circulation, a delayed onset of action, an extended duration of action, an improved resistance to proteases, and increased potency at the insulin receptor.

As used herein a "linker" is a bond, molecule or group of molecules that binds two separate entities to one another. Linkers may provide for optimal spacing of the two entities or may further supply a labile linkage that allows the two entities to be separated from each other. Labile linkages include photocleavable groups, acid-labile moieties, base-labile moieties and enzyme-cleavable groups.

As used herein an "IGF dimer" is a complex comprising two IGF YL analog peptides (each itself comprising an A chain and a B chain) covalently bound to one another via a linker. The term IGF dimer, when used absent any qualifying language, encompasses both IGF homodimers and IGF heterodimers. An IGF homodimer comprises two identical subunits, whereas an IGF heterodimer comprises two subunits that differ, although the two subunits are substantially similar to one another.

The term "$C_1$-$C_n$ alkyl" wherein n can be from 1 through 6, as used herein, represents a branched or linear alkyl group having from one to the specified number of carbon atoms. Typical $C_1$-$C_6$ alkyl groups include, but are not limited to, methyl, ethyl, n-propyl, iso-propyl, butyl, iso-Butyl, sec-butyl, tert-butyl, pentyl, hexyl and the like.

The terms "$C_2$-$C_n$ alkenyl" wherein n can be from 2 through 6, as used herein, represents an olefinically unsaturated branched or linear group having from 2 to the specified number of carbon atoms and at least one double bond. Examples of such groups include, but are not limited to, 1-propenyl, 2-propenyl (—$CH_2$—CH═$CH_2$), 1,3-butadienyl, (—CH═CHCH═$CH_2$), 1-butenyl (—CH═CHCH$_2$CH$_3$), hexenyl, pentenyl, and the like.

The term "C2-$C_n$ alkynyl" wherein n can be from 2 to 6, refers to an unsaturated branched or linear group having from 2 to n carbon atoms and at least one triple bond. Examples of such groups include, but are not limited to, 1-propynyl, 2-propynyl, 1-butynyl, 2-butynyl, 1-pentynyl, and the like.

As used herein the term "aryl" refers to a mono- or bicyclic carbocyclic ring system having one or two aromatic rings including, but not limited to, phenyl, naphthyl, tetrahydronaphthyl, indanyl, indenyl, and the like. The size of the aryl ring and the presence of substituents or linking groups are indicated by designating the number of carbons present. For example, the term "($C_1$-$C_3$ alkyl)($C_6$-$C_{10}$ aryl)" refers to a 5 to 10 membered aryl that is attached to a parent moiety via a one to three membered alkyl chain.

The term "heteroaryl" as used herein refers to a mono- or bi-cyclic ring system containing one or two aromatic rings and containing at least one nitrogen, oxygen, or sulfur atom in an aromatic ring. The size of the heteroaryl ring and the presence of substituents or linking groups are indicated by designating the number of carbons present. For example, the term "($C_1$-$C_n$ alkyl)($C_5$-$C_6$ heteroaryl)" refers to a 5 or 6 membered heteroaryl that is attached to a parent moiety via a one to "n" membered alkyl chain.

As used herein, the term "halo" refers to one or more members of the group consisting of fluorine, chlorine, bromine, and iodine.

As used herein the term "patient" without further designation is intended to encompass any warm blooded vertebrate domesticated animal (including for example, but not limited to livestock, horses, cats, dogs and other pets) and humans.

The term "isolated" as used herein means having been removed from its natural environment. In some embodiments, the analog is made through recombinant methods and the analog is isolated from the host cell.

The term "purified," as used herein relates to the isolation of a molecule or compound in a form that is substantially free of contaminants normally associated with the molecule or compound in a native or natural environment and means having been increased in purity as a result of being separated from other components of the original composition. The term "purified polypeptide" is used herein to describe a polypeptide which has been separated from other compounds including, but not limited to nucleic acid molecules, lipids and carbohydrates.

A "peptidomimetic" refers to a chemical compound having a structure that is different from the general structure of an existing peptide, but that functions in a manner similar to the existing peptide, e.g., by mimicking the biological activity of that peptide. Peptidomimetics typically comprise naturally-occurring amino acids and/or unnatural amino acids, but can also comprise modifications to the peptide backbone. For example a peptidomimetic may include a sequence of naturally-occurring amino acids with the insertion or substitution of a non-peptide moiety, e.g. a retroinverso fragment, or incorporation of non-peptide bonds such as an azapeptide bond (CO substituted by NH) or pseudo-peptide bond (e.g. NH substituted with $CH_2$), or an ester bond (e.g., depsipeptides, wherein one or more of the amide (—CONHR—) bonds are replaced by ester (COOR) bonds). Alternatively the peptidomimetic may be devoid of any naturally-occurring amino acids.

As used herein the term "charged amino acid" or "charged residue" refers to an amino acid that comprises a side chain that is negatively charged (i.e., de-protonated) or positively charged (i.e., protonated) in aqueous solution at physiological pH. For example, negatively charged amino acids include aspartic acid, glutamic acid, cysteic acid, homocysteic acid, and homoglutamic acid, whereas positively charged amino acids include arginine, lysine and histidine. Charged amino acids include the charged amino acids among the 20 amino acids commonly found in human proteins, as well as atypical or non-naturally occurring amino acids.

As used herein the term "acidic amino acid" refers to an amino acid that comprises a second acidic moiety (other than the alpha carboxylic acid of the amino acid), including for example, a side chain carboxylic acid or sulfonic acid group.

Abbreviations:

Insulin analogs will be abbreviated as follows:

The insulin A and B chains will be designated by a capital A for the A chain and a capital B for the B chain wherein a superscript 0 (e.g., $A^0$ or $B^0$) will designate the base sequence is an insulin sequence (A chain: SEQ ID NO: 1, B chain SEQ ID NO: 2) and a superscript 1 (e.g., $A^1$ or $B^1$) will designate the base sequence is an IGF-1 sequence (A chain: SEQ ID NO: 5, B chain SEQ ID NO: 6). Modifications that deviate from the native insulin and IGF sequence are indicated in parenthesis following the designation of the A or B chain (e.g., [$B^1$(H5, H10, Y16, L17): $A^1$(H8, N18, N21)]) with the single letter amino acid abbreviation indicating the substitution and the number indicating the position of the substitution in the respective A or B chain, using native insulin numbering. A colon between the A and B chain indicates a two chain insulin whereas a dash will indicate a covalent bond and thus a single chain analog. In single chain analogs a linking moiety will be included between the A and B chains and the designation C¹ refers to the native IGF 1 C peptide, SEQ ID NO: 17. The designation "position C8" in reference to the linking moiety designates an amino acid located at the position corresponding to the eighth amino acid of SEQ ID NO: 17.

Embodiments

As disclosed herein applicants have discovered high potency single chain insulin analogs. More particularly, applicants have discovered unique linking moieties that can be used to covalently link the B chain and A chain of human insulin, or analogs or derivatives thereof to form a high potency linear single chain insulin agonists. In one embodiment the linking moiety covalently bonds the carboxy terminus of the B chain to the amino terminus of the A chain.

As disclosed herein optimally sized linking moieties can be used to link human insulin A and B chains, or analogs or derivatives thereof, wherein the carboxy terminus of the B25 amino acid of the B chain is directly linked to a first end of a linking moiety, wherein the second end of the linking moiety is directly linked to the amino terminus of the A1 amino acid of the A chain via the intervening linking moiety. In one embodiment the linking moiety comprises an 8 to 17 amino acid peptide, and more particularly, in one embodiment the peptide represents an analog of the IGF-1 C peptide. In another embodiment the linking moiety comprises a relatively short bifunctional non-peptide polymer linker that approximates the length of an 8-16 amino acid sequence. In accordance with one embodiment the non-peptide linking moiety is a polyethylene glycol linker of approximately 4 to 20, 8 to 18, 8 to 16, 8 to 14, 8 to 12, 10 to 14, 10 to 12 or 11 to 13 monomers.

In one embodiment a single chain insulin agonist analog is provided that comprises the general structure B-LM-A wherein B represents an insulin B chain, A represents an insulin A chain, and LM represents a linking moiety linking the carboxy terminus of the B chain to the amino terminus of the A chain. The insulin A and B chains can be any known insulin sequence, including those disclosed herein, that when linked together as a heteroduplex form a functional insulin. Applicants have discovered a variety of linking moieties as disclosed herein that can be used to link the insulin A and B chain together to generate an active single chain insulin analog. In accordance with one embodiment the linking moiety further comprises a hydrophilic moiety linked to the side chain of an amino acid of the linking moiety and/or at a position selected from the group consisting of A9, A14 and A15 of the A chain or at the N-terminal alpha amine (positions B1, B2) or the side chain of an amino acid at positions B10, B22, B28 or B29 of the B chain. In one embodiment the hydrophilic moiety is a polyethylene chain that is linked to an amino acid of the linking moiety and/or at the N-terminal alpha amine of the B chain. In one embodiment the linking moiety (LM) comprises an amino acid sequence of no more than 17 amino acids in length and comprising the sequence $X_{51}X_{52}X_{53}X_{54}X_{55}X_{56}X_{57}X_{58}$ (SEQ ID NO: 9), wherein $X_{51}$ is selected from the group consisting of glycine, alanine, valine, leucine, isoleucine, proline, phenylalanine and methionine;

$X_{52}$ is any amino acid other than tyrosine;

$X_{53}$ through $X_{56}$ are each independently any amino acid; and $X_{57}$ and $X_{58}$ are independently arginine, lysine, cysteine, homocysteine, acetyl-phenylalanine or ornithine. In one embodiment the linking moiety further comprises a hydrophilic moiety linked to the side chain of an amino acid of the linking moiety. In one embodiment the linking moiety comprises the sequence $X_{51}X_{52}GSSSX_{57}X_{58}$ (SEQ ID NO: 29) or $X_{51}X_{52}GSSSX_{57}X_{58}APQT$ (SEQ ID NO: 46) wherein $X_{51}$ is selected from the group consisting of glycine, alanine, valine, leucine, isoleucine and proline, $X_{52}$ is alanine, valine, leucine, isoleucine or proline and $X_{57}$ or $X_{58}$ are independently arginine, lysine, cysteine, homocysteine, acetyl-phenylalanine or ornithine, wherein a hydrophilic moiety is linked to the side chain of the amino acid at position 7 or 8 of the linking moiety (i.e., at the $X_{57}$ or $X_{58}$ position). Amino acid positions of the linking moiety are designated based on the corresponding position in the native C chain of IGF 1 (SEQ ID NO: 17).

In accordance with one embodiment a single chain insulin agonist polypeptide is provided comprising a B chain and A chain of human insulin, or analogs or derivative thereof, wherein the last five carboxy amino acids of the native B chain are deleted (i.e., B26-B30), and amino acid B25 is linked to amino acid A1 of the A chain via an intervening linking moiety. In one embodiment the linking moiety has the general structure:

$Y_1$-Z wherein $Y_1$ is selected from the group consisting of a bond, $X_{46}$, $X_{46}X_{47}$, $X_{46}X_{47}X_{48}$, $X_{46}X_{47}X_{48}X_{49}$ (SEQ ID NO: 24) and $X_{46}X_{47}X_{48}X_{49}X_{50}$ (SEQ ID NO: 13) wherein each of $X_{46}$, $X_{47}$, $X_{48}$, $X_{49}$ and $X_{50}$ represent any amino acid or amino acid analog or derivative thereof; and Z represents an amino acid sequence at least 8 amino acids and no more than 16 amino acid in length and comprising the sequence $X_{51}X_{52}X_{53}X_{54}X_{55}X_{56}RR$ (SEQ ID NO: 10), wherein $X_{51}$ is selected from the group consisting of glycine, alanine, valine, leucine, isoleucine, proline, phenylalanine and methionine; and $X_{52}$ through $X_{56}$ are each independently any amino acid or amino acid analog or derivative thereof. In one embodiment $X_{52}$ is any amino acid other than tyrosine. In a further embodiment $X_{52}$ is any non-aromatic amino acid, and in one embodiment $X_{52}$ is alanine, valine, leucine, isoleucine or proline. In a further embodiment $X_{51}$ is selected from the group consisting of glycine, alanine, valine, leucine, isoleucine, proline, phenylalanine and methionine; $X_{52}$ is any amino acid other than tyrosine; and $X_{53}$, $X_{54}$, $X_{55}$ and $X_{56}$ are independently selected from the group consisting of glycine, alanine, serine, threonine and proline. In one further embodiment, $X_{51}$ is selected from the group consisting of glycine, alanine, valine, leucine, isoleucine, proline, phenylalanine and methionine; $X_{52}$ is selected from the group consisting of glycine, alanine, valine, leucine, isoleucine, serine, threonine and proline; $X_{53}$ is other than glycine; $X_{54}$, and $X_{55}$ are independently selected from the group consisting of glycine, alanine, serine, threonine and proline and $X_{56}$ is serine.

In another embodiment the linking moiety comprises the general structure:

$Y_1$-W wherein $Y_1$ is selected from the group consisting of a bond, $X_{46}$, $X_{46}X_{47}$, $X_{46}X_{47}X_{48}$, and $X_{46}X_{47}X_{48}X_{49}$ (SEQ ID NO: 24) wherein each of $X_{46}$, $X_{47}$, $X_{48}$, and $X_{49}$ represent any amino acid or amino acid analog or derivative thereof, with the proviso that $Y_1$ is not YTPKT (SEQ ID NO: 16) or FNKPT (SEQ ID NO: 76); and W represents a polyethylene glycol of 2-16 monomer units.

In one embodiment a single chain insulin analog is provided comprising an A chain and a C-terminally truncated B chain, having amino acids B26-B30 (relative to the native insulin sequence) removed, wherein said A chain and B chain are human insulin sequences, or analogs or derivatives thereof, further wherein the carboxy terminus of the B25 amino acid of the B chain is directly linked to a first end of a linking moiety and a second end of the linking moiety is directly linked to the amino terminus of the A1 amino acid of the A chain, further wherein, in one embodiment, the linking moiety does not comprise the sequence YTPKT (SEQ ID NO: 16) or FNKPT (SEQ ID NO: 76). In one embodiment the C-terminally truncated B chain comprises an analog of a peptide representing amino acids 5-25 of SEQ ID NO: 2, wherein said analog differs from the corresponding amino acids 5-25 of SEQ ID NO: 2 by 1, 1 to 2, 3 to 4, 4 to 6 or up to 8 amino acid substitutions at amino acid positions selected from 5, 9, 10, 13, 14, 21, 22 and 25. In one embodiment the C-terminally truncated B chain comprises an analog of a peptide representing amino acids 1-25 of SEQ ID NO: 2, wherein said analog differs from the corresponding amino acids 1-25 of SEQ ID NO: 2 by 1, 1 to 2, 3 to 4, 4 to 6, 4 to 8 or up to 10 amino acid substitutions at amino acid positions selected from 2, 3, 4, 5, 9, 10, 13, 14, 21, 22 and 25. In one embodiment the C-terminally truncated B chain comprises a peptide having at least 70%, 75%, 80%, 90% or 95% sequence identity with the corresponding amino acids 5-25 of SEQ ID NO: 2. In one embodiment the A chain is an analog of SEQ ID NO: 1 wherein the analog differs from SEQ ID NO: 1 by 1, 1 to 2, 3 to 4, 4 to 8 or up to 10 amino acid substitutions at amino acid positions selected from 4, 5, 8, 9, 10, 12, 14, 15, 18 and 21. In one embodiment the A chain comprises a peptide having at least 70%, 75%, 80%, 90% or 95% sequence identity with SEQ ID NO: 1.

In one embodiment the linking moiety comprising a) a polyethylene glycol of 6-16 monomer units;

b) a non-native amino acid sequence of at least 8 amino acids and no more than 17 amino acid in length and comprising the sequence GYGSSS$X_{57}$R (SEQ ID NO: 51) or $X_{51}X_{52}X_{53}X_{54}X_{55}X_{56}X_{57}X_{58}$ (SEQ ID NO: 9), or a peptidomimetic thereof; or c) a combination of said polyethylene glycol and a non-native amino acid sequence of 1 to 4 amino acids;

wherein $X_{51}$ is selected from the group consisting of glycine, alanine, valine, leucine, isoleucine, proline, phenylalanine and methionine;

$X_{52}$ is any amino acid other than tyrosine;

$X_{53}$ through $X_{56}$ are each independently any amino acid; and $X_{57}$ and $X_{58}$ are independently arginine, lysine or ornithine.

In one embodiment a single chain insulin agonist analog is provided comprising the general structure B-LM-A wherein B represents an insulin B chain comprising the sequence $X_{25}$LCG$X_{29}X_{30}$LV$X_{33}X_{34}$LYLVCGD$X_{42}$GF$X_{45}$ (SEQ ID NO: 58), A represents an insulin A chain comprising the sequence GIV$X_4X_5$CC$X_8X_9X_{10}$C$X_{12}$L$X_{14}X_{15}$L$X_{17}X_{18}X_{19}$C$X_{21}$-$R_{13}$ (SEQ ID NO: 22), and LM represents a peptide linking moiety linking the carboxy terminus of the B chain to the amino terminus of the A chain. In one embodiment the linking moiety comprises an amino acid sequence of no more than 17 amino acid in length and comprising the sequence $X_{51}X_{52}X_{53}X_{54}X_{55}X_{56}X_{57}X_{58}$ (SEQ ID NO: 9), wherein $X_4$ is glutamic acid or aspartic acid;

$X_5$ is glutamine or glutamic acid $X_8$ is histidine, threonine or phenylalanine;

$X_9$ is serine, arginine, lysine, ornithine or alanine;

$X_{10}$ is isoleucine or serine;

$X_{12}$ is serine or aspartic acid $X_{14}$ is tyrosine, arginine, lysine, ornithine or alanine;

$X_{15}$ is glutamine, glutamic acid, arginine, alanine, lysine, ornithine or leucine;

$X_{17}$ is glutamine, glutamic acid, arginine, aspartic acid or lysine, ornithine $X_{18}$ is methionine, asparagine, glutamine, aspartic acid, glutamic acid or threonine;

$X_{19}$ is tyrosine, 4-methoxy-phenylalanine or 4-amino phenylalanine;

$X_{21}$ is selected from the group consisting of alanine, glycine, serine, valine, threonine, isoleucine, leucine, glutamine, glutamic acid, asparagine, aspartic acid, histidine, tryptophan, tyrosine, and methionine;

$X_{25}$ is selected from the group consisting of histidine and threonine;

$X_{29}$ is selected from the group consisting of alanine, glycine and serine;

$X_{30}$ is selected from the group consisting of histidine, aspartic acid, glutamic acid, homocysteic acid and cysteic acid;

$X_{33}$ is selected from the group consisting of aspartic acid and glutamic acid;

$X_{34}$ is selected from the group consisting of alanine and threonine;

$X_{42}$ is selected from the group consisting of alanine, ornithine and arginine;

$X_{45}$ is selected from the group consisting of tyrosine, histidine, asparagine and phenylalanine;

$X_{51}$ is selected from the group consisting of glycine, alanine, valine, leucine, isoleucine, proline, phenylalanine and methionine;

$X_{52}$ is any amino acid other than tyrosine;

$X_{53}$ through $X_{56}$ are each independently any amino acid; and $X_{57}$ and $X_{58}$ are independently arginine, lysine, cysteine, homocysteine, acetyl-phenylalanine or ornithine. In one embodiment the single chain analog further comprises a hydrophilic moiety covalently linked to the side chain of an amino acid of the linking moiety or at the N-terminal alpha amine of the B chain, or to the side chain of an amino acid at a position selected from the group consisting of A9, A14 and A15 of the A chain or positions B1, B2, B10, B22, B28 or B29 of the B chain. In one embodiment the hydrophilic moiety (e.g., PEG) is linked to the N-terminal alpha amine of the B chain. In one embodiment one to five amino acids corresponding to B26-B30 are removed from the B chain carboxy terminus and the remaining carboxy terminal amino acid is linked directly to the amino terminus of the linking moiety. In one embodiment the B chain comprises the sequence $X_{25}$LCG$X_{29}X_{30}$LV$X_{33}X_{34}$LYLVCGD$X_{42}$GF$X_{45}$ (SEQ ID NO: 58), the linking moiety comprises the sequence $(Y_1)_k$-$X_{51}X_{52}X_{53}X_{54}X_{55}X_{56}X_{57}X_{58}(Y_2)_r$ (SEQ ID NO: 9), and the A chain comprises the sequence GIV$X_4$ECC$X_8X_9$SCDL$X_{14}X_{15}$LE$X_{18}X_{19}$C$X_{21}$-$R_{13}$ (SEQ ID NO: 19).

The Linking Moiety

Peptide Linkers

In accordance with one embodiment the linking moiety is a derivative of the IGF 1 C chain sequence (GYGSSSRRAPQT; SEQ ID NO: 17). In one embodiment the derivative is a peptide that differs from SEQ ID NO: 17 by a single amino acid substitution of a lysine, cysteine ornithine, homocysteine, or acetyl-phenylalanine residue, and in a further embodiment the lysine, cysteine ornithine, homocysteine, or acetyl-phenylalanine amino acid is pegylated. In one further embodiment the linking moiety is a peptide that differs from SEQ ID NO: 17 by a single lysine substitution. In one specific embodiment the substitution is made at position 8 of SEQ ID NO: 17. Applicants have discovered that use of the IGF 1 C chain sequence and analogs thereof as a linking moiety will generate a single chain insulin polypeptide that has near wild type insulin activity. Furthermore, use of a IGF 1 C chain sequence analog as the linking moiety, wherein position 2 of the IGF 1 C chain sequence is modified, or the carboxy terminal four amino acids are deleted from the IGF 1 C chain sequence, produces a single chain insulin polypeptide that is selective for insulin (i.e., has a higher binding and/or activity at the insulin receptor compared to the IGF-1 receptor). In one embodiment the single chain insulin polypeptide has 5×, 10×, 20×, 30×, 40×, or 50× higher affinity or activity at the insulin receptor relative to the IGF-1 receptor.

In accordance with one embodiment the linking moiety is a derivative of the IGF 1 C chain sequence (GYGSSSRRAPQT; SEQ ID NO: 17) and comprises a non-native sequence that differs from GYGSSSRR (SEQ ID NO: 18) or GAGSSSRRAPQT (SEQ ID NO: 36) by 1 to 3 amino acid substitutions, or 1 to 2 amino acid substitutions. In one embodiment at least one of the amino acid substitutions is a lysine or cysteine substitution, and in one embodiment the amino acid substitutions are conservative amino acid substitutions. In one embodiment the linking moiety is a peptide (or peptidomimetic) of 8 to 17 amino acids comprising a non-native amino acid sequence that differs from GYGSSSRR (SEQ ID NO: 18) or GAGSSSRRAPQT (SEQ ID NO: 36) by 1 amino acid substitution, including for example substitution with a lysine or cysteine. In one embodiment the linking moiety comprises the sequence GYGSSSRR (SEQ ID NO: 18) or GAGSSSRRAPQT (SEQ ID NO: 36). In one embodiment the linking moiety comprises the sequence GAGSSSRX$_{58}$APQT (SEQ ID NO: 167), GYGSSSX$_{57}$X$_{58}$APQT (SEQ ID NO: 37), or an amino acid that differs from SEQ ID NO: 167 by a single amino acid substitution, wherein X$_{57}$ is arginine and X$_{58}$ is arginine, ornithine or lysine, and in a further embodiment a polyethylene glycol chain is linked to the side chain of the amino acid at position 8 of said linking moiety. In another embodiment the linking moiety comprises the sequence GX$_{52}$GSSSRX$_{58}$APQT (SEQ ID NO: 38), wherein X$_{52}$ is any non-aromatic amino acid, including for example, alanine, valine, leucine, isoleucine or proline, and X$_{58}$ represents an amino acid that has a polyethylene chain covalently linked to its side chain. In one embodiment X$_{58}$ is a pegylated lysine. In one embodiment the linking moiety comprises the sequence GYGSSSRX$_{58}$ (SEQ ID NO: 45) or GAGSSSRX$_{58}$APQT (SEQ ID NO: 167), wherein X$_{58}$ represents an amino acid that has a polyethylene chain covalently linked to its side chain.

In accordance with one embodiment the linking moiety is a peptide or peptidomimetic of 6-18, 8-18, 8-17, 8-12, 8-10, 13-17 or 13-15 amino acids (or amino acid analogs or derivatives thereof) wherein the peptide linking moiety comprises two or more adjacent basic amino acid residues. In accordance with one embodiment the linking moiety is an 8 to 17 non-native amino acid sequence comprising the sequence X$_{51}$X$_{52}$X$_{53}$X$_{54}$X$_{55}$X$_{56}$X$_{57}$X$_{58}$ (SEQ ID NO: 9), wherein X$_{51}$, X$_{52}$, X$_{53}$, X$_{54}$, X$_{55}$ and X$_{56}$ are independently any amino acid or amino acid analog or derivative thereof, and X$_{57}$ and X$_{58}$ are basic amino acids. In accordance with one embodiment the linking moiety is an 8 to 12 non-native amino acid sequence comprising the sequence X$_{51}$AX$_{53}$X$_{54}$X$_{55}$X$_{56}$X$_{57}$X$_{58}$ (SEQ ID NO: 70) that joins a full length B chain to a full length A chain, wherein X$_{51}$, X$_{53}$, X$_{54}$, X$_{55}$ and X$_{56}$ are independently any amino acid or amino acid analog or derivative thereof, and X$_{57}$ and X$_{58}$ are basic amino analog or derivative thereof, and X$_{57}$ and X$_{58}$ are basic amino acids. In one embodiment one of X$_{57}$ and X$_{58}$ represents a pegylated lysine reside. In a further embodiment X$_{57}$ and X$_{58}$ are independently selected from the group consisting of arginine, lysine and ornithine.

In one embodiment the linking moiety is a peptide or peptidomimetic of 8-12, 8-10, 13-17 or 13-15 amino acids and comprising the sequence X$_{51}$X$_{52}$X$_{53}$X$_{54}$X$_{55}$X$_{56}$X$_{57}$R (SEQ ID NO: 25), wherein X$_{51}$, X$_{52}$, X$_{53}$, X$_{54}$ and X$_{55}$ are independently any amino acid or amino acid analog or derivative thereof and X$_{57}$ is arginine, lysine or ornithine. In one embodiment X$_{51}$ is selected from the group consisting of glycine, alanine, valine, leucine, isoleucine, proline, phenylalanine and methionine and X$_{52}$ is any amino acid other than tyrosine. In one embodiment X$_{52}$ is a non-aromatic amino acid and in one specific embodiment X$_{52}$ is alanine or proline. In one embodiment the linking moiety is pegylated at the side chain of an amino acid, and in a further embodiment the amino acid at position 8 of the linking moiety is pegylated.

In another embodiment the linking moiety is a peptide or peptidomimetic of 8-12, 8-10, 13-17 or 13-15 amino acids and comprising the sequence X$_{51}$X$_{52}$X$_{53}$X$_{54}$X$_{55}$SRR (SEQ ID NO: 26), wherein X$_{51}$, X$_{52}$, X$_{53}$, X$_{54}$ and X$_{55}$ are independently any amino acid or amino acid analog or derivative thereof. In accordance with one embodiment X$_{51}$ is selected from the group consisting of glycine, alanine, valine, leucine, isoleucine, proline, phenylalanine and methionine;

X$_{52}$ is any amino acid other than tyrosine;

X$_{53}$, X$_{54}$, X$_{55}$ and X$_{56}$ are independently selected from the group consisting of glycine, alanine, serine, threonine and proline. In one embodiment, X$_{51}$ and X$_{52}$ are independently selected from the group consisting of glycine, alanine, valine, leucine, isoleucine, and proline.

In one embodiment the linking moiety is a non-native polypeptide of 8 to 17 amino acids in length and comprising the sequence X$_{51}$X$_{52}$X$_{53}$X$_{54}$X$_{55}$X$_{56}$RR (SEQ ID NO: 10), wherein X$_{52}$ is a non-aromatic amino acid, including for example alanine. In one embodiment the linking moiety is 8 to 17 amino acids in length and comprises the sequence X$_{51}$X$_{52}$GSSSRR (SEQ ID NO: 27) wherein X$_{51}$ is selected from the group consisting of glycine, alanine, valine, leucine, isoleucine, proline and methionine, and X$_{52}$ is a non-aromatic amino acid, including for example alanine. In one embodiment the linking moiety is 8 to 17 amino acids in length and comprises a sequence that differs from X$_{51}$X$_{52}$GSSSRR (SEQ ID NO: 27) by a single amino acid substitution wherein the amino acid substitution is an amino acid that is pegylated at its side chain, further wherein X$_{51}$ is selected from the group consisting of glycine, alanine, valine, leucine, isoleucine, proline and methionine, and X$_{52}$ is a non-aromatic amino acid, including for example alanine.

In one embodiment the linking moiety is an 8 to 17 amino acid sequence comprising the sequence X$_{51}$AX$_{53}$X$_{54}$X$_{55}$X$_{56}$X$_{57}$R (SEQ ID NO: 28) or a peptidomimetic thereof, wherein X$_{51}$, X$_{53}$, X$_{54}$, X$_{55}$, X$_{56}$, and X$_{57}$ are independently any amino acid or amino acid analog or derivative thereof. In one embodiment X$_{51}$ is selected from the group consisting of glycine, alanine, valine, leucine, isoleucine, proline, phenylalanine and methionine; and X$_{53}$, X$_{54}$, X$_{55}$ and X$_{56}$ are independently selected from the group consisting of glycine, alanine, serine, threonine and proline, and X$_{57}$ is a basic amino acid, including for example, arginine, lysine or ornithine.

In one embodiment the linking moiety is an 8 to 17 amino acid sequence comprising the sequence X$_{51}$X$_{52}$GSSSX$_{57}$X$_{58}$ (SEQ ID NO: 29) or X$_{51}$X$_{52}$GSSSX$_{57}$X$_{58}$APQT (SEQ ID NO: 46) wherein X$_{51}$ is selected from the group consisting of glycine, alanine, valine, leucine, isoleucine, proline, phenylalanine and methionine, $X_{52}$ is a non-aromatic amino acid and $X_{57}$ and $X_{58}$ are independently selected from the group consisting of arginine, lysine and ornithine. In one embodiment the linking moiety further comprises a polyethylene glycol chain linked to the side chain of an amino acid of the linking moiety, including for example, the amino acid at position 8 of the linking moiety. In a further embodiment the linking moiety is an 8 to 17 amino acid sequence comprising the sequence $X_{51}X_{52}$GSSSRR (SEQ ID NO: 27), a peptidomimetic of SEQ ID NO: 27, or an amino acid sequence that differs from SEQ ID NO: 27 by a single amino acid at one of positions 3-8 of SEQ ID NO: 27, wherein $X_{51}$ is selected from the group consisting of glycine, alanine, valine, leucine, isoleucine, proline and methionine, and $X_{52}$ is any amino acid, with the proviso that when the linking peptide is longer than 8 amino acids $X_{52}$ is other than tyrosine. In one embodiment the linking moiety is an 8 to 17 amino acid sequence consisting of the sequence $X_{51}X_{52}$GSSSRR (SEQ ID NO: 27), a peptidomimetic of SEQ ID NO: 27, or an amino acid sequence that differs from SEQ ID NO: 27 by 1, 2, or 3 amino acid substitutions at one of positions 3-8 of SEQ ID NO: 27, wherein $X_{51}$ is selected from the group consisting of glycine, alanine, valine, leucine, isoleucine, proline and methionine, and $X_{52}$ is any amino acid. In one embodiment the linking moiety is a peptide of eight amino acids in length and comprises the sequence GYGSSSRR (SEQ ID NO: 18), or an amino acid sequence that differs from SEQ ID NO: 18 by a single amino acid substitution, or a derivative thereof.

In one embodiment the linking moiety is at least 8 but no more than 17 amino acids in length and comprises the sequence $(Y_1)_k$-$X_{51}X_{52}X_{53}X_{54}X_{55}X_{56}X_{57}X_{54}(Y_2)$ (SEQ ID NO: 9), wherein $X_{51}$ is selected from the group consisting of glycine, alanine, valine, leucine, isoleucine and proline;

$X_{52}$ is alanine, valine, leucine, isoleucine or proline; and $X_{53}$ through $X_{56}$ are each independently any amino acid; and $X_{57}$ and $X_{58}$ are independently arginine, lysine, cysteine, homocysteine, acetyl-phenylalanine or ornithine;

k is 0 or 1;

$Y_1$ is selected from the group $X_{46}$, $X_{46}X_{47}$, $X_{46}X_{47}X_{48}$, $X_{46}X_{47}X_{48}X_{49}$ (SEQ ID NO: 24) and $X_{46}X_{47}X_{48}X_{49}X_{50}$ (SEQ ID NO: 13);

$Y_2$ is selected from the group $X_{70}$, $X_{70}X_{71}$, $X_{70}X_{71}X_{72}$ and $X_{70}X_{71}X_{72}X_{73}$ (SEQ ID NO: 15);

$X_{46}$ through $X_{50}$ and $X_{70}$ through $X_{73}$ are each independently any amino acid. In one embodiment the linking peptide is pegylated. In one embodiment k is 0, and $Y_2$ is $X_{70}X_{71}X_{72}X_{73}$ (SEQ ID NO: 15). In an alternative embodiment k is 1 and $Y_2$ is $X_{70}X_{71}X_{72}X_{73}$ (SEQ ID NO: 15). In one embodiment $X_{46}$ is phenylalanine or tyrosine;

$X_{47}$ is asparagine or threonine;

$X_{48}$ is an aspartate-lysine dipeptide, an arginine-proline dipeptide, a lysine-proline dipeptide, or a proline-lysine dipeptide; and $X_{49}$ is threonine. In one embodiment $X_{70}$ is alanine, $X_{71}$ is proline, $X_{72}$ is glutamine and $X_{73}$ is threonine. In one embodiment k is 0, and $Y_2$ is APQT (SEQ ID NO: 82). In one embodiment, $Y_1$ is selected from the group consisting of F, Y, FN, YT, FD, FE, YD, and YE. In one embodiment when the insulin B chain is not native insulin (SEQ ID NO: 2) or native IGF-1 (SEQ ID NO: 6), $Y_1$ is FNKPT (SEQ ID NO: 76) or FNPKT SEQ ID NO: 81).

In one embodiment the linking moiety is a 12 amino acid sequence consisting of the sequence $X_{51}$AGSSSRRAPQT (SEQ ID NO: 30), or an amino acid sequence that differs from SEQ ID NO: 30 by a one to three amino acid substitutions at positions selected from positions 3-12 of SEQ ID NO: 30, wherein $X_{51}$ is selected from the group consisting of glycine, alanine, valine, leucine, isoleucine, proline and methionine, or a peptidomimetic of SEQ ID NO: 30. In one embodiment the linking moiety is a 12 amino acid sequence consisting of the sequence $X_{51}$AGSSSRRAPQT (SEQ ID NO: 30), or an amino acid sequence that differs from SEQ ID NO: 30 by a single lysine or cysteine amino acid substitution at a position selected from positions 3-10 of SEQ ID NO: 30, wherein $X_{51}$ is selected from the group consisting of glycine, alanine, valine, leucine, isoleucine, proline and methionine, or a peptidomimetic of SEQ ID NO: 30. In one embodiment the lysine or cysteine amino acid substitution is a pegylated lysine or cysteine amino acid.

In another embodiment, the linking moiety is an 8 to 17 amino acid sequence comprising the sequence G$X_{52}$GSSSRR (SEQ ID NO: 31), wherein $X_{52}$ is any amino acid, a peptidomimetic of SEQ ID NO: 31, or an analog thereof that differs from SEQ ID NO: 31 by a single amino acid substitution at any of positions 1, 3, 4, 5, 6, 7 or 8 of SEQ ID NO: 31, with the proviso that when the linking peptide is longer than 8 amino acids $X_{52}$ is other than tyrosine. In accordance with one embodiment the linking moiety comprises an 8-17 amino acid sequence selected from the group consisting of GYGSSSRR (SEQ ID NO: 18), GAGSSSRR (SEQ ID NO: 32), GAGSSSRRA (SEQ ID NO: 33), GAGSSSRRAP (SEQ ID NO: 34), GAGSSSRRAPQ (SEQ ID NO: 35), GAGSSSRRAPQT (SEQ ID NO: 36), PYGSSSRR (SEQ ID NO: 39), PAGSSSRR (SEQ ID NO: 40), PAGSSSRRA (SEQ ID NO: 41), PAGSSSRRAP (SEQ ID NO: 42), PAGSSSRRAPQ (SEQ ID NO: 43), PAGSSSRRAPQT (SEQ ID NO: 44). In accordance with one embodiment the linking moiety comprises an amino acid sequence that differs from GYGSSSRR (SEQ ID NO: 18), GAGSSSRR (SEQ ID NO: 32), GAGSSSRRA (SEQ ID NO: 33), GAGSSSRRAP (SEQ ID NO: 34), GAGSSSRRAPQ (SEQ ID NO: 35), GAGSSSRRAPQT (SEQ ID NO: 36), PYGSSSRR (SEQ ID NO: 39), PAGSSSRR (SEQ ID NO: 40), PAGSSSRRA (SEQ ID NO: 41), PAGSSSRRAP (SEQ ID NO: 42), PAGSSSRRAPQ (SEQ ID NO: 43), PAGSSSRRAPQT (SEQ ID NO: 44) by a single pegylated amino acid including for example a pegylated lysine or pegylated cysteine amino acid substitution. In one embodiment the pegylated amino acid is at position 8 of the linking moiety Non-Peptide Linkers In one embodiment the linking moiety is a relatively short bifunctional non-peptide polymer linker that approximates the length of an 8-16 amino acid sequence. In accordance with one embodiment the non-peptide linking moiety is a polyethylene glycol linker of approximately 4 to 20, 8 to 18, 8 to 16, 8 to 14, 10 to 14, 10 to 12 or 11 to 13 monomers. In one embodiment a single chain insulin agonist is provided wherein the last five carboxy amino acids of the native B chain are deleted, and amino acid B25 is directly linked to the linking moiety by a covalent bond. The second end of the linking moiety is covalently bound to amino acid A1 of the A chain thus linking the B and A chain via the linking moiety. In one embodiment the linking moiety is a linear polyethylene glycol linking moiety comprising at least 10 but no more than 16 monomer units and in another embodiment the polyethylene glycol linking moiety comprises at least 12 but no more than 16 monomer units, and in a further embodiment the polyethylene glycol linking moiety comprises at least 10 but no more than 14 monomer units.

In accordance with one embodiment the polyethylene glycol linking moiety comprises the structure:

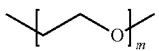

wherein m is an integer ranging from 6 to 18, 8 to 16, 10 to 14 or 11 to 13. In one embodiment m is an integer selected from 10, 11, 12, 13 or 14. In one embodiment m is 12.

In one embodiment a single chain insulin agonist is provided wherein the last five carboxy amino acids of the native B chain are deleted, and amino acid B25 is linked to amino acid A1 of the A chain via a linking moiety comprising polyethylene glycol of at least 8 but no more than 16 monomer units and an amino acid sequence of one to four amino acids. In accordance with one embodiment the linking moiety comprises a 1-4 amino acid sequence and a linear polyethylene glycol of at least 8 but less than 14 monomer units in length covalently bound to said 1-4 amino acid sequence, with the proviso that the amino acid sequence is not YTPK (SEQ ID NO: 78) or FNKP (SEQ ID NO: 77). In another embodiment a single chain insulin agonist is provided wherein the last five carboxy amino acids of the native B chain are deleted, and amino acid B25 is linked to amino acid A1 of the A chain via a linking moiety comprising a polyethylene glycol of at least 8 but less than 14 monomer units in length and a 2-5 amino acid sequence. The 2-5 amino acid sequence can be located between the B chain and the polyethylene glycol chain or between the A chain and the polyethylene glycol chain. However, when the 2-5 amino acid sequence is located between the B chain and the polyethylene glycol chain, the amino acid sequence is not YTPKT (SEQ ID NO: 16) or FNKPT (SEQ ID NO: 76).

In one embodiment the linking moiety comprises the general structure: $W_1$-$Z_1$-$Y_1$
wherein
$W_1$ and $Y_1$ are independently a bond, $X_{46}$, $X_{46}X_{47}$, $X_{46}X_{47}X_{48}$, $X_{46}X_{47}X_{48}X_{49}$ (SEQ ID NO: 24) or $X_{46}X_{47}X_{48}X_{49}X_{50}$ (SEQ ID NO: 13), with the proviso that $W_1$ is not YTPK (SEQ ID NO: 78) or FNKP (SEQ ID NO: 77) and $Z_1$ represents a polyethylene glycol of the general structure

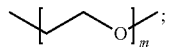

wherein m is an integer ranging from 6-14, and each of $X_{46}$, $X_{47}$, $X_{48}$, $X_{49}$ and $X_{50}$ are independently any amino acid. In one embodiment $X_{46}$, $X_{47}$, $X_{48}$, $X_{49}$ and $X_{50}$ are independently any non-native amino acid relative to positions B26-B30 of insulin or IGF-1. In one embodiment $X_{46}$, $X_{47}$, $X_{48}$, $X_{49}$ and $X_{50}$ are independently selected from the group consisting of glycine, alanine, valine, leucine, isoleucine, serine, threonine and proline, and in a further embodiment $X_{46}$, $X_{47}$, $X_{48}$, $X_{49}$ and $X_{50}$ are independently selected from the group consisting of glycine, alanine, valine, leucine and isoleucine. In one embodiment, $W_1$ is a bond and $Y_1$ is $X_{46}$, $X_{46}X_{47}$ or $X_{46}X_{47}X_{48}$ (SEQ ID NO: 24) wherein $X_{46}$, $X_{47}$ and $X_{48}$ are each alanine and Z is a polyethylene glycol of 4-14 monomer units. In one embodiment, $Y_1$ is a bond and $W_1$ is $X_{46}$, $X_{46}X_{47}$ or $X_{46}X_{47}X_{48}$ (SEQ ID NO: 24) wherein $X_{46}$, $X_{47}$ and $X_{48}$ are each alanine and Z is a polyethylene glycol of 4-14 monomer units.

In one embodiment the linking moiety comprises two polyethylene chains separated by 1, 2, 3 or 4 amino acids. In this embodiment the linking moiety comprises the general structure:

$W_2$-$Z_2$-$Y_2$ wherein
$W_2$ and $Y_2$ are independently a polyethylene glycol of the general structure

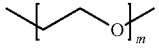

and $Z_2$ is a bond, $X_{46}$, $X_{46}X_{47}$, or $X_{46}X_{47}X_{48}$, wherein m is an integer ranging from 3-7 and each of $X_{46}$, $X_{47}$, and $X_{48}$ are independently any amino acid. In one embodiment $Z_2$ is $X_{46}$ or $X_{46}X_{47}$, and in a further embodiment $X_{46}$ and $X_{47}$ are independently Lys or Cys. In one embodiment $Z_2$ comprises a pegylated Lys or Cys amino acid. In one embodiment the linking moiety comprises a two polyethylene chains representing a total of 8-12 or 10-14 or 12 monomeric units of ethylene glycol separated by a single amino acid. In one embodiment the single amino acid is lysine or cysteine. In one embodiment $Z_2$ is a pegylated lysine.

In one embodiment a single chain insulin analog is provided comprising an A chain and a C-terminally truncated B chain, having amino acids B26-B30 (relative to the native insulin sequence) removed, wherein said A chain and B chain are human insulin sequences, or analogs or derivatives thereof, further wherein the carboxy terminus of the B25 amino acid of the B chain is directly linked to a first end of a linking moiety and a second end of the linking moiety is directly linked to the amino terminus of the A1 amino acid of the A chain. In one mebodiment the truncated B chain comprises the sequence of SEQ ID NO: 21 wherein the B25 amino acid is directly linked to the N terminus of the linking peptide. In this embodiment the linking moiety comprises either
 a) a polyethylene glycol of 6-16 monomer units;
 b) a non-native amino acid sequence of at least 8 amino acids and no more than 17 amino acid in length and comprising the sequence $(Y_1)_k$-$X_{51}AX_{53}X_{54}X_{55}X_{56}X_{57}R(Y_2)_n$ (SEQ ID NO: 28), $(Y_1)_k$-$X_{51}AX_{53}X_{54}X_{55}X_{56}RR(Y_2)_n$ (SEQ ID NO: 23), $(Y_1)_k$-GYGSSSX$_{57}$X$_{58}$(Y$_2$)$_n$ (SEQ ID NO: 85), $(Y_1)_k$-GAGSSSX$_{57}$X$_{58}$(Y$_2$)$_n$ (SEQ ID NO: 163), $(Y_1)_k$-GYGSSSX$_{57}$R (SEQ ID NO: 51) or $(Y_1)_k$-$X_{51}X_{52}$GSSSX$_{57}$X$_{58}$-(Y$_2$)$_n$ (SEQ ID NO: 29); or
 c) a combination of said polyethylene glycol and a non-native amino acid sequence of 1 to 4 amino acids;
wherein
 n is 0 or 1;
 k is 0 or 1;
 $Y_1$ is selected from the group $X_{46}$, $X_{46}X_{47}$; and
 $Y_2$ is selected from the group $X_{70}$, $X_{70}X_{71}$, $X_{70}X_{71}X_{72}$ and $X_{70}X_{71}X_{72}X_{73}$ (SEQ ID NO: 15);
 $X_{51}$ is selected from the group consisting of glycine, alanine, valine, leucine, isoleucine, proline, phenylalanine and methionine;
 $X_{52}$ is alanine, valine, leucine, isoleucine or proline;
 $X_{57}$ and $X_{58}$ are independently arginine, lysine, cysteine, homocysteine, acetyl-phenylalanine or ornithine; and
 $X_{46}$ is phenylalanine or tyrosine;
 $X_{47}$ is asparagine, glutamic acid, aspartic acid or threonine;
 $X_{70}$-$X_{73}$ are independently any amino acid, with the proviso that when k is 0, the linking peptide does not comprise the sequence YTPKT (SEQ ID NO: 16) or FNKPT (SEQ ID NO: 76). In one embodiment one of $X_{57}$ and $X_{58}$ is linked to a hydrophilic moiety or is acylated. In one embodiment one of $X_{57}$ and $X_{58}$ is pegylated. In one embodiment the linking moiety comprises the sequence $(Y_1)_k$-$X_{51}AX_{53}X_{54}X_{55}X_{56}RR(Y_2)_n$ (SEQ ID NO: 23) or $(Y_1)_k$-GYGSSSX$_{57}$R (SEQ ID NO: 51) wherein k is 0 or 1;

n is 0 or 1;

$X_{51}$ is selected from the group consisting of glycine, alanine, valine, leucine, isoleucine, proline, phenylalanine and methionine;

$X_{53}$ through $X_{56}$ are each independently any amino acid;

$X_{57}$ is lysine, ornithine or arginine;

$Y_1$ is selected from the group $X_{46}$, $X_{46}X_{47}$, and $X_{46}X_{47}X_{48}$ wherein $X_{46}$ is phenylalanine or tyrosine;

$X_{47}$ is asparagine, glutamic acid, aspartic acid or threonine;

$X_{48}$ is aspartic acid, arginine, lysine or proline; and $Y_2$ is selected from the group consisting of A, AP, APQ and APQT (SEQ ID NO: 82). In one embodiment the A chain is an amino acid sequence derivative of a sequence selected from the group consisting of GIVEQCCTSICSLYQLENYCN (SEQ ID NO: 1), GIVDECCFRSCDLRRLEMYCA (SEQ ID NO: 5) or GIVEECCFRSCDLALLETYCA (SEQ ID NO: 7) and the B chain comprises the sequence FVNQHLCGSHLVEALYLVCGERGFFYTPKT (SEQ ID NO: 2), or GPETLCGX$_{26}$ELVDX$_{27}$LYLVCGDX$_{42}$GFYFNKPT-R$_{14}$ (SEQ ID NO: 197), wherein X$_{26}$ and X$_{27}$ are each alanine and X$_{42}$ is arginine, or a carboxy shortened sequence thereof having one to five amino acids corresponding to B26, B27, B28, B29 and B30 deleted Insulin A and B Chains The single chain insulin agonists of the present invention may comprise the native B and A chain sequences of human insulin (SEQ ID NOs: 1 and 2, respectively) or any of the known analogs or derivatives thereof that exhibit insulin agonist activity when linked to one another in a heteroduplex. Such analogs include, for example, proteins that having an A-chain and a B-chain that differ from the A-chain and B-chain of human insulin by having one or more amino acid deletions, one or more amino acid substitutions, and/or one or more amino acid insertions that do not destroy the insulin activity of the insulin analog.

One type of insulin analog, "monomeric insulin analog," is well known in the art. These are fast-acting analogs of human insulin, including, for example, insulin analogs wherein:

(a) the amino acyl residue at position B28 is substituted with Asp, Lys, Leu, Val, or Ala, and the amino acyl residue at position B29 is Lys or Pro;

(b) the amino acyl residues at any of positions B27, B28, B29, and B30 are deleted or substituted with a normative amino acid. In one embodiment an insulin analog is provided comprising an Asp substituted at position B28 or a Lys substituted at position 28 and a proline substituted at position B29. Additional monomeric insulin analogs are disclosed in Chance, et al., U.S. Pat. No. 5,514,646; Chance, et al., U.S. patent application Ser. No. 08/255,297; Brems, et al., Protein Engineering, 5:527-533 (1992); Brange, et al., EPO Publication No. 214,826 (published Mar. 18, 1987); and Brange, et al., Current Opinion in Structural Biology, 1:934-940 (1991). These disclosures are expressly incorporated herein by reference for describing monomeric insulin analogs.

Insulin analogs may also have replacements of the amidated amino acids with acidic forms. For example, Asn may be replaced with Asp or Glu. Likewise, Gln may be replaced with Asp or Glu. In particular, Asn(A18), Asn(A21), or Asp (B3), or any combination of those residues, may be replaced by Asp or Glu. Also, Gln(A15) or Gln(B4), or both, may be replaced by either Asp or Glu.

As disclosed herein single chain insulin agonists are provided comprising a B chain and A chain of human insulin, or analogs or derivative thereof, wherein the carboxy terminus of the B chain is linked to the amino terminus of the A chain via a linking moiety. In one embodiment the A chain is an amino acid sequence selected from the group consisting of GIVEQCCTSICSLYQLENYCN (SEQ ID NO: 1), GIVDECCFRSCDLRRLEMYCA (SEQ ID NO: 5) or GIVEECCFRSCDLALLETYCA (SEQ ID NO: 7) and the B chain comprises the sequence FVNQHLCGSHLVEALYLVCGERGFFYTPKT (SEQ ID NO: 2), GPETLCGX$_{26}$ELVDX$_{27}$LYLVCGDX$_{42}$GFYFNKPT-R$_{14}$ (SEQ ID NO: 197), wherein X$_{26}$ and X$_{27}$ are each alanine and X$_{42}$ is arginine, or a carboxy shortened sequence thereof having one to five amino acids corresponding to B26, B27, B28, B29 and B30 deleted, and analogs of those sequences wherein each sequence is modified to comprise one to five amino acid substitutions at positions corresponding to native insulin positions (see peptide alignment shown in FIG. 5) selected from A5, A8, A9, A10, A14, A15, A17, A18, A21, B1, B2, B3, B4, B5, B9, B10, B13, B14, B20, B22, B23, B26, B27, B28, B29 and B30. In one embodiment the amino acid substitutions are conservative amino acid substitutions. Suitable amino acid substitutions at these positions that do not adversely impact insulin's desired activities are known to those skilled in the art, as demonstrated, for example, in Mayer, et al., Insulin Structure and Function, Biopolymers. 2007; 88(5):687-713, the disclosure of which is incorporated herein by reference.

In accordance with one embodiment the single chain insulin analog peptides may comprise an insulin A chain and an insulin B chain or analogs thereof, wherein the A chain comprises an amino acid sequence that shares at least 70% sequence identity (e.g., 70%, 75%, 80%, 85%, 90%, 95%) over the length of the native peptide, with at least one of GIVEQCCTSICSLYQLENYCN (SEQ ID NO: 1), GIVDECCFRSCDLRRLEMYCA (SEQ ID NO: 5) or GIVEECCFRSCDLALLETYCA (SEQ ID NO: 7) and the B chain comprises an amino acid sequence that shares at least 60% sequence identity (e.g., 60%, 65%, 70%, 75%, 80%, 85%, 90%, 95%) over the length of the native peptide, with at least one of the sequence FVNQHLCGSHLVEALYLVCGERGFFYTPKT (SEQ ID NO: 2), GPETLCGX$_{26}$ELVDX$_{27}$LYLVCGDX$_{42}$GFYFNKPT-R$_{14}$ (SEQ ID NO: 197), wherein X$_{26}$ and X$_{27}$ are each alanine and X$_{42}$ is arginine, or a carboxy shortened sequence thereof having one to four amino acids corresponding to B27, B28, B29 and B30 deleted.

Additional amino acid sequences can be added to the amino terminus of the B chain or to the carboxy terminus of the A chain of the single chain insulin agonists of the present invention. For example, a series of negatively charged amino acids can be added to the amino terminus of the B chain, including for example a peptide of 1 to 12, 1 to 10, 1 to 8 or 1 to 6 amino acids in length and comprising one or more negatively charged amino acids including for example glutamic acid and aspartic acid. In one embodiment the B chain amino terminal extension comprises 1 to 6 charged amino acids. In one embodiment the single chain insulin analog comprises a B chain amino terminal extension that comprises the sequence $X_{60}X_{61}X_{62}X_{63}X_{64}X_{65}$K (SEQ ID NO: 47), wherein $X_{60}$ is selected from the group consisting of glycine, glutamic acid and aspartic acid, and $X_{61}$, $X_{62}$, $X_{63}$ $X_{64}$ and $X_{65}$ are independently glutamic acid or aspartic acid. In one embodiment the B chain amino terminal extension comprises the sequence $GX_{61}X_{62}X_{63}X_{64}X_{65}$K (SEQ ID NO: 48) or $X_{61}X_{62}X_{63}X_{64}X_{65}$RK (SEQ ID NO: 49), wherein $X_{61}$, $X_{62}$, $X_{63}$ $X_{64}$ and $X_{65}$ are independently glutamic acid or aspartic acid. In one embodiment the B chain comprises the sequence GEEEEEKGPEHLCGAHLVDALYLVCGDX$_{42}$GFY (SEQ ID NO: 50), wherein $X_{42}$ is selected from the group consisting of alanine lysine, ornithine and arginine. In accordance with one embodiment the single chain insulin analogs disclosed comprise a C-terminal amide or ester in place of a C-terminal carboxylate on the A chain.

High potency single chain insulin analogs can also be prepared based on modified IGF I and IGF II sequences, as described in International application PCT/2009/068713, the disclosure of which is expressly incorporated herein by reference. More particularly, analogs of IGF I and IGF II that comprise a substitution of a tyrosine leucine dipeptide for the native IGF amino acids at positions corresponding to B16 and B17 of native insulin have a tenfold increase in potency at the insulin receptor. Accordingly, the single chain insulin analogs disclosed herein may include an A chain of IGF I (SEQ ID NO: 5) or IGF II (SEQ ID NO: 7) and a B chain of IGF I (SEQ ID NO: 6) or IGF II (SEQ ID NO: 8) or the B chain of native insulin (SEQ ID NO: 2). In addition, the single chain insulin analogs disclosed herein may include a native insulin A chain, or analog thereof, and a B chain of IGF I (SEQ ID NO: 6) or IGF II (SEQ ID NO: 8), as well as analogs of said B chains. In one embodiment the single chain insulin analog comprises an IGF I (SEQ ID NO: 5) A chain, or analog or derivative thereof and a B chain of IGF I (SEQ ID NO: 6), IGF II (SEQ ID NO: 8) or native insulin (SEQ ID NO: 2), or analogs or derivatives thereof.

Additional modifications to the single chain IGF or insulin A and B chains include, for example, modification of the amino acids at one or more of positions A19, B16 or B25 (relative to the native insulin A and B chains) to a 4-amino phenylalanine or one or more amino acid substitutions at positions selected from A5, A8, A9, A10, A14, A15, A17, A18, A21, B1, B2, B3, B4, B5, B9, B10, B13, B14, B20, B21, B22, B23, B26, B27, B28, B29 and B30 (relative to the native A and B chains of insulin) or deletions of any or all of positions B1-4 and B26-30. In one embodiment the substitutions at positions selected from A5, A8, A9, A10, A14, A15, A17, A18, A21, B1, B2, B3, B4, B5, B9, B10, B13, B14, B20, B21, B22, B23, B26, B27, B28, B29 and B30 are conservative amino acid substitutions relative to the native insulin sequence.

In accordance with one embodiment the B chain comprises the sequence $R_{22}$-$X_{25}$LCGX$_{29}$X$_{30}$LVX$_{33}$ X$_{34}$LYLVCGX$_{41}$X$_{42}$GFX$_{45}$(SEQ ID NO: 21), and the A chain comprises the sequence GIVX$_4$X$_5$CCX$_8$X$_9$X$_{10}$CX$_{12}$LX$_{14}$X$_{15}$LX$_{17}$X$_{18}$X$_{19}$CX$_{21}$-$R_{13}$ (SEQ ID NO: 22), wherein $X_4$ is glutamic acid or aspartic acid;
$X_5$ is glutamine or glutamic acid
$X_8$ is histidine, threonine or phenylalanine;
$X_9$ is serine, arginine, lysine, ornithine or alanine;
$X_{10}$ is isoleucine or serine;
$X_{12}$ is serine or aspartic acid
$X_{14}$ is tyrosine, arginine, lysine, ornithine or alanine;
$X_{15}$ is glutamine, glutamic acid, arginine, alanine, lysine, ornithine or leucine;
$X_{17}$ is glutamic acid, aspartic acid, asparagine, lysine, ornithine or glutamine;
$X_{18}$ is methionine, asparagine, glutamine, aspartic acid, glutamic acid or threonine;
$X_{19}$ is tyrosine, 4-methoxy-phenylalanine or 4-amino phenylalanine;
$X_{21}$ is selected from the group consisting of alanine, glycine, serine, valine, threonine, isoleucine, leucine, glutamine, glutamic acid, asparagine, aspartic acid, histidine, tryptophan, tyrosine, and methionine;
$X_{25}$ is histidine or threonine;
$X_{29}$ is selected from the group consisting of alanine, glycine and serine;
$X_{30}$ is selected from the group consisting of histidine, aspartic acid, glutamic acid, homocysteic acid and cysteic acid;
$X_{33}$ is selected from the group consisting of aspartic acid, glutamine and glutamic acid;
$X_{34}$ is selected from the group consisting of alanine and threonine;
$X_{41}$ is selected from the group consisting of glutamic acid, aspartic acid or asparagine;
$X_{42}$ is selected from the group consisting of alanine, lysine, ornithine and arginine;
$X_{45}$ is tyrosine or phenylalanine;
$R_{22}$ is selected from the group consisting of AYRPSE (SEQ ID NO: 14), FVNQ (SEQ ID NO: 12), PGPE (SEQ ID NO: 11), a tripeptide glycine-proline-glutamic acid, a tripeptide valine-asparagine-glutamine, a dipeptide proline-glutamic acid, a dipeptide asparagine-glutamine, glutamine, glutamic acid and an N-terminal amine; and $R_{13}$ is COOH or CONH$_2$. In one embodiment $X_8$, $X_{25}$ and $X_{30}$ are each histidine. In a further embodiment the single chain insulin analog peptide comprises an analog of the A chain peptide sequence of SEQ ID NO: 19 and/or a B chain peptide sequence of SEQ ID NO: 20 wherein the analog of the A chain and B chain each comprise 1-3 further amino acid substitutions.

In one embodiment a single chain insulin analog is provided that comprises the structure: IB-LM-IA, wherein IB comprises the sequence $R_{22}$-$X_{25}$LCGX$_{29}$X$_{30}$LVX$_{33}$X$_{34}$LYLVCGX$_{41}$X$_{42}$GFX$_{45}$ (SEQ ID NO: 21), LM is a linking moiety as disclosed herein that covalently links IB to IA, and IA comprises the sequence GIVX$_4$X$_5$CCX$_8$X$_9$X$_{10}$CX$_{12}$LX$_{14}$X$_{15}$LX$_{17}$X$_{18}$X$_{19}$CX$_{21}$-$R_{13}$ (SEQ ID NO: 22), wherein $X_4$ is glutamic acid or aspartic acid;
$X_5$ is glutamine or glutamic acid;
$X_8$ is histidine or phenylalanine;
$X_9$ and $X_{14}$ are independently selected from arginine, lysine, ornithine or alanine;
$X_{10}$ is isoleucine or serine;
$X_{12}$ is serine or aspartic acid;
$X_{14}$ is tyrosine, arginine, lysine, ornithine or alanine;
$X_{15}$ is arginine, lysine, ornithine or leucine;
$X_{17}$ is glutamic acid or glutamine;
$X_{18}$ is methionine, asparagine or threonine;
$X_{19}$ is tyrosine, 4-methoxy-phenylalanine or 4-amino phenylalanine;
$X_{21}$ is alanine, glycine or asparagine;
$X_{25}$ is selected from the group consisting of histidine and threonine;
$X_{29}$ is selected from the group consisting of alanine, glycine and serine;
$X_{30}$ is selected from the group consisting of histidine, aspartic acid, glutamic acid, homocysteic acid and cysteic acid;
$X_{33}$ is selected from the group consisting of aspartic acid and glutamic acid;
$X_{34}$ is selected from the group consisting of alanine and threonine;
$X_{41}$ is selected from the group consisting of glutamic acid, aspartic acid or asparagine;
$X_{42}$ is selected from the group consisting of alanine, lysine, ornithine and arginine;
$R_{22}$ is selected from the group consisting of AYRPSE (SEQ ID NO: 14), FVNQ (SEQ ID NO: 12), PGPE (SEQ ID NO: 11), a tripeptide glycine-proline-glutamic acid, a tripeptide valine-asparagine-glutamine, a dipeptide proline-glutamic acid, a dipeptide asparagine-glutamine, glutamine, glutamic acid and an N-terminal amine; and $R_{13}$ is COOH or CONH$_2$, further wherein the amino acid at the designation $X_{45}$ is directly bound to the linking moiety, LM (i.e., the designation IB-LM-IA as used herein is intended to represent that the B chain carboxyl terminus and the amino terminus of the A chain are directly linked to the linking moiety LM without any further intervening amino acids).

In accordance with one embodiment the linking moiety LM is selected from the group consisting of $(Y_1)_k$-$X_{51}AX_{53}X_{54}X_{55}X_{56}X_{57}R(Y_2)_n$ (SEQ ID NO: 28), $(Y_1)_k$-$(Y_1)_k$-$GX_{52}GSSSX_{57}R$-$(Y_2)_n$ (SEQ ID NO: 90), $(Y_1)_k$-$GYGSSSX_{57}R(Y_2)_n$ (SEQ ID NO: 51) and

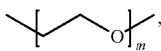

wherein $Y_1$ is selected from the group $X_{46}$, $X_{46}X_{47}$, $X_{46}X_{47}X_{48}$, $X_{46}X_{47}X_{48}X_{49}$ (SEQ ID NO: 24) and $X_{46}X_{47}X_{48}X_{49}X_{50}$ (SEQ ID NO: 13); and $Y_2$ is selected from the group $X_{70}$, $X_{70}X_{71}$, $X_{70}X_{71}X_{72}$ and $X_{70}X_{71}X_{72}X_{73}$ (SEQ ID NO: 15);

n is 0 or 1;
k is 0 or 1;
m is an integer selected from 8 to 16;

$X_{46}$ through $X_{50}$ and $X_{70}$ through $X_{73}$ are each independently any amino acid;

$X_{51}$ is selected from the group consisting of glycine, alanine, valine, leucine, isoleucine, proline, phenylalanine and methionine;

$X_{52}$ is any amino acid other than tyrosine; and $X_{53}$, $X_{54}$, $X_{55}$ and $X_{56}$ are independently selected from the group consisting of glycine, alanine, serine, threonine and proline and $X_{57}$ is arginine, lysine or ornithine. In accordance with one embodiment at least one of n or k is 1. In one embodiment $Y_2$ is selected from the group consisting of A, AP, APQ and APQT (SEQ ID NO: 82) and $Y_1$ is selected from the group consisting of F, Y, FN, YT, FNK, YTP, FNKP (SEQ ID NO: 77), FNPK (SEQ ID NO: 79), YTPK (SEQ ID NO: 78), YTPKT (SEQ ID NO: 16), YTKPT (SEQ ID NO: 80), FNPKT (SEQ ID NO: 76) and FNPKT (SEQ ID NO: 81). In one embodiment the linking moiety comprises a sequence selected from $X_{51}AX_{53}X_{54}X_{55}X_{56}X_{57}R(Y_2)_n$ (SEQ ID NO: 28), $(Y_1)_k$-$GYGSSSX_{57}R(Y_2)_n$ (SEQ ID NO: 51) and $(Y_1)_k$-$GX_{52}GSSSX_{57}R(Y_2)_n$ (SEQ ID NO: 90), wherein $X_{51}$ is selected from the group consisting of glycine, alanine, valine, leucine, isoleucine, proline, phenylalanine and methionine, $X_{52}$ is selected from the group consisting of glycine, alanine, valine, leucine, isoleucine, serine, threonine and proline, $X_{53}$ is other than glycine, $X_{54}$, and $X_{55}$ are independently selected from the group consisting of glycine, alanine, serine, threonine and proline, $X_{56}$ is serine and $X_{57}$ is arginine, lysine or ornithine. In one embodiment n is 1 and k is 0, alternatively in one embodiment k is 1 and n is 0 and in one embodiment both n and k are 1. In one embodiment the linking moiety is polyethylene glycol wherein m is an integer selected from 10 to 14.

In accordance with one embodiment an insulin analog is provided wherein the A chain of the insulin peptide comprises the sequence GIVEQCCX$_8$SICSLYQLX$_{17}$NX$_{19}$CX$_{23}$ (SEQ ID NO: 52) and the B chain comprising the sequence $X_{25}LCGX_{29}X_{30}LVEALYLVCGERGFF$ (SEQ ID NO: 53) wherein $X_8$ is selected from the group consisting of threonine and histidine;

$X_{17}$ is glutamic acid or glutamine;

$X_{19}$ is tyrosine, 4-methoxy-phenylalanine or 4-amino phenylalanine;

$X_{23}$ is asparagine or glycine;

$X_{25}$ is selected from the group consisting of histidine and threonine;

$X_{29}$ is selected from the group consisting of alanine, glycine and serine;

$X_{30}$ is selected from the group consisting of histidine, aspartic acid, glutamic acid, homocysteic acid and cysteic acid. In a further embodiment the B chain comprises the sequence $X_{22}VNQX_{25}LCGX_{29}X_{30}LVEALYLVCGERGFFYT$-$Z_1$-$B_1$ (SEQ ID NO: 54) wherein $X_{22}$ is selected from the group consisting of phenylalanine and desamino-phenylalanine;

$X_{25}$ is selected from the group consisting of histidine and threonine;

$X_{29}$ is selected from the group consisting of alanine, glycine and serine;

$X_{30}$ is selected from the group consisting of histidine, aspartic acid, glutamic acid, homocysteic acid and cysteic acid;

$Z_1$ is a dipeptide selected from the group consisting of aspartate-lysine, lysine-proline, and proline-lysine; and $B_1$ is selected from the group consisting of threonine, alanine or a threonine-arginine-arginine tripeptide.

In accordance with one embodiment a single chain insulin analog is provided that comprises the structure: IB-LM-IA, wherein IB comprises the sequence $X_{25}LCGX_{29}X_{30}LVEALYLVCG$ ERGFF (SEQ ID NO: 53), LM is a linking moiety as disclosed herein that covalently links IB to IA, and IA comprises the sequence GIVEQCCX$_8$SICSLYQLENX$_{19}$CX$_{21}$ (SEQ ID NO: 55), wherein the C-terminal phenylalanine residue of SEQ ID NO: 54 is directly covalently bound to the linking moiety, LM, in the absence of any intervening amino acids. In accordance with one embodiment linking moiety LM is selected from the group consisting of $(Y_1)_k$-$X_{51}AX_{53}X_{54}X_{55}X_{56}X_{57}R(Y_2)_n$ (SEQ ID NO: 28), $(Y_1)_k$-$GYGSSSX_{57}R(Y_2)_n$ (SEQ ID NO: 51) and

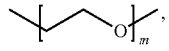

wherein $Y_1$ is selected from the group $X_{46}$, $X_{46}X_{47}$, $X_{46}X_{47}X_{48}$, $X_{46}X_{47}X_{48}X_{49}$ (SEQ ID NO: 24) and $X_{46}X_{47}X_{48}X_{49}X_{50}$ (SEQ ID NO: 13); and $Y_2$ is selected from the group $X_{70}$, $X_{70}X_{71}$, $X_{70}X_{71}X_{72}$ and $X_{70}X_{71}X_{72}X_{73}$ (SEQ ID NO: 15);

n is 0 or 1;
k is 0 or 1;
m is an integer ranging from 7 to 16;

$X_{46}$ through $X_{50}$ and $X_{70}$ through $X_{73}$ are each independently any amino acid; and $X_{57}$ is arginine, lysine or ornithine.

In accordance with one embodiment the single chain insulin analog comprises a B chain having the sequence $R_{22}$-$HLCGSX_{30}LVEALYLVCGERGFF$ (SEQ ID NO: 154) or $R_{24}$-$X_{25}$LCG$X_{29}$$X_{30}$LV$X_{33}$$X_{34}$LYLVCG$X_{41}$$X_{42}$GF$X_{45}$ (SEQ $X_{45}$ is tyrosine; and $R_{13}$ is COOH or $CONH_2$. In one embodiment at least one of n and k is 1.

In a further embodiment the A chain comprises the sequence GIVDECCHX$_9$SCDLX$_{14}$X$_{15}$LX$_{17}$X$_{18}$X$_{19}$CX$_{21}$-R$_{13}$ (SEQ ID NO: 56), and the B chain comprises the sequence X$_{25}$LCGX$_{29}$X$_{30}$LVX$_{33}$X$_{34}$LYLVCGDX$_{42}$GFX$_{45}$ (SEQ ID NO: 58) wherein $X_9$ and $X_{14}$ are independently selected from arginine, lysine, ornithine or alanine;

$X_{15}$ is arginine, lysine, ornithine or leucine;

$X_{17}$ is glutamic acid, aspartic acid, asparagine, lysine, ornithine or glutamine;

$X_{18}$ is methionine, asparagine or threonine;

$X_{19}$ is tyrosine, 4-methoxy-phenylalanine or 4-amino phenylalanine;

$X_{21}$ is alanine, glycine or asparagine;

$X_{23}$ is asparagine or glycine;

$X_{25}$ is selected from the group consisting of histidine and threonine;

$X_{29}$ is selected from the group consisting of alanine, glycine and serine;

$X_{30}$ is selected from the group consisting of histidine, aspartic acid, glutamic acid, homocysteic acid and cysteic acid;

$X_{33}$ is selected from the group consisting of aspartic acid and glutamic acid;

$X_{34}$ is selected from the group consisting of alanine and threonine;

$X_{42}$ is selected from the group consisting of alanine, lysine, ornithine and arginine;

$X_{45}$ is tyrosine or phenylalanine and $R_{13}$ is COOH or $CONH_2$. In a further embodiment the A chain comprises the sequence GIVDECCHX$_9$SCDLX$_{14}$X$_{15}$LX$_{17}$MX$_{19}$CX$_{21}$-R$_{13}$ (SEQ ID NO: 59), and the B chain comprises the sequence X$_{25}$LCGAX$_{30}$LVDALYLVCGDX$_{42}$GFX$_{45}$ (SEQ ID NO: 60) wherein $X_9$, $X_{14}$ and $X_{15}$ are independently ornithine, lysine or arginine;

$X_{17}$ is glutamic acid or glutamine;

$X_{19}$ is tyrosine, 4-methoxy-phenylalanine or 4-amino phenylalanine;

$X_{21}$ is alanine, glycine or asparagine;

$X_{25}$ is selected from the group consisting of histidine and threonine;

$X_{30}$ is selected from the group consisting of histidine, aspartic acid and glutamic acid;

$X_{42}$ is selected from the group consisting of alanine, lysine, ornithine and arginine;

$X_{45}$ is tyrosine or phenylalanine and $R_{13}$ is COOH or $CONH_2$. In one embodiment the B chain is selected from the group consisting of HLCGAELVDALYLVCGDX$_{42}$GFY (SEQ ID NO: 61), GPEHLCGAELVDALYLVCGDX$_{42}$GFY (SEQ ID NO: 62), GPEHLCGAELVDALYLVCGDX$_{42}$GFYFNPKT (SEQ ID NO: 63) and GPEHLCGAELVDALYLVCGDX$_{42}$ GFY-FNKPT (SEQ ID NO: 64), wherein $X_{42}$ is selected from the group consisting of ornithine, lysine and arginine. In a further embodiment the A chain comprises the sequence GIVDECCHX$_9$SCDLX$_{14}$X$_{15}$LQMYCN-R$_{13}$ (SEQ ID NO: 66), wherein $X_9$, $X_{14}$ and $X_{15}$ are independently ornithine, lysine or arginine.

In accordance with one embodiment the linking moiety is a peptide is selected from the group consisting of (Y$_1$)$_k$-X$_{51}$AX$_{53}$X$_{54}$X$_{55}$X$_{56}$X$_{57}$R(Y$_2$)$_n$ (SEQ ID NO: 28) and (Y$_1$)$_k$-GYGSSSX$_{57}$R (SEQ ID NO: 51), wherein $Y_1$ is selected from the group $X_{46}$, $X_{46}X_{47}$, $X_{46}X_{47}X_{48}$, $X_{46}X_{47}X_{48}X_{49}$ (SEQ ID NO: 24) and $X_{46}X_{47}X_{48}X_{49}X_{50}$ (SEQ ID NO: 13); and $Y_2$ is selected from the group $X_{70}$, $X_{70}X_{71}$, $X_{70}X_{71}X_{72}$ and $X_{70}X_{71}X_{72}X_{73}$ (SEQ ID NO: 15), n is 0 or 1 and k is 0 or 1, wherein at least one of n and k is 1. In one embodiment n is 1 and $Y_1$ is selected from the group consisting of F, Y, FN, YT, FNK, YTP, FNPK (SEQ ID NO: 79), FNKP (SEQ ID NO: 77), YTPK (SEQ ID NO: 78), YTPKT (SEQ ID NO: 16), YTKPT (SEQ ID NO: 80), FNKPT (SEQ ID NO: 76) and FNPKT (SEQ ID NO: 81). In another embodiment $Y_1$ is selected from the group consisting of F, FN, FNK, FNPK (SEQ ID NO: 79), FNKPT (SEQ ID NO: 76) and FNPKT (SEQ ID NO: 81). In one embodiment $Y_2$ is selected from the group consisting of A, AP, APQ and APQT (SEQ ID NO: 82). In a further embodiment both n and k are 1 and $Y_1$ is selected from the group consisting of F, Y, FN, YT, FNK, YTP, FNPK (SEQ ID NO: 79), FNKP (SEQ ID NO: 77), YTPK (SEQ ID NO: 78), YTPKT (SEQ ID NO: 16), YTKPT (SEQ ID NO: 80), FNKPT (SEQ ID NO: 76) and FNPKT (SEQ ID NO: 81) and $Y_2$ is selected from the group consisting of A, AP, APQ and APQT (SEQ ID NO: 82).

In one embodiment a single chain insulin analog is provided comprising the general formula IB-LM-IA wherein IB is an amino acid sequence selected from the group consisting of HLCGAELVDALYLVCGDX$_{42}$GFY (SEQ ID NO: 61), GPEHLCGAELVDALYLVCGDX$_{42}$GFY (SEQ ID NO: 62), GPEHLCGAELVDALYLVCGDX$_{42}$GFYFNPKT (SEQ ID NO: 63) and GPEHLCGAELVDALYLVCGDX$_{42}$ GFY-FNKPT (SEQ ID NO: 64), LM is a linking moiety selected from the group consisting of GAGSSSX$_{57}$RAPQT SEQ ID NO: 66), GYGSSSX$_{57}$R (SEQ ID NO: 51) and

,

IA is the amino acid sequence GIVDECCHX$_9$SCDLX$_{14}$X$_{15}$LQMYCN-R$_{13}$ (SEQ ID NO: 66), wherein $X_9$, $X_{14}$, $X_{15}$ $X_{42}$ and $X_{57}$ are independently ornithine, lysine or arginine, and m is an integer selected from the range of 10 to 12. In one further embodiment the linking moiety is GYGSSSOR (SEQ ID NO: 65).

In accordance with one embodiment a single chain insulin analog is provided that comprises the structure: IB-LM-IA, wherein IB comprises the sequence X$_{25}$LCGX$_{29}$X$_{30}$LVX$_{33}$X$_{34}$LYLVCGDX$_{42}$GFX$_{45}$ (SEQ ID NO: 58), LM is a linking moiety as disclosed herein that covalently links IB to IA, and IA comprises the sequence GIVEQCCHSICSLYQLENX$_{19}$CX$_{21}$-R$_{13}$ (SEQ ID NO: 68) or GIVDECCX$_8$X$_9$SCDLX$_{14}$X$_{15}$LX$_{17}$X$_{18}$X$_{19}$CX$_{21}$-R$_{13}$ (SEQ ID NO: 69), wherein the C-terminal phenylalanine residue of SEQ ID NO: 69 is directly covalently bound to the linking moiety, LM, in the absence of any intervening amino acids. In accordance with one embodiment a single chain insulin analog is provided that comprises the sequence X$_{25}$LCGX$_{29}$X$_{30}$LVX$_{33}$X$_{34}$LYLVCGDX$_{42}$GFX$_{45}$ (SEQ ID NO: 58)-(Y$_1$)$_k$-X$_{51}$AX$_{53}$X$_{54}$X$_{55}$X$_{56}$X$_{57}$X$_{58}$(Y$_2$)$_n$ (SEQ ID NO: 70)-GIVDECCX$_8$X$_9$SCDLX$_{14}$X$_{15}$LX$_{17}$X$_{18}$X$_{19}$CX$_{21}$-R$_{13}$ (SEQ ID NO: 56) or X$_{25}$LCGX$_{29}$X$_{30}$ LVX$_{33}$X$_{34}$LYLVCGDX$_{42}$GFX$_{45}$(Y$_1$)$_k$ (SEQ ID NO: 58)-X$_{51}$AX$_{53}$X$_{54}$X$_{55}$X$_{56}$X$_{57}$X$_{58}$(Y$_2$)$_6$ (SEQ ID NO: 70)-GIVEQCCHSICSLYQLENX$_{19}$CX$_{21}$-R$_{13}$ (SEQ ID NO: 68), wherein $X_{46}$ through $X_{56}$ and $X_{70}X_{71}X_{72}X_{73}$ (SEQ ID NO: 15) are independently any amino acid, $X_{57}$ and $X_{58}$ are independently arginine, ornithine or lysine, $Y_1$ is selected from the group $X_{46}$, $X_{46}X_{47}$, $X_{46}X_{47}X_{48}$, $X_{46}X_{47}X_{48}X_{49}$ (SEQ ID NO: 24) and $X_{46}X_{47}X_{48}X_{49}X_{50}$ (SEQ ID NO: 13), $Y_2$ is selected from the group $X_{70}$, $X_{70}X_{71}$, $X_{70}X_{71}X_{72}$ and $X_{70}X_{71}X_{72}X_{73}$ (SEQ ID NO: 15) wherein n and k are independently 0 or 1;

$X_8$ is histidine, threonine or phenylalanine;

$X_9$ is serine, arginine, lysine, ornithine or alanine;

$X_{14}$ is tyrosine, arginine, lysine, ornithine or alanine;

$X_{15}$ is glutamine, glutamic acid, arginine, alanine, lysine, ornithine or leucine;

$X_{17}$ is glutamic acid, aspartic acid, asparagine, lysine, ornithine or glutamine;

$X_{18}$ is methionine, asparagine, glutamine, aspartic acid, glutamic acid or threonine;

$X_{19}$ is tyrosine, 4-methoxy phenylalanine or 4-amino-phenylalanine;

$X_{21}$ is alanine, glycine or asparagine;

$X_{25}$ is histidine or threonine;

$X_{29}$ is selected from the group consisting of alanine, glycine and serine;

$X_{30}$ is selected from the group consisting of histidine, aspartic acid, glutamic acid, homocysteic acid and cysteic acid;

$X_{33}$ is selected from the group consisting of aspartic acid, glutamine and glutamic acid;

$X_{34}$ is selected from the group consisting of alanine and threonine;

$X_{42}$ is selected from the group consisting of alanine, lysine, ornithine and arginine; and $X_{45}$ is tyrosine or phenylalanine;

In accordance with one embodiment a single chain insulin analog is provided that comprises the structure: IB-LM-IA, wherein IB comprises the sequence $X_{25}LCGX_{29}X_{30}LVX_{33}X_{34}LYLVCGDX_{42}GFX_{45}$ (SEQ ID NO: 58), LM is a linking moiety selected from the group consisting of $(Y_1)_k$-$X_{51}AX_{53}X_{54}X_{55}X_{56}RR(Y_2)_n$ (SEQ ID NO: 23), $(Y_2)_k$-GYGSSSX$_{57}$R$(Y_2)_n$ (SEQ ID NO: 51) and

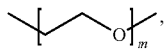

wherein $Y_1$ is selected from the group $X_{46}$, $X_{46}X_{47}$, $X_{46}X_{47}X_{48}$, $X_{46}X_{47}X_{48}X_{49}$ (SEQ ID NO: 24) and $X_{46}X_{47}X_{48}X_{49}X_{50}$ (SEQ ID NO: 13); and $Y_2$ is selected from the group $X_{70}$, $X_{70}X_{71}$, $X_{70}X_{71}X_{72}$ and $X_{70}X_{71}X_{72}X_{73}$ (SEQ ID NO: 15);

n is 0 or 1;

k is 0 or 1;

m is an integer ranging from 7 to 16; and $X_{46}$ through $X_{50}$ and $X_{70}$ through $X_{73}$ are each independently any amino acid;

$X_{51}$ is selected from the group consisting of glycine, alanine, valine, leucine, isoleucine, proline, phenylalanine and methionine;

$X_{52}$ is any amino acid other than tyrosine;

$X_{53}$ through $X_{56}$ are each independently any amino acid; and $X_{57}$ is arginine, lysine or ornithine; and the A chain comprises the sequence GIVDECCHX$_9$SCDLX$_{14}$X$_{15}$LQMYCN-R$_{13}$ (SEQ ID NO: 66), wherein $X_9$, $X_{14}$ and $X_{15}$ are independently ornithine, lysine or arginine and $R_{13}$ is COOH or CONH$_2$.

In one embodiment the B chain is selected from the group consisting of HLCGAELVDALYLVCGDOGFY (SEQ ID NO: 71), GPEHLCGAELVDALYLVCGDOGFY (SEQ ID NO: 72), GPEHLCGAELVDALYLVCGDOGFYFNPKT (SEQ ID NO: 73) and GPEHLCGAELVDALYLVCGDOG-FYFNKPT (SEQ ID NO: 74) and the A chain is GIVDECCHOSCDLOOLQMX$_{19}$CN-R$_{13}$ (SEQ ID NO: 75), wherein $X_{19}$ is tyrosine, 4-methoxy-phenylalanine or 4-amino phenylalanine. In one embodiment at least one of n and k is 1.

In one embodiment a single chain insulin analog is provided comprising the sequence $X_{25}LCGX_{29}X_{30}LVX_{33}X_{34}LYLVCGX_{41}X_{42}GFX_{45}X_{51}X_{52}X_{53}X_{54}X_{55}X_{56}X_{57}X_{58}X_{70}X_{71}X_{72}X_{73}GIVX_4X_5CCX_8X_9X_{10}CX_{12}LX_{14}X_{15}LEX_{18}X_{19}CX_{21}$-$R_{13}$ (SEQ ID NO: 168); $X_{25}LCGX_{29}X_{30}LVX_{33}X_{34}$ LYLVCGX$_{41}$X$_{42}$GFX$_{45}$X$_{51}$X$_{52}$GSSSX$_{57}$X$_{58}$APQTGIVX$_4$X$_5$CCX$_8$X$_9$X$_{10}$CX$_{12}$LX$_{14}$X$_{15}$LEX$_{18}$X$_{19}$CX$_{21}$-$R_{13}$ (SEQ ID NO: 169); $X_{25}LCGX_{29}X_{30}LVX_{33}X_{34}LYLVCGX_{41}X_{42}GFX_{45}X_{46}X_{47}X_{48}TX_{51}X_{52}GSSSX_{57}X_{58}APQTGIVX_4X_5$ CCX$_8$X$_9$X$_{10}$CX$_{12}$LX$_{14}$X$_{15}$LEX$_{18}$X$_{19}$CX$_{21}$-$R_{13}$ (SEQ ID NO: 170; $X_{25}LCGX_{29}X_{30}LVX_{33}X_{34}LYLVCGX_{41}X_{42}GFX_{45}X_{46}X_{47}X_{48}TX_{51}X_{52}GSSSX_{57}X_{58}GIVX_4X_5CCX_8X_9X_{10}CX_{12}LX_{14}X_{15}LEX_{18}X_{19}CX_{21}$-$R_{13}$ (SEQ ID NO: 171); or $X_{25}LCGX_{29}X_{30}LVX_{33}X_{34}LYLVCGX_{41}X_{42}GFX_{45}$ GAGSSSRX$_{58}$APQTGIVX$_4$X$_5$CCX$_8$X$_9$X$_{10}$CX$_{12}$LX$_{14}$X$_{15}$LEX$_{18}$X$_{19}$CX$_{21}$-$R_{13}$ (SEQ ID NO: 172); wherein $X_4$ is glutamic acid or aspartic acid;

$X_5$ is glutamic acid or glutamine $X_8$ is threonine, histidine or phenylalanine;

$X_9$ is serine, arginine, ornithine or alanine;

$X_{10}$ is serine or isoleucine;

$X_{12}$ is serine or aspartic acid;

$X_{14}$ is arginine, tyrosine, ornithine or alanine;

$X_{15}$ is glutamine, arginine, alanine, ornithine or leucine;

$X_{18}$ is methionine, asparagine or threonine;

$X_{19}$ is tyrosine, 4-methoxy-phenylalanine or 4-amino phenylalanine;

$X_{21}$ is alanine, glycine or asparagine;

$X_{25}$ is selected from the group consisting of histidine and threonine;

$X_{29}$ is selected from the group consisting of alanine, glycine and serine;

$X_{30}$ is selected from the group consisting of histidine, aspartic acid, glutamic acid, homocysteic acid and cysteic acid;

$X_{33}$ is selected from the group consisting of aspartic acid and glutamic acid;

$X_{34}$ is selected from the group consisting of alanine and threonine;

$X_{41}$ is selected from the group consisting of aspartic acid and glutamic acid;

$X_{42}$ is selected from the group consisting of alanine, ornithine and arginine;

$X_{45}$ is selected from the group consisting of tyrosine and phenylalanine;

$X_{46}$ is phenylalanine or tyrosine;

$X_{47}$ is asparagine or threonine;

$X_{48}$ is an aspartate-lysine dipeptide, an arginine-proline dipeptide, a lysine-proline dipeptide, or a proline-lysine dipeptide;

$X_{51}$ is selected from the group consisting of glycine, alanine, valine, leucine, isoleucine, proline, phenylalanine and methionine;

$X_{52}$ is any amino acid other than tyrosine;

$X_{53}$ through $X_{56}$ are each independently any amino acid; and $X_{57}$ and $X_{58}$ are independently arginine, lysine, cysteine, homocysteine, acetyl-phenylalanine or ornithine;

$X_{70}$-$X_{73}$ are independently any amino acid and $R_{13}$ is COOH or $CONH_2$. In one embodiment the single chain insulin further comprises a polyethylene glycol chain covalently linked to the side chain of an amino acid of the linking moiety and/or at a position selected from the group consisting of the N-terminal alpha amine of the B chain, the side chain of an amino acid at position A9, A14 and A15 of the A chain or positions B1, B2, B10, B22, B28 or B29 of the B chain. In one embodiment the polyethylene glycol chain is covalently linked to the side chain of an amino acid of the linking moiety and/or at the N-terminal alpha amine of the B chain (e.g. at position B1 for insulin based B chain or position B2 for IGF-1 based B chain). In one embodiment the polyethylene glycol chain is covalently linked to the side chain of an amino acid at position 8 of the linking moiety.

Pegylation of Single Chain Insulin Analogs

Applicants have surprisingly discovered that covalently linkage of a hydrophilic moiety to the insulin single chain analogs disclosed herein provide analogs having slower onset, extended duration and exhibit a basal profile of activity. In one embodiment, the single chain insulin analogs disclosed herein are further modified to comprise a hydrophilic moiety covalently linked to the side chain of an amino acid at a position selected from the group consisting of A9, A14 and A15 of the A chain or at the N-terminal alpha amine of the B chain (e.g. at position B1 for insulin based B chain or position B2 for IGF-1 based B chain) or at the side chain of an amino acid at position B1, B2, B10, B22, B28 or B29 of the B chain or at any position of the linking moiety that links the A chain and B chain. In exemplary embodiments, this hydrophilic moiety is covalently linked to a Lys, Cys, Orn, homocysteine, or acetyl-phenylalanine residue at any of these positions. In one embodiment the hydrophilic moiety is covalently linked to the side chain of an amino acid of the linking moiety.

Exemplary hydrophilic moieties include polyethylene glycol (PEG), for example, of a molecular weight of about 1,000 Daltons to about 40,000 Daltons, or about 20,000 Daltons to about 40,000 Daltons. Additional suitable hydrophilic moieties include, polypropylene glycol, polyoxyethylated polyols (e.g., POG), polyoxyethylated sorbitol, polyoxyethylated glucose, polyoxyethylated glycerol (POG), polyoxyalkylenes, polyethylene glycol propionaldehyde, copolymers of ethylene glycol/propylene glycol, monomethoxy-polyethylene glycol, mono-($C_1$-$C_{10}$) alkoxy- or aryloxy-polyethylene glycol, carboxymethylcellulose, polyacetals, polyvinyl alcohol (PVA), polyvinyl pyrrolidone, poly-1,3-dioxolane, poly-1,3,6-trioxane, ethylene/maleic anhydride copolymer, poly (beta-amino acids) (either homopolymers or random copolymers), poly(n-vinyl pyrrolidone)polyethylene glycol, propropylene glycol homopolymers (PPG) and other polyakylene oxides, polypropylene oxide/ethylene oxide copolymers, colonic acids or other polysaccharide polymers, Ficoll or dextran and mixtures thereof.

The hydrophilic moiety, e.g., polyethylene glycol chain in accordance with some embodiments has a molecular weight selected from the range of about 500 to about 40,000 Daltons. In one embodiment the hydrophilic moiety, e.g. PEG, has a molecular weight selected from the range of about 500 to about 5,000 Daltons, or about 1,000 to about 5,000 Daltons. In another embodiment the hydrophilic moiety, e.g., PEG, has a molecular weight of about 10,000 to about 20,000 Daltons. In yet other exemplary embodiment the hydrophilic moiety, e.g., PEG, has a molecular weight of about 20,000 to about 40,000 Daltons. In one embodiment the hydrophilic moiety, e.g. PEG, has a molecular weight of about 20,000 Daltons. In one embodiment a single chain insulin analog is provided wherein one or more amino acids of the analog are pegylated, and the combined molecular weight of the covalently linked PEG chains is about 20,000 Daltons.

In one embodiment dextrans are used as the hydrophilic moiety. Dextrans are polysaccharide polymers of glucose subunits, predominantly linked by α1-6 linkages. Dextran is available in many molecular weight ranges, e.g., about 1 kD to about 100 kD, or from about 5, 10, 15 or 20 kD to about 20, 30, 40, 50, 60, 70, 80 or 90 kD.

Linear or branched polymers are contemplated. Resulting preparations of conjugates may be essentially monodisperse or polydisperse, and may have about 0.5, 0.7, 1, 1.2, 1.5 or 2 polymer moieties per peptide.

In one embodiment the hydrophilic moiety is a polyethylene glycol (PEG) chain, optionally linked to the side chain of an amino acid at a position selected from the group consisting of A9, A14 and A15 of the A chain, positions B1, B2, B10, B22, B28 or B29 of the B chain, at the N-terminal alpha amine of the B chain, or at any position of the linking moiety that links the A chain and B chain, including for example at position C8. In one embodiment the single chain insulin analog comprises a peptide linking moiety of 8 to 12 amino acids, wherein one of the amino acids of the linking moiety has a polyethylene chain covalently bound to its side chain. In one embodiment the single chain insulin analog comprises a peptide linking moiety of 8 to 12 amino acids, wherein an amino acid of the linking moiety is pegylated and one or more amino acid at a position selected from the group consisting of A9, A14 and A15 of the A chain, positions B1, B2, B10, B22, B28 or B29 of the B chain is also pegylated. In one embodiment the total molecular weight of the covalently linked PEG chain(s) is about 20,000 Daltons.

In one embodiment a single chain insulin analog comprises a linking moiety of 8 to 12 amino acids, wherein one of the amino acids of the linking moiety has a 20,000 Dalton polyethylene chain covalently bound to its side chain. In another embodiment a insulin analog comprises a peptide linking moiety of 8 to 12 amino acids, wherein one of the amino acids of the linking moiety has a polyethylene chain covalently bound to its side chain and a second PEG chain is linked to the N-terminal alpha amine of the B chain (e.g. at position B1 for insulin based B chain or position B2 for IGF-1 based B chain) or at the side chain of an amino acid at position B1, B2 and B29 of the B chain. In one embodiment when two PEG chains are linked to the single chain insulin analog, each PEG chain has a molecular weight of about 10,000 Daltons. In one embodiment when the PEG chain is linked to an 8 to 12 amino acid linking moiety, the PEG chain is linked at position C7 or C8 of the linking moiety and in one embodiment the PEG chain is linked at position C8 of the linking moiety. In one embodiment when two PEG chains are linked to the single chain insulin analog, with one PEG chain linked at position C8 and the second PEG is linked at A9, A14, A15, B1, B2, B10, B22, B28 or B29.

Hydrophilic moieties such as polyethylene glycol can be attached to the single chain insulin analog under any suitable conditions used to react a protein with an activated polymer molecule. Any means known in the art can be used, including via acylation, reductive alkylation, Michael addition, thiol alkylation or other chemoselective conjugation/ligation methods through a reactive group on the PEG moiety (e.g., an aldehyde, amino, ester, thiol, α-haloacetyl, maleimido or hydrazino group) to a reactive group on the target compound (e.g., an aldehyde, amino, ester, thiol, α-haloacetyl, maleimido or hydrazino group). Activating groups which can be used to link the water soluble polymer to one or more proteins include without limitation sulfone, maleimide, sulfhydryl, thiol, triflate, tresylate, azidirine, oxirane and 5-pyridyl. If attached to the peptide by reductive alkylation, the polymer selected should have a single reactive aldehyde so that the degree of polymerization is controlled. See, for example, Kinstler et al., *Adv. Drug. Delivery Rev.* 54: 477-485 (2002); Roberts et al., *Adv. Drug Delivery Rev.* 54: 459-476 (2002); and Zalipsky et al., *Adv. Drug Delivery Rev.* 16: 157-182 (1995).

In a specific aspect of the invention, an amino acid residue on the single chain analog having a thiol is modified with a hydrophilic moiety such as PEG. In some embodiments, the thiol is modified with maleimide-activated PEG in a Michael addition reaction to result in a PEGylated peptide comprising the thioether linkage shown below:

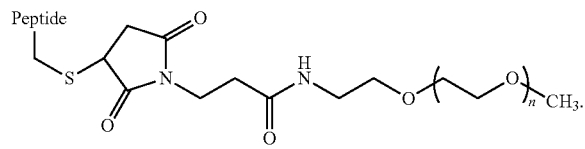

In some embodiments, the thiol is modified with a haloacetyl-activated PEG in a nucleophilic substitution reaction to result in a PEGylated peptide comprising the thioether linkage shown below:

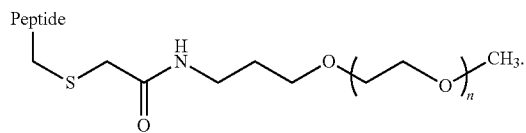

Acylation of Single Chain Insulin Analogs

In some embodiments, the single chain insulin analog is modified to comprise an acyl group. The acyl group can be covalently linked directly to an amino acid of the single chain insulin analog, or indirectly to an amino acid of the single chain insulin analog via a spacer, wherein the spacer is positioned between the amino acid of the single chain insulin analog and the acyl group. The single chain insulin analog may be acylated at the same amino acid position where a hydrophilic moiety is linked, or at a different amino acid position. For example, acylation may occur at any position including any of amino acid of the A or B chains as well as a position within the linking moiety, provided that the activity exhibited by the non-acylated single chain insulin analog is retained upon acylation. Nonlimiting examples include acylation at positions A14 and A15 of the A chain, positions position B1 for insulin based B chain or position B2 for IGF-1 based B chain or positions B10, B22, B28 or B29 of the B chain or at any position of the linking moiety.

In one specific aspect of the invention, the single chain insulin analog (or derivative or conjugate thereof) is modified to comprise an acyl group by direct acylation of an amine, hydroxyl, or thiol of a side chain of an amino acid of the single chain insulin analog. In some embodiments, the single chain insulin analog is directly acylated through the side chain amine, hydroxyl, or thiol of an amino acid. In some embodiments, acylation is at position B28 or B29 (according to the amino acid numbering of the native insulin A and B chain sequences). In this regard, a single chain insulin analog can be provided that has been modified by one or more amino acid substitutions in the A or B chain sequence, including for example at positions A14, A15, B1, B2, B10, B22, B28 or B29 (according to the amino acid numbering of the native insulin A and B chain sequences) or at any position of the linking moiety with an amino acid comprising a side chain amine, hydroxyl, or thiol. In some specific embodiments of the invention, the direct acylation of the single chain insulin analog occurs through the side chain amine, hydroxyl, or thiol of the amino acid at position B28 or B29 (according to the amino acid numbering of the native insulin A and B chain sequences).

In one embodiment, the single chain insulin analog comprises an amino acid of Formula I:

In some exemplary embodiments, the amino acid of Formula I, is the amino acid wherein n is 4 (Lys) or n is 3 (Orn).

In another embodiment, the single chain insulin analog comprises an amino acid of Formula II:

In some exemplary embodiments, the amino acid of Formula II is the amino acid wherein n is 1 (Ser).

In yet another embodiment, the single chain insulin analog comprises a side chain thiol is an amino acid of Formula III:

In some exemplary embodiments, the amino acid of Formula III is the amino acid wherein n is 1 (Cys).

In yet another embodiment, the single chain insulin analog comprises a disubstituted amino acid comprising the same structure of Formula I, Formula II, or Formula III, except that the hydrogen bonded to the alpha carbon of the amino acid of Formula I, Formula II, or Formula III is replaced with a second side chain.

In accordance with one embodiment, the acylated single chain insulin analogs comprise a spacer between the peptide and the acyl group. In some embodiments, the single chain insulin analog is covalently bound to the spacer, which is covalently bound to the acyl group. In some exemplary embodiments, the single chain insulin analog is modified to comprise an acyl group by acylation of an amine, hydroxyl, or thiol of a spacer, which spacer is attached to a side chain of an amino acid at position B28 or B29 (according to the amino acid numbering of the A or B chain of native insulin), or at any position of the spacer moiety. The amino acid of the single chain insulin analog to which the spacer is attached can be any amino acid comprising a moiety which permits linkage to the spacer. For example, an amino acid comprising a side chain —NH$_2$, —OH, or —COOH (e.g., Lys, Orn, Ser, Asp, or Glu) is suitable.

In some embodiments, the spacer between the single chain insulin analog and the acyl group is an amino acid comprising a side chain amine, hydroxyl, or thiol (or a dipeptide or tripeptide comprising an amino acid comprising a side chain amine, hydroxyl, or thiol). In some embodiments, the spacer comprises a hydrophilic bifunctional spacer. In a specific embodiment, the spacer comprises an amino poly(alkyloxy) carboxylate. In this regard, the spacer can comprise, for example, NH$_2$(CH$_2$CH$_2$O)$_n$(CH$_2$)$_m$COOH, wherein m is any integer from 1 to 6 and n is any integer from 2 to 12, such as, e.g., 8-amino-3,6-dioxaoctanoic acid, which is commercially available from Peptides International, Inc. (Louisville, Ky.). In one embodiment, the hydrophilic bifunctional spacer comprises two or more reactive groups, e.g., an amine, a hydroxyl, a thiol, and a carboxyl group or any combinations thereof. In certain embodiments, the hydrophilic bifunctional spacer comprises a hydroxyl group and a carboxylate. In other embodiments, the hydrophilic bifunctional spacer comprises an amine group and a carboxylate. In other embodiments, the hydrophilic bifunctional spacer comprises a thiol group and a carboxylate.

In some embodiments, the spacer between peptide the single chain insulin analog and the acyl group is a hydrophobic bifunctional spacer. Hydrophobic bifunctional spacers are known in the art. See, e.g., Bioconjugate Techniques, G. T. Hermanson (Academic Press, San Diego, Calif., 1996), which is incorporated by reference in its entirety. In certain embodiments, the hydrophobic bifunctional spacer comprises two or more reactive groups, e.g., an amine, a hydroxyl, a thiol, and a carboxyl group or any combinations thereof. In certain embodiments, the hydrophobic bifunctional spacer comprises a hydroxyl group and a carboxylate. In other embodiments, the hydrophobic bifunctional spacer comprises an amine group and a carboxylate. In other embodiments, the hydrophobic bifunctional spacer comprises a thiol group and a carboxylate. Suitable hydrophobic bifunctional spacers comprising a carboxylate and a hydroxyl group or a thiol group are known in the art and include, for example, 8-hydroxyoctanoic acid and 8-mercaptooctanoic acid.

In accordance with certain embodiments the bifunctional spacer can be a synthetic or naturally occurring amino acid comprising an amino acid backbone that is 3 to 10 atoms in length (e.g., 6-amino hexanoic acid, 5-aminovaleric acid, 7-aminoheptanoic acid, and 8-aminooctanoic acid). Alternatively, the spacer can be a dipeptide or tripeptide spacer having a peptide backbone that is 3 to 10 atoms (e.g., 6 to 10 atoms) in length. Each amino acid of the dipeptide or tripeptide spacer attached to the single chain insulin analog can be independently selected from the group consisting of: naturally-occurring and/or non-naturally occurring amino acids, including, for example, any of the D or L isomers of the naturally-occurring amino acids (Ala, Cys, Asp, Glu, Phe, Gly, His, Ile, Lys, Leu, Met, Asn, Pro, Arg, Ser, Thr, Val, Trp, Tyr), or any D or L isomers of the non-naturally occurring amino acids selected from the group consisting of: β-alanine (β-Ala), N-α-methyl-alanine (Me-Ala), aminobutyric acid (Abu), α-aminobutyric acid (γ-Abu), aminohexanoic acid (e-Ahx), aminoisobutyric acid (Aib), aminomethylpyrrole carboxylic acid, aminopiperidinecarboxylic acid, aminoserine (Ams), aminotetrahydropyran-4-carboxylic acid, arginine N-methoxy-N-methyl amide, β-aspartic acid (β-Asp), azetidine carboxylic acid, 3-(2-benzothiazolyl)alanine, α-tert-butylglycine, 2-amino-5-ureido-n-valeric acid (citrulline, Cit), β-Cyclohexylalanine (Cha), acetamidomethyl-cysteine, diaminobutanoic acid (Dab), diaminopropionic acid (Dpr), dihydroxyphenylalanine (DOPA), dimethylthiazolidine (DMTA), γ-Glutamic acid (γ-Glu), homoserine (Hse), hydroxyproline (Hyp), isoleucine N-methoxy-N-methyl amide, methyl-isoleucine (MeIle), isonipecotic acid (Isn), methyl-leucine (MeLeu), methyl-lysine, dimethyl-lysine, trimethyl-lysine, methanoproline, methionine-sulfoxide (Met(O)), methionine-sulfone (Met(O2)), norleucine (Nle), methyl-norleucine (Me-Nle), norvaline (Nva), ornithine (Orn), para-aminobenzoic acid (PABA), penicillamine (Pen), methylphenylalanine (MePhe), 4-Chlorophenylalanine (Phe(4-Cl)), 4-fluorophenylalanine (Phe(4-F)), 4-nitrophenylalanine (Phe(4-NO2)), 4-cyanophenylalanine ((Phe(4-CN)), phenylglycine (Phg), piperidinylalanine, piperidinylglycine, 3,4-dehydroproline, pyrrolidinylalanine, sarcosine (Sar), selenocysteine (Sec), U-Benzyl-phosphoserine, 4-amino-3-hydroxy-6-methylheptanoic acid (Sta), 4-amino-5-cyclohexyl-3-hydroxypentanoic acid (ACHPA), 4-amino-3-hydroxy-5-phenylpentanoic acid (AHPPA), 1,2,3,4,-tetrahydro-isoquinoline-3-carboxylic acid (Tic), tetrahydropyranglycine, thienylalanine (Thi), U-Benzyl-phosphotyrosine, O-Phosphotyrosine, methoxytyrosine, ethoxytyrosine, O-(bis-dimethylamino-phosphono)-tyrosine, tyrosine sulfate tetrabutylamine, methyl-valine (Me-Val), 1-amino-1-cyclohexane carboxylic acid (Acx), aminovaleric acid, beta-cyclopropyl-alanine (Cpa), propargylglycine (Prg), allylglycine (Alg), 2-amino-2-cyclohexyl-propanoic acid (2-Cha), tertbutylglycine (Tbg), vinylglycine (Vg), 1-amino-1-cyclopropane carboxylic acid (Acp), 1-amino-1-cyclopentane carboxylic acid (Acpe), alkylated 3-mercaptopropionic acid, 1-amino-1-cyclobutane carboxylic acid (Acb). In some embodiments the dipeptide spacer is selected from the group consisting of: Ala-Ala, β-Ala-β-Ala, Leu-Leu, Pro-Pro, γ-aminobutyric acid-γ-aminobutyric acid, and γ-Glu-γ-Glu.

The peptide the single chain insulin analog can be modified to comprise an acyl group by acylation of a long chain alkane. In specific aspects, the long chain alkane comprises an amine, hydroxyl, or thiol group (e.g. octadecylamine, tetradecanol, and hexadecanethiol) which reacts with a carboxyl group, or activated form thereof, of the single chain insulin analog. The carboxyl group, or activated form thereof, of the single chain insulin analog can be part of a side chain of an amino acid (e.g., glutamic acid, aspartic acid) of the single chain insulin analog or can be part of the peptide backbone.

In certain embodiments, the single chain insulin analog is modified to comprise an acyl group by acylation of the long chain alkane by a spacer which is attached to the single chain insulin analog. In specific aspects, the long chain alkane comprises an amine, hydroxyl, or thiol group which reacts with a carboxyl group, or activated form thereof, of the spacer. Suitable spacers comprising a carboxyl group, or activated form thereof, are described herein and include, for example, bifunctional spacers, e.g., amino acids, dipeptides, tripeptides, hydrophilic bifunctional spacers and hydrophobic bifunctional spacers. As used herein, the term "activated form of a carboxyl group" refers to a carboxyl group with the general formula R(C═O)X, wherein X is a leaving group and R is the single chain insulin analog or the spacer. For example, activated forms of a carboxyl groups may include, but are not limited to, acyl chlorides, anhydrides, and esters. In some embodiments, the activated carboxyl group is an ester with a N-hydroxysuccinimide (NHS) leaving group.

With regard to these aspects of the invention, in which a long chain alkane is acylated by the peptide the single chain insulin analog or the spacer, the long chain alkane may be of any size and can comprise any length of carbon chain. The long chain alkane can be linear or branched. In certain aspects, the long chain alkane is a $C_4$ to $C_{30}$ alkane. For example, the long chain alkane can be any of a $C_4$ alkane, $C_6$ alkane, $C_8$ alkane, $C_{10}$ alkane, $C_{12}$ alkane, $C_{14}$ alkane, $C_{16}$ alkane, $C_{18}$ alkane, $C_{20}$ alkane, $C_{22}$ alkane, $C_{24}$ alkane, $C_{26}$ alkane, $C_{28}$ alkane, or a $C_{30}$ alkane. In some embodiments, the long chain alkane comprises a $C_8$ to $C_{20}$ alkane, e.g., a $C_{14}$ alkane, $C_{16}$ alkane, or a $C_{18}$ alkane.

In some embodiments, an amine, hydroxyl, or thiol group of the single chain insulin analog is acylated with a cholesterol acid. In a specific embodiment, the peptide is linked to the cholesterol acid through an alkylated des-amino Cys spacer, i.e., an alkylated 3-mercaptopropionic acid spacer. Suitable methods of peptide acylation via amines, hydroxyls, and thiols are known in the art. See, for example, Miller, Biochem Biophys Res Commun 218: 377-382 (1996); Shimohigashi and Stammer, Int J Pept Protein Res 19: 54-62 (1982); and Previero et al., Biochim Biophys Acta 263: 7-13 (1972) (for methods of acylating through a hydroxyl); and San and Silvius, J Pept Res 66: 169-180 (2005) (for methods of acylating through a thiol); Bioconjugate Chem. "Chemical Modifications of Proteins: History and Applications" pages 1, 2-12 (1990); Hashimoto et al., Pharmacuetical Res. "Synthesis of Palmitoyl Derivatives of Insulin and their Biological Activity" Vol. 6, No: 2 pp. 171-176 (1989).

The acyl group of the acylated peptide the single chain insulin analog can be of any size, e.g., any length carbon chain, and can be linear or branched. In some specific embodiments of the invention, the acyl group is a $C_4$ to $C_{30}$ fatty acid. For example, the acyl group can be any of a $C_4$ fatty acid, $C_6$ fatty acid, $C_8$ fatty acid, $C_{10}$ fatty acid, $C_{12}$ fatty acid, $C_{14}$ fatty acid, $C_{16}$ fatty acid, $C_{18}$ fatty acid, $C_{20}$ fatty acid, $C_{22}$ fatty acid, $C_{24}$ fatty acid, $C_{26}$ fatty acid, $C_{28}$ fatty acid, or a $C_{30}$ fatty acid. In some embodiments, the acyl group is a $C_8$ to $C_{20}$ fatty acid, e.g., a C14 fatty acid or a $C_{16}$ fatty acid.

In an alternative embodiment, the acyl group is a bile acid. The bile acid can be any suitable bile acid, including, but not limited to, cholic acid, chenodeoxycholic acid, deoxycholic acid, lithocholic acid, taurocholic acid, glycocholic acid, and cholesterol acid.

The acylated single chain insulin analog described herein can be further modified to comprise a hydrophilic moiety. In some specific embodiments the hydrophilic moiety can comprise a polyethylene glycol (PEG) chain. The incorporation of a hydrophilic moiety can be accomplished through any suitable means, such as any of the methods described herein. In some embodiments the acylated single chain analog comprises an amino acid selected from the group consisting of a Cys, Lys, Orn, homo-Cys, or Ac-Phe, and the side chain of the amino acid is covalently bonded to a hydrophilic moiety (e.g., PEG). In one embodiment, the acyl group is attached to position A14, A15, B1 (for insulin based B chains), B2 (for IGF-1 based B chains), B10, B22, B28 or B29 (according to the amino acid numbering of the A and B chains of native insulin), optionally via a spacer comprising Cys, Lys, Orn, homo-Cys, or Ac-Phe.

Alternatively, the acylated single chain insulin analog comprises a spacer, wherein the spacer is both acylated and modified to comprise the hydrophilic moiety. Nonlimiting examples of suitable spacers include a spacer comprising one or more amino acids selected from the group consisting of Cys, Lys, Orn, homo-Cys, and Ac-Phe.

Alkylation of the Single Chain Insulin Analog

In some embodiments, the single chain insulin analog is modified to comprise an alkyl group. The alkyl group can be covalently linked directly to an amino acid of the single chain insulin analog, or indirectly to an amino acid of the single chain insulin analog via a spacer, wherein the spacer is positioned between the amino acid of the single chain insulin analog and the alkyl group. The alkyl group can be attached to the single chain insulin analog via an ether, thioether, or amino linkage. For example, the single chain insulin analog may be alkylated at the same amino acid position where a hydrophilic moiety is linked, or at a different amino acid position. Alkylation can be carried out at any position within the single chain insulin analog, including for example in the C-terminal region of the B chain or at a position in the linking moiety, provided that insulin activity is retained. In a specific aspect of the invention, the single chain insulin analog is modified to comprise an alkyl group by direct alkylation of an amine, hydroxyl, or thiol of a side chain of an amino acid of the single chain insulin analog. In some embodiments, the single chain insulin analog is directly alkylated through the side chain amine, hydroxyl, or thiol of an amino acid. In some specific embodiments of the invention, the direct alkylation of the single chain insulin analog occurs through the side chain amine, hydroxyl, or thiol of the amino acid at position A14, A15, B1 (for insulin based B chains), B2 (for IGF-1 based b chains), B10, B22, B28 or B29 (according to the amino acid numbering of the A and B chain of native insulin).

In some embodiments, the amino acid of the single chain insulin analog comprises an amino acid selected from of Formula I, Formula II, and Formula III, and the alkyl group is linked through the amino, hydroxyl or thiol group contained in Formula I, Formula II, and Formula III, respectively. In some exemplary embodiments, the amino acid of Formula I, is the amino acid wherein n is 4 (Lys) or n is 3 (Orn). In some exemplary embodiments, the amino acid of Formula II is the amino acid wherein n is 1 (Ser). In some exemplary embodiments, the amino acid of Formula II is the amino acid wherein n is 1 (Cys). In yet other embodiments, the amino acid of peptide the single chain insulin analog comprising a side chain amine, hydroxyl, or thiol is a disubstituted amino acid comprising the same structure of Formula I, Formula II, or Formula III, except that the hydrogen bonded to the alpha carbon of the amino acid of Formula I, Formula II, or Formula III is replaced with a second side chain.

In some embodiments of the invention, the single chain insulin analog comprises a spacer between the peptide and the alkyl group. In some embodiments, the single chain insulin analog is covalently bound to the spacer, which is covalently bound to the alkyl group. In some exemplary embodiments, the single chain insulin analog is modified to comprise an alkyl group by alkylation of an amine, hydroxyl, or thiol of a spacer, wherein the spacer is attached to a side chain of an amino acid at position A14, A15, B1 (for insulin based b chains), B2 (for IGF-1 based B chains), B10, B22, B28 or B29 (according to the amino acid numbering of the A and B chains of native insulin). The amino acid of the single chain insulin analog to which the spacer is attached can be any amino acid (e.g., a singly α-substituted amino acid or an α,α-disubstituted amino acid) comprising a moiety which permits linkage to the spacer. An amino acid of the single chain insulin analog comprising a side chain —NH$_2$, —OH, or —COOH (e.g., Lys, Orn, Ser, Asp, or Glu) is suitable. In some embodiments, the spacer between the peptide the single chain insulin analog and the alkyl group is an amino acid comprising a side chain amine, hydroxyl, or thiol or a dipeptide or tripeptide comprising an amino acid comprising a side chain amine, hydroxyl, or thiol.

In the instance in which the alpha amine is alkylated, the spacer amino acid can be any amino acid. For example, the spacer amino acid can be a hydrophobic amino acid, e.g., Gly, Ala, Val, Leu, Ile, Trp, Met, Phe, Tyr. Alternatively, the spacer amino acid can be an acidic residue, e.g., Asp and Glu. In exemplary embodiments, the spacer amino acid can be a hydrophobic amino acid, e.g., Gly, Ala, Val, Leu, Ile, Trp, Met, Phe, Tyr, 6-amino hexanoic acid, 5-aminovaleric acid, 7-aminoheptanoic acid, 8-aminooctanoic acid. Alternatively, the spacer amino acid can be an acidic residue, e.g., Asp and Glu, provided that the alkylation occurs on the alpha amine of the acidic residue. In the instance in which the side chain amine of the spacer amino acid is alkylated, the spacer amino acid is an amino acid comprising a side chain amine, e.g., an amino acid of Formula I (e.g., Lys or Orn). In this instance, it is possible for both the alpha amine and the side chain amine of the spacer amino acid to be alkylated, such that the peptide is dialkylated. Embodiments of the invention include such dialkylated molecules.

When alkylation occurs through a hydroxyl group of the amino acid of the spacer, the amino acid or one of the amino acids of the spacer can be an amino acid of Formula II. In a specific exemplary embodiment, the amino acid is Ser.

When alkylation occurs through a thiol group of the amino acid of the spacer, the amino acid or one of the amino acids of the spacer can be an amino acid of Formula III. In a specific exemplary embodiment, the amino acid is Cys.

In some embodiments, the spacer comprises a hydrophilic bifunctional spacer. In a specific embodiment, the spacer comprises an amino poly(alkyloxy)carboxylate. In this regard, the spacer can comprise, for example, $NH_2(CH_2CH_2O)_n(CH_2)_mCOOH$, wherein m is any integer from 1 to 6 and n is any integer from 2 to 12, such as, e.g., 8-amino-3,6-dioxaoctanoic acid, which is commercially available from Peptides International, Inc. (Louisville, Ky.). In some embodiments, the spacer between peptide the single chain insulin analog and the alkyl group is a hydrophilic bifunctional spacer. In certain embodiments, the hydrophilic bifunctional spacer comprises two or more reactive groups, e.g., an amine, a hydroxyl, a thiol, and a carboxyl group or any combinations thereof. In certain embodiments, the hydrophilic bifunctional spacer comprises a hydroxyl group and a carboxylate. In other embodiments, the hydrophilic bifunctional spacer comprises an amine group and a carboxylate. In other embodiments, the hydrophilic bifunctional spacer comprises a thiol group and a carboxylate.

In some embodiments, the spacer between peptide the single chain insulin analog and the alkyl group is a hydrophobic bifunctional spacer. In certain embodiments, the hydrophobic bifunctional spacer comprises two or more reactive groups, e.g., an amine, a hydroxyl, a thiol, and a carboxyl group or any combinations thereof. In certain embodiments, the hydrophobic bifunctional spacer comprises a hydroxyl group and a carboxylate. In other embodiments, the hydrophobic bifunctional spacer comprises an amine group and a carboxylate. In other embodiments, the hydrophobic bifunctional spacer comprises a thiol group and a carboxylate. Suitable hydrophobic bifunctional spacers comprising a carboxylate and a hydroxyl group or a thiol group are known in the art and include, for example, 8-hydroxyoctanoic acid and 8-mercaptooctanoic acid.

The spacer (e.g., amino acid, dipeptide, tripeptide, hydrophilic bifunctional spacer, or hydrophobic bifunctional spacer) is 3 to 10 atoms (e.g., 6 to 10 atoms, (e.g., 6, 7, 8, 9, or 10 atoms)) in length. In more specific embodiments, the spacer is about 3 to 10 atoms (e.g., 6 to 10 atoms) in length and the alkyl is a $C_{12}$ to $C_{18}$ alkyl group, e.g., $C_{14}$ alkyl group, $C_{16}$ alkyl group, such that the total length of the spacer and alkyl group is 14 to 28 atoms, e.g., about 14, 15, 16, 17, 18, 19, 20, 21, 22, 23, 24, 25, 26, 27, or 28 atoms. In some embodiments the length of the spacer and alkyl is 17 to 28 (e.g., 19 to 26, 19 to 21) atoms.

In accordance with one embodiment the bifunctional spacer is a synthetic or non-naturally occurring amino acid comprising an amino acid backbone that is 3 to 10 atoms in length (e.g., 6-amino hexanoic acid, 5-aminovaleric acid, 7-aminoheptanoic acid, and 8-aminooctanoic acid). Alternatively, the spacer can be a dipeptide or tripeptide spacer having a peptide backbone that is 3 to 10 atoms (e.g., 6 to 10 atoms) in length. The dipeptide or tripeptide spacer attached to the single chain insulin analog can be composed of naturally-occurring and/or non-naturally occurring amino acids, including, for example, any of the amino acids taught herein. In some embodiments the spacer comprises an overall negative charge, e.g., comprises one or two negatively charged amino acids. In some embodiments the dipeptide spacer is selected from the group consisting of: Ala-Ala, β-Ala-β-Ala, Leu-Leu, Pro-Pro, γ-aminobutyric acid-γ-aminobutyric acid, and γ-Glu-γ-Glu. In one embodiment the dipeptide spacer is γ-Glu-γ-Glu.

Suitable methods of peptide alkylation via amines, hydroxyls, and thiols are known in the art. For example, a Williamson ether synthesis can be used to form an ether linkage between the insulin peptide and the alkyl group. Also, a nucleophilic substitution reaction of the peptide with an alkyl halide can result in any of an ether, thioether, or amino linkage. The alkyl group of the alkylated peptide the single chain insulin analog can be of any size, e.g., any length carbon chain, and can be linear or branched. In some embodiments of the invention, the alkyl group is a $C_4$ to $C_{30}$ alkyl. For example, the alkyl group can be any of a $C_4$ alkyl, $C_6$ alkyl, $C_8$ alkyl, $C_{10}$ alkyl, $C_{12}$ alkyl, $C_{14}$ alkyl, $C_{16}$ alkyl, $C_{18}$ alkyl, $C_{20}$ alkyl, $C_{22}$ alkyl, $C_{24}$ alkyl, $C_{26}$ alkyl, $C_{28}$ alkyl, or a $C_{30}$ alkyl. In some embodiments, the alkyl group is a $C_8$ to $C_{20}$ alkyl, e.g., a $C_{14}$ alkyl or a $C_{16}$ alkyl.

In some specific embodiments, the alkyl group comprises a steroid moiety of a bile acid, e.g., cholic acid, chenodeoxycholic acid, deoxycholic acid, lithocholic acid, taurocholic acid, glycocholic acid, and cholesterol acid.

In some embodiments the single chain insulin analog is modified to comprise an alkyl group by reacting a nucleophilic, long chain alkane with the single chain insulin analog, wherein the single chain insulin analog comprises a leaving group suitable for nucleophilic substitution. In specific aspects, the nucleophilic group of the long chain alkane comprises an amine, hydroxyl, or thiol group (e.g. octadecylamine, tetradecanol, and hexadecanethiol). The leaving group of the single chain insulin analog can be part of a side chain of an amino acid or can be part of the peptide backbone. Suitable leaving groups include, for example, N-hydroxysuccinimide, halogens, and sulfonate esters.

In certain embodiments, the single chain insulin analog is modified to comprise an alkyl group by reacting the nucleophilic, long chain alkane with a spacer, which is attached to the single chain insulin analog, wherein the spacer comprises the leaving group. In specific aspects, the long chain alkane comprises an amine, hydroxyl, or thiol group. In certain embodiments, the spacer comprising the leaving group can be any spacer discussed herein, e.g., amino acids, dipeptides, tripeptides, hydrophilic bifunctional spacers and hydrophobic bifunctional spacers further comprising a suitable leaving group.

When a long chain alkane is alkylated by the single chain insulin analog or the spacer, the long chain alkane may be of any size and can comprise any length of carbon chain. The long chain alkane can be linear or branched. In certain aspects, the long chain alkane is a $C_4$ to $C_{30}$ alkane. For example, the long chain alkane can be any of a $C_4$ alkane, $C_6$ alkane, $C_8$ alkane, $C_{10}$ alkane, $C_{12}$ alkane, $C_{14}$ alkane, $C_{16}$ alkane, $C_{18}$ alkane, $C_{20}$ alkane, $C_{22}$ alkane, $C_{24}$ alkane, $C_{26}$ alkane, $C_{28}$ alkane, or a $C_{30}$ alkane. In some embodiments the long chain alkane comprises a $C_8$ to $C_{20}$ alkane, e.g., a $C_{14}$ alkane, $C_{16}$ alkane, or a $C_{18}$ alkane.

Also, in some embodiments alkylation can occur between the single chain insulin analog and a cholesterol moiety. For example, the hydroxyl group of cholesterol can displace a leaving group on the long chain alkane to form a cholesterol-insulin peptide product. The alkylated single chain insulin analogs described herein can be further modified to comprise a hydrophilic moiety. In some specific embodiments the hydrophilic moiety can comprise a polyethylene glycol (PEG) chain. The incorporation of a hydrophilic moiety can be accomplished through any suitable means, such as any of the methods described herein. In some embodiments the single chain insulin analog can comprise an amino acid selected from Cys, Lys, Orn, homo-Cys, or Ac-Phe, wherein the side chain of the amino acid is covalently bonded to a hydrophilic moiety (e.g., PEG). In some embodiments the alkyl group is attached to position A14, A15, B1 (for insulin based B chains), B2 (for IGF-1 based B chains), B10, B22, B28 or B29 (according to the amino acid numbering of the A or B chain of native insulin), optionally via a spacer comprising Cys, Lys, Orn, homo-Cys, or Ac-Phe, and optionally further comprising a hydrophilic moiety linked to the side chain of another amino acid. Alternatively, the alkylated single chain insulin analog can comprise a spacer, wherein the spacer is both alkylated and modified to comprise the hydrophilic moiety. Nonlimiting examples of suitable spacers include a spacer comprising one or more amino acids selected from the group consisting of Cys, Lys, Orn, homo-Cys, and Ac-Phe.

Conjugates

In some embodiments, the single chain insulin analogs described herein are glycosylated, amidated, carboxylated, phosphorylated, esterified, N-acylated, cyclized via, e.g., a disulfide bridge, or converted into a salt (e.g., an acid addition salt, a basic addition salt), and/or optionally dimerized, multimerized, or polymerized, or conjugated. The present disclosure also encompasses conjugates in which the single chain insulin analog is linked to a heterologous moiety. The conjugation between the single chain insulin analog and the heterologous moiety can be through covalent bonding, non-covalent bonding (e.g. electrostatic interactions, hydrogen bonds, van der Waals interactions, salt bridges, hydrophobic interactions, and the like), or both types of bonding. A variety of non-covalent coupling systems may be used, including biotin-avidin, ligand/receptor, enzyme/substrate, nucleic acid/nucleic acid binding protein, lipid/lipid binding protein, cellular adhesion molecule partners; or any binding partners or fragments thereof which have affinity for each other. In some aspects, the covalent bonds are peptide bonds. The conjugation of the single chain insulin analog to the heterologous moiety may be indirect or direct conjugation, the former of which may involve a linker or spacer. Suitable linkers and spacers are known in the art and include, but not limited to, any of the linkers or spacers described.

As used herein, the term "heterologous moiety" is synonymous with the term "conjugate moiety" and refers to any molecule (chemical or biochemical, naturally-occurring or non-coded) which is different from the single chain insulin analog to which it is attached. Exemplary conjugate moieties that can be linked to the single chain insulin analog include but are not limited to a heterologous peptide or polypeptide (including for example, a plasma protein), a targeting agent, an immunoglobulin or portion thereof (e.g., variable region, CDR, or Fc region), a diagnostic label such as a radioisotope, fluorophore or enzymatic label, a polymer including water soluble polymers, or other therapeutic or diagnostic agents. In some embodiments a conjugate is provided comprising the single chain insulin analog and a plasma protein, wherein the plasma protein is selected from the group consisting of albumin, transferin, fibrinogen and globulins. In some embodiments the plasma protein moiety of the conjugate is albumin or transferin. In one embodiment the heterologous moiety is albumin, including for example, albumins such as human serum albumin (HSA) and recombinant human albumin (rHA). The conjugate in some embodiments comprises the single chain insulin analog and one or more of a polypeptide, a nucleic acid molecule, an antibody or fragment thereof, a polymer, a the single chain insulin analoguantum dot, a small molecule, a toxin, a diagnostic agent, a carbohydrate, an amino acid.

Polymer Heterologous Moiety

In some embodiments, the heterologous moiety conjugated to the single chain insulin analog is a polymer. In some embodiments, the polymer is selected from the group consisting of: polyamides, polycarbonates, polyalkylenes and derivatives thereof including, polyalkylene glycols, polyalkylene oxides, polyalkylene terepthalates, polymers of acrylic and methacrylic esters, including poly(methyl methacrylate), poly(ethyl methacrylate), poly(butylmethacrylate), poly(isobutyl methacrylate), poly(hexylmethacrylate), poly(isodecyl methacrylate), poly(lauryl methacrylate), poly(phenyl methacrylate), poly(methyl acrylate), poly(isopropyl acrylate), poly(isobutyl acrylate), and poly(octadecyl acrylate), polyvinyl polymers including polyvinyl alcohols, polyvinyl ethers, polyvinyl esters, polyvinyl halides, poly(vinyl acetate), and polyvinylpyrrolidone, polyglycolides, polysiloxanes, polyurethanes and co-polymers thereof, celluloses including alkyl cellulose, hydroxyalkyl celluloses, cellulose ethers, cellulose esters, nitro celluloses, methyl cellulose, ethyl cellulose, hydroxypropyl cellulose, hydroxy-propyl methyl cellulose, hydroxybutyl methyl cellulose, cellulose acetate, cellulose propionate, cellulose acetate butyrate, cellulose acetate phthalate, carboxylethyl cellulose, cellulose triacetate, and cellulose sulphate sodium salt, polypropylene, polyethylenes including poly(ethylene glycol), poly(ethylene oxide), and poly(ethylene terephthalate), and polystyrene.

In some aspects, the polymer is a biodegradable polymer, including a synthetic biodegradable polymer (e.g., polymers of lactic acid and glycolic acid, polyanhydrides, poly(ortho) esters, polyurethanes, poly(butic acid), poly(valeric acid), and poly(lactide-cocaprolactone)), and a natural biodegradable polymer (e.g., alginate and other polysaccharides including dextran and cellulose, collagen, chemical derivatives thereof (substitutions, additions of chemical groups, for example, alkyl, alkylene, hydroxylations, oxidations, and other modifications routinely made by those skilled in the art), albumin and other hydrophilic proteins (e.g., zein and other prolamines and hydrophobic proteins)), as well as any copolymer or mixture thereof. In general, these materials degrade either by enzymatic hydrolysis or exposure to water in vivo, by surface or bulk erosion.

In some aspects, the polymer is a bioadhesive polymer, such as a bioerodible hydrogel described by H. S. Sawhney, C. P. Pathak and J. A. Hubbell in Macromolecules, 1993, 26, 581-587, the teachings of which are incorporated herein, polyhyaluronic acids, casein, gelatin, glutin, polyanhydrides, polyacrylic acid, alginate, chitosan, poly(methyl methacrylates), poly(ethyl methacrylates), poly(butylmethacrylate), poly(isobutyl methacrylate), poly(hexylmethacrylate), poly(isodecyl methacrylate), poly(lauryl methacrylate), poly(phenyl methacrylate), poly(methyl acrylate), poly(isopropyl acrylate), poly(isobutyl acrylate), and poly(octadecyl acrylate).

In some embodiments, the polymer is a water-soluble polymer or a hydrophilic polymer. Hydrophilic polymers are further described herein under "Hydrophilic Heterologous Moieties." Suitable water-soluble polymers are known in the art and include, for example, polyvinylpyrrolidone, hydroxypropyl cellulose (HPC; Klucel), hydroxypropyl methylcellulose (HPMC; Methocel), nitrocellulose, hydroxypropyl ethylcellulose, hydroxypropyl butylcellulose, hydroxypropyl pentylcellulose, methyl cellulose, ethylcellulose (Ethocel), hydroxyethyl cellulose, various alkyl celluloses and hydroxyalkyl celluloses, various cellulose ethers, cellulose acetate, carboxymethyl cellulose, sodium carboxymethyl cellulose, calcium carboxymethyl cellulose, vinyl acetate/crotonic acid copolymers, poly-hydroxyalkyl methacrylate, hydroxymethyl methacrylate, methacrylic acid copolymers, polymethacrylic acid, polymethylmethacrylate, maleic anhydride/methyl vinyl ether copolymers, poly vinyl alcohol, sodium and calcium polyacrylic acid, polyacrylic acid, acidic carboxy polymers, carboxypolymethylene, carboxyvinyl polymers, polyoxyethylene polyoxypropylene copolymer, polymethylvinylether co-maleic anhydride, carboxymethylamide, potassium methacrylate divinylbenzene co-polymer, polyoxyethyleneglycols, polyethylene glycol, and derivatives, salts, and combinations thereof.

In one embodiment, the polymer is a polyalkylene glycol, including, for example, polyethylene glycol (PEG). In some embodiments, the heterologous moiety is a carbohydrate. In some embodiments, the carbohydrate is a monosaccharide (e.g., glucose, galactose, fructose), a disaccharide (e.g., sucrose, lactose, maltose), an oligosaccharide (e.g., raffinose, stachyose), a polysaccharide (a starch, amylase, amylopectin, cellulose, chitin, callose, laminarin, xylan, mannan, fucoidan, galactomannan.

In some embodiments, the heterologous moiety is a lipid. The lipid, in some embodiments, is a fatty acid, eicosanoid, prostaglandin, leukotriene, thromboxane, N-acyl ethanolamine), glycerolipid (e.g., mono-, di-, tri-substituted glycerols), glycerophospholipid (e.g., phosphatidylcholine, phosphatidylinositol, phosphatidylethanolamine, phosphatidylserine), sphingolipid (e.g., sphingosine, ceramide), sterol lipid (e.g., steroid, cholesterol), prenol lipid, saccharolipid, or a polyketide, oil, wax, cholesterol, sterol, fat-soluble vitamin, monoglyceride, diglyceride, triglyceride, a phospholipid.

Fc Fusion Heterologous Moiety

As noted above, in some embodiments the single chain insulin analog is conjugated, e.g., fused to an immunoglobulin or portion thereof (e.g. variable region, CDR, or Fc region). Known types of immunoglobulins (Ig) include IgG, IgA, IgE, IgD or IgM. The Fc region is a C-terminal region of an Ig heavy chain, which is responsible for binding to Fc receptors that carry out activities such as recycling (which results in prolonged half-life), antibody dependent cell-mediated cytotoxicity (ADCC), and complement dependent cytotoxicity (CDC).

For example, according to some definitions the human IgG heavy chain Fc region stretches from Cys226 to the C-terminus of the heavy chain. The "hinge region" generally extends from Glu216 to Pro230 of human IgG1 (hinge regions of other IgG isotypes may be aligned with the IgG1 sequence by aligning the cysteines involved in cysteine bonding). The Fc region of an IgG includes two constant domains, CH2 and CH3. The CH2 domain of a human IgG Fc region usually extends from amino acids 231 to amino acid 341. The CH3 domain of a human IgG Fc region usually extends from amino acids 342 to 447. References made to amino acid numbering of immunoglobulins or immunoglobulin fragments, or regions, are all based on Kabat et al. 1991, Sequences of Proteins of Immunological Interest, U.S. Department of Public Health, Bethesda, Md. In a related embodiment, the Fc region may comprise one or more native or modified constant regions from an immunoglobulin heavy chain, other than CH1 for example, the CH2 and CH3 regions of IgG and IgA, or the CH3 and CH4 regions of IgE.

Suitable conjugate moieties include portions of immunoglobulin sequence that include the FcRn binding site. FcRn, a salvage receptor, is responsible for recycling immunoglobulins and returning them to circulation in blood. The region of the Fc portion of IgG that binds to the FcRn receptor has been described based on X-ray crystallography (Burmeister et al. 1994, Nature 372:379). The major contact area of the Fc with the FcRn is near the junction of the CH2 and CH3 domains. Fc-FcRn contacts are all within a single Ig heavy chain. The major contact sites include amino acid residues 248, 250-257, 272, 285, 288, 290-291, 308-311, and 314 of the CH2 domain and amino acid residues 385-387, 428, and 433-436 of the CH3 domain.

Some conjugate moieties may or may not include FcγR binding site(s). FcγR are responsible for ADCC and CDC. Examples of positions within the Fc region that make a direct contact with FcγR are amino acids 234-239 (lower hinge region), amino acids 265-269 (B/C loop), amino acids 297-299 (C'/E loop), and amino acids 327-332 (F/G) loop (Sondermann et al., Nature 406: 267-273, 2000). The lower hinge region of IgE has also been implicated in the FcRI binding (Henry, et al., Biochemistry 36, 15568-15578, 1997). Residues involved in IgA receptor binding are described in Lewis et al., (J. Immunol. 175:6694-701, 2005). Amino acid residues involved in IgE receptor binding are described in Sayers et al. (J Biol. Chem. 279(34):35320-5, 2004).

Amino acid modifications may be made to the Fc region of an immunoglobulin. Such variant Fc regions comprise at least one amino acid modification in the CH3 domain of the Fc region (residues 342-447) and/or at least one amino acid modification in the CH2 domain of the Fc region (residues 231-341). Mutations believed to impart an increased affinity for FcRn include T256A, T307A, E380A, and N434A (Shields et al. 2001, J. Biol. Chem. 276:6591). Other mutations may reduce binding of the Fc region to FcγRI, FcγRIIA, FcγRIIB, and/or FcγRIIIA without significantly reducing affinity for FcRn. For example, substitution of the Asn at position 297 of the Fc region with Ala or another amino acid removes a highly conserved N-glycosylation site and may result in reduced immunogenicity with concomitant prolonged half-life of the Fc region, as well as reduced binding to FcγRs (Routledge et al. 1995, Transplantation 60:847; Friend et al. 1999, Transplantation 68:1632; Shields et al. 1995, J. Biol. Chem. 276:6591). Amino acid modifications at positions 233-236 of IgG1 have been made that reduce binding to FcγRx (Ward and Ghetie 1995, Therapeutic Immunology 2:77 and Armour et al. 1999, Eur. J. Immunol. 29:2613). Some exemplary amino acid substitutions are described in U.S. Pat. Nos. 7,355,008 and 7,381,408, each incorporated by reference herein in its entirety.

Hydrophilic Heterologous Moiety

In some embodiments, the single chain insulin analog described herein is covalently bonded to a hydrophilic moiety. Hydrophilic moieties can be attached to the single chain insulin analog under any suitable conditions used to react a protein with an activated polymer molecule. Any means known in the art can be used, including via acylation, reductive alkylation, Michael addition, thiol alkylation or other chemoselective conjugation/ligation methods through a reactive group on the hydrophilic moiety (e.g., an aldehyde, amino, ester, thiol, α-haloacetyl, maleimido or hydrazino group) to a reactive group on the target compound (e.g., an aldehyde, amino, ester, thiol, α-haloacetyl, maleimido or hydrazino group). Activating groups which can be used to link the water soluble polymer to one or more proteins include without limitation sulfone, maleimide, sulfhydryl, thiol, triflate, tresylate, azidirine, oxirane, 5-pyridyl, and alpha-halogenated acyl group (e.g., alpha-iodo acetic acid, alpha-bromoacetic acid, alpha-chloroacetic acid). If attached to the peptide by reductive alkylation, the polymer selected should have a single reactive aldehyde so that the degree of polymerization is controlled. See, for example, Kinstler et al., Adv. Drug. Delivery Rev. 54: 477-485 (2002); Roberts et al., Adv. Drug Delivery Rev. 54: 459-476 (2002); and Zalipsky et al., Adv. Drug Delivery Rev. 16: 157-182 (1995). The hydrophilic moiety, e.g., polyethylene glycol chain, in accordance with some embodiments has a molecular weight selected from the range of about 500 to about 40,000 Daltons. In some embodiments the polyethylene glycol chain has a molecular weight selected from the range of about 500 to about 5,000 Daltons, or about 1,000 to about 5,000 Daltons. In another embodiment the hydrophilic moiety, e.g., polyethylene glycol chain, has a molecular weight of about 10,000 to about 20,000 Daltons. In yet other exemplary embodiments the hydrophilic moiety, e.g. polyethylene glycol chain, has a molecular weight of about 20,000 to about 40,000 Daltons. Linear or branched hydrophilic polymers are contemplated. Resulting preparations of conjugates may be essentially monodisperse or polydisperse, and may have about 0.5, 0.7, 1, 1.2, 1.5 or 2 polymer moieties per peptide.

In some embodiments, the native amino acid of the peptide is substituted with an amino acid having a side chain suitable for crosslinking with hydrophilic moieties, to facilitate linkage of the hydrophilic moiety to the peptide. Exemplary amino acids include Cys, Lys, Orn, homo-Cys, or acetyl phenylalanine (Ac-Phe). In other embodiments, an amino acid modified to comprise a hydrophilic group is added to the peptide at the N-terminus or C-terminus. In some embodiments, the peptide of the conjugate is conjugated to a hydrophilic moiety, e.g. PEG, via covalent linkage between a side chain of an amino acid of the peptide and the hydrophilic moiety.

rPEG Heterologous Moiety

In some embodiments, the conjugate comprises a single chain insulin analog fused to an accessory peptide which is capable of forming an extended conformation similar to chemical PEG (e.g., a recombinant PEG (rPEG) molecule), such as those described in International Patent Application Publication No. WO2009/023270 and U.S. Patent Application Publication No. US2008/0286808. The rPEG molecule is not polyethylene glycol. The rPEG molecule in some aspects is a polypeptide comprising one or more of glycine, serine, glutamic acid, aspartic acid, alanine, or proline. In some aspects, the rPEG is a homopolymer, e.g., poly-glycine, poly-serine, poly-glutamic acid, poly-aspartic acid, poly-alanine, or poly-proline. In other embodiments, the rPEG comprises two types of amino acids repeated, e.g., poly(Gly-Ser), poly(Gly-Glu), poly(Gly-Ala), poly(Gly-Asp), poly(Gly-Pro), poly(Ser-Glu), etc. In some aspects, the rPEG comprises three different types of amino acids, e.g., poly(Gly-Ser-Glu). In specific aspects, the rPEG increases the half-life of the single chain insulin analog. In some aspects, the rPEG comprises a net positive or net negative charge. The rPEG in some aspects lacks secondary structure. In some embodiments, the rPEG is greater than or equal to 10 amino acids in length and in some embodiments is about 40 to about 50 amino acids in length. The accessory peptide in some aspects is fused to the N- or C-terminus of the peptide of the invention through a peptide bond or a proteinase cleavage site. The rPEG in some aspects comprises an affinity tag or is linked to a PEG that is greater than 5 kDa. In some embodiments, the rPEG confers the conjugate of the invention with an increased hydrodynamic radius, serum half-life, protease resistance, or solubility and in some aspects confers the conjugate with decreased immunogenicity.

The conjugate moieties can be linked to the single chain insulin analog via direct covalent linkage by reacting targeted amino acid residues of the peptide with an organic derivatizing agent that is capable of reacting with selected side chains or the N- or C-terminal residues of these targeted amino acids. Reactive groups on the peptide or conjugate moiety include, e.g., an aldehyde, amino, ester, thiol, α-haloacetyl, maleimido or hydrazino group. Derivatizing agents include, for example, maleimidobenzoyl sulfosuccinimide ester (conjugation through cysteine residues), N-hydroxysuccinimide (through lysine residues), glutaraldehyde, succinic anhydride or other agents known in the art. Alternatively, the conjugate moieties can be linked to the peptide indirectly through intermediate carriers, such as polysaccharide or polypeptide carriers. Examples of polysaccharide carriers include aminodextran. Examples of suitable polypeptide carriers include polylysine, polyglutamic acid, polyaspartic acid, co-polymers thereof, and mixed polymers of these amino acids and others, e.g., serines, to confer desirable solubility properties on the resultant loaded carrier.

Multimers

The single chain insulin analog may be part of a dimer, trimer or higher order multimer comprising at least two, three, or more peptides bound via a linker, wherein at least one or both peptides is a single chain insulin analog. In one embodiment a single chain insulin analog is linked to either the A chain or the B chain of a second insulin polpeptide that is either a heteroduplex comprising the A and B chain or a second single chain insulin analog. The dimer may be a homodimer or heterodimer In some embodiments, the linker is selected from the group consisting of a bifunctional thiol crosslinker and a bi-functional amine crosslinker. In certain embodiments, the linker is PEG, e.g., a 5 kDa PEG, 20 kDa PEG. In some embodiments, the linker is a disulfide bond. For example, each monomer of the dimer may comprise a Cys residue (e.g., a terminal or internally positioned Cys) and the sulfur atom of each Cys residue participates in the formation of the disulfide bond. In some aspects of the invention, the monomers are connected via terminal amino acids (e.g., N-terminal or C-terminal), via internal amino acids, or via a terminal amino acid of at least one monomer and an internal amino acid of at least one other monomer. In specific aspects, the monomers are not connected via an N-terminal amino acid. In some aspects, the monomers of the multimer are attached together in a "tail-to-tail" orientation in which the C-terminal amino acids of each monomer are attached together. In one embodiment the dimer comprises two single chain insulin analogs wherein the two insulin analogs are linked to one another via the amino acid side chains of an amino acid present in the linking moiety of each single chain insulin analog. A conjugate moiety may be covalently linked to any of the single chain insulin analogs described herein, including a dimer, trimer or higher order multimer.

In accordance with one embodiment a multimer is provided that comprises an IGF YL B chain analog disclosed herein (including prodrug and depot derivatives thereof). The multimer (e.g., a dimer) may be a homodimer or heterodimer, comprising peptides selected from the group consisting of native insulin, native IGF-1, native IGF-II, an insulin analog peptide and IGF analog peptides. In some embodiments, the linker is selected from the group consisting of a bifunctional thiol crosslinker and a bi-functional amine crosslinker. In certain embodiments, the linker is PEG, e.g., a 5 kDa PEG, 20 kDa PEG. In some embodiments, the linker is a disulfide bond.

Controlled Release Formulations

Alternatively, the single chain insulin analogs described herein can be modified into a depot form, such that the manner in which the conjugate of the present disclosure is released into the body to which it is administered is controlled with respect to time and location within the body (see, for example, U.S. Pat. No. 4,450,150). Depot forms of the conjugates of the present disclosures can be, for example, an implantable composition comprising the conjugate of the present disclosure and a porous or non-porous material, such as a polymer, wherein the conjugate of the present disclosures is encapsulated by or diffused throughout the material and/or degradation of the non-porous material. The depot is then implanted into the desired location within the body and the conjugate of the present disclosures are released from the implant at a predetermined rate.

Alternatively, a large depot polymer can be linked to a self cleaving dipeptide element that is covalently bound to the single chain insulin analog as described herein. In this embodiment, the depot polymer effectively sequesters the single chain insulin analog at its site of administration until it is subsequently cleaved from the single chain analog via a non-enzymatic reaction at a predetermined rate. Depot formulations of insulin analogs using a self cleaving dipeptide have been described in PCT/US2009/068713, the disclosure of which is incorporated herein. In one embodiment a single chain insulin analog is provided comprising a dipeptide prodrug element wherein the dipeptide prodrug element is linked to a large polymer such as PEG or dextran. In one embodiment a self cleaving dipeptide element comprising a large depot polymer (including for example, PEG) is linked to the side chain of an amino acid of the linking moiety, including for example, the amino acid at position C8 of the linking moiety.

Pharmaceutical compositions can be prepared that comprise the single chain analogs and are formulated to have a desired in vivo release profile. In some aspects, the pharmaceutical composition is an immediate release, controlled release, sustained release, extended release, delayed release, or bi-phasic release formulation. Methods of formulating peptides or conjugates for controlled release are known in the art. See, for example, J Pharm 374: 46-52 (2009) and International Patent Application Publication Nos. WO 2008/130158, WO2004/033036; WO2000/032218; and WO 1999/040942. The instant compositions may further comprise, for example, micelles or liposomes, or some other encapsulated form, or may be administered in an extended release form to provide a prolonged storage and/or delivery effect. The disclosed pharmaceutical formulations may be administered according to any regime including, for example, daily (1 time per day, 2 times per day, 3 times per day, 4 times per day, 5 times per day, 6 times per day), every two days, every three days, every four days, every five days, every six days, weekly, bi-weekly, every three weeks, monthly, or bi-monthly.

Prodrug Derivatives of Single Chain Insulin Analogs

The present disclosure also encompasses prodrug analogs of the single chain insulin analog peptides disclosed herein. Advantageously, the prodrug formulations improve the therapeutic index of the underlying peptide and delay onset of action and enhance the half life of the single chain insulin analog peptide. The disclosed prodrug chemistry can be chemically conjugated to active site amines to form amides that revert to the parent amine upon diketopiperazine formation and release of the prodrug element (see International patent application PCT/US2009/068713, the disclosure of which is expressly incorporated herein). This novel biologically friendly prodrug chemistry spontaneously degrades under physiological conditions (e.g. pH of about 7, at 37° C. in an aqueous environment) and is not reliant on enzymatic degradation. The duration of the prodrug analog is determined by the selection of the dipeptide prodrug sequence, and thus allows for flexibility in prodrug formulation.

In one embodiment a prodrug is provided having a non-enzymatic activation half time (t½) of between 1-100 hrs under physiological conditions. Physiological conditions as disclosed herein are intended to include a temperature of about 35 to 40° C. and a pH of about 7.0 to about 7.4 and more typically include a pH of 7.2 to 7.4 and a temperature of 36 to 38° C. in an aqueous environment. In one embodiment a dipeptide, capable of undergoing diketopiperazine formation under physiological conditions, is covalently linked through an amide or ester linkage to the single chain insulin analog (see International applications WO 2009/099763 and PCT/US2009/068713 the disclosures of which are incorporated herein).

Advantageously, the rate of cleavage, and thus activation of the prodrug, depends on the structure and stereochemistry of the dipeptide pro-moiety and also on the strength of the nucleophile. The prodrugs disclosed herein will ultimately be chemically converted to structures that can be recognized by the insulin/IGF receptor, wherein the speed of this chemical conversion will determine the time of onset and duration of in vivo biological action. The prodrug chemistry disclosed in this application relies upon an intramolecular chemical reaction that is not dependent upon additional chemical additives, or enzymes. The speed of conversion is controlled by the chemical nature of the dipeptide substituent and its cleavage under physiological conditions. Since physiological pH and temperature are tightly regulated within a highly defined range, the speed of conversion from prodrug to drug will exhibit high intra and interpatient reproducibility. In one embodiment a prodrug derivative of the single chain analog is provided wherein the single chain insulin analog comprises a linking moiety of 8-17 amino acids wherein one of the amino acids of the linking moiety is pegylated. Alternatively, or in addition to the pegylation of the amino acid of the linking moiety, one of the two amino acids of the dipeptide prodrug element can be pegylated. Alternatively, or in any combination with the above mentioned pegylated sites, the single chain insulin prodrug derivative can be pegylated at a position selected from the group consisting of A9, A14 and A15 of the A chain, or positions B1 (for insulin based B chains), B2 (for IGF-1 based B chains), B10, B22, B28 or B29 of the B chain. In one embodiment the insulin prodrug is pegylated at the N-terminal alpha amine of the B chain (e.g. at position B1 for insulin based B chain or position B2 for IGF-1 based B chain).

As disclosed herein prodrugs are provided wherein the single chain insulin analog peptides have extended half lives of at least 1 hour, and more typically greater than 20 hours but less than 100 hours, and are converted to the active form at physiological conditions through a non-enzymatic reaction driven by inherent chemical instability. In one embodiment the a non-enzymatic activation t½ time of the prodrug is between 1-100 hrs, and more typically between 12 and 72 hours, and in one embodiment the t½ is between 24-48 hrs as measured by incubating the prodrug in a phosphate buffer solution (e.g., PBS) at 37° C. and pH of 7.2. In one embodiment the half life of the prodrugs is about 1, 8, 12, 20, 24, 48 or 72 hours. In one embodiment the half life of the prodrugs is about 100 hours or greater including half lives of up to about 168, 336, 504, 672 or 720 hours, and are converted to the active form at physiological conditions through a non-enzymatic reaction driven by inherent chemical instability. The half lives of the various prodrugs are calculated by using the formula $t_{1/2}=0.693/k$, where 'k' is the first order rate constant for the degradation of the prodrug. In one embodiment, activation of the prodrug occurs after cleavage of an amide bond linked dipeptide, and formation of a diketopiperazine or diketomorpholine, and the active single chain insulin analog peptide.

In another embodiment, the dipeptide prodrug element is covalently bound to the single chain insulin analog peptide via an amide linkage, and the dipeptide further comprises a depot polymer linked to dipeptide. In one embodiment two or more depot polymers are linked to a single dipeptide element. In one embodiment the depot polymer is linked to the side chain of one of the amino acids comprising the dipeptide prodrug element. The depot polymer is selected to be biocompatible and of sufficient size that the single chain insulin analog, modified by covalent attachment of the dipeptide, remains sequestered at an injection site and/or incapable of interacting with its corresponding receptor upon administration to a patient. Subsequent cleavage of the dipeptide releases the single chain insulin analog to interact with its intended target. The depot bearing dipeptide element can be linked to the single chain insulin analog via an amide bond through any convenient amine group of the single chain insulin analog, including an N-terminal amine or an amine bearing side chain of an internal natural or synthetic amino acid of the single chain insulin analog. In one embodiment the depot bearing dipeptide element is linked to the amino group of a 4-amino phenylalanine present at position A19 of the single chain analog.

In accordance with one embodiment the depot polymer is selected from biocompatible polymers known to those skilled in the art. The depot polymers typically have a size selected from a range of about 20,000 to 120,000 Daltons. In one embodiment the depot polymer has a size selected from a range of about 40,000 to 100,000 or about 40,000 to 80,000 Daltons. In one embodiment the depot polymer has a size of about 40,000, 50,000, 60,000, 70,000 or 80,000 Daltons. Suitable depot polymers include but are not limited to dextrans, polylactides, polyglycolides, caprolactone-based polymers, poly(caprolactone), polyanhydrides, polyamines, polyesteramides, polyorthoesters, polydioxanones, polyacetals, polyketals, polycarbonates, polyphosphoesters, polyesters, polybutylene terephthalate, polyorthocarbonates, polyphosphazenes, succinates, poly(malic acid), poly(amino acids), polyvinylpyrrolidone, polyethylene glycol, polyhydroxycellulose, polysaccharides, chitin, chitosan, hyaluronic acid, and copolymers, terpolymers and mixtures thereof, and biodegradable polymers and their copolymers including caprolactone-based polymers, polycaprolactones and copolymers which include polybutylene terephthalate. In one embodiment the depot polymer is selected from the group consisting of polyethylene glycol, dextran, polylactic acid, polyglycolic acid and a copolymer of lactic acid and glycolic acid, and in one specific embodiment the depot polymer is polyethylene glycol. In one embodiment the depot polymer is polyethylene glycol and the combined molecular weight of depot polymer(s) linked to the dipeptide element is about 40,000 to 80,000 Daltons.

Specific dipeptides composed of natural or synthetic amino acids have been identified that facilitate intramolecular decomposition under physiological conditions to release the active single chain insulin analog. The dipeptide can be linked (via an amide bond) to an amino group present on the single chain insulin analog, or an amino group introduced into the single chain insulin analog by modification of the peptide sequence. In one embodiment the dipeptide structure is selected to resist cleavage by peptidases present in mammalian sera, including for example dipeptidyl peptidase IV (DPP-IV). Accordingly, in one embodiment the rate of cleavage of the dipeptide prodrug element from the bioactive peptide is not substantially enhanced (e.g., greater than 2×) when the reaction is conducted using physiological conditions in the presence of serum proteases relative to conducting the reaction in the absence of the proteases. Thus the cleavage half-life of the dipeptide prodrug element from the single chain insulin analog (in PBS under physiological conditions) is not more than two, three, four or five fold the cleavage half-life of the dipeptide prodrug element from the single chain insulin analog in a solution comprising a DPP-IV protease. In one embodiment the solution comprising a DPP-IV protease is serum, more particularly mammalian serum, including human serum.

In accordance with one embodiment the dipeptide prodrug element comprises the structure U-B, wherein U is an amino acid or a hydroxyl acid and B is an N-alkylated amino acid. The structure of U-B is selected, in one embodiment, wherein chemical cleavage of U-B from the single chain insulin analog is at least about 90% complete within about 1 to about 720 hours in PBS under physiological conditions. In one embodiment the chemical cleavage half-life ($t_{1/2}$) of U-B from the single chain insulin analog peptide is at least about 1 hour to about 1 week in PBS under physiological conditions. In one embodiment U, B, or the amino acid of the single chain insulin analog to which U-B is linked is a non-coded amino acid. In some embodiments U and/or B is an amino acid in the D stereoisomer configuration. In some exemplary embodiments, U is an amino acid in the D stereoisomer configuration and B is an amino acid in the L stereoisomer configuration. In some exemplary embodiments, U is an amino acid in the L stereoisomer configuration and B is an amino acid in the D stereoisomer configuration. In some exemplary embodiments, U is an amino acid in the D stereoisomer configuration and B is an amino acid in the D stereoisomer configuration. In one embodiment B is an N-alkylated amino acid but is not proline. In one embodiment the N-alkylated group of amino acid B is a $C_1$-$C_{18}$ alkyl, and in one embodiment the N-alkylated group is $C_1$-$C_6$ alkyl. In one embodiment U is an amino acid having a disubstitution at the alpha carbon.

In one embodiment one or more dipeptide elements are linked to single chain insulin analog through an amide bond formed through one or more amino groups selected from the N-terminal amino group of the B chain, or the side chain amino group of an amino acid present in the single chain insulin analog. In one embodiment the single chain insulin analog comprises two dipeptide elements, wherein the dipeptide elements are optionally pegylated, alkylated, acylated or linked to a depot polymer. In accordance with one embodiment the dipeptide extension is covalently linked to a single chain insulin analog through the side chain amine of a lysine residue that resides at or near the active site. In one embodiment the dipeptide extension is attached through a synthetic amino acid or a modified amino acid, wherein the synthetic amino acid or modified amino acid exhibits a functional group suitable for covalent attachment of the dipeptide extension (e.g., the aromatic amine of an amino-phenylalanine). In accordance with one embodiment one or more dipeptide elements are linked to the single chain insulin analog at an amino group selected from the N-terminal amino group of the B chain, or the side chain amino group of an aromatic amine of a 4-amino-phenylalanine residue present at a position corresponding to position A19, B16 or B25 of native insulin.

The dipeptide prodrug element is designed to spontaneously cleave its amide linkage to the insulin analog under physiological conditions and in the absence of enzymatic activity. In one embodiment the N-terminal amino acid of the dipeptide prodrug element comprises a C-alkylated amino acid (e.g. amino isobutyric acid). In one embodiment the C-terminal amino acid of the dipeptide prodrug element comprises an N-alkylated amino acid (e.g., proline or N-methyl glycine). In one embodiment the dipeptide comprises the sequence of an N-terminal C-alkylated amino acid followed by an N-alkylated amino acid.

Figure 3:
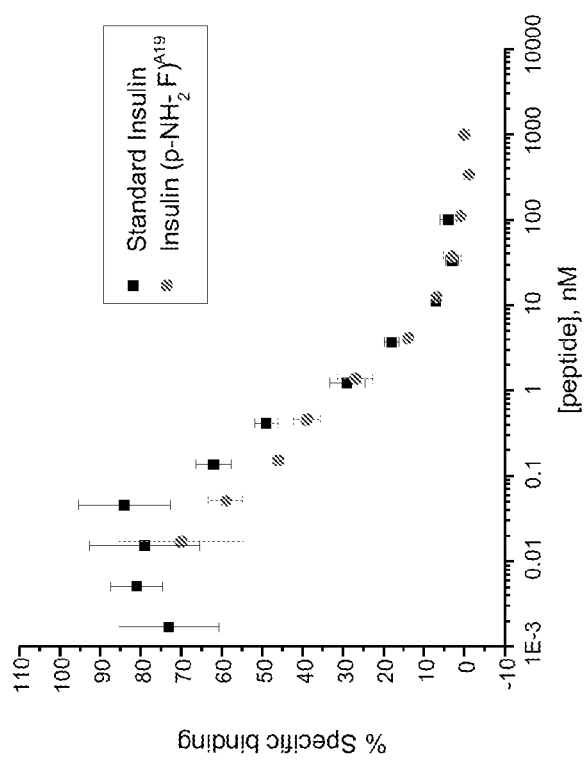
FIG. 3 is a graph comparing relative insulin receptor binding of native insulin and the A19 insulin analog (Insulin(p-$NH_2$—F)$^{19}$). As indicated by the data presented in the graph, the two molecules have similar binding activities.

Applicants have discovered that the selective insertion of a 4-amino phenylalanine amino acid moiety for the native tyrosine at position 19 of the A chain can be accommodated without loss in potency of the insulin peptide (see FIG. 3). Subsequent chemical amidation of this active site amino group with the dipeptide prodrug element disclosed herein dramatically lessens insulin receptor binding activity and thus provides a suitable prodrug of insulin (see FIG. 7-12, data provided for the IGF1Y$^{16}$L$^{17}$ (p-NH$_2$—F)$^{A19}$ analog which has been demonstrated to have comparable activity as insulin (p-NH$_2$—F)$^{A19}$, see FIG. 4). Applicants have discovered that a similar modification can be made to the IGF$^{B16B17}$ analog peptides to provide a suitable attachment site for prodrug chemistry. Accordingly, in one embodiment the dipeptide prodrug element is linked to the aromatic ring of an A19 4-aminophenylalanine of an insulin (p-NH$_2$—F)$^{A19}$ or IGF$^{B16B17}$ single chain insulin analog peptide via an amide bond, wherein the C-terminal amino acid of the dipeptide comprises an N-alkylated amino acid and the N-terminal amino acid of the dipeptide is any amino acid.

The dipeptide prodrug moiety can also be attached to additional sites of an insulin (p-NH$_2$—F)$^{A19}$ or IGF$^{B16B17}$ single chain insulin analog peptide to prepare insulin (p-NH$_2$—F)$^{A19}$ or IGF$^{B16B17}$ single chain insulin analog prodrug derivatives. In accordance with one embodiment an IGF$^{B16B17}$ single chain insulin analog prodrug derivative is provided comprising an IGF$^{B16B17}$ B chain with a dipeptide prodrug element linked via an amide bond to the N-terminal amino group of the B chain, or the side chain amino group of an aromatic amine of a 4-amino-phenylalanine residue present at a position corresponding to A19, B16 or B25 of native insulin or present in the linking moiety. The IGF$^{B16B17}$ single chain insulin analog prodrug derivative may comprise a native insulin A chain or a native IGF-1 A chain or any analogs thereof disclosed herein. In one embodiment the dipeptide comprises an N-terminal C-alkylated amino acid followed by an N-alkylated amino acid. In accordance with one embodiment a single chain insulin analog prodrug derivative is provided wherein the A chain and B chain comprising the analog comprises the sequence of SEQ ID NO: 1 and SEQ ID NO: 2, respectively, or may comprise an analog of SEQ ID NO: 1 and/or SEQ ID NO: 2 wherein the analogs include substitution of the amino acid at position A19, B16 or B25 with a 4-amino phenylalanine and/or one or more amino acid substitutions at positions corresponding to positions A5, A8, A9, A10, A14, A15, A17, A18, A19 and A21, B1, B2, B3, B4, B5, B9, B10, B13, B14, B20, B22, B23, B26, B27, B28, B29 and B30 of native insulin, or deletions of any or all of corresponding positions B1-4 and B26-30, relative to native insulin. In one embodiment the dipeptide is linked to an N-terminal amino group of the B chain of the single chain insulin analog, wherein the C-terminal amino acid of the dipeptide comprises an N-alkylated amino acid and the N-terminal amino acid of the dipeptide is any amino acid, with the proviso that when the C-terminal amino acid of the dipeptide is proline, the N-terminal amino acid of the dipeptide comprises a C-alkylated amino acid.

In one embodiment the dipeptide prodrug element comprises the general structure of Formula X:

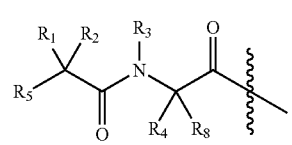

X wherein $R_1$, $R_2$, $R_4$ and $R_8$ are independently selected from the group consisting of H, $C_1$-$C_{18}$ alkyl, $C_2$-$C_{18}$ alkenyl, ($C_1$-$C_{18}$ alkyl)OH, ($C_1$-$C_{18}$ alkyl)SH, ($C_2$-$C_3$ alkyl)SCH$_3$, ($C_1$-$C_4$ alkyl)CONH$_2$, ($C_1$-$C_4$ alkyl)COOH, ($C_1$-$C_4$ alkyl)NH$_2$, ($C_1$-$C_4$ alkyl)NHC(NH$_2$$^+$)NH$_2$, ($C_0$-$C_4$ alkyl)($C_3$-$C_6$ cycloalkyl), ($C_0$-$C_4$ alkyl)($C_2$-$C_5$ heterocyclic), ($C_0$-$C_4$ alkyl)($C_6$-$C_{10}$ aryl)$R_7$, ($C_1$-$C_4$ alkyl)($C_3$-$C_9$ heteroaryl), and $C_1$-$C_{12}$ alkyl (W)$C_1$-$C_{12}$ alkyl, wherein W is a heteroatom selected from the group consisting of N, S and O, or $R_1$ and $R_2$ together with the atoms to which they are attached form a $C_3$-$C_{12}$ cycloalkyl or aryl; or $R_4$ and $R_8$ together with the atoms to which they are attached form a $C_3$-$C_6$ cycloalkyl;

$R_3$ is selected from the group consisting of $C_1$-$C_{18}$ alkyl, ($C_1$-$C_{18}$ alkyl)OH, ($C_1$-$C_{18}$ alkyl)NH$_2$, ($C_1$-$C_{18}$ alkyl)SH, ($C_0$-$C_4$ alkyl)($C_3$-$C_6$)cycloalkyl, ($C_0$-$C_4$ alkyl)($C_2$-$C_5$ heterocyclic), ($C_0$-$C_4$ alkyl)($C_6$-$C_{10}$ aryl)$R_7$, and ($C_1$-$C_4$ alkyl)($C_3$-$C_9$ heteroaryl) or $R_4$ and $R_3$ together with the atoms to which they are attached form a 4, 5 or 6 member heterocyclic ring;

$R_5$ is NHR$_6$ or OH;

$R_6$ is H, $C_1$-$C_8$ alkyl or $R_6$ and $R_2$ together with the atoms to which they are attached form a 4, 5 or 6 member heterocyclic ring; and $R_7$ is selected from the group consisting of H and OH. In one embodiment when the prodrug element is linked to the N-terminal amine of the single chain insulin analog and $R_4$ and $R_3$ together with the atoms to which they are attached form a 4, 5 or 6 member heterocyclic ring, then at least one of $R_1$ and $R_2$ are other than H.

In one embodiment the prodrug element of Formula X is provided wherein $R_1$ is selected from the group consisting of H and $C_1$-$C_8$ alkyl; and $R_2$, $R_8$ and $R_4$ are independently selected from the group consisting of H, $C_1$-$C_8$ alkyl, $C_2$-$C_8$ alkenyl, ($C_1$-$C_4$ alkyl)OH, ($C_1$-$C_4$ alkyl)SH, ($C_2$-$C_3$ alkyl)SCH$_3$, ($C_1$-$C_4$ alkyl)CONH$_2$, ($C_1$-$C_4$ alkyl)COOH, ($C_1$-$C_4$ alkyl)NH$_2$, ($C_1$-$C_4$ alkyl)NHC(NH$_2$$^+$) NH$_2$, ($C_0$-$C_4$ alkyl)($C_3$-$C_6$ cycloalkyl), ($C_0$-$C_4$ alkyl)($C_6$-$C_{10}$ aryl)$R_7$, and $CH_2$($C_5$-$C_9$ heteroaryl), or $R_1$ and $R_2$ together with the atoms to which they are attached form a $C_3$-$C_8$ cycloalkyl ring;

$R_3$ is selected from the group consisting of $C_1$-$C_8$ alkyl, ($C_1$-$C_4$ alkyl)OH, ($C_1$-$C_4$ alkyl)SH, ($C_1$-$C_4$ alkyl)$NH_2$, ($C_3$-$C_6$)cycloalkyl or $R_4$ and $R_3$ together with the atoms to which they are attached form a 5 or 6 member heterocyclic ring;

$R_5$ is $NHR_6$ or OH;

$R_6$ is H, or $R_6$ and $R_2$ together with the atoms to which they are attached form a 5 or 6 member heterocyclic ring; and $R_7$ is selected from the group consisting of H and OH and $R_8$ is H. In one embodiment $R_3$ is $C_1$-$C_8$ alkyl and $R_4$ is selected from the group consisting of H, $C_1$-$C_6$ alkyl, $CH_2OH$, ($C_0$-$C_4$ alkyl)($C_6$-$C_{10}$ aryl)$R_7$, and $CH_2$($C_5$-$C_9$ heteroaryl) or $R_4$ and $R_3$ together with the atoms to which they are attached form a 5 or 6 member heterocyclic ring. In a further embodiment $R_5$ is $NHR_6$ and $R_8$ is H.

In accordance with one embodiment the dipeptide element comprises a compound having the general structure of Formula X:

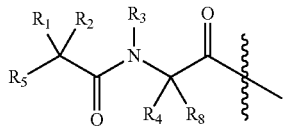

wherein $R_1$, $R_2$, $R_4$ and $R_8$ are independently selected from the group consisting of H, $C_1$-$C_{18}$ alkyl, $C_2$-$C_{18}$ alkenyl, ($C_1$-$C_{18}$ alkyl)OH, ($C_1$-$C_{18}$ alkyl)SH, ($C_2$-$C_3$ alkyl)$SCH_3$, ($C_1$-$C_4$ alkyl)$CONH_2$, ($C_1$-$C_4$ alkyl)COOH, ($C_1$-$C_4$ alkyl)$NH_2$, ($C_1$-$C_4$ alkyl)NHC($NH_2^+$)$NH_2$, ($C_0$-$C_4$ alkyl)($C_3$-$C_6$ cycloalkyl), ($C_0$-$C_4$ alkyl)($C_2$-$C_5$ heterocyclic), ($C_0$-$C_4$ alkyl)($C_6$-$C_{10}$ aryl)$R_7$, ($C_1$-$C_4$ alkyl)($C_3$-$C_9$ heteroaryl), and $C_1$-$C_{12}$ alkyl($W_1$)$C_1$-$C_{12}$ alkyl, wherein $W_1$ is a heteroatom selected from the group consisting of N, S and O, or $R_1$ and $R_2$ together with the atoms to which they are attached form a $C_3$-$C_{12}$ cycloalkyl; or $R_4$ and $R_8$ together with the atoms to which they are attached form a $C_3$-$C_6$ cycloalkyl;

$R_3$ is selected from the group consisting of $C_1$-$C_{18}$ alkyl, ($C_1$-$C_{18}$ alkyl)OH, ($C_1$-$C_{18}$ alkyl)$NH_2$, ($C_1$-$C_{18}$ alkyl)SH, ($C_0$-$C_4$ alkyl)($C_3$-$C_6$)cycloalkyl, ($C_0$-$C_4$ alkyl)($C_2$-$C_5$ heterocyclic), ($C_0$-$C_4$ alkyl)($C_6$-$C_{10}$ aryl)$R_7$, and ($C_1$-$C_4$ alkyl)($C_3$-$C_9$ heteroaryl) or $R_4$ and $R_3$ together with the atoms to which they are attached form a 4, 5 or 6 member heterocyclic ring;

$R_5$ is $NHR_6$ or OH;

$R_6$ is H, $C_1$-$C_8$ alkyl or $R_6$ and $R_1$ together with the atoms to which they are attached form a 4, 5 or 6 member heterocyclic ring; and $R_7$ is selected from the group consisting of H, OH, $C_1$-$C_{18}$ alkyl, $C_2$-$C_{18}$ alkenyl, ($C_0$-$C_4$ alkyl)$CONH_2$, ($C_0$-$C_4$ alkyl)COOH, ($C_0$-$C_4$ alkyl)$NH_2$, ($C_0$-$C_4$ alkyl)OH, and halo.

In another embodiment the dipeptide prodrug element comprises the general structure:

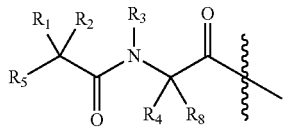

wherein $R_1$ and $R_8$ are independently H or $C_1$-$C_8$ alkyl;

$R_2$ and $R_4$ are independently selected from the group consisting of H, $C_1$-$C_8$ alkyl, $C_2$-$C_8$ alkenyl, ($C_1$-$C_4$ alkyl)OH, ($C_1$-$C_4$ alkyl)SH, ($C_2$-$C_3$ alkyl)$SCH_3$, ($C_1$-$C_4$ alkyl)$CONH_2$, ($C_1$-$C_4$ alkyl)COOH, ($C_1$-$C_4$ alkyl)$NH_2$, ($C_1$-$C_4$ alkyl)NHC($NH_2^+$)$NH_2$, ($C_0$-$C_4$ alkyl)($C_3$-$C_6$ cycloalkyl), ($C_0$-$C_4$ alkyl)($C_2$-$C_5$ heterocyclic), ($C_0$-$C_4$ alkyl)($C_6$-$C_{10}$ aryl)$R_7$, and $CH_2$($C_3$-$C_9$ heteroaryl), or $R_1$ and $R_2$ together with the atoms to which they are attached form a $C_3$-$C_{12}$ cycloalkyl;

$R_3$ is selected from the group consisting of $C_1$-$C_8$ alkyl, ($C_1$-$C_4$ alkyl)OH, ($C_1$-$C_4$ alkyl)$NH_2$, ($C_1$-$C_4$ alkyl)SH, ($C_3$-$C_6$)cycloalkyl or $R_4$ and $R_3$ together with the atoms to which they are attached form a 5 or 6 member heterocyclic ring;

$R_5$ is $NHR_6$ or OH;

$R_6$ is H, $C_1$-$C_8$ alkyl, or $R_6$ and $R_2$ together with the atoms to which they are attached form a 5 or 6 member heterocyclic ring; and $R_7$ is selected from the group consisting of H, OH, $C_1$-$C_{18}$ alkyl, $C_2$-$C_{18}$ alkenyl, ($C_0$-$C_4$ alkyl)$CONH_2$, ($C_0$-$C_4$ alkyl)COOH, ($C_0$-$C_4$ alkyl)$NH_2$, ($C_0$-$C_4$ alkyl)OH and halo, provided that when $R_4$ and $R_3$ together with the atoms to which they are attached form a 5 or 6 member heterocyclic ring, both $R_1$ and $R_2$ are not H. In one embodiment $R_7$ is H or OH. In one embodiment either the first amino acid and/or the second amino acid of the dipeptide prodrug element is an amino acid in the D stereoisomer configuration.

In a further embodiment the prodrug element of Formula X is provided wherein $R_1$ is selected from the group consisting of H and $C_1$-$C_8$ alkyl; and $R_2$ and $R_4$ are independently selected from the group consisting of H, $C_1$-$C_8$ alkyl, $C_2$-$C_8$ alkenyl, ($C_1$-$C_4$ alkyl)OH, ($C_1$-$C_4$ alkyl)SH, ($C_2$-$C_3$ alkyl)$SCH_3$, ($C_1$-$C_4$ alkyl)$CONH_2$, ($C_1$-$C_4$ alkyl)COOH, ($C_1$-$C_4$ alkyl)$NH_2$, ($C_1$-$C_4$ alkyl)NHC($NH_2^+$) $NH_2$, ($C_0$-$C_4$ alkyl)($C_3$-$C_6$ cycloalkyl), ($C_0$-$C_4$ alkyl)($C_6$-$C_{10}$ aryl)$R_7$, and $CH_2$($C_5$-$C_9$ heteroaryl), or $R_1$ and $R_2$ together with the atoms to which they are attached form a $C_3$-$C_8$ cycloalkyl ring;

$R_3$ is selected from the group consisting of $C_1$-$C_8$ alkyl, ($C_1$-$C_4$ alkyl)OH, ($C_1$-$C_4$ alkyl)SH, ($C_1$-$C_4$ alkyl)$NH_2$, ($C_3$-$C_6$)cycloalkyl or $R_4$ and $R_3$ together with the atoms to which they are attached form a 5 or 6 member heterocyclic ring;

$R_5$ is $NHR_6$ or OH;

$R_6$ is H, or $R_6$ and $R_2$ together with the atoms to which they are attached form a 5 or 6 member heterocyclic ring;

$R_7$ is selected from the group consisting of hydrogen, $C_1$-$C_{18}$ alkyl, $C_2$-$C_{18}$ alkenyl, ($C_0$-$C_4$ alkyl)$CONH_2$, ($C_0$-$C_4$ alkyl)COOH, ($C_0$-$C_4$ alkyl)$NH_2$, ($C_0$-$C_4$ alkyl)OH and halo, and $R_8$ is H, provided that when the dipeptide element is linked to an N-terminal amine and $R_4$ and $R_3$ together with the atoms to which they are attached form a 5 or 6 member heterocyclic ring, both $R_1$ and $R_2$ are not H. In one embodiment either the first amino acid and/or the second amino acid of the dipeptide prodrug element is an amino acid in the D stereoisomer configuration.

In other embodiments the dipeptide prodrug element has the structure of Formula X, wherein $R_1$ and $R_8$ are independently H or $C_1$-$C_8$ alkyl;

$R_2$ and $R_4$ are independently selected from the group consisting of H, $C_1$-$C_8$ alkyl, $C_2$-$C_8$ alkenyl, ($C_1$-$C_4$ alkyl)OH, ($C_1$-$C_4$ alkyl)SH, ($C_2$-$C_3$ alkyl)$SCH_3$, ($C_1$-$C_4$ alkyl)$CONH_2$, ($C_1$-$C_4$ alkyl)COOH, ($C_1$-$C_4$ alkyl)$NH_2$, ($C_1$-$C_4$ alkyl)NHC($NH_2^+$) $NH_2$, ($C_0$-$C_4$ alkyl)($C_3$-$C_6$ cycloalkyl), ($C_0$-$C_4$ alkyl)($C_2$-$C_5$ heterocyclic), ($C_0$-$C_4$ alkyl)($C_6$-$C_{10}$ aryl)$R_7$, and $CH_2$ ($C_3$-$C_9$ heteroaryl), or $R_1$ and $R_2$ together with the atoms to which they are attached form a $C_3$-$C_{12}$ cycloalkyl;

$R_3$ is $C_1$-$C_{18}$ alkyl;

$R_5$ is $NHR_6$;

$R_6$ is H or $C_1$-$C_8$ alkyl; and $R_7$ is selected from the group consisting of hydrogen, $C_1$-$C_{18}$ alkyl, $C_2$-$C_{18}$ alkenyl, ($C_0$-$C_4$ alkyl)$CONH_2$, ($C_0$-$C_4$ alkyl)COOH, ($C_0$-$C_4$ alkyl)$NH_2$, ($C_0$-$C_4$ alkyl)OH, and halo.

In a further embodiment the dipeptide prodrug element has the structure of Formula X, wherein $R_1$ and $R_2$ are independently $C_1$-$C_{18}$ alkyl or ($C_0$-$C_4$ alkyl)($C_6$-$C_{10}$ aryl)$R_7$; or $R_1$ and $R_2$ are linked through —($CH_2$)$_p$, wherein p is 2-9;

$R_3$ is $C_1$-$C_{18}$ alkyl;

$R_4$ and $R_8$ are each hydrogen;

$R_5$ is $NH_2$; and $R_7$ is selected from the group consisting of hydrogen, $C_1$-$C_{18}$ alkyl, $C_2$-$C_{18}$ alkenyl, ($C_0$-$C_4$ alkyl)$CONH_2$, ($C_0$-$C_4$ alkyl)COOH, ($C_0$-$C_4$ alkyl)$NH_2$, ($C_0$-$C_4$ alkyl)OH, and halo.

In a further embodiment the dipeptide prodrug element has the structure of Formula X, wherein $R_1$ and $R_2$ are independently selected from the group consisting of hydrogen, $C_1$-$C_{18}$ alkyl, ($C_1$-$C_{18}$ alkyl)OH, ($C_1$-$C_4$ alkyl)$NH_2$, and ($C_0$-$C_4$ alkyl)($C_6$-$C_{10}$ aryl)$R_7$, or $R_1$ and $R_2$ are linked through ($CH_2$)$_p$, wherein p is 2-9;

$R_3$ is $C_1$-$C_{18}$ alkyl or $R_3$ and $R_4$ together with the atoms to which they are attached form a 4-12 heterocyclic ring;

$R_4$ and $R_8$ are independently selected from the group consisting of hydrogen, $C_1$-$C_s$ alkyl and ($C_0$-$C_4$ alkyl)($C_6$-$C_{10}$ aryl)$R_7$;

$R_5$ is $NH_2$; and $R_7$ is selected from the group consisting of H, $C_1$-$C_{18}$ alkyl, $C_2$-$C_{18}$ alkenyl, ($C_0$-$C_4$ alkyl)$CONH_2$, ($C_0$-$C_4$ alkyl)COOH, ($C_0$-$C_4$ alkyl)$NH_2$, ($C_0$-$C_4$ alkyl)OH, and halo, with the proviso that both $R_1$ and $R_2$ are not hydrogen and provided that at least one of $R_4$ or $R_8$ is hydrogen.

In another embodiment the dipeptide prodrug element has the structure of Formula X, wherein $R_1$ and $R_2$ are independently selected from the group consisting of hydrogen, $C_1$-$C_s$ alkyl and ($C_1$-$C_4$ alkyl)$NH_2$, or $R_1$ and $R_2$ are linked through ($CH_2$)$_p$, wherein p is 2-9;

$R_3$ is $C_1$-$C_8$ alkyl or $R_3$ and $R_4$ together with the atoms to which they are attached form a 4-6 heterocyclic ring;

$R_4$ is selected from the group consisting of hydrogen and $C_1$-$C_8$ alkyl;

$R_8$ is hydrogen; and $R_5$ is $NH_2$, with the proviso that both $R_1$ and $R_2$ are not hydrogen.

In a further embodiment the dipeptide prodrug element has the structure of Formula X, wherein $R_1$ and $R_2$ are independently selected from the group consisting of hydrogen, $C_1$-$C_8$ alkyl and ($C_1$-$C_4$ alkyl)$NH_2$;

$R_3$ is $C_1$-$C_6$ alkyl;

$R_4$ and $R_8$ are each hydrogen; and $R_5$ is $NH_2$, with the proviso that both $R_1$ and $R_2$ are not hydrogen.

In another embodiment the dipeptide prodrug element has the structure of Formula X, wherein $R_1$ and $R_2$ are independently selected from the group consisting of hydrogen and $C_1$-$C_8$ alkyl, ($C_1$-$C_4$ alkyl)$NH_2$, or $R_1$ and $R_2$ are linked through ($CH_2$)$_p$, wherein p is 2-9;

$R_3$ is $C_1$-$C_8$ alkyl;

$R_4$ is ($C_0$-$C_4$ alkyl)($C_6$-$C_{10}$ aryl)$R_7$;

$R_5$ is $NH_2$;

$R_7$ is selected from the group consisting of hydrogen, $C_1$-$C_8$ alkyl and ($C_0$-$C_4$ alkyl)OH; and $R_8$ is hydrogen, with the proviso that both $R_1$ and $R_2$ are not hydrogen.

In another embodiment the dipeptide prodrug element has the structure of Formula X, wherein $R_1$ is selected from the group consisting of hydrogen, $C_1$-$C_8$ alkyl and ($C_0$-$C_4$ alkyl)($C_6$-$C_{10}$ aryl)$R_7$;

$R_2$ is hydrogen;

$R_3$ is $C_1$-$C_{18}$ alkyl;

$R_4$ and $R_8$ are each hydrogen;

$R_5$ is $NHR_6$ or OH;

$R_6$ is H, $C_1$-$C_8$ alkyl, or $R_6$ and $R_1$ together with the atoms to which they are attached form a 4, 5 or 6 member heterocyclic ring; and $R_7$ is selected from the group consisting of hydrogen, $C_1$-$C_{18}$ alkyl, $C_2$-$C_{18}$ alkenyl, ($C_0$-$C_4$ alkyl)$CONH_2$, ($C_0$-$C_4$ alkyl)COOH, ($C_0$-$C_4$ alkyl)$NH_2$, ($C_0$-$C_4$ alkyl)OH, and halo, with the proviso that, if $R_1$ is alkyl or ($C_0$-$C_4$ alkyl)($C_6$-$C_{10}$ aryl)$R_7$, then $R_1$ and $R_6$ together with the atoms to which they are attached form a 4-11 heterocyclic ring.

In one embodiment a single chain insulin analog is provided comprising an A chain and a B chain wherein the carboxy terminus of the B chain is linked to the amino terminus of said A chain via a linking moiety. In one embodiment a single chain insulin analog is provided that comprises the structure: IB-LM-IA, wherein IB comprises the sequence $R_{22}$-$X_{25}$LCGX$_{29}$X$_{30}$LVX$_{33}$X$_{34}$LYLVCGX$_{41}$X$_{42}$GFX$_{45}$ (SEQ ID NO: 21), LM is a linking moiety as disclosed herein that covalently links IB to IA, and IA comprises the sequence GIVX$_4$X$_5$CCX$_8$X$_9$X$_{10}$CX$_{12}$LX$_{14}$X$_{15}$LX$_{17}$X$_{18}$X$_{19}$CX$_{21}$-$R_{13}$ (SEQ ID NO: 22), wherein the amino acid at the designation $X_{45}$ is phenylalanine or tyrosine that is directly bound to the linking moiety, LM. In one embodiment a single chain insulin analog is provided that comprises the structure: IB-LM-IA, wherein IB comprises the sequence J-$R_{23}$-$R_{22}$-$X_{25}$LCGX$_{29}$X$_{30}$LVX$_{33}$X$_{34}$LX$_{36}$LVCGX$_{41}$X$_{42}$GFX$_{45}$ (SEQ ID NO: 20) or a sequence that differs from SEQ ID NO: 20 by 1 to 3 amino acid modifications selected from positions 5, 6, 9, 10, 16, 18, 19 and 21 of SEQ ID NO: 20, LM is a linking moiety as disclosed herein and IA comprises the sequence GIVX$_4$X$_5$CCX$_8$X$_9$X$_{10}$CX$_{12}$LX$_{14}$X$_{15}$LX$_{17}$X$_{18}$X$_{19}$CX$_{21}$-$R_{13}$ (SEQ ID NO: 22) or a sequence that differs from SEQ ID NO: 19 by 1 to 3 amino acid modifications selected from positions 5, 8, 9, 10, 14, 15, 17, 18 and 21 of SEQ ID NO: 20, wherein J is H or a dipeptide element comprising the general structure of U-B, wherein U is an amino acid or a hydroxyl acid and B is an N-alkylated amino acid linked through an amide bond;

$X_4$ is glutamic acid or aspartic acid;

$X_5$ is glutamine or glutamic acid $X_8$ is histidine, threonine or phenylalanine;

$X_9$ is serine, arginine, ornithine, lysine or alanine;

$X_{10}$ is isoleucine or serine;

$X_{12}$ is serine or aspartic acid $X_{14}$ is tyrosine, arginine, ornithine, lysine or alanine;

$X_{15}$ is glutamine, glutamic acid, arginine, alanine, ornithine, lysine or leucine;

$X_{17}$ is glutamic acid or glutamine;

$X_{18}$ is methionine, asparagine, glutamine, aspartic acid, glutamic acid or threonine;

$X_{19}$ is an amino acid of the general structure:

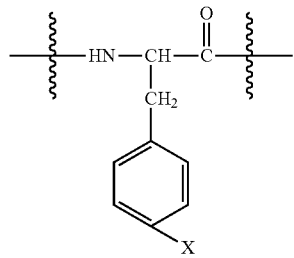

wherein X is selected from the group consisting of OH or $NHR_{10}$, wherein $R_{10}$ is H or a dipeptide element comprising the general structure U-B, wherein U is an amino acid or a hydroxyl acid and B is an N-alkylated amino acid;

$X_{21}$ is selected from the group consisting of alanine, glycine, serine, valine, threonine, isoleucine, leucine, glutamine, glutamic acid, asparagine, aspartic acid, histidine, tryptophan, tyrosine, and methionine;

$X_{25}$ is histidine or threonine;

$X_{29}$ is selected from the group consisting of alanine, glycine and serine;

$X_{30}$ is selected from the group consisting of histidine, aspartic acid, glutamic acid, homocysteic acid and cysteic acid;

$X_{33}$ is selected from the group consisting of aspartic acid, glutamine and glutamic acid;

$X_{34}$ is selected from the group consisting of alanine and threonine;

$X_{36}$ is an amino acid of the general structure

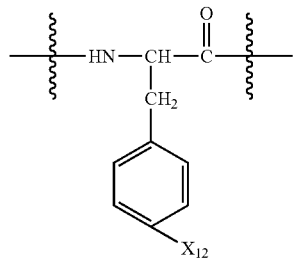

wherein $X_{12}$ is selected from the group consisting of OH and $NHR_{11}$, wherein $R_{11}$ is a dipeptide element comprising the general structure U-B;

$X_{41}$ is selected from the group consisting of glutamic acid, aspartic acid or asparagine;

$X_{42}$ is selected from the group consisting of alanine, ornithine, lysine and arginine;

$X_{45}$ is an amino acid of the general structure

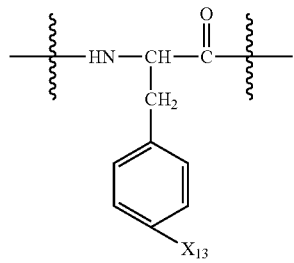

wherein $X_{13}$ is selected from the group consisting of H, OH and $NHR_{12}$, wherein $R_{12}$ is H or dipeptide element comprising the general structure U-B;

$R_{22}$ is selected from the group consisting of AYRPSE (SEQ ID NO: 14), FVNQ (SEQ ID NO: 12), PGPE (SEQ ID NO: 11), a tripeptide glycine-proline-glutamic acid, a tripeptide valine-asparagine-glutamine, a dipeptide proline-glutamic acid, a dipeptide asparagine-glutamine, glutamine, glutamic acid and an N-terminal amine;

$R_{23}$ is a bond or an amino sequence comprising 1 to 6 charged amino acids; and $R_{13}$ is COOH or $CONH_2$. In one embodiment, only one of J, $R_{10}$, $R_{11}$ and $R_{12}$ is U-B. In one embodiment $X_{12}$ is OH and $X_{13}$ is H or OH and J and/or X is U-B. In one embodiment $X_{12}$ is OH and $X_{13}$ is OH, $R_{23}$ is a bond, J is H and X is U-B. In a further embodiment $X_8$, $X_{25}$ and $X_{30}$ are each histidine. In another embodiment the single chain insulin analog peptide comprises an A chain peptide sequence of SEQ ID NO: 19 and a B chain peptide sequence of SEQ ID NO: 20. In one embodiment $R_{23}$ is a bond or comprises an amino sequence $X_{60}(X_{61}X_{62})_dX_{63}K$ (SEQ ID NO: 192) wherein $X_{60}$ is selected from the group consisting of glycine, glutamic acid and aspartic acid, $X_{61}$ and $X_{62}$ are independently selected from the group consisting of glutamic acid and aspartic acid, $X_{63}$ is selected from the group consisting of arginine aspartic acid and glutamic acid and d is an integer ranging from 1-3.

In one embodiment a single chain insulin analog is provided wherein IB comprises the sequence J-$R_{23}R_{22}$-$X_{25}LCGX_{29}X_{30}LVX_{33}X_{34}LX_{36}LVCGX_{41}X_{42}GFX_{45}$ (SEQ ID NO: 20) or J-$R_{23}R_{22}$-$X_{25}LCGX_{29}X_{30}LVEALYLVCG$ ERGFF (SEQ ID NO: 53) wherein the carboxy terminus of the B25 amino acid of IB is directly linked to a first end of the linking moiety (LM) and a second end of the linking moiety is directly linked to the amino terminus of the A1 amino acid of the IA chain, further wherein, in one embodiment, the linking moiety does not comprise the sequence YTPKT (SEQ ID NO: 16) or FNKPT (SEQ ID NO: 76). In one embodiment a single chain insulin analog is provided wherein IB comprises the sequence J-$R_{23}R_{22}$-$X_{25}LCGX_{29}X_{30}LVX_{33}X_{34}LX_{36}LVCGX_{41}X_{42}GFX_{45}$ (SEQ ID NO: 20), J-$R_{23}R_{22}$-$X_{25}LCGX_{29}X_{30}LVEALYLVCG$ ERGFF (SEQ ID NO: 53), $R_{23}R_{22}$-$X_{25}LCGX_{29}X_{30}LVX_{33}X_{34}LX_{36}LVCGX_{41}X_{42}GFX_{45}$ (SEQ ID NO: 20) or $R_{23}R_{22}$-$X_{25}LCGX_{29}X_{39}LVEALYLVCG$ ERGFF (SEQ ID NO: 53) and the linking moiety is a peptide linker of the general structure $(Y_1)_k$-$X_{51}AX_{53}X_{54}X_{55}X_{56}X_{57}R(Y_2)_n$ (SEQ ID NO: 28), $(Y_1)_k$-$X_{51}AX_{53}X_{54}X_{55}X_{56}RR(Y_2)_n$ (SEQ ID NO: 23), $(Y_1)_k$-$GYGSSSX_{57}X_{58}(Y_2)_n$ (SEQ ID NO: 85), $(Y_1)_k$-$GAGSSSX_{57}X_{58}(Y_2)_n$ (SEQ ID NO: 163), $(Y_1)_k$-$GYGSSSX_{57}R$ (SEQ ID NO: 51) or $(Y_1)_k$-$X_{51}X_{52}GSSSX_{57}X_{58}$-$(Y_2)_n$ (SEQ ID NO: 29) wherein $Y_1$ is selected from the group $X_{46}$, and $X_{46}X_{47}$/with the proviso that when k is 0, then, the linking peptide does not comprise the sequence YTPKT (SEQ ID NO: 16) or FNKPT (SEQ ID NO: 76).

In one embodiment a single chain insulin analog is provided that comprises the structure: IB-LM-IA, wherein IB comprises the sequence J-$R_{23}R_{22}$-$X_{25}LCGX_{29}X_{30}LVEALYLVCG$ ERGFF (SEQ ID NO: 53), LM is a linking moiety as disclosed herein and IA comprises the sequence $GIVEQCCX_8SICSLYQLX_{17}NX_{19}CX_{23}$ (SEQ ID NO: 52) wherein $X_8$ is selected from the group consisting of threonine and histidine;

$X_{17}$ is glutamic acid or glutamine;

$X_{19}$ is an amino acid of the general structure:

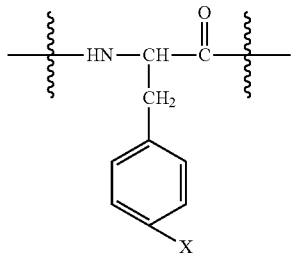

wherein X is selected from the group consisting of OH or $NHR_{10}$, wherein $R_{10}$ is H or a dipeptide element comprising the general structure U-B, wherein U is an amino acid or a hydroxyl acid and B is an N-alkylated amino acid;

$X_{23}$ is asparagine or glycine;

$X_{25}$ is selected from the group consisting of histidine and threonine;

$X_{29}$ is selected from the group consisting of alanine, glycine and serine;

$X_{30}$ is selected from the group consisting of histidine, aspartic acid, glutamic acid, homocysteic acid and cysteic acid;

$R_{22}$ is selected from the group consisting of FVNQ (SEQ ID NO: 12), a tripeptide valine-asparagine-glutamine, a dipeptide asparagine-glutamine, glutamine, glutamic acid and an N-terminal amine; and $R_{23}$ is a bond or an amino sequence comprising 1 to 6 charged amino acids.

In a further embodiment the B chain comprises the sequence $X_{22}VNQX_{25}LCGX_{29}X_{30}LVEALYLVCGERGFFYT\text{-}Z_1\text{-}B_1$ (SEQ ID NO: 54) wherein $X_{22}$ is selected from the group consisting of phenylalanine and desamino-phenylalanine;

$X_{25}$ is selected from the group consisting of histidine and threonine;

$X_{29}$ is selected from the group consisting of alanine, glycine and serine;

$X_{30}$ is selected from the group consisting of histidine, aspartic acid, glutamic acid, homocysteic acid and cysteic acid;

$Z_1$ is a dipeptide selected from the group consisting of aspartate-lysine, lysine-proline, and proline-lysine; and $B_1$ is selected from the group consisting of threonine, alanine or a threonine-arginine-arginine tripeptide.

In accordance with one embodiment a single chain insulin analog is provided that comprises the structure: IB-LM-IA, wherein IB comprises the sequence $X_{25}LCGX_{29}X_{30}LVEALYLVCG$ ERGFF (SEQ ID NO: 53), LM is a linking moiety as disclosed herein that covalently links IB to IA, and IA comprises the sequence $GIVEQCCX_8SICSLYQLENX_{19}CX_{21}$ (SEQ ID NO: 55), wherein the C-terminal phenylalanine residue of SEQ ID NO: 53 is directly covalently bound to the linking moiety, LM, in the absence of any intervening amino acids.

In one embodiment a single chain insulin analog is provided that comprises the structure: IB-LM-IA, wherein IB comprises the sequence $J\text{-}R_{23}\text{-}R_{22}\text{-}X_{25}LCGX_{29}X_{30}LVX_{33}X_{34}LYLVCGDX_{42}GFX_{45}$ (SEQ ID NO: 58), LM is a linking moiety as disclosed herein and IA comprises the sequence $GIVX_4ECCX_8X_9SCDLX_{14}X_{15}LX_{17}X_{18}X_{19}CX_{21}\text{-}R_{13}$ (SEQ ID NO: 19) wherein J is H or a dipeptide element comprising the general structure of U-B, wherein U is an amino acid or a hydroxyl acid and B is an N-alkylated amino acid linked through an amide bond;

$X_4$ is aspartic acid or glutamic acid;

$X_8$ is histidine or phenylalanine;

$X_9$ and $X_{14}$ are independently selected from arginine, ornithine, lysine or alanine;

$X_{15}$ is arginine, lysine, ornithine or leucine;

$X_{17}$ is glutamic acid or glutamine;

$X_{18}$ is methionine, asparagine or threonine;

$X_{19}$ is an amino acid of the general structure:

wherein X is selected from the group consisting of OH or $NHR_{10}$, wherein $R_{10}$ is H or a dipeptide element comprising the general structure U-B, wherein U is an amino acid or a hydroxyl acid and B is an N-alkylated amino acid;

$X_{21}$ is alanine, glycine or asparagine;

$R_{22}$ is selected from the group consisting of a covalent bond, AYRPSE (SEQ ID NO: 14), a glycine-proline-glutamic acid tripeptide, a proline-glutamic acid dipeptide and glutamic acid;

$R_{23}$ is a bond or an amino sequence comprising 1 to 6 charged amino acids;

$X_{25}$ is selected from the group consisting of histidine and threonine;

$X_{29}$ is selected from the group consisting of alanine, glycine and serine;

$X_{30}$ is selected from the group consisting of histidine, aspartic acid, glutamic acid, homocysteic acid and cysteic acid;

$X_{33}$ is selected from the group consisting of aspartic acid and glutamic acid;

$X_{34}$ is selected from the group consisting of alanine and threonine;

$X_{42}$ is selected from the group consisting of alanine, lysine ornithine and arginine;

$X_{45}$ is an amino acid of the general structure wherein $X_{13}$ is selected from the group consisting of H, OH and $NHR_{12}$, wherein $R_{12}$ is a dipeptide element comprising the general structure U-B;

and $R_{13}$ is COOH or $CONH_2$, with the proviso that one and only one of J, X, and $X_{13}$, comprises U-B. In one embodiment J is H, and $X_{13}$ is OH, and X is NH-U-B.

In one embodiment U and B of the dipeptide prodrug element U-B are selected to inhibit enzymatic cleavage of the U-B dipeptide from an insulin peptide by enzymes found in mammalian serum. In one embodiment U and/or B are selected such that the cleavage half-life of U-B from the insulin peptide, in PBS under physiological conditions, is not more than two fold the cleavage half-life of U-B from the insulin peptide in a solution comprising a DPP-IV protease (i.e., cleavage of U-B from the insulin prodrug does not occur at a rate more than 2× faster in the presence of DPP-IV protease and physiological conditions relative to identical conditions in the absence of the enzyme). In one embodiment U, B, or the amino acid of the insulin peptide to which U-B is linked is a non-coded amino acid. In one embodiment U and/or B is an amino acid in the D stereoisomer configuration. In some exemplary embodiments, U is an amino acid in the D stereoisomer configuration and B is an amino acid in the L stereoisomer configuration. In some exemplary embodiments, U is an amino acid in the L stereoisomer configuration and B is an amino acid in the D stereoisomer configuration. In some exemplary embodiments, U is an amino acid in the D stereoisomer configuration and B is an amino acid in the D stereoisomer configuration. In one embodiment U-B is a dipeptide comprising the structure of Formula X as defined herein. In one embodiment B is an N-alkylated amino acid but is not proline.

In accordance with one embodiment a single chain insulin agonist polypeptide comprising a B chain and A chain of human insulin, or analogs or derivative thereof is provided, wherein the carboxy terminus of the B chain is linked to the amino terminus of the A chain via a linking moiety. In one embodiment the linking moiety comprises a polyethylene glycol of 6-16 monomer units, an amino acid sequence of at least 8 amino acids and no more than 12 amino acid in length (or a peptidomimetic thereof), or a combination of said polyethylene glycol and amino acid sequence. More particularly, in one embodiment the linking moiety comprises an amino acid sequence, $X_{51}X_{52}X_{53}X_{54}X_{55}X_{56}RR$ (SEQ ID NO: 10), wherein $X_{51}$ is selected from the group consisting of glycine, alanine, valine, leucine, isoleucine, proline, phenylalanine and methionine; $X_{52}$ is any amino acid other than tyrosine, including for example any non-aromatic amino acid; and $X_3$ through $X_6$ are each independently any amino acid.

In one embodiment the single chain insulin analog comprises the structure IB-LM-IA, wherein IB comprises the sequence $J-R_{23}R_{22}-X_{25}LCGX_{29}X_{30}LVX_{33}X_{34}LX_{36}LVCGX_{41}X_{42}GFX_{45}$ SEQ ID NO: 20);

LM is a linking moiety is selected from the group consisting of $(Y_1)_k-X_{51}X_{52}X_{53}X_{54}X_{55}X_{56}X_{57}X_{58}(Y_2)_n$ (SEQ ID NO: 9), $(Y_1)_k-X_{511}AX_{53}X_{54}X_{55}X_{56}RR(Y_2)_n$ (SEQ ID NO: 23), $(Y_1)_k$-$GYGSSSX_{57}X_{58}(Y_2)_n$ (SEQ ID NO: 85) and

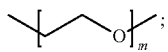

IA comprises the sequence $GIVX_4X_5CCX_8X_9X_{10}CX_{12}LX_{14}X_{15}LX_{17}X_{18}X_{19}CX_{21}-R_{13}$ (SEQ ID NO: 22) wherein J is H or a dipeptide comprising the general structure of U-B, wherein U is an amino acid or a hydroxyl acid and B is an N-alkylated amino acid linked through an amide bond;

$Y_1$ is selected from the group $X_{46}$, $X_{46}X_{47}$, $X_{46}X_{47}X_{48}$, $X_{46}X_{47}X_{48}X_{49}$ (SEQ ID NO: 24) and $X_{46}X_{47}X_{48}X_{49}X_{50}$ (SEQ ID NO: 13); and $Y_2$ is selected from the group $X_{70}$, $X_{70}X_{71}$, $X_{70}X_{71}X_{72}$ and $X_{70}X_{71}X_{72}X_{73}$ (SEQ ID NO: 15) wherein n is 0 or 1;

k is 0 or 1;

m is an integer ranging from 5 to 15;

$X_4$ is glutamic acid or aspartic acid;

$X_5$ is glutamine or glutamic acid $X_8$ is histidine, threonine or phenylalanine;

$X_9$ is serine, arginine, lysine, ornithine or alanine;

$X_{10}$ is isoleucine or serine;

$X_{12}$ is serine or aspartic acid $X_{14}$ is tyrosine, arginine, lysine, ornithine or alanine;

$X_{15}$ is glutamine, glutamic acid, arginine, alanine, lysine, ornithine or leucine;

$X_{17}$ is glutamic acid or glutamine;

$X_{18}$ is methionine, asparagine, glutamine, aspartic acid, glutamic acid or threonine;

$X_{19}$ is an amino acid of the general structure:

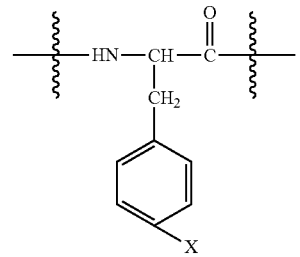

wherein X is selected from the group consisting of OH, $OCH_3$ or $NHR_{10}$, wherein $R_{10}$ is H or a dipeptide element comprising the general structure U-B, wherein U is an amino acid or a hydroxyl acid and B is an N-alkylated amino acid;

$X_{21}$ is selected from the group consisting of alanine, glycine, serine, valine, threonine, isoleucine, leucine, glutamine, glutamic acid, asparagine, aspartic acid, histidine, tryptophan, tyrosine, and methionine;

$X_{25}$ is histidine or threonine;

$X_{29}$ is selected from the group consisting of alanine, glycine and serine;

$X_{30}$ is selected from the group consisting of histidine, aspartic acid, glutamic acid, homocysteic acid and cysteic acid;

$X_{33}$ is selected from the group consisting of aspartic acid, glutamine and glutamic acid;

$X_{34}$ is selected from the group consisting of alanine and threonine;

$X_{36}$ is an amino acid of the general structure

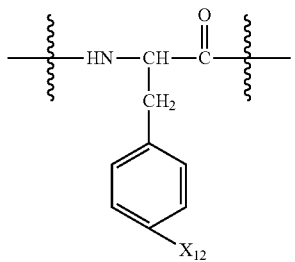

wherein $X_{12}$ is selected from the group consisting of OH and $NHR_{11}$, wherein $R_{11}$ is a dipeptide element comprising the general structure U-B;

$X_{41}$ is selected from the group consisting of glutamic acid, aspartic acid or asparagine;

$X_{42}$ is selected from the group consisting of alanine, lysine, ornithine and arginine;

$X_{45}$ is an amino acid of the general structure

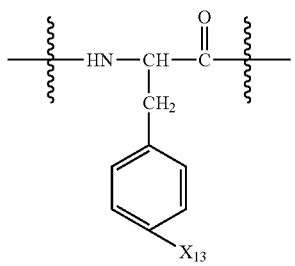

wherein $X_{13}$ is selected from the group consisting of H, OH and $NHR_{12}$, wherein $R_{12}$ is H or dipeptide element comprising the general structure U-B;

$X_{51}$ is selected from the group consisting of glycine, alanine, valine, leucine, isoleucine, proline, phenylalanine and methionine;

$X_{52}$ is any amino acid other than tyrosine;

$X_{46}$ through $X_{56}$ and $X_{70}$ through $X_{73}$ are each independently any amino acid or amino acid analog or derivative thereof;

$X_{57}$ and $X_{58}$ are independently selected from the group arginine, ornithine and lysine.

$R_{22}$ is selected from the group consisting of AYRPSE (SEQ ID NO: 14), FVNQ (SEQ ID NO: 12), PGPE (SEQ ID NO: 11), a tripeptide glycine-proline-glutamic acid, a tripeptide valine-asparagine-glutamine, a dipeptide proline-glutamic acid, a dipeptide asparagine-glutamine, glutamine, glutamic acid and a bond;

$R_{23}$ is a bond or an amino sequence comprising 1 to 6 charged amino acids; and $R_{13}$ is COOH or $CONH_2$, with the proviso that U, B, or the amino acid of the single chain insulin agonist to which U-B is linked is a non-coded amino acid. In one embodiment at least one of n or k is 1.

In one embodiment a single chain insulin analog is provided comprising the structure IB-LM-IA, wherein IB comprises the sequence $R_{23}R_{22}$-$X_{25}LCGX_{29}X_{30}LVX_{33}X_{34}LYLVCGX_{41}X_{42}GFX_{45}$ (SEQ ID NO: 21);

LM is a linking moiety is selected from the group consisting of $(Y_1)_k$-$X_{51}X_{52}X_{53}X_{54}X_{55}X_{56}X_{57}X_{58}(Y_2)_n$ (SEQ ID NO: 9), $(Y_1)_k$-$X_{51}AX_{53}X_{54}X_{55}X_{56}RR(Y_2)_n$ (SEQ ID NO: 23), $(Y_1)_k$-$GYGSSSX_{57}X_5$) (SEQ ID NO: 85) and

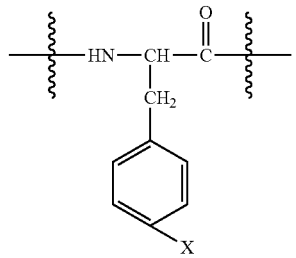

and

IA comprises the sequence $GIVX_4X_5CCX_8X_9X_{10}CX_{12}LX_{14}X_{15}LX_{17}X_{18}X_{19}CX_{21}$-$R_{13}$ (SEQ ID NO: 22) wherein $Y_1$ is selected from the group $X_{46}$, $X_{46}X_{47}$, $X_{46}X_{47}X_{48}$, $X_{46}X_{47}X_{48}X_{49}$ (SEQ ID NO: 24) and $X_{46}X_{47}X_{48}X_{49}X_{50}$ (SEQ ID NO: 13); and $Y_2$ is selected from the group $X_{70}$, $X_{70}X_{71}$, $X_{70}X_{71}X_{72}$ and $X_{70}X_{71}X_{72}X_{73}$ (SEQ ID NO: 15) wherein n is 0 or 1;
k is 0 or 1;
m is an integer ranging from 5 to 15;
$X_4$ is glutamic acid or aspartic acid;
$X_5$ is glutamine or glutamic acid
$X_8$ is histidine, threonine or phenylalanine;
$X_9$ is serine, arginine, lysine, ornithine or alanine;
$X_{10}$ is isoleucine or serine;
$X_{12}$ is serine or aspartic acid
$X_{14}$ is tyrosine, arginine, lysine, ornithine or alanine;
$X_{15}$ is glutamine, glutamic acid, arginine, alanine, lysine, ornithine or leucine;
$X_{17}$ is glutamic acid or glutamine;
$X_{18}$ is methionine, asparagine, glutamine, aspartic acid, glutamic acid or threonine;
$X_{19}$ is an amino acid of the general structure:

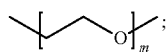

wherein X is selected from the group consisting of OH or $NHR_{10}$, wherein $R_{10}$ is H or a dipeptide element comprising the general structure U-B, wherein U is an amino acid or a hydroxyl acid and B is an N-alkylated amino acid;

$X_{21}$ is selected from the group consisting of alanine, glycine, serine, valine, threonine, isoleucine, leucine, glutamine, glutamic acid, asparagine, aspartic acid, histidine, tryptophan, tyrosine, and methionine;

$X_{25}$ is histidine or threonine;

$X_{29}$ is selected from the group consisting of alanine, glycine and serine;

$X_{30}$ is selected from the group consisting of histidine, aspartic acid, glutamic acid, homocysteic acid and cysteic acid;

$X_{33}$ is selected from the group consisting of aspartic acid, glutamine and glutamic acid;

$X_{34}$ is selected from the group consisting of alanine and threonine;

$X_{45}$ is tyrosine or phenylalanine;

$X_{51}$ is selected from the group consisting of glycine, alanine, valine, leucine, isoleucine, proline, phenylalanine and methionine;

$X_{52}$ is any amino acid other than tyrosine;

$X_{46}$ through $X_{56}$ and $X_{70}$ through $X_{73}$ are each independently any amino acid or amino acid analog or derivative thereof;

$X_{57}$ and $X_{58}$ are independently selected from the group arginine, ornithine and lysine;

$R_{22}$ is selected from the group consisting of AYRPSE (SEQ ID NO: 14), FVNQ (SEQ ID NO: 12), PGPE (SEQ ID NO: 11), a tripeptide glycine-proline-glutamic acid, a tripeptide valine-asparagine-glutamic acid, a dipeptide proline-glutamic acid, a dipeptide asparagine-glutamine, glutamine, glutamic acid and a bond;

$R_{23}$ is a H or an amino sequence comprising 1 to 6 charged amino acids; and $R_{13}$ is COOH or CONH$_2$. In one embodiment at least one of n or k is 1. In one embodiment both n and k are 1. In a further embodiment $Y_2$ is selected from the group consisting of A, AP, APQ and APQT and $Y_1$ is selected from the group consisting of F, Y, FN, YT, FNK, YTP, FNPK (SEQ ID NO: 79), FNKP (SEQ ID NO: 77), YTPK (SEQ ID NO: 78), YTPKT (SEQ ID NO: 16), YTKPT (SEQ ID NO: 80), FNKPT (SEQ ID NO: 76) and FNPKT (SEQ ID NO: 81). In one embodiment $R_{23}$ is a bond and $R_{22}$ is selected from the group consisting of AYRPSE (SEQ ID NO: 14), PGPE (SEQ ID NO: 11), a tripeptide glycine-proline-glutamic acid, a dipeptide proline-glutamic acid, glutamine, glutamic acid and H.

In one embodiment $R_{23}$ is H or an amino sequence of 4 to 7 amino acids wherein the N-terminal amino acid is selected from the group consisting of glycine, glutamic acid and aspartic acid, the C-terminal amino acid is a lysine and the other amino acids of the sequence are independently selected from the group consisting of glutamic acid and aspartic acid and $R_{22}$ is selected from the group consisting of AYRPSE (SEQ ID NO: 14), PGPE (SEQ ID NO: 11), a tripeptide glycine-proline-glutamic acid, a dipeptide proline-glutamic acid, glutamine, glutamic acid and H.

In one embodiment U-B comprises the structure of Formula X:

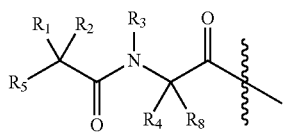

wherein $R_1$, $R_2$, $R_4$ and $R_8$ are independently selected from the group consisting of H, $C_1$-$C_{18}$ alkyl, $C_2$-$C_{18}$alkenyl, ($C_1$-$C_{18}$ alkyl)OH, ($C_1$-$C_{18}$ alkyl)SH, ($C_2$-$C_3$ alkyl)SCH$_3$, ($C_1$-$C_4$ alkyl)CONH$_2$, ($C_1$-$C_4$ alkyl)COOH, ($C_1$-$C_4$ alkyl)NH$_2$, ($C_1$-$C_4$ alkyl)NHC(NH$_2^+$)NH$_2$, ($C_0$-$C_4$ alkyl)($C_3$-$C_6$ cycloalkyl), ($C_0$-$C_4$alkyl)($C_2$-$C_5$ heterocyclic), ($C_0$-$C_4$alkyl)($C_6$-$C_{10}$ aryl)R$_7$, ($C_1$-$C_4$ alkyl)($C_3$-$C_9$ heteroaryl), and $C_1$-$C_{12}$ alkyl(W$_1$)$C_1$-$C_{12}$ alkyl, wherein W$_1$ is a heteroatom selected from the group consisting of N, S and O, or $R_1$ and $R_2$ together with the atoms to which they are attached form a $C_3$-$C_{12}$ cycloalkyl or aryl; or $R_4$ and $R_8$ together with the atoms to which they are attached form a $C_3$-$C_6$ cycloalkyl;

$R_3$ is selected from the group consisting of $C_1$-$C_{18}$ alkyl, ($C_1$-$C_{18}$ alkyl)OH, ($C_1$-$C_{18}$ alkyl)NH$_2$, ($C_1$-$C_{18}$ alkyl)SH, ($C_0$-$C_4$ alkyl)($C_3$-$C_6$)cycloalkyl, ($C_0$-$C_4$ alkyl)($C_2$-$C_5$ heterocyclic), ($C_0$-$C_4$ alkyl)($C_6$-$C_{10}$ aryl)R$_7$, and ($C_1$-$C_4$ alkyl)($C_3$-$C_9$ heteroaryl) or $R_4$ and $R_3$ together with the atoms to which they are attached form a 4, 5 or 6 member heterocyclic ring;

$R_5$ is NHR$_6$ or OH;

$R_6$ is H, $C_1$-$C_8$ alkyl or $R_6$ and $R_1$ together with the atoms to which they are attached form a 4, 5 or 6 member heterocyclic ring; and $R_7$ is selected from the group consisting of H, OH, $C_1$-$C_{18}$ alkyl, $C_2$-$C_{18}$ alkenyl, ($C_0$-$C_4$ alkyl)CONH$_2$, ($C_0$-$C_4$ alkyl)COOH, ($C_0$-$C_4$ alkyl)NH$_2$, ($C_0$-$C_4$ alkyl)OH, and halo.

In another embodiment a single chain insulin analog is provided comprising the structure IB-LM-IA, wherein IB comprises the sequence J-$R_{22}$-$X_{25}$LCGX$_{29}$X$_{30}$LVX$_{33}$X$_{34}$LYLVCGX$_{41}$X$_{42}$GFX$_{45}$ (SEQ ID NO: 21);

LM comprises the sequence $(Y_1)_k$-GYGSSSGX$_{57}$R$(Y_2)_n$ (SEQ ID NO: 91) or $(Y_1)_k$-X$_{51}$AX$_{53}$X$_{54}$X$_{55}$X$_{56}$X$_{57}$R$(Y_2)_n$ (SEQ ID NO: 28); and IA comprises the sequence GIVX$_4$X$_5$CCX$_8$X$_9$X$_{10}$CX$_{12}$LX$_{14}$X$_{15}$LX$_{17}$X$_{18}$X$_{19}$CX$_{21}$-R$_{13}$ (SEQ ID NO: 22) wherein J is H or a dipeptide comprising the general structure of U-B, wherein U is an amino acid or a hydroxyl acid and B is an N-alkylated amino acid linked through an amide bond;

$Y_1$ is selected from the group X$_{46}$, X$_{46}$X$_{47}$, X$_{46}$X$_{47}$X$_{48}$, X$_{46}$X$_{47}$X$_{48}$X$_{49}$ (SEQ ID NO: 24) and X$_{46}$X$_{47}$X$_{48}$X$_{49}$X$_{50}$ (SEQ ID NO: 13); and $Y_2$ is selected from the group X$_{70}$, X$_{70}$X$_{71}$, X$_{70}$X$_{71}$X$_{72}$ and X$_{70}$X$_{71}$X$_{72}$X$_{73}$ (SEQ ID NO: 15) wherein n is 0 or 1;

k is 0 or 1;

$X_4$ is glutamic acid or aspartic acid;

$X_5$ is glutamine or glutamic acid $X_8$ is histidine, threonine or phenylalanine;

$X_9$ is serine, arginine, lysine, ornithine or alanine;

$X_{10}$ is isoleucine or serine;

$X_{12}$ is serine or aspartic acid $X_{14}$ is tyrosine, arginine, lysine, ornithine or alanine;

$X_{15}$ is glutamine, glutamic acid, arginine, alanine, lysine, ornithine or leucine;

$X_{17}$ is glutamic acid or glutamine;

$X_{18}$ is methionine, asparagine, glutamine, aspartic acid, glutamic acid or threonine;

$X_{19}$ is an amino acid of the general structure:

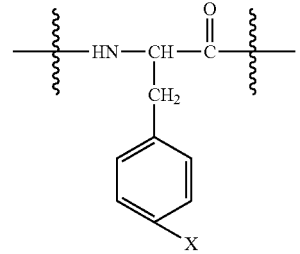

wherein X is selected from the group consisting of OH or NHR$_{10}$, wherein R$_{10}$ is H or a dipeptide element comprising the general structure U-B, wherein U is an amino acid or a hydroxyl acid and B is an N-alkylated amino acid;

$X_{21}$ is selected from the group consisting of alanine, glycine, serine, valine, threonine, isoleucine, leucine, glutamine, glutamic acid, asparagine, aspartic acid, histidine, tryptophan, tyrosine, and methionine;

$X_{25}$ is histidine or threonine;

$X_{29}$ is selected from the group consisting of alanine, glycine and serine;

$X_{30}$ is selected from the group consisting of histidine, aspartic acid, glutamic acid, homocysteic acid and cysteic acid;

$X_{33}$ is selected from the group consisting of aspartic acid, glutamine and glutamic acid;

$X_{34}$ is selected from the group consisting of alanine and threonine;

$X_{41}$ is selected from the group consisting of glutamic acid, aspartic acid or asparagine;

$X_{42}$ is selected from the group consisting of alanine, lysine, ornithine and arginine;

$X_{45}$ is an amino acid of the general structure

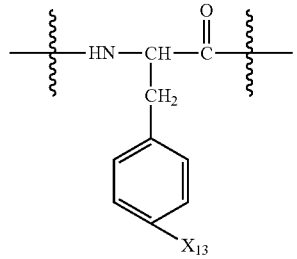

wherein $X_{13}$ is selected from the group consisting of H, OH and $NHR_{12}$, wherein $R_{12}$ is H or dipeptide element comprising the general structure U-B;

$X_{51}$ is selected from the group consisting of glycine, alanine, valine, leucine, isoleucine, proline, phenylalanine and methionine;

$X_{52}$ is any amino acid other than tyrosine;

$X_{46}$ through $X_{56}$ and $X_{70}$ through $X_{73}$ are each independently any amino acid or amino acid analog or derivative thereof; and $X_{57}$ is arginine, lysine, ornithine or lysine;

$R_{22}$ is selected from the group consisting of AYRPSE (SEQ ID NO: 14), FVNQ (SEQ ID NO: 12), PGPE (SEQ ID NO: 11), a tripeptide glycine-proline-glutamic acid, a tripeptide valine-asparagine-glutamine, a dipeptide proline-glutamic acid, a dipeptide asparagine-glutamine, glutamine, glutamic acid and a bond;

$R_{23}$ is a bond or an amino sequence comprising 1 to 6 charged amino acids; and $R_{13}$ is COOH or $CONH_2$. In one embodiment k is 0, in another embodiment n is 0 and in one further embodiment both k and n are 0. In one embodiment the linking moiety is GYGSSSRR (SEQ ID NO: 18) or $GX_{52}GSSSRRAPQT$ (SEQ ID NO: 83), wherein $X_{52}$ is a non-aromatic amino acid.

In another embodiment the single chain insulin analogs comprise the structure IB-LM-IA, wherein IB comprises sequence $J-R_{23}-R_{22}-X_{25}LCGX_{29}X_{30}LVX_{33}X_{34}LYLVCGX_{41}X_{42}GFX_{45}$ (SEQ ID NO: 21);

LM comprises the structure:

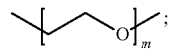

and

IA comprises the sequence $GIVX_4X_5CCX_8X_9X_{10}CX_{12}LX_{14}X_{15}LX_{17}X_{18}X_{19}CX_{21}-R_{13}$ (SEQ ID NO: 22) wherein J is H or a dipeptide element comprising the general structure of U-B, wherein U is an amino acid or a hydroxyl acid and B is an N-alkylated amino acid linked through an amide bond;

m is an integer ranging from 5 to 15;

$X_4$ is glutamic acid or aspartic acid;

$X_5$ is glutamine or glutamic acid $X_8$ is histidine, threonine or phenylalanine;

$X_9$ is serine, arginine, lysine, ornithine or alanine;

$X_{10}$ is isoleucine or serine;

$X_{12}$ is serine or aspartic acid $X_{14}$ is tyrosine, arginine, lysine, ornithine or alanine;

$X_{15}$ is glutamine, glutamic acid, arginine, alanine, lysine, ornithine or leucine;

$X_{17}$ is glutamic acid or glutamine;

$X_{18}$ is methionine, asparagine, glutamine, aspartic acid, glutamic acid or threonine;

$X_{19}$ is an amino acid of the general structure:

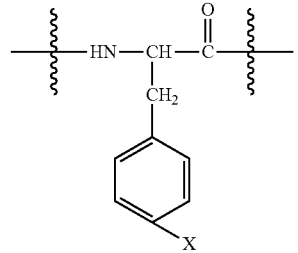

wherein X is selected from the group consisting of OH or $NHR_{10}$, wherein $R_{10}$ is H or a dipeptide element comprising the general structure U-B, wherein U is an amino acid or a hydroxyl acid and B is an N-alkylated amino acid;

$X_{21}$ is selected from the group consisting of alanine, glycine, serine, valine, threonine, isoleucine, leucine, glutamine, glutamic acid, asparagine, aspartic acid, histidine, tryptophan, tyrosine, and methionine;

$X_{25}$ is histidine or threonine;

$X_{29}$ is selected from the group consisting of alanine, glycine and serine;

$X_{30}$ is selected from the group consisting of histidine, aspartic acid, glutamic acid, homocysteic acid and cysteic acid;

$X_{33}$ is selected from the group consisting of aspartic acid, glutamine and glutamic acid;

$X_{34}$ is selected from the group consisting of alanine and threonine;

$X_{41}$ is selected from the group consisting of glutamic acid, aspartic acid or asparagine;

$X_{42}$ is selected from the group consisting of alanine, lysine, ornithine and arginine;

$X_{45}$ is an amino acid of the general structure

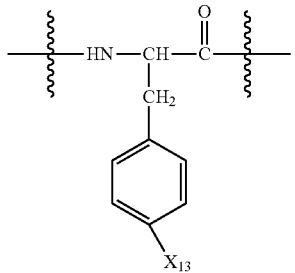

wherein $X_{13}$ is selected from the group consisting of H, OH and $NHR_{12}$, wherein $R_{12}$ is H or dipeptide element comprising the general structure U-B;

$X_{51}$ is selected from the group consisting of glycine, alanine, valine, leucine, isoleucine, proline, phenylalanine and methionine;

$X_{52}$ is any amino acid other than tyrosine;

$X_{46}$ through $X_{56}$ and $X_{70}$ through $X_{73}$ are each independently any amino acid or amino acid analog or derivative thereof;

$R_{22}$ is selected from the group consisting of AYRPSE (SEQ ID NO: 14), FVNQ (SEQ ID NO: 12), PGPE (SEQ ID NO: 11), a tripeptide glycine-proline-glutamic acid, a tripeptide valine-asparagine-glutamine, a dipeptide proline-glutamic acid, a dipeptide asparagine-glutamine, glutamine, glutamic acid and an N-terminal amine;

$R_{23}$ is a bond or $X_{60}(X_{61}X_{62})_dX_{63}K$ (SEQ ID NO: 192) wherein $X_{60}$ is selected from the group consisting of glycine, glutamic acid and aspartic acid;

$X_{61}$ and $X_{62}$ are independently selected from the group consisting of glutamic acid and aspartic acid;

$X_{63}$ is selected from the group consisting of arginine aspartic acid and glutamic acid;

d is an integer ranging from 1-3; and $R_{13}$ is COOH or $CONH_2$.

In one embodiment the single chain insulin analog comprises the structure IB-LM-IA, wherein IB comprises sequence J-$R_{23}$-$R_{22}$-$X_{25}LCGX_{29}X_{30}LVX_{33}X_{34}LX_{36}LVCGX_{41}X_{42}GFX_{45}$ SEQ ID NO: 20);

LM comprises the sequence $(Y_1)_k$-$X_{51}AX_{53}X_{54}X_{55}X_{56}RR(Y_2)_n$ (SEQ ID NO: 23); and IA comprises the sequence $GIVX_4X_5CCX_8X_9X_{10}CX_{12}LX_{14}X_{15}LX_{17}X_{18}X_{19}CX_{21}$-$R_{13}$ (SEQ ID NO: 22), wherein n is 1 and at least one of $X_{46}$, $X_{47}$, $X_{48}$, $X_{49}$, and/or $X_{50}$ is an amino acid selected from the group of formula I, II or III. In one embodiment $Y_1$ is selected from the group consisting of F, Y, FN, YT, FNK, YTP, FNPK (SEQ ID NO: 79), FNKP (SEQ ID NO: 77), YTPK (SEQ ID NO: 78), YTPKT (SEQ ID NO: 16), YTKPT (SEQ ID NO: 80), FNKPT (SEQ ID NO: 76) and FNPKT (SEQ ID NO: 81). In another embodiment $Y_1$ is selected from the group consisting of F, FN, FNK, FNPK (SEQ ID NO: 79), FNKPT (SEQ ID NO: 76) and FNPKT (SEQ ID NO: 81). In one embodiment $Y_2$ is selected from the group consisting of A, AP, APQ and APQT (SEQ ID NO: 82). In a further embodiment n is 0. In one embodiment $X_{53}$, $X_{54}$, $X_{55}$ and $X_{56}$ are each independently selected from the group consisting of glycine, alanine, serine, threonine and proline. In one embodiment wherein IB comprises sequence J-$R_{23}$-$R_{22}$-$X_{25}LCGX_{29}X_{30}LVX_{33}$-$X_{34}LX_{36}LVCGX_{41}X_{42}GFX_{45}$ (SEQ ID NO: 20), LM comprises a sequence selected from the group consisting of $FX_{51}AX_{53}X_{54}X_{55}X_{56}RR$ (SEQ ID NO: 94),
$FX_{51}AX_{53}X_{54}X_{55}X_{56}RRA$ (SEQ ID NO: 95),
$FX_{51}AX_{53}X_{54}X_{55}X_{56}RRAP$ (SEQ ID NO: 96),
$FX_{51}AX_{53}X_{54}X_{55}X_{56}RRAPQ$ (SEQ ID NO: 97),
$FNX_{51}AX_{53}X_{54}X_{55}X_{56}RRAPQT$ (SEQ ID NO: 98),
$FNX_{51}AX_{53}X_{54}X_{55}X_{56}RR$ (SEQ ID NO: 99),
$FNX_{51}AX_{53}X_{54}X_{55}X_{56}RRA$ (SEQ ID NO: 100),
$FNX_{51}AX_{53}X_{54}X_{55}X_{56}RRAP$ (SEQ ID NO: 101),
$FNX_{51}AX_{53}X_{54}X_{55}X_{56}RRAPQ$ (SEQ ID NO: 102),
$FNX_{51}AX_{53}X_{54}X_{55}X_{56}RRAPQT$ (SEQ ID NO: 103),
$FNKX_{51}AX_{53}X_{54}X_{55}X_{56}RR$ (SEQ ID NO: 104),
$FNKX_{51}AX_{53}X_{54}X_{55}X_{56}RRA$ (SEQ ID NO: 105),
$FNKX_{51}AX_{53}X_{54}X_{55}X_{56}RRAP$ (SEQ ID NO: 106),
$FNKX_{51}AX_{53}X_{54}X_{55}X_{56}RRAPQ$ (SEQ ID NO: 107),
$FNKX_{51}AX_{53}X_{54}X_{55}X_{56}RRAPQT$ (SEQ ID NO: 108),
$FNKPX_{51}AX_{53}X_{54}X_{55}X_{56}RR$ (SEQ ID NO: 109),
$FNKPX_{51}AX_{53}X_{54}X_{55}X_{56}RRA$ (SEQ ID NO: 110),
$FNKPX_{51}AX_{53}X_{54}X_{55}X_{56}RRAP$ (SEQ ID NO: 111),
$FNKPX_{51}AX_{53}X_{54}X_{55}X_{56}RRAPQ$ (SEQ ID NO: 112),
$FNKPX_{51}AX_{53}X_{54}X_{55}X_{56}RRAPQT$ (SEQ ID NO: 113),
$FNKPTX_{51}AX_{53}X_{54}X_{55}X_{56}RR$ (SEQ ID NO: 114),
$FNKPTX_{51}AX_{53}X_{54}X_{55}X_{56}RRA$ (SEQ ID NO: 115),
$FNKPTX_{51}AX_{53}X_{54}X_{55}X_{56}RRAP$ (SEQ ID NO: 116),
$FNKPTX_{51}AX_{53}X_{54}X_{55}X_{56}RRAPQ$ (SEQ ID NO: 117),
$FNKPTX_{51}AX_{53}X_{54}X_{55}X_{56}RRAPQT$ (SEQ ID NO: 118),
$FX_{51}X_{52}GSSSRR$ (SEQ ID NO: 119), $FX_{51}X_{52}GSSSRRA$ (SEQ ID NO: 120), $FX_{51}X_{52}GSSSRRAP$ (SEQ ID NO: 121),
$FX_{51}X_{52}GSSSRRAPQ$ (SEQ ID NO: 122),
$FNX_{51}X_{52}GSSSRRAPQT$ (SEQ ID NO: 123),
$FNX_{51}X_{52}GSSSRR$ (SEQ ID NO: 124),
$FNX_{51}X_{52}GSSSRRA$ (SEQ ID NO: 125),
$FNX_{51}X_{52}GSSSRRAP$ (SEQ ID NO: 126),
$FNX_{51}X_{52}GSSSRRAPQ$ (SEQ ID NO: 127),
$FNX_{51}X_{52}GSSSRRAPQT$ (SEQ ID NO: 128),
$FNKX_{51}X_{52}GSSSRR$ (SEQ ID NO: 129),
$FNKX_{51}X_{52}GSSSRRA$ (SEQ ID NO: 130),
$FNKX_{51}X_{52}GSSSRRAP$ (SEQ ID NO: 131),
$FNKX_{51}X_{52}GSSSRRAPQ$ (SEQ ID NO: 132),
$FNKX_{51}X_{52}GSSSRRAPQT$ (SEQ ID NO: 133),
$FNKPX_{51}X_{52}GSSSRR$ (SEQ ID NO: 134),
$FNKPX_{51}X_{52}GSSSRRA$ (SEQ ID NO: 135),
$FNKPX_{51}X_{52}GSSSRRAP$ (SEQ ID NO: 136),
$FNKPX_{51}X_{52}GSSSRRAPQ$ (SEQ ID NO: 137),
$FNKPX_{51}X_{52}GSSSRRAPQT$ (SEQ ID NO: 138),
$FNKPTX_{51}X_{52}GSSSRR$ (SEQ ID NO: 139),
$FNKPTX_{51}X_{52}GSSSRRA$ (SEQ ID NO: 140),
$FNKPTX_{51}X_{52}GSSSRRAP$ (SEQ ID NO: 141),
$FNKPTX_{51}X_{52}GSSSRRAPQ$ (SEQ ID NO: 142), and
$FNKPTX_{51}X_{52}GSSSRRAPQT$ (SEQ ID NO: 143), wherein $X_{51}$ is selected from the group consisting of glycine, alanine, valine, leucine, isoleucine, proline, phenylalanine and methionine, $X_{52}$ is any amino acid other than tyrosine and $X_{46}$ through $X_{56}$ are each independently any amino acid or amino acid analog or derivative thereof. In one embodiment linking moiety of SEQ ID NO: 94-143 is pegylated and in a further embodiment an arginine residue of the linking moiety of SEQ ID NO: 94-143 is substituted with a pegylated lysine. In one embodiment the pegylated lysine is located at position 8 relative to the native IGF 1 C peptide (SEQ ID NO: 17). In one embodiment $X_{52}$ is any non-aromatic amino acid. In one embodiment wherein IB comprises sequence J-$R_{23}$-$R_{22}$-$X_{25}LCGX_{29}X_{30}LVX_{33}X_{34}LX_{36}LVCGX_{41}X_{42}GFX_{45}$ (SEQ ID NO: 20), LM consists of the sequence $GAGSSSX_{57}X_{58}$ (SEQ ID NO: 163), $GAGSSSRX_{58}APQ$ (SEQ ID NO: 167), TGYGSSSRR (SEQ ID NO: 18), TGYGSSSRR (SEQ ID NO: 144), KTGYGSSSRR (SEQ ID NO: 145), PKT-GYGSSSRR (SEQ ID NO: 146), TPKTGYGSSSRR (SEQ ID NO: 147), TKPTGYGSSSRR(SEQ ID NO: 148) or SRPAGYGSSSRR (SEQ ID NO: 149), wherein $X_{57}$ and $X_{58}$ are independently selected from arginine, ornithine and lysine.

In one embodiment the single chain insulin analog comprises a sequence selected from the group consisting of a) J-$R_{23}$-$R_{22}$-$X_{25}$LCG$X_{29}$$X_{30}$LV$X_{33}$$X_{34}$LYLVCG$X_{41}$$X_{42}$GF$X_{45}$ (SEQ ID NO: 21)-$X_{51}$$X_{52}$GSSSRR (SEQ ID NO: 27)-GIV$X_{4}$$X_{5}$CC$X_{8}$$X_{9}$$X_{10}$C$X_{12}$L$X_{14}$$X_{15}$L$X_{17}$$X_{18}$$X_{19}$C$X_{21}$-$R_{13}$ (SEQ ID NO: 22);

b) J-$R_{23}$-$R_{22}$-$X_{25}$LCG$X_{29}$$X_{30}$LV$X_{33}$$X_{34}$LYLVCG$X_{41}$$X_{42}$GF$X_{45}$ (SEQ ID NO: 21)-$X_{46}$$X_{47}$$X_{48}$$X_{49}$$X_{50}$$X_{51}$$X_{52}$GSSSRR (SEQ ID NO: 86)-GIV$X_{4}$$X_{5}$CC$X_{8}$$X_{9}$$X_{10}$C$X_{12}$L$X_{14}$$X_{15}$L$X_{17}$$X_{18}$$X_{19}$C$X_{21}$-$R_{13}$ (SEQ ID NO: 22);

c) J-$R_{23}$-$R_{22}$-$X_{25}$LCG$X_{29}$$X_{30}$LV$X_{33}$$X_{34}$LYLVCG$X_{41}$$X_{42}$GF$X_{45}$ (SEQ ID NO: 21)-$X_{51}$$X_{52}$GSSSRR (SEQ ID NO: 27)-APQT (SEQ ID NO: 82)-GIV$X_{4}$$X_{5}$CC$X_{8}$$X_{9}$$X_{10}$C$X_{12}$L$X_{14}$$X_{15}$L$X_{17}$$X_{18}$$X_{19}$C$X_{21}$-$R_{13}$ (SEQ ID NO: 22);

d) J-$R_{23}$-$R_{22}$-$X_{25}$LCG$X_{29}$$X_{30}$LV$X_{33}$$X_{34}$LYLVCG$X_{41}$$X_{42}$GF$X_{45}$ (SEQ ID NO: 21)-$X_{46}$$X_{47}$$X_{48}$$X_{49}$$X_{50}$$X_{51}$$X_{52}$GSSSR$X_{58}$APQT (SEQ ID NO: 87)-GIV$X_{4}$$X_{5}$CC$X_{8}$$X_{9}$$X_{10}$C$X_{12}$L$X_{14}$$X_{15}$L$X_{17}$$X_{18}$$X_{19}$C$X_{21}$-$R_{13}$ (SEQ ID NO: 22);

e) J-$R_{23}$-$R_{22}$-$X_{25}$LCG$X_{29}$$X_{30}$LVEALYLVCGERGFF (SEQ ID NO: 53)-$X_{51}$$X_{52}$GSSS$X_{57}$$X_{58}$APQT (SEQ ID NO: 46)-GIVEQCC$X_{8}$SICSLYQLEN$X_{19}$C$X_{21}$-$R_{13}$ (SEQ ID NO: 55);

f) J-$R_{23}$-$R_{22}$-$X_{25}$LCG$X_{29}$$X_{30}$LVEALYLVCGERGFF (SEQ ID NO: 53)-$X_{51}$$X_{52}$GSSSRR (SEQ ID NO: 27)-GIVEQCC$X_{8}$SICSLYQLEN$X_{19}$C$X_{21}$-$R_{13}$ (SEQ ID NO: 55);

g) J-$R_{23}$-$R_{22}$-$X_{25}$LCG$X_{29}$$X_{30}$LVEALYLVCGERGFF (SEQ ID NO: 53)-$X_{46}$$X_{47}$$X_{48}$$X_{49}$$X_{50}$$X_{51}$$X_{52}$GSSSR$X_{58}$ APQT (SEQ ID NO: 87)-GIVEQCC$X_{8}$SICSLYQLEN$X_{19}$C$X_{21}$-$R_{13}$ (SEQ ID NO: 55);

h) J-$R_{23}$-$R_{22}$-$X_{25}$LCG$X_{29}$$X_{30}$LVEALYLVCGERGFF (SEQ ID NO: 53)-$X_{46}$$X_{47}$$X_{48}$$X_{49}$$X_{50}$$X_{51}$$X_{52}$GSSSRR (SEQ ID NO: 87)-GIVEQCC$X_{8}$SICSLYQLEN$X_{19}$C$X_{21}$-$R_{13}$ (SEQ ID NO: 55);

i) J-$R_{23}$-$R_{22}$-$X_{25}$LCG$X_{29}$$X_{30}$LV$X_{33}$$X_{34}$LYLVCG$X_{41}$$X_{42}$GF$X_{45}$ (SEQ ID NO: 21)-GYGSSSRR (SEQ ID NO: 18)-GIV$X_{4}$$X_{5}$CC$X_{8}$$X_{9}$$X_{10}$C$X_{12}$L$X_{14}$$X_{15}$LE$X_{18}$$X_{19}$C$X_{21}$-$R_{13}$ (SEQ ID NO: 152);

j) J-$R_{23}$-$R_{22}$-$X_{25}$LCG$X_{29}$$X_{30}$LV$X_{33}$$X_{34}$LYLVCG$X_{41}$$X_{42}$GF$X_{45}$ (SEQ ID NO: 21)-GYGSSSRR (SEQ ID NO: 18)-GIVEQCC$X_{8}$SICSLYQLEN$X_{19}$C$X_{21}$-$R_{13}$ (SEQ ID NO: 55); and wherein J is H or a dipeptide element comprising the general structure of U-B, wherein U is an amino acid or a hydroxyl acid and B is an N-alkylated amino acid linked through an amide bond;

$X_{4}$ is glutamic acid or aspartic acid;
$X_{5}$ is glutamine or glutamic acid
$X_{8}$ is histidine, threonine or phenylalanine;
$X_{9}$ is serine, arginine, lysine, ornithine or alanine;
$X_{10}$ is isoleucine or serine;
$X_{12}$ is serine or aspartic acid
$X_{14}$ is tyrosine, arginine, lysine, ornithine or alanine;
$X_{15}$ is glutamine, glutamic acid, arginine, alanine, lysine, ornithine or leucine;
$X_{17}$ is glutamic acid or glutamine;
$X_{18}$ is methionine, asparagine, glutamine, aspartic acid, glutamic acid or threonine;
$X_{19}$ is an amino acid of the general structure:

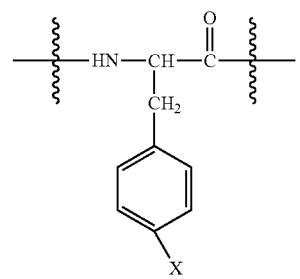

wherein X is selected from the group consisting of OH or $NHR_{10}$, wherein $R_{10}$ is H or a dipeptide element comprising the general structure U-B, wherein U is an amino acid or a hydroxyl acid and B is an N-alkylated amino acid;

$X_{21}$ is selected from the group consisting of alanine, glycine, serine, valine, threonine, isoleucine, leucine, glutamine, glutamic acid, asparagine, aspartic acid, histidine, tryptophan, tyrosine, and methionine;

$X_{25}$ is histidine or threonine;

$X_{29}$ is selected from the group consisting of alanine, glycine and serine;

$X_{30}$ is selected from the group consisting of histidine, aspartic acid, glutamic acid, homocysteic acid and cysteic acid;

$X_{33}$ is selected from the group consisting of aspartic acid, glutamine and glutamic acid;

$X_{34}$ is selected from the group consisting of alanine and threonine;

$X_{41}$ is selected from the group consisting of glutamic acid, aspartic acid or asparagine;

$X_{42}$ is selected from the group consisting of alanine, lysine, ornithine and arginine;

$X_{45}$ is an amino acid of the general structure

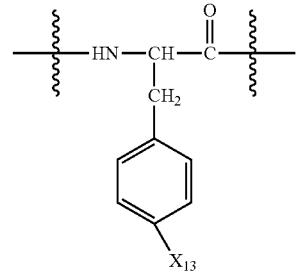

wherein $X_{13}$ is selected from the group consisting of H, OH and $NHR_{12}$, wherein $R_{12}$ is H or dipeptide element comprising the general structure U-B;

$X_{46}$ through $X_{50}$ are each independently any amino acid or amino acid analog or derivative thereof;

$X_{51}$ is selected from the group consisting of glycine, alanine, valine, leucine, isoleucine, proline, phenylalanine and methionine;

$X_{52}$ is any amino acid other than tyrosine;

$X_{57}$ and $X_{58}$ are independently arginine or lysine;

$R_{22}$ is selected from the group consisting of AYRPSE (SEQ ID NO: 14), FVNQ (SEQ ID NO: 12), PGPE (SEQ ID NO: 11), a tripeptide glycine-proline-glutamic acid, a tripeptide valine-asparagine-glutamine, a dipeptide proline-glutamic acid, a dipeptide asparagine-glutamine, glutamine, glutamic acid and an N-terminal amine;

$R_{23}$ is a bond or a 1 to 8 amino acid sequence comprising charged amino acids, including for example negatively charged amino acids; and $R_{13}$ is COOH or $CONH_2$. In one embodiment J is H and $X_{45}$ is phenylalanine or tyrosine. In a further embodiment $R_{22}$ is a bond or $GX_{60}X_{61}X_{62}X_{63}X_{64}K$ (SEQ ID NO: 153), wherein $X_{60}$, $X_{61}$, $X_{62}$, $X_{63}$ and $X_{64}$ are independently glutamic acid or aspartic acid. In a further embodiment the single chain insulin analog comprises the sequence $R_{23}$-$R_{22}$-$X_{25}LCGX_{29}X_{30}LVX_{33}X_{34}LYLVCGX_{41}X_{42}GFX_{45}$ (SEQ ID NO: 21)-$X_{51}X_{52}GSSSRR$ (SEQ ID NO: 27)-$GIVX_4X_5CCX_8X_9X_{10}CX_{12}LX_{14}X_{15}LX_{17}X_{18}X_{19}CX_{21}$-$R_{13}$ (SEQ ID NO: 22) or $R_{23}$-$R_{22}$-$X_{25}LCGX_{29}X_{30}LVX_{33}X_{34}LYLVCGX_{41}X_{42}GFX_{45}$ (SEQ ID NO: 21)-$GX_{52}GSSSRX_{58}APQT$ (SEQ ID NO: 38)-$GIVX_4X_5CCX_8X_9X_{10}CX_{12}LX_{14}X_{15}LX_{17}X_{18}X_{19}CX_{21}$-$R_{13}$ (SEQ ID NO: 22)

wherein $X_4$ is glutamic acid or aspartic acid;

$X_5$ is glutamine or glutamic acid $X_8$ is histidine, threonine or phenylalanine;

$X_9$ is serine, arginine, lysine, ornithine or alanine;

$X_{10}$ is isoleucine or serine;

$X_{12}$ is serine or aspartic acid $X_{14}$ is tyrosine, arginine, lysine, ornithine or alanine;

$X_{15}$ is glutamine, glutamic acid, arginine, alanine, lysine, ornithine or leucine;

$X_{17}$ is glutamic acid or glutamine;

$X_{18}$ is methionine, asparagine, glutamine, aspartic acid, glutamic acid or threonine;

$X_{19}$ is an amino acid of the general structure:

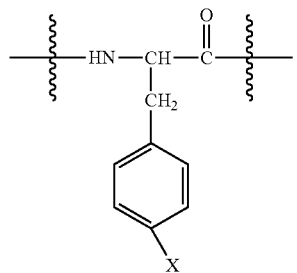

wherein X is selected from the group consisting of OH or $NHR_{10}$, wherein $R_{10}$ is H or a dipeptide element comprising the general structure U-B, wherein U is an amino acid or a hydroxyl acid and B is an N-alkylated amino acid;

$X_{21}$ is selected from the group consisting of alanine, glycine, serine, valine, threonine, isoleucine, leucine, glutamine, glutamic acid, asparagine, aspartic acid, histidine, tryptophan, tyrosine, and methionine;

$X_{25}$ is histidine or threonine;

$X_{29}$ is selected from the group consisting of alanine, glycine and serine;

$X_{30}$ is selected from the group consisting of histidine, aspartic acid, glutamic acid, homocysteic acid and cysteic acid;

$X_{33}$ is selected from the group consisting of aspartic acid, glutamine and glutamic acid;

$X_{34}$ is selected from the group consisting of alanine and threonine;

$X_{41}$ is selected from the group consisting of glutamic acid, aspartic acid or asparagine;

$X_{42}$ is selected from the group consisting of alanine, lysine, ornithine and arginine;

$X_{45}$ is phenylalanine or tyrosine;

$X_{51}$ is selected from the group consisting of glycine, alanine, valine, leucine, isoleucine and proline;

$X_{52}$ is alanine;

$X_{58}$ is arginine or lysine;

$R_{22}$ is selected from the group consisting of AYRPSE (SEQ ID NO: 14), FVNQ (SEQ ID NO: 12), PGPE (SEQ ID NO: 11), a tripeptide glycine-proline-glutamic acid, a tripeptide valine-asparagine-glutamine, a dipeptide proline-glutamic acid, a dipeptide asparagine-glutamine, glutamine, glutamic acid and an N-terminal amine;

$R_{23}$ is a bond or a 1 to 8 amino acid sequence comprising one or more negatively charged amino acids; and $R_{13}$ is COOH or $CONH_2$. In one embodiment $R_{23}$ is an N-terminal amine, a peptide comprising $X_{60}(X_{61}X_{62})_dX_{63}K$ (SEQ ID NO: 192), wherein d is an integer ranging from 1-3, or a peptide selected form the group consisting of GEK, GEEK (SEQ ID NO: 179), GEEEK (SEQ ID NO: 178), GEEEEEK (SEQ ID NO: 177), GEEEEEK (SEQ ID NO: 176), GEEEEEEEK (SEQ ID NO: 175), GDK, GDDK (SEQ ID NO: 190), GDDDK (SEQ ID NO: 189), GDDDDK (SEQ ID NO: 188), GDDDDDK (SEQ ID NO: 187), GDDDDDDK (SEQ ID NO: 186), GERK (SEQ ID NO: 174), GEERK (SEQ ID NO: 173), GEEERK (SEQ ID NO: 172), GEEEERK (SEQ ID NO: 171), GEEEEERK (SEQ ID NO: 170), GEEEEEEERK (SEQ ID NO: 169), GDRK (SEQ ID NO: 185, GDDRK (SEQ ID NO: 184), GDDDRK (SEQ ID NO: 183), GDDDDRK (SEQ ID NO: 182), GDDDDDRK (SEQ ID NO: 181), or GDDDDDDRK (SEQ ID NO: 180). In accordance with one embodiment the dipeptide element U-B comprises the structure of Formula X:

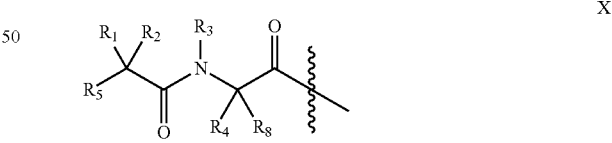

wherein (a) $R_1$, $R_2$, $R_4$ and $R_8$ are independently selected from the group consisting of H, $C_1$-$C_{18}$ alkyl, $C_2$-$C_{18}$ alkenyl, ($C_1$-$C_{18}$ alkyl)OH, ($C_1$-$C_{18}$ alkyl)SH, ($C_2$-$C_3$ alkyl)$SCH_3$, ($C_1$-$C_4$ alkyl)$CONH_2$, ($C_1$-$C_4$ alkyl)COOH, ($C_1$-$C_4$ alkyl)$NH_2$, ($C_1$-$C_4$ alkyl)$NHC(NH_2^+)NH_2$, ($C_0$-$C_4$ alkyl)($C_3$-$C_6$ cycloalkyl), ($C_0$-$C_4$ alkyl)($C_2$-$C_5$ heterocyclic), ($C_0$-$C_4$ alkyl)($C_6$-$C_{10}$ aryl)$R_7$, ($C_1$-$C_4$ alkyl)($C_3$-$C_9$ heteroaryl), and $C_1$-$C_{12}$ alkyl (W1)$C_1$-$C_{12}$ alkyl, wherein W1 is a heteroatom selected from the group consisting of N, S and O, or (ii) $R_1$ and $R_2$ together with the atoms to which they are attached form a C3-C12 cycloalkyl or aryl; or (iii) $R_4$ and $R_8$ together with the atoms to which they are attached form a $C_3$-$C_6$ cycloalkyl;

(b) $R_3$ is selected from the group consisting of $C_1$-$C_{18}$ alkyl, ($C_1$-$C_{18}$ alkyl)OH, ($C_1$-$C_{18}$ alkyl)NH$_2$, ($C_1$-$C_{18}$ alkyl)SH, ($C_0$-$C_4$ alkyl)($C_3$-$C_6$)cycloalkyl, ($C_0$-$C_4$ alkyl)($C_2$-$C_5$ heterocyclic), ($C_0$-$C_4$ alkyl)($C_6$-$C_{10}$ aryl)$R_7$, and ($C_1$-$C_4$ alkyl)($C_3$-$C_9$ heteroaryl) or $R_4$ and $R_3$ together with the atoms to which they are attached form a 4, 5 or 6 member heterocyclic ring;

(c) $R_5$ is NHR$_6$ or OH;

(d) $R_6$ is H, $C_1$-$C_8$ alkyl or $R_6$ and $R_2$ together with the atoms to which they are attached form a 4, 5 or 6 member heterocyclic ring; and (e) $R_7$ is selected from the group consisting of H and OH.

In accordance with one embodiment the dipeptide element U-B comprises the structure:

$$\underset{R_5}{\overset{R_1\ R_2}{\phantom{X}}} \cdots \underset{R_4\ R_8}{N} \cdots X$$

wherein $R_1$, $R_2$, $R_4$ and $R_8$ are independently selected from the group consisting of H, $C_1$-$C_{18}$ alkyl, $C_2$-$C_{18}$ alkenyl, ($C_1$-$C_{18}$ alkyl)OH, ($C_1$-$C_{18}$ alkyl)SH, ($C_2$-$C_3$ alkyl)SCH$_3$, ($C_1$-$C_4$ alkyl)CONH$_2$, ($C_1$-$C_4$ alkyl)COOH, ($C_1$-$C_4$ alkyl)NH$_2$, ($C_1$-$C_4$ alkyl)NHC(NH$_2^+$)NH$_2$, ($C_0$-$C_4$ alkyl)($C_3$-$C_6$ cycloalkyl), ($C_0$-$C_4$ alkyl)($C_2$-$C_5$ heterocyclic), ($C_0$-$C_4$ alkyl)($C_6$-$C_{10}$ aryl)$R_7$, ($C_1$-$C_4$ alkyl)($C_3$-$C_9$ heteroaryl), and $C_1$-$C_{12}$ alkyl (W$_1$)$C_1$-$C_{12}$ alkyl, wherein W$_1$ is a heteroatom selected from the group consisting of N, S and O, or $R_1$ and $R_2$ together with the atoms to which they are attached form a $C_3$-$C_{12}$ cycloalkyl; or $R_4$ and $R_8$ together with the atoms to which they are attached form a $C_3$-$C_6$ cycloalkyl;

$R_3$ is selected from the group consisting of $C_1$-$C_{18}$ alkyl, ($C_1$-$C_{18}$ alkyl)OH, ($C_1$-$C_{18}$ alkyl)NH$_2$, ($C_1$-$C_{18}$ alkyl)SH, ($C_0$-$C_4$ alkyl)($C_3$-$C_6$)cycloalkyl, ($C_0$-$C_4$ alkyl)($C_2$-$C_5$ heterocyclic), ($C_0$-$C_4$ alkyl)($C_6$-$C_{10}$ aryl)$R_7$, and ($C_1$-$C_4$ alkyl)($C_3$-$C_9$ heteroaryl) or $R_4$ and $R_3$ together with the atoms to which they are attached form a 4, 5 or 6 member heterocyclic ring;

$R_5$ is NHR$_6$ or OH;

$R_6$ is H, $C_1$-$C_8$ alkyl or $R_6$ and $R_1$ together with the atoms to which they are attached form a 4, 5 or 6 member heterocyclic ring; and $R_7$ is selected from the group consisting of hydrogen, $C_1$-$C_{18}$ alkyl, $C_2$-$C_{18}$ alkenyl, ($C_0$-$C_4$ alkyl)CONH$_2$, ($C_0$-$C_4$ alkyl)COOH, ($C_0$-$C_4$ alkyl)NH$_2$, ($C_0$-$C_4$ alkyl)OH, and halo.

In one specific embodiment the dipeptide element comprises the structure of Formula X wherein $R_1$ and $R_2$ are independently C1-C18 alkyl or aryl;

$R_3$ is $C_1$-$C_{18}$ alkyl or $R_3$ and $R_4$ together with the atoms to which they are attached form a 4-12 heterocyclic ring;

$R_4$ and $R_8$ are independently selected from the group consisting of hydrogen, $C_1$-$C_{18}$ alkyl and aryl; and $R_5$ is an amine or a hydroxyl.

In another specific embodiment the dipeptide element comprises the structure of Formula X wherein $R_1$ is selected from the group consisting of hydrogen, $C_1$-$C_{18}$ alkyl and aryl, or $R_1$ and $R_2$ are linked through —(CH2)p-, wherein p is 2-9;

$R_3$ is $C_1$-$C_{18}$ alkyl or $R_3$ and $R_4$ together with the atoms to which they are attached form a 4-6 heterocyclic ring;

$R_4$ and $R_8$ are independently selected from the group consisting of hydrogen, $C_1$-$C_{18}$ alkyl and aryl; and $R_5$ is an amine or N-substituted amine.

In another specific embodiment the dipeptide element comprises the structure of Formula X wherein $R_1$ and $R_2$ are independently selected from the group consisting of hydrogen, $C_1$-C8 alkyl and aryl;

$R_3$ is $C_1$-$C_{18}$ alkyl or $R_3$ and $R_4$ together with the atoms to which they are attached form a 4-6 heterocyclic ring;

$R_4$ and $R_8$ are each hydrogen; and $R_5$ is selected from the group consisting of amine, N-substituted amine and hydroxyl.

In one embodiment a prodrug form of a single chain insulin analog comprises the structure IB-LM-IA, wherein IB comprises sequence J-$R_{23}$-$R_{22}$-$X_{25}$LCGX$_{29}$X$_{30}$LVX$_{33}$X$_{34}$LX$_{36}$LVCGX$_{41}$X$_{42}$GFX$_{45}$ (SEQ ID NO: 20);

LM comprises the structure:

$$\underset{}{\overset{}{\phantom{X}}}\!\!\!\left[\text{O}\right]_m\!\!;$$

and

IA comprises the sequence GIVX$_4$X$_5$CCX$_8$X$_9$X$_{10}$CX$_{12}$LX$_{14}$X$_{15}$LX$_{17}$X$_{18}$X$_{19}$CX$_{21}$-$R_{13}$ (SEQ ID NO: 22), wherein m is an integer ranging from 5 to 15. In a further embodiment m is an integer ranging from 7 to 13.

In one embodiment the single chain insulin analog comprises a sequence selected from the group consisting of a) J-$R_{23}$-$R_{22}$-X$_{25}$LCGX$_{29}$X$_{30}$LVX$_{33}$X$_{34}$LYLVCGX$_{41}$X$_{42}$GFX$_{45}$ (SEQ ID NO: 21)-(PEG)$_{8\text{-}14}$-GIVX$_4$X$_5$CCX$_8$X$_9$X$_{10}$CX$_{12}$LX$_{14}$X$_{15}$LX$_{17}$X$_{18}$X$_{19}$CX$_{21}$-$R_{13}$ (SEQ ID NO: 22)

b) J-$R_{23}$-$R_{22}$-X$_{25}$LCGX$_{29}$X$_{30}$LVEALYLVCGERGFF (SEQ ID NO: 53)-(PEG)$_{8\text{-}14}$-GIVEQCCX$_8$SICSLYQLENX$_{19}$CX$_{21}$-$R_{13}$ (SEQ ID NO: 55)

c) J-$R_{23}$-$R_{22}$-X$_{25}$LCGX$_{29}$X$_{30}$LVEALYLVCGERGFF (SEQ ID NO: 53)-(PEG)$_{8\text{-}14}$-GIVX$_4$X$_5$CCX$_8$X$_9$X$_{10}$CX$_{12}$LX$_{14}$X$_{15}$LX$_{17}$X$_{18}$X$_{19}$CX$_{21}$-$R_{13}$ (SEQ ID NO: 22); and d) J-$R_{23}$-$R_{22}$-X$_{25}$LCGX$_{29}$X$_{30}$LVX$_{33}$X$_{34}$LYLVCGX$_{41}$X$_{42}$GFX$_{45}$ (SEQ ID NO: 21)-(PEG)$_{8\text{-}14}$-GIVEQCCX$_8$SICSLYQLENX$_{19}$CX$_{21}$-$R_{13}$ (SEQ ID NO: 55)

wherein

J is H or a dipeptide element comprising the general structure of U-B, wherein U is an amino acid or a hydroxyl acid and B is an N-alkylated amino acid linked through an amide bond;

$X_4$ is glutamic acid or aspartic acid;

$X_5$ is glutamine or glutamic acid $X_8$ is histidine, threonine or phenylalanine;

$X_9$ is serine, arginine, lysine, ornithine or alanine;

$X_{10}$ is isoleucine or serine;

$X_{12}$ is serine or aspartic acid $X_{14}$ is tyrosine, arginine, lysine, ornithine or alanine;

$X_{15}$ is glutamine, glutamic acid, arginine, alanine, lysine, ornithine or leucine;

$X_{17}$ is glutamic acid or glutamine;

$X_{18}$ is methionine, asparagine, glutamine, aspartic acid, glutamic acid or threonine;

$X_{19}$ is an amino acid of the general structure:

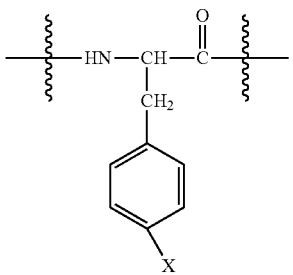

wherein X is selected from the group consisting of OH or $NHR_{10}$, wherein $R_{10}$ is H or a dipeptide element comprising the general structure U-B, wherein U is an amino acid or a hydroxyl acid and B is an N-alkylated amino acid;

$X_{21}$ is selected from the group consisting of alanine, glycine, serine, valine, threonine, isoleucine, leucine, glutamine, glutamic acid, asparagine, aspartic acid, histidine, tryptophan, tyrosine, and methionine;

$X_{25}$ is histidine or threonine;

$X_{29}$ is selected from the group consisting of alanine, glycine and serine;

$X_{30}$ is selected from the group consisting of histidine, aspartic acid, glutamic acid, homocysteic acid and cysteic acid;

$X_{33}$ is selected from the group consisting of aspartic acid, glutamine and glutamic acid;

$X_{34}$ is selected from the group consisting of alanine and threonine;

$X_{41}$ is selected from the group consisting of glutamic acid, aspartic acid or asparagine;

$X_{42}$ is selected from the group consisting of alanine, lysine, ornithine and arginine;

$X_{45}$ is an amino acid of the general structure

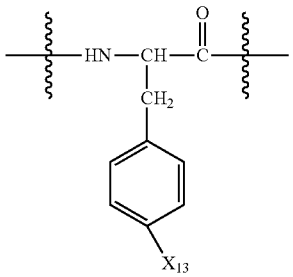

wherein $X_{13}$ is selected from the group consisting of H, OH and $NHR_{12}$, wherein $R_{12}$ is H or dipeptide element comprising the general structure U-B;

$R_{22}$ is selected from the group consisting of AYRPSE (SEQ ID NO: 14), FVNQ (SEQ ID NO: 12), PGPE (SEQ ID NO: 11), a tripeptide glycine-proline-glutamic acid, a tripeptide valine-asparagine-glutamic acid, a dipeptide proline-glutamic acid, a dipeptide asparagine-glutamine, glutamine, glutamic acid and a bond;

$R_{23}$ is a bond or $G(X_{60})_d(X_{61})_gK$ (SEQ ID NO: 191) wherein $X_{60}, X_{61}$ are independently glutamic acid or aspartic acid; and d and g are integers independently ranging from 1-6; and $R_{13}$ is COOH or $CONH_2$. As used herein the designation "$(PEG)_n$" is intended to represent a polyethylene glycol having the number of monomers indicated by the subscript number, or range of numbers, provided outside the parenthesis. In one embodiment J is H and $X_{45}$ is phenylalanine or tyrosine. In a further embodiment $R_{23}$ is a bond or $GX_{60}X_{61}X_{62}X_{63}X_{64}K$ (SEQ ID NO: 193, wherein $X_{60}, X_{61}, X_{62}, X_{63}$ and $X_{64}$ are independently glutamic acid or aspartic acid.

In accordance with one embodiment a prodrug form of a single chain insulin analog comprises the structure IB-LM-IA, wherein IB comprises the sequence $R_{22}$HLCGSX$_{30}$LVEALYLVCG ERGFF (SEQ ID NO: 154) or $X_{22}$VNQX$_{25}$LCGX$_{29}$X$_{30}$LVEALYLVCGERGFFYT-Z$_1$-B$_1$ (SEQ ID NO: 54);

LM is a linking moiety as disclosed herein and IA comprises the sequence GIVEQCCX$_8$SICSLYQLENX$_{19}$CX$_{21}$-R$_{13}$ (SEQ ID NO: 55) or GIVX$_4$ECCX$_8$X$_9$SCDLX$_{14}$X$_{15}$LX$_{17}$X$_{18}$X$_{19}$CX$_{21}$-R$_{13}$ (SEQ ID NO: 19), wherein $X_4$ is glutamic acid or aspartic acid;

$X_8$ is histidine, threonine or phenylalanine;

$X_9$ is arginine, lysine, ornithine or alanine;

$X_{14}$ is arginine, lysine, ornithine or alanine;

$X_{15}$ is glutamine, glutamic acid, arginine, alanine, lysine, ornithine or leucine;

$X_{17}$ is glutamic acid or glutamine;

$X_{18}$ is methionine, asparagine, glutamine, aspartic acid, glutamic acid or threonine;

$X_{19}$ is an amino acid of the general structure

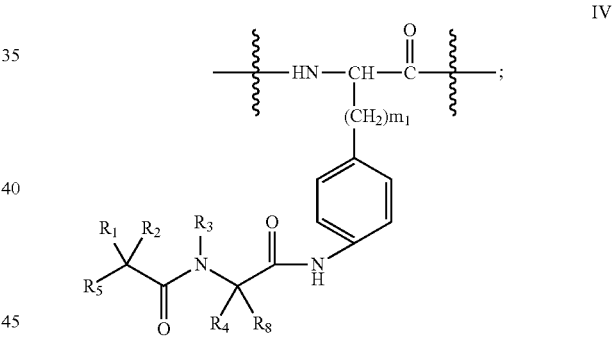

wherein $m_1$ is an integer ranging from 1 to 3;

$R_1, R_2, R_4$ and $R_8$ are independently selected from the group consisting of H, $C_1$-$C_{18}$ alkyl, $C_2$-$C_{18}$ alkenyl, ($C_1$-$C_{18}$ alkyl)OH, ($C_1$-$C_{18}$ alkyl)SH, ($C_2$-$C_3$ alkyl)SCH$_3$, ($C_1$-$C_4$ alkyl)CONH$_2$, ($C_1$-$C_4$ alkyl)COOH, ($C_1$-$C_4$ alkyl)NH$_2$, ($C_1$-$C_4$ alkyl)NHC(NH$_2$)NH$_2$, ($C_0$-$C_4$ alkyl)($C_3$-$C_6$ cycloalkyl), ($C_0$-$C_4$ alkyl)($C_2$-$C_5$ heterocyclic), ($C_0$-$C_4$ alkyl)($C_6$-$C_{10}$ aryl)R$_7$, ($C_1$-$C_4$ alkyl)($C_3$-$C_9$ heteroaryl), and $C_1$-$C_{12}$ alkyl(W$_1$)C$_1$-C$_{12}$ alkyl, wherein W$_1$ is a heteroatom selected from the group consisting of N, S and O, or R$_1$ and R$_2$ together with the atoms to which they are attached form a C$_3$-C$_{12}$ cycloalkyl; or R$_4$ and R$_8$ together with the atoms to which they are attached form a C$_3$-C$_6$ cycloalkyl;

$R_3$ is selected from the group consisting of $C_1$-$C_{18}$ alkyl, ($C_1$-$C_{18}$ alkyl)OH, ($C_1$-$C_{18}$ alkyl)NH$_2$, ($C_1$-$C_{18}$ alkyl)SH, ($C_0$-$C_4$ alkyl)($C_3$-$C_6$)cycloalkyl, ($C_0$-$C_4$ alkyl) ($C_2$-$C_5$ heterocyclic), ($C_0$-$C_4$ alkyl)($C_6$-$C_{10}$ aryl)R$_7$, and (C₁-C₄ alkyl)(C₃-C₉ heteroaryl) or R₄ and R₃ together with the atoms to which they are attached form a 4, 5 or 6 member heterocyclic ring;

R₅ is NHR₆ or OH;

R₆ is H, C₁-C₈ alkyl or R₆ and R₁ together with the atoms to which they are attached form a 4, 5 or 6 member heterocyclic ring; and R₇ is selected from the group consisting of hydrogen, C₁-C₁₈ alkyl, C₂-C₁₈ alkenyl, (C₀-C₄ alkyl)CONH₂, (C₀-C₄ alkyl)COOH, (C₀-C₄ alkyl)NH₂, (C₀-C₄ alkyl)OH, and halo;

X₂₁ is selected from the group consisting of alanine, glycine, serine, valine, threonine, isoleucine, leucine, glutamine, glutamic acid, asparagine, aspartic acid, histidine, tryptophan, tyrosine, and methionine;

X₂₂ is selected from the group consisting of phenylalanine and desamino-phenylalanine;

X₂₃ is asparagine or glycine;

X₂₅ is histidine or threonine;

X₂₉ is selected from the group consisting of alanine, glycine and serine;

X₃₀ is selected from the group consisting of histidine, aspartic acid, glutamic acid, homocysteic acid and cysteic acid;

Z₁ is a dipeptide selected from the group consisting of aspartate-lysine, lysine-proline, and proline-lysine; and B₁ is selected from the group consisting of threonine, alanine or a threonine-arginine-arginine tripeptide.

R₂₂ is selected from the group consisting of X₂₂VNQ (SEQ ID NO: 84), a tripeptide valine-asparagine-glutamine, a dipeptide asparagine-glutamine, glutamine, and an N-terminal amine; and R₁₃ is COOH or CONH₂. In one embodiment m₁ is 1. In accordance with one embodiment the single chain insulin analog comprises the structure IB-LM-IA, wherein IB comprises the sequence X₂₂VNQX₂₅LCGX₂₉X₃₀LVEALYLVCGERGFFYT-Z₁-B₁ (SEQ ID NO: 54), LM is a linking moiety as disclosed herein and IA comprises the sequence GIVX₄ECCX₈X₉SCDLX₁₄X₁₅LX₁₇X₁₈X₁₉CX₂₁-R₁₃ (SEQ ID NO: 19).

In one embodiment the single chain insulin analog comprises a compound of the formula: IB-LM-IA, wherein IB represents an IGF YL B chain comprising the sequence GPETLCGX₂₆ELVDX₂₇LYLVCGDX₄₂GFYFNKPT-R₁₄ (SEQ ID NO: 197), wherein X₂₆ and X₂₇ are each alanine and X₄₂ is arginine, or GPETLCGAELVDALYLVCGDRGFYFNPKT (SEQ ID NO: 89), LM represents a linking moiety as disclosed herein and IA represents an IGF A chain comprising the sequence GIVDECCHRSCDLRRLEMX₁₉CA-R₁₃ (SEQ ID NO: 155) or GIVDECCHOSCDLOOLQMX₁₉CN-R₁₃ (SEQ ID NO: 75) or the native insulin sequence GIVEQCCTSICSLYQLENX₁₉CN-R₁₃ (SEQ ID NO: 194) wherein X₈ is histidine or phenylalanine;

X₁₉ is an amino acid of the general structure

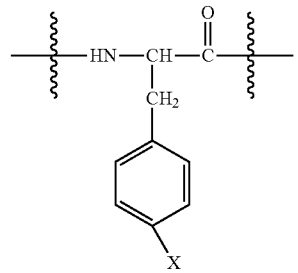

wherein X is selected from the group consisting of OH or NHR₁₀, wherein R₁₀ is a dipeptide comprising the general structure:

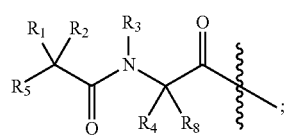

R₁ is selected from the group consisting of H and C₁-C₈ alkyl;

R₂ and R₄ are independently selected from the group consisting of H, C₁-Cₛ alkyl, C₂-C₈ alkenyl, (C₁-C₄ alkyl)OH, (C₁-C₄ alkyl)SH, (C₂-C₃ alkyl)SCH₃, (C₁-C₄ alkyl)CONH₂, (C₁-C₄ alkyl)COOH, (C₁-C₄ alkyl)NH₂, (C₁-C₄ alkyl)NHC(NH₂⁺)NH₂, (C₀-C₄ alkyl)(C₃-C₆ cycloalkyl), (C₀-C₄ alkyl)(C₆-C₁₀ aryl)R₇, and CH₂(C₅-C₉ heteroaryl), or R₁ and R₂ together with the atoms to which they are attached form a C₃-C₆ cycloalkyl;

R₃ is selected from the group consisting of C₁-C₈ alkyl, (C₁-C₄ alkyl)OH, (C₁-C₄ alkyl)NH₂, (C₁-C₄ alkyl)SH, and (C₃-C₆)cycloalkyl or R₄ and R₃ together with the atoms to which they are attached form a 5 or 6 member heterocyclic ring;

R₅ is NHR₆ or OH;

R₆ is H, or R₆ and R₂ together with the atoms to which they are attached form a 5 or 6 member heterocyclic ring;

R₇ is selected from the group consisting of H and OH; and

R₈ is H; and

R₁₃ and R₁₄ are independently COOH or CONH₂. The present invention also encompasses any combination of insulin analog A chain and B chain peptides, as disclosed herein, linked together via a linking moiety as disclosed herein as a single chain insulin analog of the formula IB-LM-IA.

The Dipeptide Prodrug Element

The substituents of the dipeptide prodrug element, and its site of attachment to the single chain insulin analog, can be selected to provide the desired half life of a prodrug analog of the single chain insulin analogs disclosed herein. For example, when a dipeptide prodrug element comprising the structure:

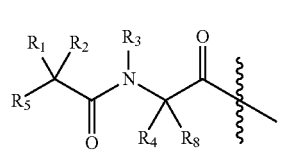

is linked to the alpha amino group of the N-terminal amino acid of the single chain insulin analog B chain, compounds having a $t_{1/2}$ of about 1 hour in PBS under physiological conditions are provided when $R_1$ and $R_2$ are independently $C_1$-$C_{18}$ alkyl or aryl; or $R_1$ and $R_2$ are linked through —$(CH_2)_p$—, wherein p is 2-9;

$R_3$ is $C_1$-$C_{18}$ alkyl;

$R_4$ and $R_8$ are each hydrogen; and $R_5$ is an amine.

In other embodiments, prodrugs linked at the N-terminus and having a $t_{1/2}$ of, e.g., about 1 hour comprise a dipeptide prodrug element with the structure:

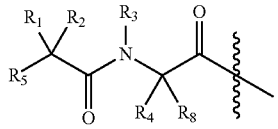

wherein
$R_1$ and $R_2$ are independently $C_1$-$C_{18}$ alkyl or $(C_0$-$C_4$ alkyl)$(C_6$-$C_{10}$ aryl)$R_7$; or $R_1$ and $R_2$ are linked through —$(CH_2)_p$—, wherein p is 2-9;

$R_3$ is $C_1$-$C_{18}$ alkyl;

$R_4$ and $R_8$ are each hydrogen;

$R_5$ is $NH_2$;

$R_7$ is selected from the group consisting of hydrogen, $C_1$-$C_{18}$ alkyl, $C_2$-$C_{18}$ alkenyl, $(C_0$-C4 alkyl)$CONH_2$, $(C_0$-$C_4$ alkyl)COOH, $(C_0$-$C_4$ alkyl)$NH_2$, $(C_0$-$C_4$ alkyl)OH, and halo; and $R_8$ is H.

Alternatively, in one embodiment a single chain insulin analog prodrug derivative is provided wherein the dipeptide prodrug is linked to the alpha amino group of the N-terminal amino acid of the single chain insulin analog B chain, and the prodrug has a $t_{1/2}$ between about 6 to about 24 hours in PBS under physiological conditions. In one embodiment a single chain insulin analog prodrug derivative having a $t_{1/2}$ between about 6 to about 24 hours in PBS under physiological conditions is provided wherein the prodrug element has the structure of Formula X and $R_1$ and $R_2$ are independently selected from the group consisting of hydrogen, $C_1$-$C_{18}$ alkyl and aryl, or $R_1$ and $R_2$ are linked through —$(CH_2)_p$—, wherein p is 2-9;

$R_3$ is $C_1$-$C_{18}$ alkyl or $R_3$ and $R_4$ together with the atoms to which they are attached form a 4-12 heterocyclic ring;

$R_4$ and $R_8$ are independently selected from the group consisting of hydrogen, $C_1$-$C_8$ alkyl and aryl; and $R_5$ is an amine, with the proviso that both $R_1$ and $R_2$ are not hydrogen and provided that one of $R_4$ or $R_8$ is hydrogen.

In a further embodiment a single chain insulin analog prodrug derivative is provided wherein the dipeptide prodrug is linked to the alpha amino group of the N-terminal amino acid of the single chain insulin analog B chain, and the prodrug has a $t_{1/2}$ between about 72 to about 168 hours in PBS under physiological conditions. In one embodiment a single chain insulin analog prodrug derivative having a $t_{1/2}$ between about 72 to about 168 hours in PBS under physiological conditions is provided wherein the prodrug element has the structure of Formula X and $R_1$ is selected from the group consisting of hydrogen, $C_1$-$C_8$ alkyl and aryl;

$R_2$ is H;

$R_3$ is $C_1$-$C_{18}$ alkyl;

$R_4$ and $R_8$ are each hydrogen; and $R_5$ is an amine or N-substituted amine or a hydroxyl;

with the proviso that, if $R_1$ is alkyl or aryl, then $R_1$ and $R_5$ together with the atoms to which they are attached form a 4-11 heterocyclic ring.

In some embodiments, prodrugs having the dipeptide prodrug element linked to the N-terminal alpha amino acid of the single chain insulin analog B chain peptide and having a $t_{1/2}$, e.g., between about 12 to about 72 hours, or in some embodiments between about 12 to about 48 hours, comprise a dipeptide prodrug element with the structure:

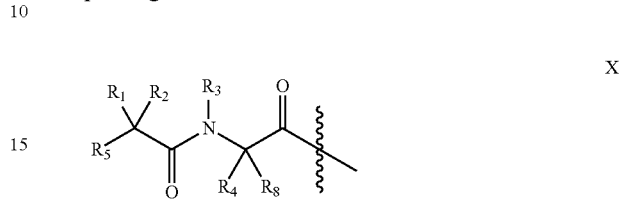

wherein $R_1$ and $R_2$ are independently selected from the group consisting of hydrogen, $C_1$-$C_{18}$ alkyl, $(C_1$-$C_{18}$ alkyl)OH, $(C_1$-$C_4$ alkyl)$NH_2$, and $(C_0$-$C_4$ alkyl)$(C_6$-$C_{10}$ aryl)$R_7$, or $R_1$ and $R_2$ are linked through $(CH_2)_p$, wherein p is 2-9;

$R_3$ is $C_1$-$C_{18}$ alkyl or $R_3$ and $R_4$ together with the atoms to which they are attached form a 4-12 heterocyclic ring;

$R_4$ and $R_8$ are independently selected from the group consisting of hydrogen, $C_1$-$C_s$ alkyl and $(C_0$-$C_4$ alkyl)$(C_6$-$C_{10}$ aryl)$R_7$;

$R_5$ is $NH_2$; and $R_7$ is selected from the group consisting of H, $C_1$-$C_{18}$ alkyl, $C_2$-$C_{18}$ alkenyl, $(C_0$-$C_4$ alkyl)$CONH_2$, $(C_0$-$C_4$ alkyl)COOH, $(C_0$-$C_4$ alkyl)$NH_2$, $(C_0$-$C_4$ alkyl)OH, and halo;

with the proviso that both $R_1$ and $R_2$ are not hydrogen and provided that at least one of $R_4$ or $R_8$ is hydrogen.

In some embodiments, prodrugs having the dipeptide prodrug element linked to the N-terminal amino acid of the single chain insulin analog B chain peptide and having a $t_{1/2}$, e.g., between about 12 to about 72 hours, or in some embodiments between about 12 to about 48 hours, comprise a dipeptide prodrug element with the structure:

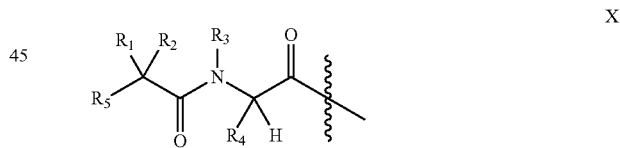

wherein $R_1$ and $R_2$ are independently selected from the group consisting of hydrogen, $C_1$-$C_8$ alkyl and $(C_1$-$C_4$ alkyl)$NH_2$, or $R_1$ and $R_2$ are linked through $(CH_2)_p$, wherein p is 2-9;

$R_3$ is $C_1$-$C_8$ alkyl or $R_3$ and $R_4$ together with the atoms to which they are attached form a 4-6 heterocyclic ring;

$R_4$ is selected from the group consisting of hydrogen and $C_1$-$C_8$ alkyl; and $R_5$ is $NH_2$;

with the proviso that both $R_1$ and $R_2$ are not hydrogen.

In other embodiments, prodrugs having the dipeptide prodrug element linked to the N-terminal amino acid of the single chain insulin analog B chain peptide and having a $t_{1/2}$, e.g., between about 12 to about 72 hours, or in some embodiments between about 12 to about 48 hours, comprise a dipeptide prodrug element with the structure:

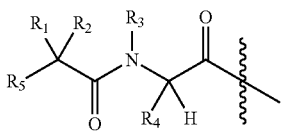

wherein
$R_1$ and $R_2$ are independently selected from the group consisting of hydrogen, $C_1$-$C_8$ alkyl and ($C_1$-$C_4$ alkyl)$NH_2$;
$R_3$ is $C_1$-$C_6$ alkyl;
$R_4$ is hydrogen; and
$R_5$ is $NH_2$,
with the proviso that both $R_1$ and $R_2$ are not hydrogen.

In some embodiments, prodrugs having the dipeptide prodrug element linked to the N-terminal amino acid of the single chain insulin analog B chain peptide and having a $t_{1/2}$, e.g., between about 12 to about 72 hours, or in some embodiments between about 12 to about 48 hours, comprise a dipeptide prodrug element with the structure:

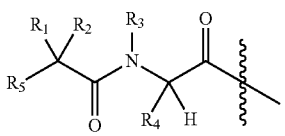

wherein
$R_1$ and $R_2$ are independently selected from the group consisting of hydrogen and $C_1$-$C_8$ alkyl, ($C_1$-$C_4$ alkyl)$NH_2$, or $R_1$ and $R_2$ are linked through $(CH_2)_p$, wherein p is 2-9;
$R_3$ is $C_1$-$C_8$ alkyl;
$R_4$ is ($C_0$-$C_4$ alkyl)($C_6$-$C_{10}$ aryl)$R_7$;
$R_5$ is $NH_2$; and
$R_7$ is selected from the group consisting of hydrogen, $C_1$-$C_8$ alkyl and ($C_0$-$C_4$ alkyl)OH;
with the proviso that both $R_1$ and $R_2$ are not hydrogen.

In addition a prodrug having the dipeptide prodrug element linked to the N-terminal alpha amino acid of the single chain insulin analog and having a $t_{1/2}$, e.g., of about 72 to about 168 hours is provided wherein the dipeptide prodrug element has the structure:

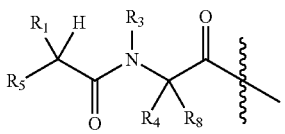

wherein $R_1$ is selected from the group consisting of hydrogen, $C_1$-$C_8$ alkyl and ($C_0$-$C_4$ alkyl)($C_6$-$C_{10}$ aryl)$R_7$;
$R_3$ is $C_1$-$C_{18}$ alkyl;
$R_4$ and $R_8$ are each hydrogen;
$R_5$ is $NHR_6$ or OH;
$R_6$ is H, $C_1$-$C_8$ alkyl, or $R_6$ and $R_1$ together with the atoms to which they are attached form a 4, 5 or 6 member heterocyclic ring; and
$R_7$ is selected from the group consisting of hydrogen, $C_1$-$C_{18}$ alkyl, $C_2$-$C_{18}$ alkenyl, ($C_0$-$C_4$ alkyl)$CONH_2$, ($C_0$-$C_4$ alkyl)COOH, ($C_0$-$C_4$ alkyl)$NH_2$, ($C_0$-$C_4$ alkyl)OH, and halo;

with the proviso that, if $R_1$ is alkyl or ($C_0$-$C_4$ alkyl)($C_6$-$C_{10}$ aryl)$R_7$, then $R_1$ and $R_5$ together with the atoms to which they are attached form a 4-11 heterocyclic ring.

In some embodiments the dipeptide prodrug element is linked to a side chain amine of an internal amino acid of the single chain insulin analog. In this embodiment prodrugs having a $t_{1/2}$, e.g., of about 1 hour have the structure:

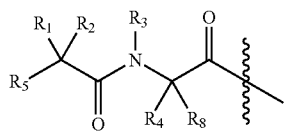

wherein
$R_1$ and $R_2$ are independently $C_1$-$C_8$ alkyl or ($C_0$-$C_4$ alkyl)($C_6$-$C_{10}$ aryl)$R_7$; or $R_1$ and $R_2$ are linked through $-(CH_2)_p-$, wherein p is 2-9;
$R_3$ is $C_1$-$C_{18}$ alkyl;
$R_4$ and $R_8$ are each hydrogen;
$R_5$ is $NH_2$; and
$R_7$ is selected from the group consisting of hydrogen, $C_1$-$C_{18}$ alkyl, $C_2$-$C_{18}$ alkenyl, ($C_0$-C4 alkyl)$CONH_2$, ($C_0$-$C_4$ alkyl)COOH, ($C_0$-$C_4$ alkyl)$NH_2$, ($C_0$-$C_4$ alkyl)OH, and halo.

Furthermore, prodrugs having a $T_{1/2}$, e.g., between about 6 to about 24 hours and having the dipeptide prodrug element linked to an internal amino acid side chain are provided wherein the prodrug comprises a dipeptide prodrug element with the structure:

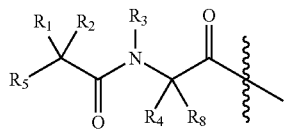

wherein $R_1$ and $R_2$ are independently selected from the group consisting of hydrogen, $C_1$-$C_8$ alkyl, and ($C_0$-$C_4$ alkyl)($C_6$-$C_{10}$ aryl)$R_7$, or $R_1$ and $R_2$ are linked through $-(CH_2)_p-$, wherein p is 2-9;
$R_3$ is $C_1$-$C_{18}$ alkyl or $R_3$ and $R_4$ together with the atoms to which they are attached form a 4-12 heterocyclic ring;
$R_4$ and $R_8$ are independently hydrogen, $C_1$-$C_{18}$ alkyl or ($C_0$-$C_4$ alkyl)($C_6$-$C_{10}$ aryl)$R_7$;
$R_5$ is $NHR_6$;
$R_6$ is H or $C_1$-$C_8$ alkyl, or $R_6$ and $R_2$ together with the atoms to which they are attached form a 4, 5 or 6 member heterocyclic ring; and
$R_7$ is selected from the group consisting of hydrogen, $C_1$-$C_{18}$ alkyl, $C_2$-$C_{18}$ alkenyl, ($C_0$-$C_4$ alkyl)$CONH_2$, ($C_0$-$C_4$ alkyl)COOH, ($C_0$-$C_4$ alkyl)$NH_2$, ($C_0$-$C_4$ alkyl)OH, and halo;
with the proviso that both $R_1$ and $R_2$ are not hydrogen and provided that at least one of $R_4$ or $R_8$ is hydrogen.

In addition a prodrug having a $t_{1/2}$, e.g., of about 72 to about 168 hours and having the dipeptide prodrug element linked to a internal amino acid side chain of the single chain insulin analog is provided wherein the dipeptide prodrug element has the structure:

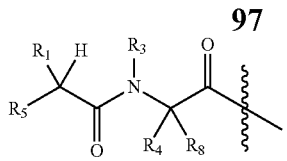

wherein $R_1$ is selected from the group consisting of hydrogen, $C_1$-$C_{18}$ alkyl and $(C_0$-$C_4$ alkyl$)(C_6$-$C_{10}$ aryl$)R_7$;

$R_3$ is $C_1$-$C_{18}$ alkyl;

$R_4$ and $R_8$ are each hydrogen;

$R_5$ is $NHR_6$ or $OH$;

$R_6$ is H or $C_1$-$C_8$ alkyl, or $R_6$ and $R_1$ together with the atoms to which they are attached form a 4, 5 or 6 member heterocyclic ring; and $R_7$ is selected from the group consisting of hydrogen, $C_1$-$C_{18}$ alkyl, $C_2$-$C_{18}$ alkenyl, $(C_0$-$C_4$ alkyl$)CONH_2$, $(C_0$-$C_4$ alkyl$)COOH$, $(C_0$-$C_4$ alkyl$)NH_2$, $(C_0$-$C_4$ alkyl$)OH$, and halo; with the proviso that, if $R_1$ and $R_2$ are both independently an alkyl or $(C_0$-$C_4$ alkyl$)(C_6$-$C_{10}$ aryl$)R_7$, either $R_1$ or $R_2$ is linked through $(CH_2)_p$ to $R_5$, wherein p is 2-9.

In some embodiments the dipeptide prodrug element is linked to a side chain amine of an internal amino acid of the single chain insulin analog wherein the internal amino acid comprises the structure of Formula V

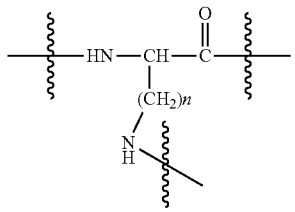

wherein n is an integer selected from 1 to 4. In some embodiments n is 3 or 4 and in some embodiments the internal amino acid is lysine. In some embodiments the dipeptide prodrug element is linked to a primary amine on a side chain of an amino acid located at position 28, or 29 of the B-chain of the single chain insulin analog.

In embodiments where the dipeptide prodrug element of formula X is linked to an amino substituent of an aryl group of an aromatic amino acid, prodrug, the substituents of the prodrug element can be selected to provide the desired time of activation. For example, the half life of a prodrug analog of any of the single chain insulin analogs disclosed herein comprising an amino acid of the structure of Formula IV:

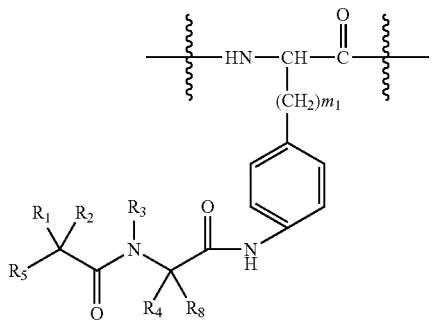

wherein $m_1$ is an integer from 0 to 3, can be selected by altering the substituents of $R_1$, $R_2$, $R_3$, $R_4$, $R_5$, and $R_8$. In one embodiment the amino acid of formula V is present at an amino acid corresponding to position A19, B16 or B25 of native insulin, and in one specific example the amino acid of formula V is located at position A19 of the single chain insulin analog, and $m_1$ is 1. In one embodiment a single chain insulin analog prodrug derivative comprising the structure of Formula IV and having a t½ of about 1 hour in PBS under physiological conditions is provided. In one embodiment the single chain insulin analog prodrug derivative having a t½ of about 1 hour in PBS under physiological conditions comprises the structure of formula IV wherein, $R_1$ and $R_2$ are independently $C_1$-$C_{18}$ alkyl or aryl;

$R_3$ is $C_1$-$C_{18}$ alkyl or $R_3$ and $R_4$ together with the atoms to which they are attached form a 4-12 heterocyclic ring;

$R_4$ and $R_8$ are independently selected from the group consisting of hydrogen, $C_1$-$C_{18}$ alkyl and aryl; and $R_5$ is an amine or a hydroxyl. In one embodiment $m_1$ is 1.

In one embodiment, the dipeptide prodrug element is linked to the single chain insulin analog via an amine present on an aryl group of an aromatic amino acid of the single chain insulin analog, wherein the prodrug has a $t_{1/2}$, e.g., of about 1 hour has a dipeptide structure of:

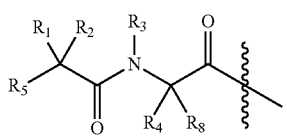

wherein $R_1$ and $R_2$ are independently $C_1$-$C_{18}$ alkyl or $(C_0$-$C_4$ alkyl$)(C_6$-$C_{10}$ aryl$)R_7$;

$R_3$ is $C_1$-$C_{18}$ alkyl or $R_3$ and $R_4$ together with the atoms to which they are attached form a 4-12 heterocyclic ring;

$R_4$ and $R_8$ are independently selected from the group consisting of hydrogen, $C_1$-$C_{18}$ alkyl and $(C_0$-$C_4$ alkyl$)(C_6$-$C_{10}$ aryl$)R_7$;

$R_5$ is $NH_2$ or $OH$; and $R_7$ is selected from the group consisting of hydrogen, $C_1$-$C_{18}$ alkyl, $C_2$-$C_{18}$ alkenyl, $(C_0$-$C_4$ alkyl$)CONH_2$, $(C_0$-$C_4$ alkyl$)COOH$, $(C_0$-$C_4$ alkyl$)NH_2$, $(C_0$-$C_4$ alkyl$)OH$, and halo.

In another embodiment a single chain insulin analog prodrug derivative comprising the structure of Formula IV, wherein $m_1$ is an integer from 0 to 3 and having a t½ of about 6 to about 24 hours in PBS under physiological conditions, is provided. In one embodiment where the single chain insulin analog prodrug having a t½ of about 6 to about 24 hours in PBS under physiological conditions comprises the structure of formula IV wherein, $R_1$ is selected from the group consisting of hydrogen, $C_1$-$C_{18}$ alkyl and aryl, or $R_1$ and $R_2$ are linked through —$(CH_2)_p$—, wherein p is 2-9;

$R_3$ is $C_1$-$C_{18}$ alkyl or $R_3$ and $R_4$ together with the atoms to which they are attached form a 4-6 heterocyclic ring;

$R_4$ and $R_8$ are independently selected from the group consisting of hydrogen, $C_1$-$C_{18}$ alkyl and aryl; and $R_5$ is an amine or N-substituted amine. In one embodiment $m_1$ is 1.

In one embodiment, prodrugs having the dipeptide prodrug element linked via an aromatic amino acid and having a $t_{1/2}$, e.g., of about 6 to about 24 hours are provided wherein the dipeptide comprises a structure of:

$$\text{R}_5\text{--}\underset{\underset{\text{O}}{\|}}{\text{C}}(\text{R}_1)(\text{H})\text{--C(O)--N(R}_3)\text{--C(R}_4)(\text{R}_8)\text{--}$$

wherein

R₁ is selected from the group consisting of hydrogen, $C_1$-$C_{18}$ alkyl, ($C_1$-$C_{18}$ alkyl)OH, ($C_1$-$C_4$ alkyl)NH$_2$, and ($C_0$-$C_4$ alkyl)($C_6$-$C_{10}$ aryl)R$_7$;

$R_3$ is $C_1$-$C_{18}$ alkyl or $R_3$ and $R_4$ together with the atoms to which they are attached form a 4-6 heterocyclic ring;

$R_4$ and $R_8$ are independently selected from the group consisting of hydrogen, $C_1$-$C_{18}$ alkyl and ($C_0$-$C_4$ alkyl)($C_6$-$C_{10}$ aryl)R$_7$;

$R_5$ is NHR$_6$;

$R_6$ is H, $C_1$-$C_8$ alkyl, or $R_6$ and $R_1$ together with the atoms to which they are attached form a 4, 5 or 6 member heterocyclic ring; and $R_7$ is selected from the group consisting of hydrogen, $C_1$-$C_{18}$ alkyl, $C_2$-$C_{18}$ alkenyl, ($C_0$-$C_4$ alkyl)CONH$_2$, ($C_0$-$C_4$ alkyl)COOH, ($C_0$-$C_4$ alkyl)NH$_2$, ($C_0$-$C_4$ alkyl)OH, and halo.

In another embodiment a single chain insulin analog prodrug derivative comprising the structure of Formula IV, wherein $m_1$ is an integer from 0 to 3 and having a t½ of about 72 to about 168 hours in PBS under physiological conditions, is provided. In one embodiment where the single chain insulin analog prodrug derivative having a t½ of about 72 to about 168 hours in PBS under physiological conditions comprises the structure of formula IV wherein, $R_1$ and $R_2$ are independently selected from the group consisting of hydrogen, $C_1$-$C_8$ alkyl and aryl;

$R_3$ is $C_1$-$C_{18}$ alkyl or $R_3$ and $R_4$ together with the atoms to which they are attached form a 4-6 heterocyclic ring;

$R_4$ and $R_8$ are each hydrogen; and $R_5$ is selected from the group consisting of amine, N-substituted amine and hydroxyl. In one embodiment $m_1$ is 1.

In one embodiment, prodrugs having the dipeptide prodrug element linked via an aromatic amino acid and having a $t_{1/2}$, e.g., of about 72 to about 168 hours are provided wherein the dipeptide comprises a structure of:

$$\text{R}_5\text{--C(R}_1)(\text{H})\text{--C(O)--N(R}_3)\text{--C(R}_4)(\text{R}_8)\text{--}$$

wherein $R_1$ and $R_2$ are independently selected from the group consisting of hydrogen, $C_1$-$C_8$ alkyl, ($C_1$-$C_4$ alkyl)COOH, and ($C_0$-$C_4$ alkyl)($C_6$-$C_{10}$ aryl)R$_7$, or $R_1$ and $R_5$ together with the atoms to which they are attached form a 4-11 heterocyclic ring;

$R_3$ is $C_1$-$C_{18}$ alkyl or $R_3$ and $R_4$ together with the atoms to which they are attached form a 4-6 heterocyclic ring;

$R_4$ is hydrogen or forms a 4-6 heterocyclic ring with $R_3$;

$R_8$ is hydrogen;

$R_5$ is NHR$_6$ or OH;

$R_6$ is H or $C_1$-$C_8$ alkyl, or $R_6$ and $R_1$ together with the atoms to which they are attached form a 4, 5 or 6 member heterocyclic ring; and $R_7$ is selected from the group consisting of hydrogen, $C_1$-$C_{18}$ alkyl, $C_2$-$C_{18}$ alkenyl, ($C_0$-$C_4$ alkyl)CONH$_2$, ($C_0$-$C_4$ alkyl)COOH, ($C_0$-$C_4$ alkyl)NH$_2$, ($C_0$-$C_4$ alkyl)OH, and halo.

In accordance with one embodiment the dipeptide of Formula X is further modified to comprise a large polymer that interferes with the single chain insulin analog's ability to interact with the insulin or IGF-1 receptor. Subsequent cleavage of the dipeptide releases the single chain insulin analog from the dipeptide complex wherein the released single chain insulin analog is fully active. In accordance with one embodiment the dipeptide of Formula X is further modified to comprises a large polymer that interferes with the bound single chain insulin analog's ability to interact with the insulin or IGF-1 receptor. In accordance with one embodiment the single chain insulin analog comprises a dipeptide of the general structure of Formula X:

$$\text{R}_5\text{--C(R}_1)(\text{R}_2)\text{--C(O)--N(R}_3)\text{--C(R}_4)(\text{R}_8)\text{--} \quad\quad X$$

wherein one of the amino acid side chains of the dipeptide of Formula X is pegylated or acylated.

In one embodiment a single chain insulin analog is provided that comprises the structure IB-LM-IA, wherein IB comprises sequence J-R$_{23}$-R$_{22}$-X$_{25}$LCGX$_{29}$X$_{30}$LVX$_{33}$X$_{34}$LX$_{36}$LVCGX$_{41}$X$_{42}$GFX$_{45}$ (SEQ ID NO: 20);

LM comprises a linking moiety as described herein; and

IA comprises the sequence GIVX$_4$X$_5$CCX$_8$X$_9$X$_{10}$CX$_{12}$LX$_{14}$X$_{18}$LEX$_{18}$X$_{19}$CX$_{21}$-R$_{13}$ (SEQ ID NO: 152), wherein J is H or a dipeptide element of formula X;

X$_4$ is glutamic acid or aspartic acid;

X$_5$ is glutamine or glutamic acid

X$_8$ is histidine, threonine or phenylalanine;

X$_9$ is serine, arginine, lysine, ornithine or alanine;

X$_{10}$ is isoleucine or serine;

X$_{12}$ is serine or aspartic acid

X$_{14}$ is tyrosine, arginine, lysine, ornithine or alanine;

X$_{15}$ is glutamine, glutamic acid, arginine, alanine, lysine, ornithine or leucine;

X$_{18}$ is methionine, asparagine, glutamine, aspartic acid, glutamic acid or threonine;

X$_{19}$ is an amino acid of the general structure:

$$\text{--HN--CH(CH}_2\text{-C}_6\text{H}_4\text{-X)--C(O)--}$$

wherein X is selected from the group consisting of OH or NHR$_{10}$, wherein R$_{10}$ is H or a dipeptide element comprising the general structure of Formula X;

X$_{21}$ is selected from the group consisting of alanine, glycine, serine, valine, threonine, isoleucine, leucine, glutamine, glutamic acid, asparagine, aspartic acid, histidine, tryptophan, tyrosine, and methionine;

$X_{25}$ is histidine or threonine;

$X_{29}$ is selected from the group consisting of alanine, glycine and serine;

$X_{30}$ is selected from the group consisting of histidine, aspartic acid, glutamic acid, homocysteic acid and cysteic acid;

$X_{33}$ is selected from the group consisting of aspartic acid, glutamine and glutamic acid;

$X_{34}$ is selected from the group consisting of alanine and threonine;

$X_{41}$ is selected from the group consisting of glutamic acid, aspartic acid or asparagine;

$X_{42}$ is selected from the group consisting of alanine, lysine, ornithine and arginine;

$X_{45}$ is an amino acid of the general structure

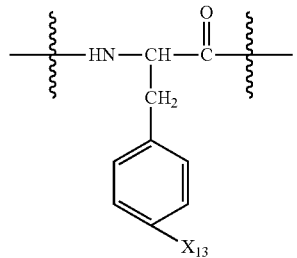

wherein $X_{13}$ is selected from the group consisting of H, OH and $NHR_{12}$, wherein $R_{12}$ is H or dipeptide element comprising the general structure of Formula X;

$R_{22}$ is selected from the group consisting of AYRPSE (SEQ ID NO: 14), FVNQ (SEQ ID NO: 12), PGPE (SEQ ID NO: 11), a tripeptide glycine-proline-glutamic acid, a tripeptide valine-asparagine-glutamine, a dipeptide proline-glutamic acid, a dipeptide asparagine-glutamine, glutamine, glutamic acid and an N-terminal amine;

$R_{23}$ is a bond or $G(X_{60})_d(X_{61})_gK$ (SEQ ID NO: 191) wherein $X_{60}, X_{61}$ are independently glutamic acid or aspartic acid; and d and g are integers independently ranging from 1-6; and $R_{13}$ is COOH or CONH, further wherein the dipeptide of Formula X is acylated or pegylated. In one embodiment J comprises an acylated or pegylated dipeptide of Formula X.

The single chain insulin analogs and prodrug derivative thereof disclosed herein can be further modified to improve the peptide's solubility in aqueous solutions at physiological pH, while enhancing the effective duration of the peptide by preventing renal clearance of the peptide. Peptides are easily cleared because of their relatively small molecular size when compared to plasma proteins. Increasing the molecular weight of a peptide above 40 kDa exceeds the renal threshold and significantly extends duration in the plasma. Accordingly, in one embodiment the peptide prodrugs are further modified to comprise a covalently linked hydrophilic moiety.

In one embodiment the hydrophilic moiety is a plasma protein, polyethylene glycol chain or the Fc portion of an immunoglobin. Therefore, in one embodiment the presently disclosed insulin analogs are further modified to comprise one or more hydrophilic groups covalently linked to the side chains of amino acids.

In accordance with one embodiment the insulin prodrugs disclosed herein are further modified by linking a hydrophilic moiety to either the N-terminal amino acid of the B chain or to the side chain of a lysine amino acid (or other suitable amino acid) located at the carboxy terminus of the B chain, including for example, at position 28 of SEQ ID NO: 89. In one embodiment a single-chain insulin prodrug derivative is provided wherein one of the amino acids of the linking moiety is modified by linking a hydrophilic moiety to the side chain of the peptide linker. In one embodiment the modified amino acid is cysteine, lysine or acetyl phenylalanine.

In accordance with one embodiment a prodrug derivative of the single chain insulin analog is provided wherein the dipeptide element of Formula X further comprises an polyethylene glycol, alkyl or acyl group. In one embodiment one or more polyethylene glycol chains are linked to the dipeptide of Formula X wherein the combined molecular weight of the polyethylene glycol chains ranges from about 20,000 to about 80,000 Daltons, or 40,000 to 80,000 Daltons or 40,000 to 60,000 Daltons. In one embodiment at least one polyethylene glycol chain having a molecular weight of about 40,000 Daltons is linked to the dipeptide of Formula X. In another embodiment the dipeptide of Formula X is acylated with an acyl group of sufficient size to bind serum albumin and thus inactivate the $IGF^{B16B17}$ analog peptide upon administration. The acyl group can be linear or branched, and in one embodiment is a C16 to C30 fatty acid. For example, the acyl group can be any of a C16 fatty acid, C18 fatty acid, C20 fatty acid, C22 fatty acid, C24 fatty acid, C26 fatty acid, C28 fatty acid, or a C30 fatty acid. In some embodiments, the acyl group is a C16 to C20 fatty acid, e.g., a C18 fatty acid or a C20 fatty acid.

In another embodiment the single chain insulin analog peptides, and their prodrug analogs, disclosed herein are further modified by the addition of a modified amino acid to the carboxy or amino terminus of the A chain or the amino terminus of the B chain of the single chain insulin analog peptide, wherein the added amino acid is modified to comprise a hydrophilic moiety linked to the amino acid. In one embodiment the amino acid added to the C-terminus is a modified cysteine, lysine or acetyl phenylalanine. In one embodiment the hydrophilic moiety is selected from the group consisting of a plasma protein, polyethylene glycol chain and an Fc portion of an immunoglobin.

In one embodiment the hydrophilic group is a polyethylene glycol chain, and in one embodiment two or more polyethylene glycol chains are covalently attached to two or more amino acid side chains of the single chain insulin analog. In accordance with one embodiment the hydrophilic moiety is covalently attached to an amino acid side chain of a single chain insulin analog disclosed herein at a position corresponding to A10, B28, B29, the C-terminus of the A chain or the N-terminus of the B chain (positions relative to native insulin). For single chain insulin analogs and their prodrug derivatives having multiple polyethylene glycol chains, the polyethylene glycol chains can be attached at the N-terminal amino acid of the B chain or to the side chain of a lysine amino acid located at the carboxy terminus of the B chain, or by the addition of a single amino acid at the C-terminus of the peptide wherein the added amino acid has a polyethylene glycol chain linked to its side chain. In accordance with one embodiment a prodrug derivative is provided wherein the polyethylene glycol chain or other hydrophilic moiety is linked to the side chain of one of the two amino acids comprising the dipeptide prodrug element. In one embodiment the dipeptide prodrug element comprises a lysine (in the D or L stereoisomer configuration) with a polyethylene glycol chain attached to the side chain amine of the lysine.

In accordance with one embodiment, the single chain insulin analog peptides, or prodrug derivatives thereof, disclosed herein are further modified by amino acid substitutions, wherein the substituting amino acid comprises a side chain suitable for crosslinking with hydrophilic moieties, including for example, polyethylene glycol. For example, in one embodiment a native amino acid at a position corresponding to A5, A8, A9, A10, A12, A14, A15, A17, A18, B1, B2, B3, B4, B5, B13, B14, B17, B21, B22, B26, B27, B28, B29 and B30 of native insulin is substituted with a lysine, cysteine or acetyl phenylalanine residue (or a lysine, cysteine or acetyl phenylalanine residue is added to the C-terminus) to allow for the covalent attachment of a polyethylene glycol chain.

In one embodiment the single chain insulin analog, or prodrug derivative thereof, has a single cysteine substitution or a single cysteine residue added to the amino or carboxy terminus of the single chain insulin analog, or an amino acid within the linking moiety or the dipeptide element of an insulin prodrug derivative is substituted with at least one cysteine residue, wherein the side chain of the cysteine residue is further modified with a thiol reactive reagent, including for example, maleimido, vinyl sulfone, 2-pyridylthio, haloalkyl, and haloacyl. These thiol reactive reagents may contain carboxy, keto, hydroxyl, and ether groups as well as other hydrophilic moieties such as polyethylene glycol units. In an alternative embodiment, the single chain insulin analog, or prodrug derivative thereof, has a single lysine substitution or a single lysine residue added to the amino or carboxy terminus of the single chain insulin analog, or an amino acid within the linking moiety or the dipeptide element of an insulin prodrug derivative is substituted with lysine, and the side chain of the substituting lysine residue is further modified using amine reactive reagents such as active esters (succinimido, anhydride, etc) of carboxylic acids or aldehydes of hydrophilic moieties such as polyethylene glycol.

In accordance with one embodiment a pharmaceutical composition is provided comprising any of the novel single chain insulin analogs disclosed herein, preferably at a purity level of at least 90%, 91%, 92%, 93%, 94%, 95%, 96%, 97%, 98% or 99%, and a pharmaceutically acceptable diluent, carrier or excipient. Such compositions may contain a single chain insulin analog as disclosed herein at a concentration of at least 0.5 mg/ml, 1 mg/ml, 2 mg/ml, 3 mg/ml, 4 mg/ml, 5 mg/ml, 6 mg/ml, 7 mg/ml, 8 mg/ml, 9 mg/ml, 10 mg/ml, 11 mg/ml, 12 mg/ml, 13 mg/ml, 14 mg/ml, 15 mg/ml, 16 mg/ml, 17 mg/ml, 18 mg/ml, 19 mg/ml, 20 mg/ml, 21 mg/ml, 22 mg/ml, 23 mg/ml, 24 mg/ml, 25 mg/ml or higher. In one embodiment the pharmaceutical compositions comprise aqueous solutions that are sterilized and optionally stored contained within various package containers. In other embodiments the pharmaceutical compositions comprise a lyophilized powder. The pharmaceutical compositions can be further packaged as part of a kit that includes a disposable device for administering the composition to a patient. The containers or kits may be labeled for storage at ambient room temperature or at refrigerated temperature.

In one embodiment, a composition is provided comprising a mixture of a first and second single chain insulin analog prodrug derivative, wherein the first and second single chain insulin analog prodrug derivatives differ from one another based on the structure of the prodrug element. More particularly, the first single chain insulin analog prodrug derivative may comprise a dipeptide prodrug element that has a half life substantially different from the dipeptide prodrug element of the second single chain insulin analog prodrug derivative. Accordingly, selection of different combinations of substituents on the dipeptide element will allow for the preparation of compositions that comprise a mixture of single chain insulin analog prodrug derivatives that are activated in a controlled manner over a desired time frame and at specific time intervals. For example, the compositions can be formulated to release active single chain insulin analog peptide at mealtimes followed by a subsequent activation single chain insulin analog peptide during nighttime with suitable dosages being released based on time of activation.

In another embodiment the pharmaceutical composition comprises a mixture of a single chain insulin analog prodrug derivative disclosed herein and native insulin, or a known bioactive analog of insulin. The mixture in one embodiment can be in the form of a heteroduplex linking a single chain insulin analog and a native insulin, or a known bioactive analog of insulin. The dimers may comprise a single chain insulin analog peptide linked to another single chain insulin analog or to a disulfide linked A chain to B chain insulin heteroduplex. The mixtures may comprise one or more of the single chain insulin analogs, native insulin, or a known bioactive analog of insulin, in prodrug derivatives thereof or depot derivative thereof or other conjugate forms, and any combination thereof, as disclosed herein.

The disclosed single chain insulin analogs, and their corresponding prodrug derivatives, are believed to be suitable for any use that has previously been described for insulin peptides. Accordingly, the single chain insulin analogs, and their corresponding prodrug derivatives, described herein can be used to treat hyperglycemia, or treat other metabolic diseases that result from high blood glucose levels. Accordingly, the present invention encompasses pharmaceutical compositions comprising a single chain insulin analog as disclosed herein, or a prodrug derivative thereof, and a pharmaceutically acceptable carrier for use in treating a patient suffering from high blood glucose levels. In accordance with one embodiment the patient to be treated using a single chain insulin analog disclosed herein is a domesticated animal, and in another embodiment the patient to be treated is a human.

One method of treating hyperglycemia in accordance with the present disclosure comprises the steps of administering the presently disclosed single chain insulin analog, or depot or prodrug derivative thereof, to a patient using any standard route of administration, including parenterally, such as intravenously, intraperitoneally, subcutaneously or intramuscularly, intrathecally, transdermally, rectally, orally, nasally or by inhalation. In one embodiment the composition is administered subcutaneously or intramuscularly. In one embodiment, the composition is administered parenterally and the single chain insulin analog, or prodrug derivative thereof, is prepackaged in a syringe.

The single chain insulin analog disclosed herein, and depot or prodrug derivative thereof, may be administered alone or in combination with other anti-diabetic agents. Anti-diabetic agents known in the art or under investigation include native insulin, native glucagon and functional analogs thereof, sulfonylureas, such as tolbutamide (Orinase), acetohexamide (Dymelor), tolazamide (Tolinase), chlorpropamide (Diabinese), glipizide (Glucotrol), glyburide (Diabeta, Micronase, Glynase), glimepiride (Amaryl), or gliclazide (Diamicron); meglitinides, such as repaglinide (Prandin) or nateglinide (Starlix); biguanides such as metformin (Glucophage) or phenformin; thiazolidinediones such as rosiglitazone (Avandia), pioglitazone (Actos), or troglitazone (Rezulin), or other PPARγ inhibitors; alpha glucosidase inhibitors that inhibit carbohydrate digestion, such as miglitol (Glyset), acarbose (Precose/Glucobay); exenatide (Byetta) or pramlintide; Dipeptidyl peptidase-4 (DPP-4) inhibitors such as vildagliptin or sitagliptin; SGLT (sodium-dependent glucose transporter 1) inhibitors; or FBPase (fructose 1,6-bisphosphatase) inhibitors.

Pharmaceutical compositions comprising the single chain insulin analogs disclosed herein, or depot or prodrug derivatives thereof, can be formulated and administered to patients using standard pharmaceutically acceptable carriers and routes of administration known to those skilled in the art. Accordingly, the present disclosure also encompasses pharmaceutical compositions comprising one or more of the single chain insulin analogs disclosed herein (or prodrug derivative thereof), or a pharmaceutically acceptable salt thereof, in combination with a pharmaceutically acceptable carrier. In one embodiment the pharmaceutical composition comprises a 1 mg/ml concentration of the single chain insulin analog at a pH of about 4.0 to about 7.0 in a phosphate buffer system. The pharmaceutical compositions may comprise the single chain insulin analog as the sole pharmaceutically active component, or the single chain insulin analog peptide can be combined with one or more additional active agents.

All therapeutic methods, pharmaceutical compositions, kits and other similar embodiments described herein contemplate that single chain insulin analog peptides, or prodrug derivatives thereof, include all pharmaceutically acceptable salts thereof.

In one embodiment the kit is provided with a device for administering the single chain insulin analog composition to a patient. The kit may further include a variety of containers, e.g., vials, tubes, bottles, and the like. Preferably, the kits will also include instructions for use.

In accordance with one embodiment the device of the kit is an aerosol dispensing device, wherein the composition is prepackaged within the aerosol device. In another embodiment the kit comprises a syringe and a needle, and in one embodiment the single chain insulin analog composition is prepackaged within the syringe.

The compounds of this invention may be prepared by standard synthetic methods, recombinant DNA techniques, or any other methods of preparing peptides and fusion proteins. Although certain non-natural amino acids cannot be expressed by standard recombinant DNA techniques, techniques for their preparation are known in the art. Compounds of this invention that encompass non-peptide portions may be synthesized by standard organic chemistry reactions, in addition to standard peptide chemistry reactions when applicable.

EXAMPLE 1

Synthesis of Insulin A & B Chains

Insulin A & B chains were synthesized on 4-methylbenzhyryl amine (MBHA) resin or 4-Hydroxymethyl-phenylacetamidomethyl (PAM) resin using Boc chemistry. The peptides were cleaved from the resin using HF/p-cresol 95:5 for 1 hour at 0° C. Following HF removal and ether precipitation, peptides were dissolved into 50% aqueous acetic acid and lyophilized. Alternatively, peptides were synthesized using Fmoc chemistry. The peptides were cleaved from the resin using Trifluoroacetic acid (TFA)/Triisopropylsilane (TIS)/$H_2O$ (95:2.5:2.5), for 2 hour at room temperature. The peptide was precipitated through the addition of an excessive amount of diethyl ether and the pellet solubilized in aqueous acidic buffer. The quality of peptides were monitored by RP-HPLC and confirmed by Mass Spectrometry (ESI or MALDI).

Insulin A chains were synthesized with a single free cysteine at amino acid 7 and all other cysteines protected as acetamidomethyl A-$(SH)^7(Acm)^{6,11,20}$. Insulin B chains were synthesized with a single free cysteine at position 7 and the other cysteine protected as acetamidomethyl B-$(SH)^7$ $(Acm)^{19}$. The crude peptides were purified by conventional RP-HPLC.

The synthesized A and B chains were linked to one another through their native disulfide bond linkage in accordance with the general procedure outlined in FIG. 1. The respective B chain was activated to the $Cys^7$-Npys analog through dissolution in DMF or DMSO and reacted with 2,2'-Dithiobis (5-nitropyridine) (Npys) at a 1:1 molar ratio, at room temperature. The activation was monitored by RP-HPLC and the product was confirmed by ESI-MS.

Figure 2:
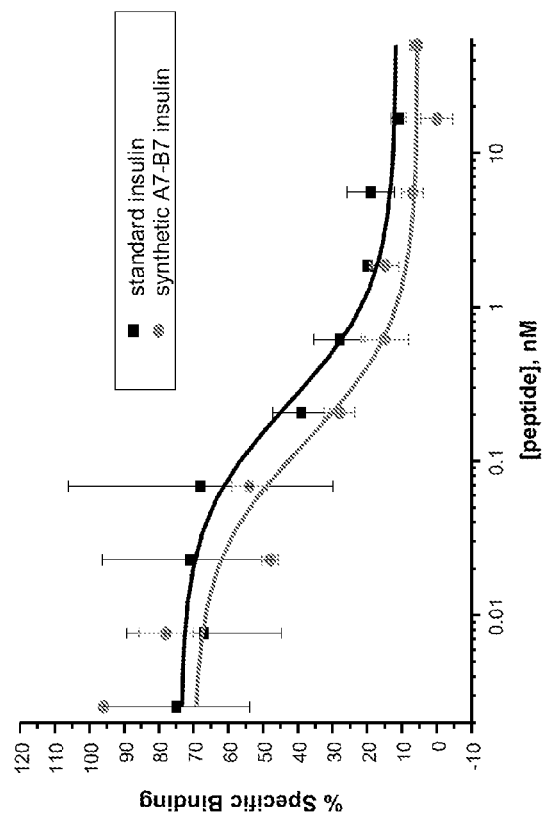
FIG. 2 is a graph comparing insulin receptor specific binding of synthetic human insulin relative to purified native insulin. The synthetic insulin was produced by the approach detailed in FIG. 1 where the $A^7$-$B^7$ bond is the first disulfide formed. As indicated by the data presented in the graph, the two molecules have similar binding activities.

The first B7-A7 disulfide bond was formed by dissolution of the respective A-$(SH)^7(Acm)^{6,11,20}$ and B-$(Npys)^7(Acm)^{19}$ at 1:1 molar ratio to a total peptide concentration of 10 mg/ml. When the chain combination reaction was complete the mixture was diluted to a concentration of 50% aqueous acetic acid. The last two disulfide bonds were formed simultaneously through the addition of iodine. A 40 fold molar excess of iodine was added to the solution and the mixture was stirred at room temperature for an additional hour. The reaction was terminated by the addition of an aqueous ascorbic acid solution. The mixture was purified by RP-HPLC and the final compound was confirmed by MALDI-MS. As shown in FIG. 2 and the data in Table 1, the synthetic insulin prepared in accordance with this procedure compares well with purified insulin for insulin receptor binding.

Insulin peptides comprising a modified amino acid (such as 4-amino phenylalanine at position A19) can also be synthesized in vivo using a system that allows for incorporation of non-coded amino acids into proteins, including for example, the system taught in U.S. Pat. Nos. 7,045,337 and 7,083,970.

TABLE 1

Activity of synthesized insulin relative to native insulin

|  | Insulin Standard | | A7-B7 Insulin | |
| --- | --- | --- | --- | --- |
|  | AVER. | STDEV | AVER. | STDEV |
| $IC_{50}$(nM) | 0.24 | 0.07 | 0.13 | 0.08 |
| % of Insulin Activity | 100 | | 176.9 | |

EXAMPLE 2

Pegylation of Amine Groups (N-Terminus and Lysine) by Reductive Alkylation a. Synthesis Insulin (or an insulin analog), mPEG20k-Aldyhyde, and $NaBH_3CN$, in a molar ratio of 1:2:30, were dissolved in acetic acid buffer at a pH of 4.1-4.4. The reaction solution was composed of 0.1 N NaCl, 0.2 N acetic acid and 0.1 N $Na_2CO_3$. The insulin peptide concentration was approximately 0.5 mg/ml. The reaction occurs over six hours at room temperature. The degree of reaction was monitored by RP-HPLC and the yield of the reaction was approximately 50%.

b. Purification

The reaction mixture was diluted 2-5 fold with 0.1% TFA and applied to a preparative RP-HPLC column. HPLC condition: C4 column; flow rate 10 ml/min; A buffer 10% ACN and 0.1% TFA in water; B buffer 0.1% TFA in ACN; A linear gradient B % from 0-40% (0-80 min); PEG-insulin or analogues was eluted at approximately 35% buffer B. The desired compounds were verified by MALDI-TOF, following chemical modification through sulftolysis or trypsin degradation.

Pegylation of Amine Groups (N-Terminus and Lysine) by N-Hydroxysuccinimide Acylation a. Synthesis Insulin (or an insulin analog) along with mPEG20k-NHS were dissolved in 0.1 N Bicine buffer (pH 8.0) at a molar ratio of 1:1. The insulin peptide concentration was approximately 0.5 mg/ml. Reaction progress was monitored by HPLC. The yield of the reaction is approximately 90% after 2 hours at room temperature.

b. Purification

The reaction mixture was diluted 2-5 fold and loaded to RP-HPLC. HPLC condition: C4 column; flow rate 10 ml/min; A buffer 10% ACN and 0.1% TFA in water; B buffer 0.1% TFA in ACN; A linear gradient B % from 0-40% (0-80 min); PEG-insulin or analogues was collected at approximately 35% B. The desired compounds were verified by MALDI-TOF, following chemical modification through sulftolysis or trypsin degradation.

Reductive Aminated Pegylation of Acetyl Group on the Aromatic Ring Of The Phenylalanine a. Synthesis Insulin (or an insulin analogue), mPEG20k-Hydrazide, and $NaBH_3CN$ in a molar ratio of 1:2:20 were dissolved in acetic acid buffer (pH of 4.1 to 4.4). The reaction solution was composed of 0.1 N NaCl, 0.2 N acetic acid and 0.1 N $Na_2CO_3$. Insulin or insulin analogue concentration was approximately 0.5 mg/ml. at room temperature for 24 h. The reaction process was monitored by HPLC. The conversion of the reaction was approximately 50%. (calculated by HPLC)

b. Purification

The reaction mixture was diluted 2-5 fold and loaded to RP-HPLC. HPLC condition: C4 column; flow rate 10 ml/min; A buffer 10% ACN and 0.1% TFA in water; B buffer 0.1% TFA in ACN; A linear gradient B % from 0-40% (0-80 min); PEG-insulin, or the PEG-insulin analogue was collected at approximately 35% B. The desired compounds were verified by MALDI-TOF, following chemical modification through sulftolysis or trypsin degradation.

EXAMPLE 3

Insulin Receptor Binding Assay

The affinity of each peptide for the insulin or IGF-1 receptor was measured in a competition binding assay utilizing scintillation proximity technology. Serial 3-fold dilutions of the peptides were made in Tris-Cl buffer (0.05 M Tris-HCl, pH 7.5, 0.15 M NaCl, 0.1% w/v bovine serum albumin) and mixed in 96 well plates (Corning Inc., Acton, Mass.) with 0.05 nM (3-[125I]-iodotyrosyl) A TyrA14 insulin or (3-[125I]-iodotyrosyl) IGF-1 (Amersham Biosciences, Piscataway, N.J.). An aliquot of 1-6 micrograms of plasma membrane fragments prepared from cells over-expressing the human insulin or IGF-1 receptors were present in each well and 0.25 mg/well polyethylene imine-treated wheat germ agglutinin type A scintillation proximity assay beads (Amersham Biosciences, Piscataway, N.J.) were added. After five minutes of shaking at 800 rpm the plate was incubated for 12 h at room temperature and radioactivity was measured with MicroBeta1450 liquid scintillation counter (Perkin-Elmer, Wellesley, Mass.). Non-specifically bound (NSB) radioactivity was measured in the wells with a four-fold concentration excess of "cold" native ligand than the highest concentration in test samples. Total bound radioactivity was detected in the wells with no competitor. Percent specific binding was calculated as following: % Specific Binding=(Bound-NSB/Total bound-NSB)×100. IC50 values were determined by using Origin software (OriginLab, Northampton, Mass.).

EXAMPLE 4

Insulin Receptor Phosphorylation Assay

To measure receptor phosphorylation of insulin or insulin analog, receptor transfected HEK293 cells were plated in 96 well tissue culture plates (Costar #3596, Cambridge, Mass.) and cultured in Dulbecco's modified Eagle medium (DMEM) supplemented with 100 IU/ml penicillin, 100 ng/ml streptomycin, 10 mM HEPES and 0.25% bovine growth serum (HyClone SH30541, Logan, Utah) for 16-20 hrs at 37° C., 5% $CO_2$ and 90% humidity. Serial dilutions of insulin or insulin analogs were prepared in DMEM supplemented with 0.5% bovine serum albumin (Roche Applied Science #100350, Indianapolis, Ind.) and added to the wells with adhered cells. After 15 min incubation at 37° C. in humidified atmosphere with 5% $CO_2$ the cells were fixed with 5% paraformaldehyde for 20 min at room temperature, washed twice with phosphate buffered saline pH 7.4 and blocked with 2% bovine serum albumin in PBS for 1 hr. The plate was then washed three times and filled with horseradish peroxidase-conjugated antibody against phosphotyrosine (Upstate biotechnology #16-105, Temecula, Calif.) reconstituted in PBS with 2% bovine serum albumin per manufacturer's recommendation. After 3 hrs incubation at room temperature the plate was washed 4 times and 0.1 ml of TMB single solution substrate (Invitrogen, #00-2023, Carlbad, Calif.) was added to each well. Color development was stopped 5 min later by adding 0.05 ml 1 N HCl. Absorbance at 450 nm was measured on Titertek Multiscan MCC340 (ThermoFisher, Pittsburgh, Pa.). Absorbance vs. peptide concentration dose response curves were plotted and $EC_{50}$ values were determined by using Origin software (OriginLab, Northampton, Mass.).

EXAMPLE 5

Determination of Rate of Model Dipeptide Cleavage (in PBS)

A specific hexapeptide (HSRGTF-$NH_2$; SEQ ID NO: 156) was used as a model peptide upon which the rate of cleavage of dipeptide N-terminal extensions could be studied. The dipeptide-extended model peptides were prepared Boc-protected sarcosine and lysine were successively added to the model peptide-bound resin to produce peptide A (Lys-Sar-HSRGTF-$NH_2$; SEQ ID NO: 157). Peptide A was cleaved by HF and purified by preparative HPLC.

Preparative Purification Using HPLC:

Purification was performed using HPLC analysis on a silica based 1×25 cm Vydac C18 (5μ particle size, 300 A° pore size) column. The instruments used were: Waters Associates model 600 pump, Injector model 717, and UV detector model 486. A wavelength of 230 nm was used for all samples. Solvent A contained 10% $CH_3CN$/0.1% TFA in distilled water, and solvent B contained 0.1% TFA in $CH_3CN$. A linear gradient was employed (0 to 100% B in 2 hours). The flow rate was 10 ml/min and the fraction size was 4 ml. From ~150 mgs of crude peptide, 30 mgs of the pure peptide was obtained.

Peptide A was dissolved at a concentration of 1 mg/ml in PBS buffer. The solution was incubated at 37° C. Samples were collected for analysis at 5 h, 8 h, 24 h, 31 h, and 47 h. The dipeptide cleavage was quenched by lowering the pH with an equal volume of 0.1% TFA. The rate of cleavage was qualitatively monitored by LC-MS and quantitatively studied by HPLC. The retention time and relative peak area for the prodrug and the parent model peptide were quantified using Peak Simple Chromatography software.

Analysis Using Mass Spectrometry

The mass spectra were obtained using a Sciex API-III electrospray quadrapole mass spectrometer with a standard ESI ion source. Ionization conditions that were used are as follows: ESI in the positive-ion mode; ion spray voltage, 3.9 kV; orifice potential, 60 V. The nebulizing and curtain gas used was nitrogen flow rate of 0.9 L/min. Mass spectra were recorded from 600-1800 Thompsons at 0.5 Th per step and 2 msec dwell time. The sample (about 1 mg/mL) was dissolved in 50% aqueous acetonitrile with 1% acetic acid and introduced by an external syringe pump at the rate of 5 µL/min. Peptides solubilized in PBS were desalted using a ZipTip solid phase extraction tip containing 0.6 µL C4 resin, according to instructions provided by the manufacturer (Millipore Corporation, Billerica, Mass.) prior to analysis.

Analysis Using HPLC

The HPLC analyses were performed using a Beckman System Gold Chromatography system equipped with a UV detector at 214 nm and a 150 mm×4.6 mm C8 Vydac column. The flow rate was 1 ml/min. Solvent A contained 0.1% TFA in distilled water, and solvent B contained 0.1% TFA in 90% $CH_3CN$. A linear gradient was employed (0% to 30% B in 10 minutes). The data were collected and analyzed using Peak Simple Chromatography software.

The rate of cleavage was determined for the respective propeptides. The concentrations of the propeptides and the model parent peptide were determined by their respective peak areas. The first order dissociation rate constants of the prodrugs were determined by plotting the logarithm of the concentration of the prodrug at various time intervals. The slope of this plot provides the rate constant 'k'. The half lives for cleavage of the various prodrugs were calculated by using the formula $t_{1/2}=0.693/k$. The half life of the Lys-Sar extension to this model peptide HSRGTF-NH$_2$ (SEQ ID NO: 156) was determined to be 14.0 h.

EXAMPLE 6

Rate of Dipeptide Cleavage Half Time in Plasma as Determined with an all d-isoform Model Peptide An additional model hexapeptide (dHdTdRGdTdF-NH$_2$ SEQ ID NO: 158) was used to determine the rate of dipeptide cleavage in plasma. The d-isomer of each amino acid was used to prevent enzymatic cleavage of the model peptide, with the exception of the prodrug extension. This model d-isomer hexapeptide was synthesized in an analogous fashion to the 1-isomer. The sarcosine and lysine were successively added to the N-terminus as reported previously for peptide A to prepare peptide B (dLys-dSar-dHdTdRGdTdF-NH$_2$ SEQ ID NO: 159)

The rate of cleavage was determined for the respective propeptides. The concentrations of the propeptides and the model parent peptide were determined by their respective peak areas. The first order dissociation rate constants of the prodrugs were determined by plotting the logarithm of the concentration of the prodrug at various time intervals. The slope of this plot provides the rate constant 'k'. The half life of the Lys-Sar extension to this model peptide dHdT-dRGdTdF-NH$_2$ (SEQ ID NO: 158) was determined to be 18.6 h.

EXAMPLE 7

The rate of cleavage for additional dipeptides linked to the model hexapeptide (HSRGTF-NH$_2$; SEQ ID NO: 156) were determined using the procedures described in Example 5. The results generated in these experiments are presented in Tables 2 and 3.

TABLE 2

Cleavage of the Dipeptide U-B that are linked to the side chain of an N-terminal para-amino-Phe from the Model Hexapeptide (HSRGTF-NH$_2$; SEQ ID NO: 156) in PBS

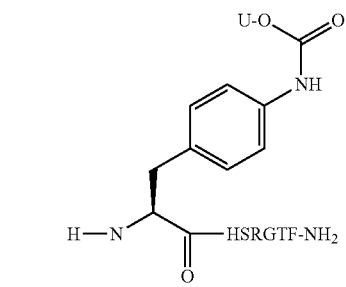

| Compounds | U (amino acid) | O (amino acid) | $t_{1/2}$ |
|---|---|---|---|
| 1 | F | P | 58 h |
| 2 | Hydroxyl-F | P | 327 h |
| 3 | d-F | P | 20 h |
| 4 | d-F | d-P | 39 h |
| 5 | G | P | 72 h |
| 6 | Hydroxyl-G | P | 603 h |
| 7 | L | P | 62 h |
| 8 | tert-L | P | 200 h |
| 9 | S | P | 34 h |
| 10 | P | P | 97 h |
| 11 | K | P | 33 h |
| 12 | dK | P | 11 h |
| 13 | E | P | 85 h |
| 14 | Sar | P | ≈1000 h |
| 15 | Aib | P | 69 min |
| 16 | Hydroxyl-Aib | P | 33 h |
| 17 | cyclohexane | P | 6 min |
| 18 | G | G | No cleavage |
| 19 | Hydroxyl-G | G | No cleavage |
| 20 | S | N-Methyl-Gly | 4.3 h |
| 21 | K | N-Methyl-Gly | 5.2 h |
| 22 | Aib | N-Methyl-Gly | 7.1 min |
| 23 | Hydroxyl-Aib | N-Methyl-Gly | 1.0 h |

TABLE 3

Cleavage of the Dipeptides U-B linked to histidine (or histidine analog) at position 1 (X) from the Model Hexapeptide (XSRGTF-NH$_2$; SEQ ID NO: 160) in PBS
NH$_2$-U-B-XSRGTF-NH$_2$ (SEQ ID NO: 160)

| Comd. | U (amino acid) | O (amino acid) | X (amino acid) | $t_{1/2}$ |
|---|---|---|---|---|
| 1 | F | P | H | No cleavage |
| 2 | Hydroxyl-F | P | H | No cleavage |

TABLE 3-continued

Cleavage of the Dipeptides U-B linked to histidine (or histidine analog) at position 1 (X) from the Model Hexapeptide (XSRGTF-NH$_2$; SEQ ID NO: 160) in PBS NH$_2$-U-B-XSRGTF-NH$_2$ (SEQ ID NO: 160)

| Comd. | U (amino acid) | O (amino acid) | X (amino acid) | t$_{1/2}$ |
|---|---|---|---|---|
| 3 | G | P | H | No cleavage |
| 4 | Hydroxyl-G | P | H | No cleavage |
| 5 | A | P | H | No cleavage |
| 6 | C | P | H | No cleavage |
| 7 | S | P | H | No cleavage |
| 8 | P | P | H | No cleavage |
| 9 | K | P | H | No cleavage |
| 10 | E | P | H | No cleavage |
| 11 | Dehydro V | P | H | No cleavage |
| 12 | P | d-P | H | No cleavage |
| 13 | d-P | P | H | No cleavage |
| 14 | Aib | P | H | 32 h |
| 15 | Aib | d-P | H | 20 h |
| 16 | Aib | P | d-H | 16 h |
| 17 | Cyclohexyl- | P | H | 5 h |
| 18 | Cyclopropyl- | P | H | 10 h |
| 19 | N-Me-Aib | P | H | >500 h |
| 20 | α, α-diethyl-Gly | P | H | 46 h |
| 21 | Hydroxyl-Aib | P | H | 61 |
| 22 | Aib | P | A | 58 |
| 23 | Aib | P | N-Methyl-His | 30 h |
| 24 | Aib | N-Methyl-Gly | H | 49 min |
| 25 | Aib | N-Hexyl-Gly | H | 10 min |
| 26 | Aib | Azetidine-2-carboxylic acid | H | >500 h |
| 27 | G | N-Methyl-Gly | H | 104 h |
| 28 | Hydroxyl-G | N-Methyl-Gly | H | 149 h |
| 29 | G | N-Hexyl-Gly | H | 70 h |
| 30 | dK | N-Methyl-Gly | H | 27 h |
| 31 | dK | N-Methyl-Ala | H | 14 h |
| 32 | dK | N-Methyl-Phe | H | 57 h |
| 33 | K | N-Methyl-Gly | H | 14 h |
| 34 | F | N-Methyl-Gly | H | 29 h |
| 35 | S | N-Methyl-Gly | H | 17 h |
| 36 | P | N-Methyl-Gly | H | 181 h |

EXAMPLE 8

Identification of an Insulin Analog with Structure Suitable for Prodrug Construction Position 19 of the A chain is known to be an important site for insulin activity. Modification at this site to allow the attachment of a prodrug element is therefore desirable. Specific analogs of insulin at A19 have been synthesized and characterized for their activity at the insulin receptors. Two highly active structural analogs have been identified at A19, wherein comparable structural changes at a second active site aromatic residue (B24) were not successful in identification of similarly full activity insulin analogs.

Tables 4 and 5 illustrate the high structural conservation at position A19 for full activity at the insulin receptor (receptor binding determined using the assay described in Example 3). Table 4 demonstrates that only two insulin analogs with modifications at A19 have receptor binding activities similar to native insulin. For the 4-amino insulin analog, data from three separate experiments is provided. The column labeled "Activity (in test)" compares the percent binding of the insulin analog relative to native insulin for two separate experiments conducted simultaneously. The column labeled "Activity (0.60 nM)" is the relative percent binding of the insulin analog relative to the historical average value obtained for insulin binding using this assay. Under either analysis, two A19 insulin analogs (4-amino phenylalanine and 4-methoxy phenylalanine) demonstrate receptor binding approximately equivalent to native insulin. FIG. 3 represents a graph demonstrating the respective specific binding of native insulin and the A19 insulin analog to the insulin receptor. Table 5 presents data showing that the two A19 insulin analogs (4-amino and 4-methoxy) that demonstrate equivalent binding activities as native insulin also demonstrate equivalent activity at the insulin receptor (receptor activity determined using the assay described in Example 4).

TABLE 4

Insulin Receptor Binding Activity of A19 Insulin Analogs

| | Insulin Receptor | | | |
|---|---|---|---|---|
| Analogue | $IC_{50}$ | STDev | % native ligand Activity (in test) | % native ligand Activity (0.60 nM) |
| 4-OH (native insulin) | 0.64 | 0.15 | 100.0 | 100.0 |
| 4-COCH$_3$ | 31.9 | 9.47 | 0.6 | 1.9 |
| 4-NH$_2$ | 0.31 | 0.12 | 203.0 | 193.5 |
| | 0.83 | 0.15 | 103.0 | 72.3 |
| | 0.8 | 0.1 | 94.0 | 75.0 |
| 4-NO$_2$ | 215.7 | 108.01 | 0.3 | 1.3 |
| 3,4,5-3F | 123.29 | 31.10 | 0.5 | 0.5 |
| 4-OCH$_3$ | 0.5 | 0.50 | 173.0 | 120.0 |
| 3-OCH$_3$ | 4.74 | 1.09 | 28.0 | 12.7 |
| | 5.16 | 3.88 | 18.0 | 11.6 |
| 4-OH, 3,5-2Br | 1807.17 | 849.72 | 0.0 | 0.0 |
| 4-OH, 3,5-2 NO$_2$ | 2346.2 | 338.93 | 0.0 | 0.0 |

TABLE 5

Insulin Receptor Phosphorylation Activity of A19 Insulin Analogs

| | Insulin Receptor | | |
|---|---|---|---|
| Analogue | $EC_{50}$ | STDev | % native ligand Activity (in test) |
| 4-OH (native insulin) | 1.22 | 0.4 | 100.0 |
| 4-NH$_2$ | 0.31 | 0.14 | 393.5 |
| 4-OCH$_3$ | 0.94 | 0.34 | 129.8 |

EXAMPLE 9

Insulin like Growth Factor (IGF) Analog IGF1 ($Y^{B16}L^{B17}$)

Figure 4:
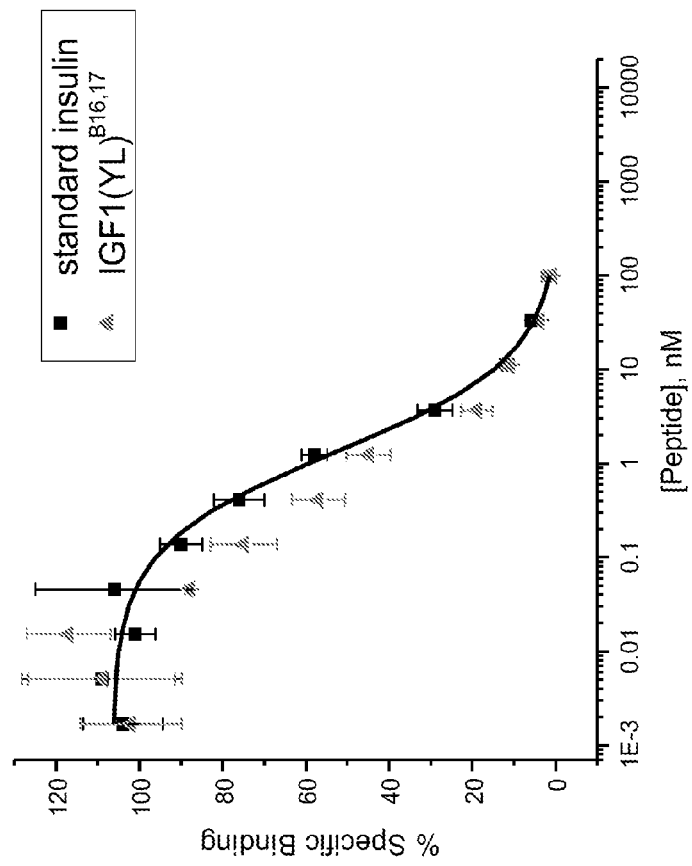
FIG. 4 is a graph comparing relative insulin receptor binding of native insulin and the IGF1($Y^{B16}L^{B17}$) analog. As indicated by the data presented in the graph, the two molecules have similar binding activities.

Applicants have discovered an IGF analog that demonstrates similar activity at the insulin receptor as native insulin. More particularly, the IGF analog (IGF1 ($Y^{B16}L^{B17}$) comprises the native IGF A chain (SEQ ID NO: 5) and the modified B chain (SEQ ID NO: 6), wherein the native glutamine and phenylalanine at positions 15 and 16 of the native IGF B-chain (SEQ ID NO: 3) have been replaced with tyrosine and leucine residues, respectively. As shown in FIG. 4 and Table 6 below the binding activities of IGF1 ($Y^{B16}L^{17}$) and native insulin demonstrate that each are highly potent agonists of the insulin receptor.

TABLE 6

| | Insulin Standard | | IGF1($Y^{B16}L^{B17}$) | |
|---|---|---|---|---|
| | AVER. | STDEV | AVER. | STDEV |
| $IC_{50}$(nM) | 1.32 | 0.19 | 0.51 | 0.18 |
| % of Insulin Activity | 100 | | 262 | |

EXAMPLE 10

IGF Prodrug Analogs

Figure 6:
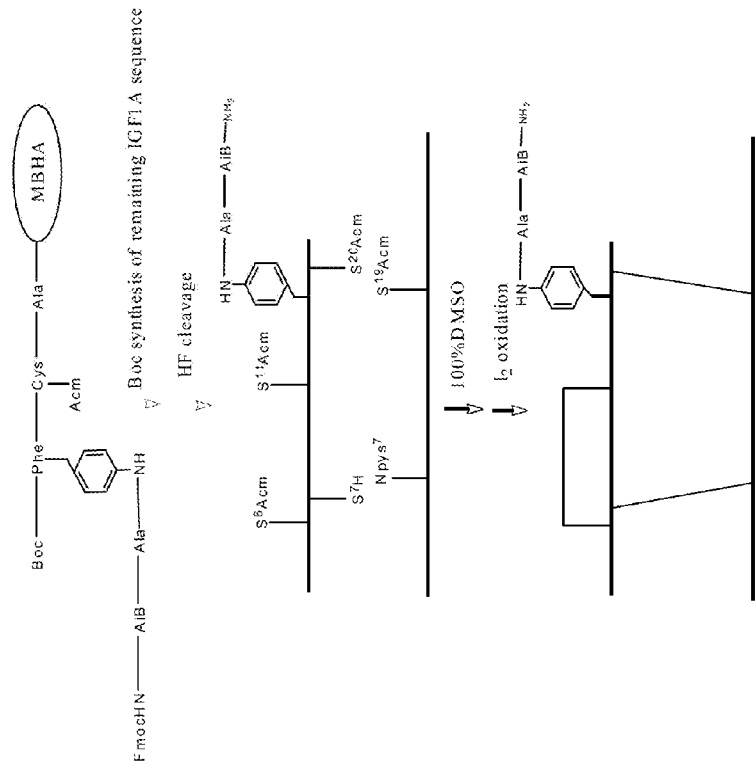
FIG. 6 is a schematic drawing of the synthetic scheme used to prepare the IGF1($Y^{B16}L^{B17}$)(p-$NH_2$—F)$^{A19}$ prodrug derivatives. The specific derivative is p-$NH_2$—F where the aromatic amine is acylated with the dipeptide Aib-Ala, which serves as a negative control since this dipeptide does not cleave under physiological conditions.
Figure 7:
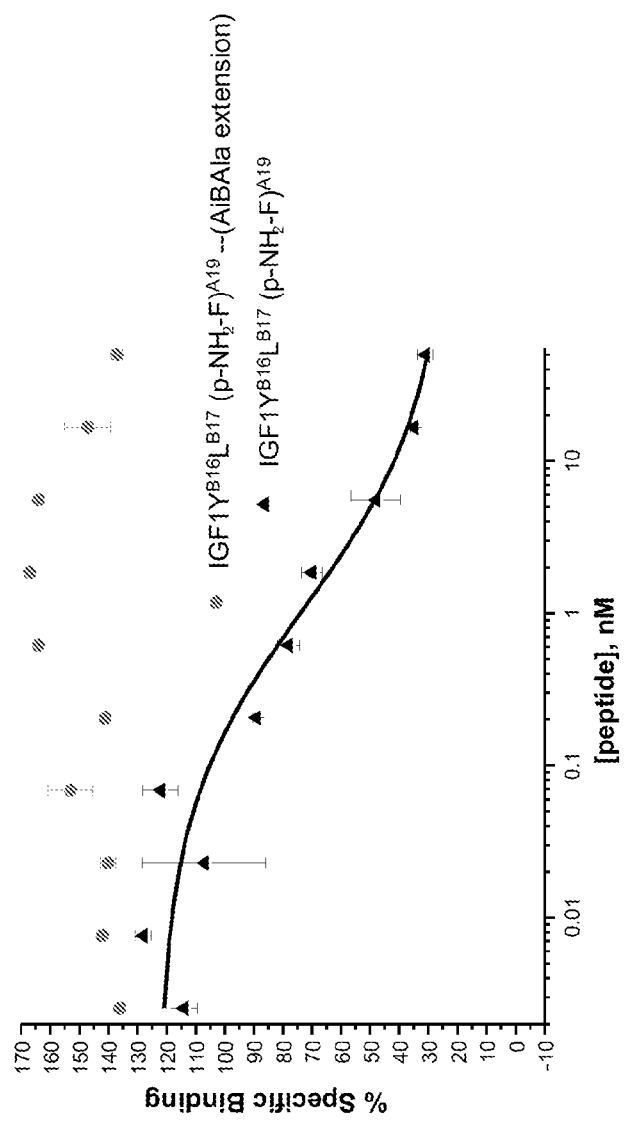
FIG. 7 is a graph comparing relative insulin receptor binding of IGF1($Y^{B16}L^{B17}$)(p-$NH_2$—F)$^{A19}$ and the dipeptide extended form of IGF1($Y^{B16}L^{B17}$)(p$NH_2$—F)$^{A19}$-AibAla. The synthesis of this prodrug is shown in FIG. 6 where the dipeptide AibAla is bound at position A19 (i.e. IGF1($Y^{B16}L^{B17}$)(AibAla)). The dipeptide does not readily cleave under physiological conditions and thus the activity is extremely low which demonstrates the ability of acylation at this site with dipeptide to silence bioactivity. This constitutes one of the two central ingredients of a prodrug, low activity in the prodrug form.
Figure 8A:
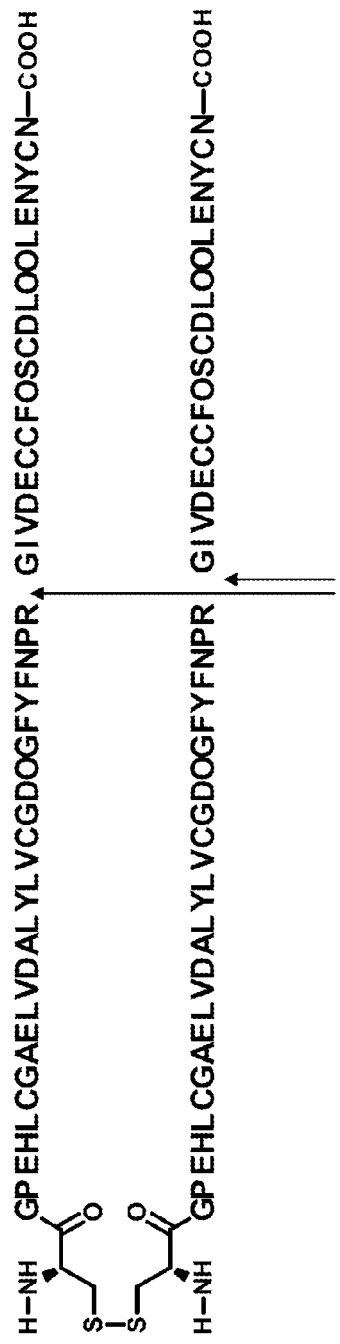

Based on the activity of the A19 insulin analog (see Example 5), a similar modification was made to the IGF1 A:B($Y^{B16}L^{17}$) analog and its ability to bind and stimulate insulin receptor activity was investigated. FIG. 6 provides the general synthetic scheme for preparing IGF1 A:B($Y^{B16}L^{17}$) wherein the native tyrosine is replace with a 4-amino phenylalanine [IGF1 A:B($Y^{B16}L^{17}$)(p-NH$_2$—F)$^{A19}$amide] as well as the preparation of its dipeptide extended analog [IGF1 A:B($Y^{B16}L^{17}$)$^{A19}$-AibAla amide], wherein a dipeptide comprising Aib and Ala are linked to the peptide through an amide linkage to the A19 4-amino phenylalanine. As shown in FIG. 7 and Table 7, the IGF analog, IGF1 ($Y^{B16}L^{17}$)A(p-NH$_2$—F)$^{19}$ specifically binds to the insulin receptor wherein the dipeptide extended analog of that analog fails to specifically bind the insulin receptor. Note the dipeptide extension lacks the proper structure to allow for spontaneous cleavage of the dipeptide (absence of an N-alkylated amino acid at the second position of the dipeptide) and therefore there is no restoration of insulin receptor binding.

IGF A:B($Y^{B16}L^{17}$) insulin analog peptides comprising a modified amino acid (such as 4-amino phenylalanine at position A19) can also be synthesized in vivo using a system that allows for incorporation of non-coded amino acids into proteins, including for example, the system taught in U.S. Pat. Nos. 7,045,337 and 7,083,970.

TABLE 7

|  | Insulin Standard | | IGF1($Y^{B16}L^{B17}$) (p-NH$_2$—F)$^{A19}$ amide | | IGF1($Y^{B16}L^{B17}$) (AibAla)$^{A19}$amide | |
| --- | --- | --- | --- | --- | --- | --- |
|  | AVER. | STDEV | AVER. | STDEV. | AVER. | STDEV |
| IC$_{50}$(nM) | 0.24 | 0.07 | 1.08 | .075 | No Activity | |
| % of Insulin Activity | 100 | | 22 | | | |

A further prodrug analog of an IGF$^{B16B17}$ analog peptide was prepared wherein the dipeptide prodrug element (alanine-proline) was linked via an amide bond to the amino terminus of the A chain (IGF1($Y^{B16}L^{B17}$)(AlaPro)$^{A-1,0}$). As shown in Table 8, the IGF1($Y^{B16}L^{B17}$)(AlaPro)$^{A-1,10}$ has reduced affinity for the insulin receptor. Note, based on the data of Table 3, the dipeptide prodrug element lacks the proper structure to allow for spontaneous cleavage of the dipeptide prodrug element, and therefore the detected insulin receptor binding is not the result of cleavage of the prodrug element.

TABLE 8

|  | Insulin Standard | | IGF1($Y^{B16}L^{B17}$) (AlaPro)$^{A-1,0}$ | |
| --- | --- | --- | --- | --- |
|  | AVER. | STDEV | AVER. | STDEV. |
| IC$_{50}$(nM) | 0.72 | 0.09 | 1.93 | .96 |
| % of Insulin Activity | 100 | | 37.12 | |

EXAMPLE 11

Additional IGF Insulin Analogs

Further modifications of the IGF1 ($Y^{B16}L^{B17}$)peptide sequence reveal additional IGF insulin analogs that vary in their potency at the insulin and IGF-1 receptor. Binding data is presented in Table 9 for each of these analogs (using the assay of Example 3), wherein the position of the modification is designated based on the corresponding position in the native insulin peptide (DPI=des B26-30). For example, a reference herein to "position B28" absent any further elaboration would mean the corresponding position B27 of the B chain of an insulin analog in which the first amino acid of SEQ ID NO: 2 has been deleted. Thus a generic reference to "B(Y16)" refers to a substitution of a tyrosine residue at position 15 of the B chain of the native IGF-1 sequence (SEQ ID NO: 3). Data regarding the relative receptor binding of insulin and IGF analogs is provided in Table 9, and data regarding IGF analog stimulated phosphorylation (using the assay of Example 4) is provided in Table 10.

TABLE 9

Receptor Binding Affinity of Insulin and IGF Analogues

| | Insulin Receptor | | | | | IGF-1 Receptor | | | | | |
| --- | --- | --- | --- | --- | --- | --- | --- | --- | --- | --- | --- |
| Analogue | nM IC$_{50}$: | STDev | Date | % insulin (in test) | % native insulin activity (0.6 nM) | IC$_{50}$: | STDev | Date | % IGF-1 (in test) | % native IGF-1 activity (0.55 nM) | Ratio |
| IGF-1 A:B | 10.41 | 1.65 | Sep. 4, 2007 | 5.8 | 5.8 | | | | | | |
| IGF-1 A:B(E10Y16L17) | 0.66 | 0.36 | May 22, 2007 | 58.7 | 90.9 | 7.85 | 1.98 | Jun. 4, 2007 | 6.8 | 7.0 | 11.9 |
| | 0.51 | 0.18 | May 29, 2007 | 98.8 | 117.6 | 12.19 | 2.17 | Sep. 18, 2007 | 5.0 | 4.5 | |
| IGF-1 A:B(E10 Y16L17)-E31E32B-COOH | 1.22 | 0.30 | Mar. 20, 2008 | 36.5 | 50.0 | 17.50 | 2.25 | Apr. 4, 2007 | 3.0 | 3.1 | 14.3 |
| IGF-1 A:B(D10Y16L17) DPI A-COOH | 0.26 | 0.02 | Nov. 9, 2007 | 301.0 | 231.0 | 6.79 | 1.50 | Apr. 4, 2008 | 7.7 | 8.1 | |
| | 0.2 | 0.02 | Dec. 4, 2007 | 380.1 | 300.0 | | | | | | |
| | 0.42 | 0.06 | Jun. 5, 2008 | 174.1 | 144.1 | | | | | | |
| IGF-1 A:B (E10Y16L17) DPI | 0.38 | 0.08 | Aug. 10, 2007 | 51.1 | 157.9 | 22.89 | 5.26 | Sep. 18, 2007 | 3.3 | 2.4 | 60.2 |
| IGF-1 A:B (H5D10Y16L17) DPI | 0.16 | 0.07 | Nov. 9, 2007 | 479.0 | | 4.66 | 0.77 | Apr. 4, 2008 | 11.2 | 11.8 | 29.1 |
| IGF-1 A:B (H5D10Y16L17) (S═O) DPI | 0.25 | 0.04 | Nov. 9, 2007 | 316.0 | | | | | | | |
| IGF-1 A (H8 A9 N21): B(H5D10Y16L17) DPI A-COOH | 0.05 | 0.01 | Dec. 4, 2007 | 1576.7 | | 4.03 | 0.50 | Apr. 4, 2008 | 12.9 | 13.6 | 80.6 |
| | 0.09 | 0.02 | Dec. 14, 2007 | 1667.0 | | | | | | | |
| IGF-1 A (H8 A9 N21): B(H5D10Y16L17 A22) DPI A-COOH | 0.12 | 0.02 | Dec. 14, 2007 | 1171.4 | | 22.83 | 3.53 | Apr. 4, 2008 | 2.3 | 2.4 | 190.3 |
| IGF-1 A (H8 A9 N21): B(H5D10Y16L17A22) (S═O) DPI A-COOH | 0.36 | 0.10 | Dec. 14, 2007 | 400.7 | | | | | | | |
| IGF-1 A: IGF-1 B(1-8)-In (9-17)-IGF-1 B(18-30) | 1.59 | 0.62 | May 22, 2007 | 19.1 | 37.7 | 131.30 | 58.05 | Jun. 4, 2007 | 0.3 | 0.4 | 82.6 |
| IGF-1 A: In (1-17)-IGF-1 B (18-30) | 2.77 | 1.19 | May 22, 2007 | 14.0 | 21.7 | 62.50 | 30.28 | Jun. 4, 2007 | 0.9 | 0.9 | 22.6 |

TABLE 9-continued

Receptor Binding Affinity of Insulin and IGF Analogues

| Analogue | Insulin Receptor | | | | | IGF-1 Receptor | | | | | |
|---|---|---|---|---|---|---|---|---|---|---|---|
| | nM IC$_{50}$: | STDev | Date | % insulin (in test) | % native insulin activity (0.6 nM) | IC$_{50}$: | STDev | Date | % IGF-1 (in test) | % native IGF-1 activity (0.55 nM) | Ratio |
| | 2.67 | 0.67 | May 18, 2007 | 11.3 | 22.5 | | | | | | |
| | 2.48 | 1.35 | May 29, 2007 | 20.1 | 24.2 | | | | | | |
| IGF-1 A: In B(1-5)-IGF-1 B(YL)(6-30) | 0.31 | 0.19 | Aug. 10, 2007 | 62.4 | 193.5 | 27.54 | 6.57 | Sep. 25, 2007 | 3.6 | 2 | 88.8 |
| IGF-2 native | | | | | | 13.33 | 1.85 | Sep. 25, 2007 | 7.5 | 4.5 | |
| IGF-2 AB | | | | | | | | | | | |
| IGF-2 AB(YL) | 6.81 | 3.81 | Oct. 10, 2007 | 8.4 | 8.8 | | | | | | |
| In A: IGF-1 B(YL) | 82.62 | 31.75 | Sep. 4, 2007 | 0.9 | 0.7 | | | | | | |
| | 107.24 | 65.38 | Sep. 4, 2007 | 0.7 | 0.6 | | | | | | |
| In A-IGF-2 D: In B-IGF-2 C | 0.53 | 0.11 | Sep. 4, 2007 | 141.0 | 113.0 | 1.59 | 0.34 | Sep. 18, 2007 | 47.6 | 34.6 | |
| | 0.37 | 0.05 | Oct. 13, 2007 | 179.1 | 162.2 | 14.69 | 3.02 | Sep. 25, 2007 | 6.8 | 3.7 | 39.7 |

**All C terminals are amides (DPI) unless specified otherwise

TABLE 10

Total Phosphorylation by IGF-1 & IGF-2 Analogues

| Analogue | Insulin Receptor | | | | IGF-1 Receptor | | | | Selective |
|---|---|---|---|---|---|---|---|---|---|
| | EC50: | STDev | Date | % Insulin | EC50: | STDev | Date | % IGF | Ratio |
| Insulin | 1.26 | 0.098 | Dec. 14, 2007 | | 114.88 | 46.66 | Jan. 23, 2008 | | 90.89 |
| | 1.43 | 0.72 | Apr. 1, 2008 | | 86.02 | 29.35 | May 20, 2008 | | |
| | 1.12 | 0.11 | Mar. 31, 2008 | | | | | | |
| | 1.53 | 0.13 | Apr. 11, 2008 | | | | | | |
| | 2.70 | 0.71 | Apr. 16, 2008 | | | | | | |
| | 1.22 | 0.40 | May 20, 2008 | | | | | | |
| IGF-1 | 54.39 | 21.102 | Dec. 14, 2007 | 2.3 | 0.87 | 0.16 | Jan. 23, 2008 | 100 | 0.02 |
| | | | | | 0.49 | 0.13 | May 20, 2008 | | |
| | | | | | 0.97 | 0.48 | Jul. 23, 2008 | | |
| IGF-1 AB | | | | | | | | | |
| IGF-1 A: B(E10Y16L17) | 2.57 | 0.59 | Mar. 31, 2008 | 49.2 | 7.42 | 5.59 | Jul. 23, 2008 | 13 | |
| IGF-1 A:B(E10 Y16L17)-E31E32B-COOH | 7.00 | 2.82 | Mar. 31, 2008 | 18.1 | | | | | |
| | 8.52 | 4.34 | Apr. 16, 2008 | 31.7 | | | | | |
| IGF-1 AB(D10Y16L17) DPI A-COOH | 0.08 | 0.006 | Dec. 14, 2007 | 1575 | 0.78 | 0.17 | Jan. 23, 2008 | 111.538 | 9.75 |
| | 4.38 | 2.98 | Apr. 16, 2008 | ?? | | | | | |
| IGF-1 AB (E10Y16L17) DPI | | | | | | | | | |
| IGF-1 AB (H5D10Y16L17) DPI | | | | | 12.22 | 5.46 | Jan. 23, 2008 | 7.1 | |
| IGF-1 AB (H5D10Y16L17) (S=O)DPI | | | | | | | | | |
| IGF-1 A (H8 A9 N21) B(H5D10Y16L17) DPI A-COOH | 0.15 | 0.054 | Dec. 14, 2007 | 840 | 0.43 | 0.44 | Jan. 23, 2008 | 181.395 | 2.81 |
| | 0.25 | 0.2 | Apr. 16, 2008 | 1080 | | | | | |
| IGF-1 A (H8 A9 N21) B(H5D10Y16L17A22) DPI A-COOH | 0.35 | 0.064 | Dec. 14, 2007 | 360 | 11.26 | 2.55 | Jan. 23, 2008 | 7.7 | 32.54 |
| | 0.44 | 0.17 | Apr. 16, 2008 | 614 | | | | | |
| IGF-1 A (H8 A9 N21) B(H5D10Y16L17A22) (S=O) DPI A-COOH | 0.72 | 0.098 | Dec. 14, 2007 | | | | | | |

*All C-terminals are amides unless specified otherwise.

EXAMPLE 12

Dipeptide Half Life on IGF1 Dipeptide Extended (p-NH$_2$—F)$^{419}$Amide Analogs The cleavage of an (pNH2-Phe) amide linked dipeptide AibPro from various IGF-1 peptides was measured to determine the impact of the peptide sequence or heteroduplex on the dipeptide cleavage. Results for the tested peptides is shown in Table 12 and the data reveals that the IGF1-A chain alone represents a good model for the study of prodrug half life for IGF1 B:A ($Y^{B16}L^{B17}$) peptides.

TABLE 12

| Parent Peptide | Half Life (hr) |
|---|---|
| IGF1A(Ala)$^{6,11,20}$(pNH$_2$-Phe)$^{A19}$ | 2.2 |
| IGF1A(Acm)$^{6,11,20}$(pNH$_2$-Phe)$^{A19}$ | 1.8 |
| IGF1 B:A(S—S)$^{A7,B7}$(Acm)$^{A6,11,20,B19}$(pNH$_2$-Phe)$^{A19}$ | 1.8 |
| IGF1 B:A(pNH$_2$-Phe)$^{A19}$ | 1.6 |

Comparison of prodrug analogs of the IGF A-chain relative to the disulfide bound A chain and B chain construct (IGF1 A:B($Y^{B16}L^{B17}$)) revealed the two compounds had similar half lives for the prodrug form. The AibAla analog does not cleave and thus is not a prodrug, but serves to show the modification can inactivate the insulin analog IGF1 A:B($Y^{B16}L^{B17}$)(p-

$NH_2$—F)$^{419}$amide. Accordingly, the IGF1A chain alone was determined to be a good model for the study of pro-drug half life on IGF1 B:A (Y$^{B16}$L$^{B17}$) analog peptides. The AibAla analog does not cleave and thus is not a prodrug, but serves to show the modification can inactivate the insulin analog IGF1 A:B(Y$^{B16}$L$^{17}$)(p-NH$_2$—F)$^{419}$amide. For simplicity, prodrug half lives were determined using only the IGF 1 A chain in the absence of the B chain. The half lives of each propeptide was determined as described in Example 5. The data is presented in Table 13:

TABLE 13

Dipeptide half life on IGF1 dipeptide extended (p-NH$_2$—F)$^{419}$amide analogs

| Dipeptide | | Half Life (hr) |
| --- | --- | --- |
| Aib | Pro | 2.2 |
| AibOH | Pro | 165.0 |
| Aib | dPro | 1.9 |
| AibOH | Sar | 2.3 |
| dK(acetyl) | Sar | 16.3 |
| K | Sar | 21.8 |
| K(acetyl) | N-methyl Ala | 23.6 |
| dK(acetyl) | N-methyl Ala | 35.3 |

The data shows that by altering the substituents on the dipeptide prodrug element that the half life of prodrug can be varied from 2 hrs to >100 hrs.

Additional prodrug analog peptides were prepared using an IGF1-A(pNH2-F)$^{19}$ base peptide and altering the amino acid composition of the dipeptide prodrug element linked through the 4-amino phenylalanine at position A19. Dipeptide half lives were measured for different constructs both in PBS and in 20% plasma/PBS (i.e. in the presence of serum enzymes. The results are provided in Table 14. The results indicate that three of the four peptides tested were not impacted by serum enzymes.

TABLE 14

Dipeptide half life on IGF1-A(pNH2—F)$^{19}$

| | | Half Life (hr) | |
| --- | --- | --- | --- |
| | | PBS | 20% Plasma/PBS |
| Aib | Pro | 2.2 | 2.1 |
| Aib | dPro | 2.1 | 2.2 |
| AiBOH | Sar | 2.3 | |
| dK | N-isobutyl Gly | 4.4 | 4.1 |
| dK | N-hexyl Gly | 10.6 | |
| dK(acetyl) | Sar | 17.2 | |
| K | Sar | 21.8 | 5.9 |
| K(acetyl) | N-methyl Ala | 23.6 | |
| dK(acetyl) | N-methyl Ala | 35.3 | |
| AibOH | Pro | 165.0 | |
| K(acetyl) | Azetidine-2-carboxylic acid | Not cleavable | |
| dK(acetyl) | Azetidine-2-carboxylic acid | Not cleavable | |

EXAMPLE 13

Receptor Binding of IGF$^{B16B17}$ Analog Peptides over Time

Prodrug formulations of IGF$^{B16B17}$ Analog Peptides were prepared and their degradation over time was measured using the insulin receptor binding assay of Example 3. Peptides used in the assay were prepared as follows:

Dipeptide-IGF1A analogs

If not specified, Boc-chemistry was applied in the synthesis of designed peptide analogs. Selected dipeptide H$_2$N-AA1-AA2-COOH was added to (pNH$_2$-Phe)$^{19}$ on IGF1A (Ala)$^{6,7,11,20}$. The IGF-1 A chain C-terminal tripeptide Boc (Fmoc-pNH-Phe)-Ala-Ala was synthesized on MBHA resin. After removal of Fmoc by the treatment with 20% piperidine/DMF at room temperature for 30 minutes, Fmoc-AA2 was coupled to the p-amino benzyl side chain at A19 by using a threefold excess of amino acid, PyBop, DIEA and catalytic amount of pyridine. The Boc-synthesis of the remaining IGF-1 A chain (Ala)$^{6,7,11,20}$ sequence was completed using an Applied Biosystems 430A Peptide Synthesizer, yielding IGF-1 A chain (Boc)$^0$(Ala)$^{6,7,11,20}$(Fmoc-AA2-pNH-Phe)$^{19}$-MBHA. After the Fmoc group was removed from the N-terminus of AA2, Boc-AA1 was then coupled to the amine using threefold excess of amino acid, DEPBT and DIEA. Removal of the two Boc groups remaining on the A chain by TFA was followed by HF cleavage, yielding IGF-1 A-chain (Ala)$^{6,7,11,20}$(H$_2$N-AA1-AA2-pNH-Phe)$^{19}$amide. In the case of AA1 being d-lysine, acetylation on the ε-amine was performed prior to Boc removal. Dipeptide-IGF-1 A chain analogs were purified by semi-preparative RP-HPLC and characterized by analytical RP-HPLC and MALDI mass spectrometry.

Dipeptide-IGF-1 (YL) Analogs

A selected dipeptide H$_2$N-AA1-AA2-COOH was added to (pNH$_2$-Phe)$^{19}$ on IGF-1 A chain (Acm)$^{6,11,20}$ as described immediately above except PAM resin was used for the synthesis of IGF-1 A chain to yield a C terminal acid upon HF-cleavage. IGF-1 B chain (Y$^{B16}$L$^{B17}$)(Acm)$^{19}$ was synthesized on MBHA resin to yield a C terminal amide. The free thiol on Cys$^{B7}$ was modified by Npys through reaction with DTNP at a 1:1 molar ratio in 100% DMSO. Purified dipeptide-IGF-1 A chain and IGF-1 B chain (Y$^{B16}$L$^{B17}$) analogs were assembled using the "1+2" two step chain combination strategy illustrated in Scheme 1. Intermediate and final purifications were performed on semi-preparative RP-HPLC and characterized by analytical RP-HPLC and MALDI mass spectrometry.

Figures 9A, 9B, 9C:
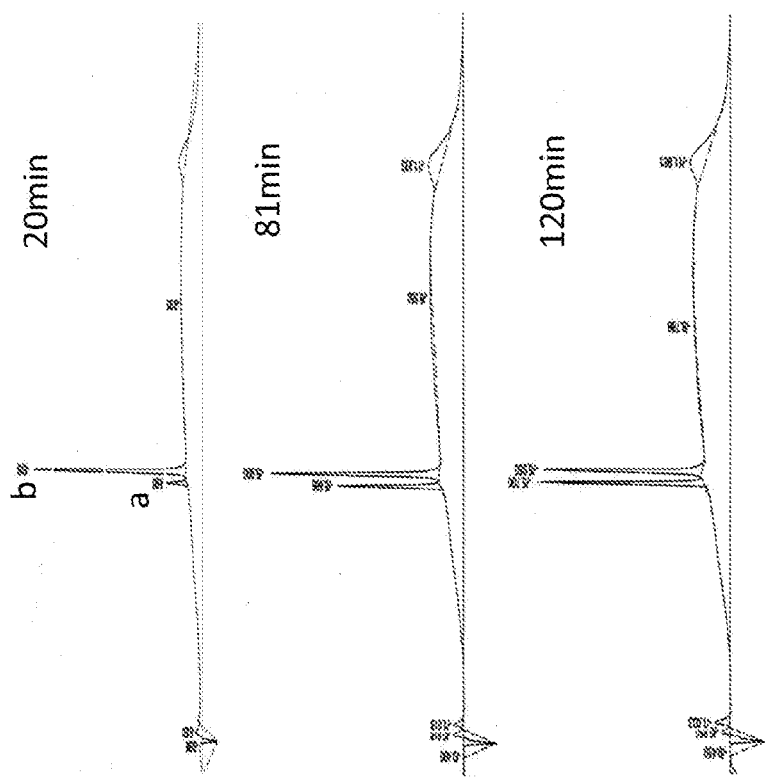
FIG. 9A-9C shows the degradation of a prodrug form of an IGF A chain peptide: (Aib-Pro on (p$NH_2$—F)$^{19}$ of IGF1A (Ala)$^{6,7,11,20}$amide. The dipeptide was incubated in PBS, pH 7.4 at 37° C. for predetermined lengths of time. Aliquots were taken at 20 minutes (FIG. 9A), 81 minutes (FIG. 9B) and 120 minutes (FIG. 9C) after beginning the incubation, were quenched with 0.1% TFA and tested by analytical HPLC. Peak a (IGF1A(Ala)$^{6,7,11,20}$(p$NH_2$—F)$^1$amide) and b (IGF1A(Ala)$^{6,7,11,20}$(Aib-Pro-pNH—F)$^{19}$amide) were identified with LC-MS and quantified by integration of peak area. The data indicate the spontaneous, non-enzymatic conversion of IGF1A(Ala)$^{6,7,11,20}$(Aib-Pro-pNH—F)$^{19}$amide to IGF1A (Ala)$^{6,7,11,20}$(p$NH_2$—F)$^1$amide over time.

The IGF$^{B16B17}$ analog peptide prodrugs were incubated in PBS, pH 7.4 at 37° C. and at predetermined time intervals an aliquot was taken and further degradation was quenched with 0.1% TFA and the aliquot was subjected to analytical HPLC analysis. Peaks a and b, representing the prodrug and active forms of the IGF$^{B16B17}$ analog peptide were identified with LC-MS and quantified by integration of peak area an HPLC. FIGS. 9A-9C show the output of an HPLC analysis of the degradation of the IGF$^{B16B17}$ analog peptide prodrug: IGF1A (Ala)$^{6,7,11,20}$(Aib-Pro-pNH—F)$^{19}$. Aliquots were taken at 20 minutes (FIG. 9A), 81 minutes (FIG. 9B) and 120 minutes (FIG. 9C) after beginning the incubation of the prodrug in PBS. The data indicate the spontaneous, non enzymatic conversion of IGF1A(Ala)$^{6,7,11,20}$(Aib-Pro-pNH—F)$^{19}$amide to IGF1A(Ala)$^{6,7,11,20}$(pNH$_2$—F)$^1$ amide over time.

Figure 10A:
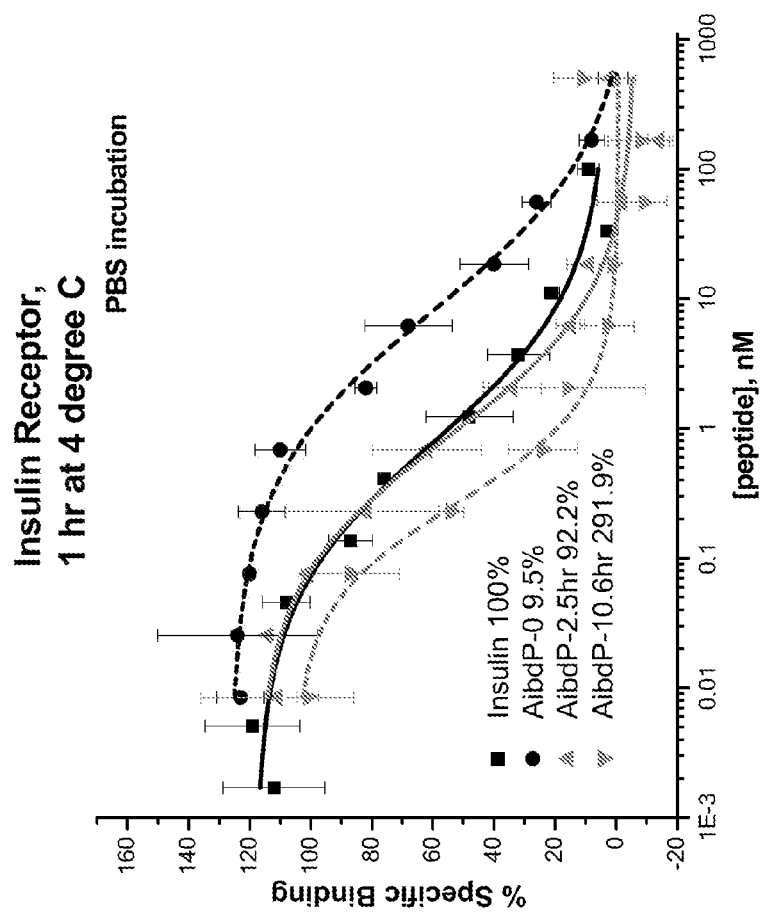
FIGS. 10A & 10B are graphs depicting the in vitro activity of the prodrug Aib, dPro-IGF1YL (dipeptide linked through the A19 4-aminoPhe).
Figure 10B:
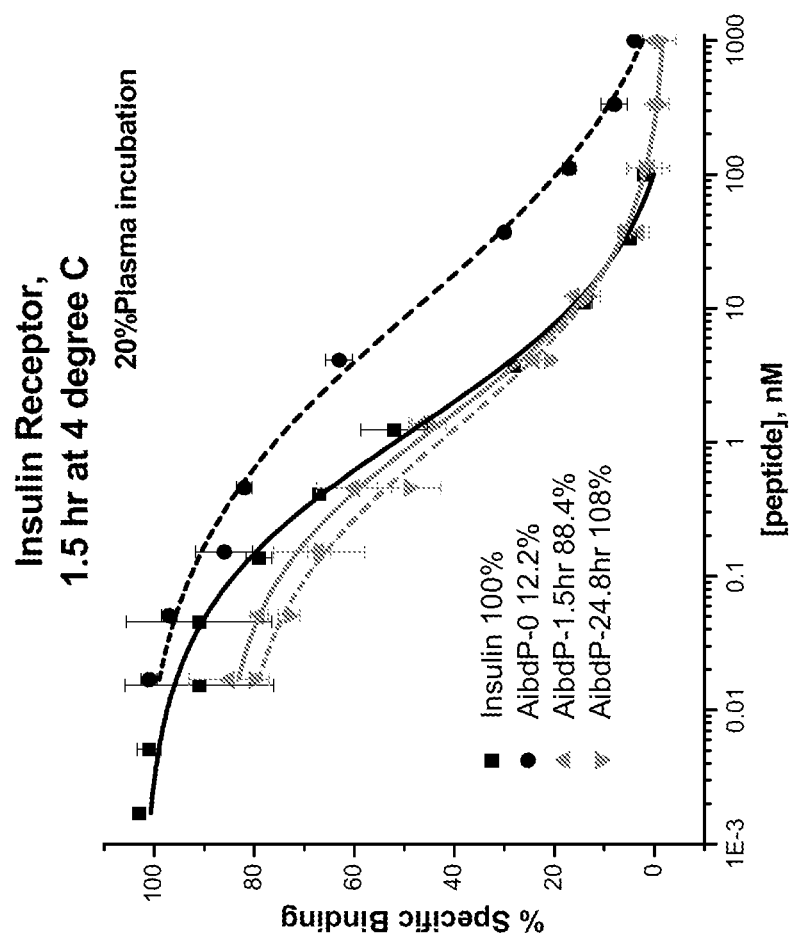

The degradation of the prodrug forms of IGF$^{B16B17}$ analog peptides to their active form was also measured based on the compounds ability to bind to the insulin receptor as measured using the in vitro assay of Example 3. FIGS. 10A & 10B are graphs depicting the in vitro activity of the prodrug Aib, dPro-IGF1YL (dipeptide linked through the A19 4-aminoPhe). FIG. 10A is a graph comparing relative insulin receptor binding of native insulin (measured at 1 hour at 4° C.) and the A19 IGF prodrug derivative (Aib, dPro-IGF1YL) over time (0 hours, 2.5 hours and 10.6 hours) incubated in PBS. FIG. 10B is a graph comparing relative insulin receptor binding of native insulin and the A19 IGF prodrug derivative (Aib, dPro-IGF1YL) over time (0 hours, 1.5 hours and 24.8 hours) incubated in 20% plasma/PBS at 37° C. As indicated by the data presented in the graph, increased activity is recovered form the A19 IGF prodrug derivative sample as the prodrug form is converted to the active IGF1YL peptide. The activity of the IGF$^{B16B17}$ analog peptides was measured relative to insulin receptor binding, and since the underlying IGF$^{B16B17}$ analog peptides have more activity than native insulin, activity of greater than 100% relative to insulin is possible.

Figure 11A:
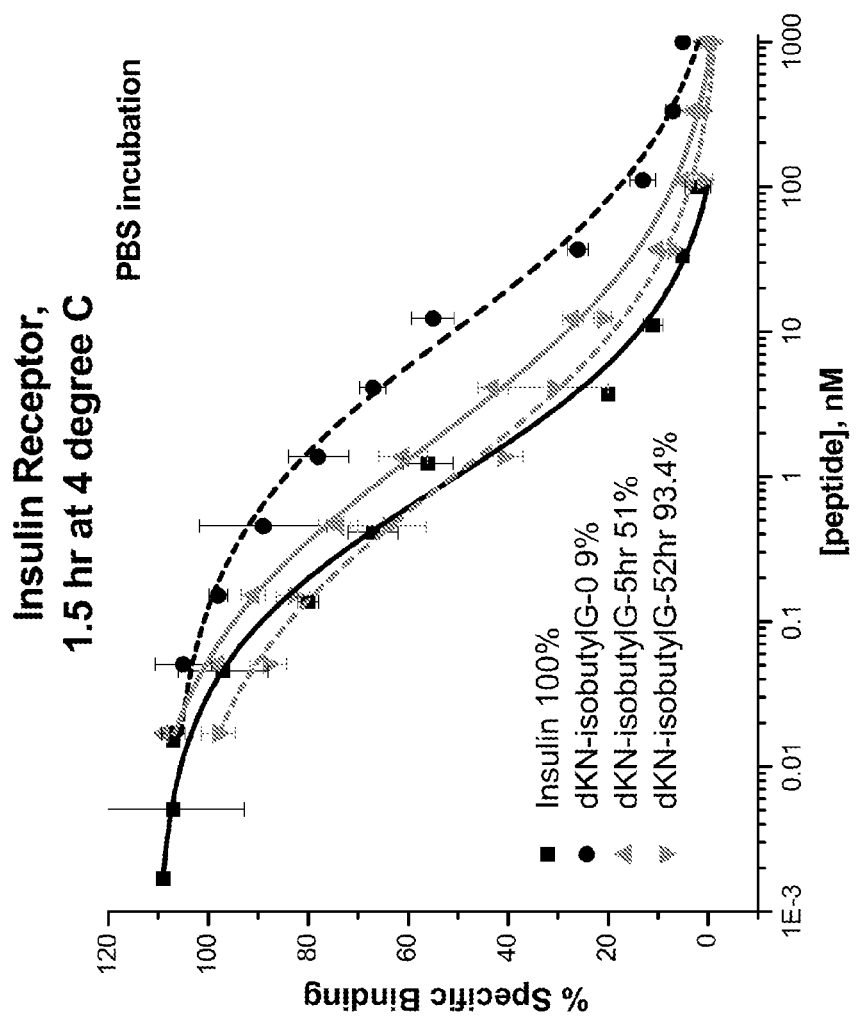
FIGS. 11A & 11B are graphs depicting the in vitro activity of the prodrug dK, (N-isobutylG)-IGF1YL (dipeptide linked through the A19 4-aminoPhe).
Figure 11B:
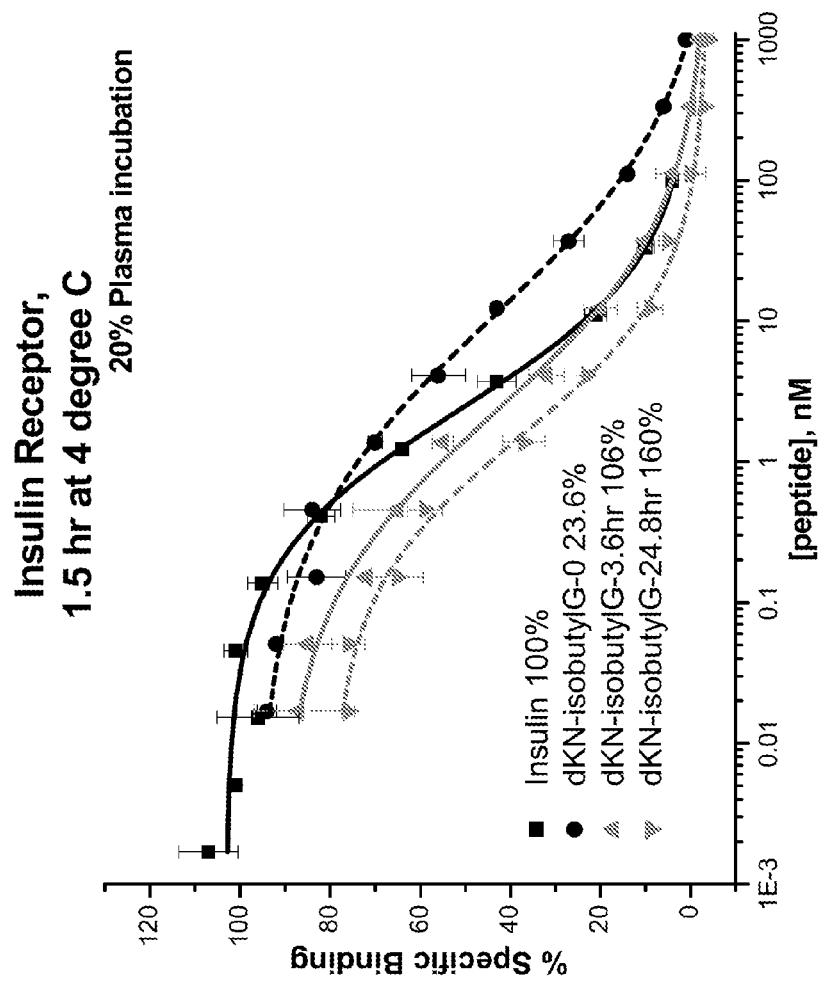

FIGS. 11A & 11B are graphs depicting the in vitro activity of the prodrug dK, (N-isobutylG)-IGF1YL (dipeptide linked through the A19 4-aminoPhe). FIG. 11A is a graph comparing relative insulin receptor binding of native insulin (measured at 1 hour at 4° C.) and the A19 IGF prodrug derivative (IGF1YL: dK, (N-isobutylG) over time (0 hours, 5 hours and 52 hours) incubated in PBS. FIG. 11B is a graph comparing relative insulin receptor binding of native insulin and the A19 IGF prodrug derivative (IGF1YL: dK, (N-isobutylG) over time (0 hours, 3.6 hours and 24.8 hours) incubated in 20% plasma/PBS at 37° C. As indicated by the data presented in the graph, increased activity is recovered form the A19 IGF prodrug derivative sample as the prodrug form is converted to the active IGF1YL peptide.

Figure 12A:
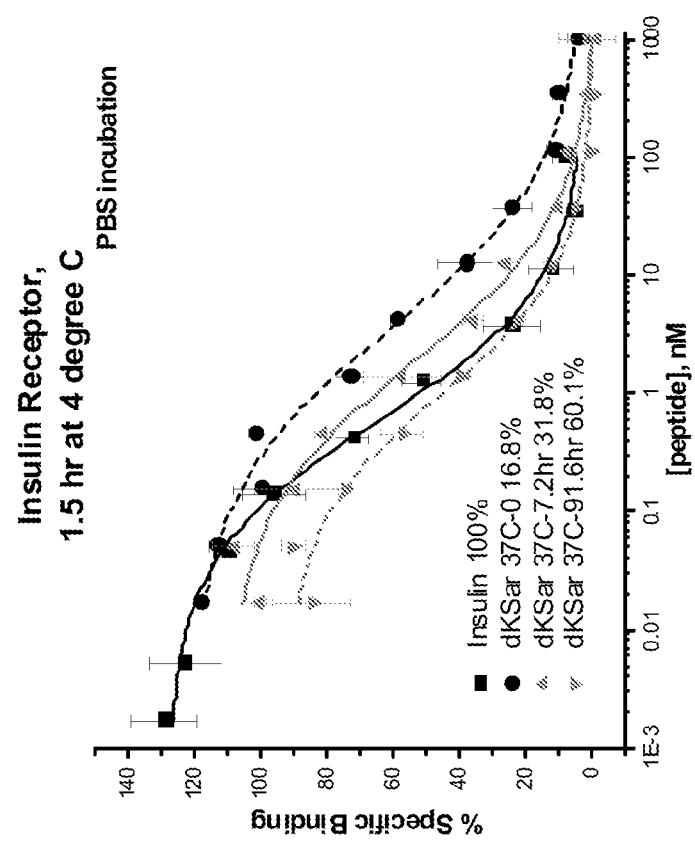
FIGS. 12A & 12B are graphs depicting the in vitro activity of the prodrug dK(e-acetyl), Sar)-IGF1YL (dipeptide linked through the A19 4-aminoPhe).
Figure 12B:
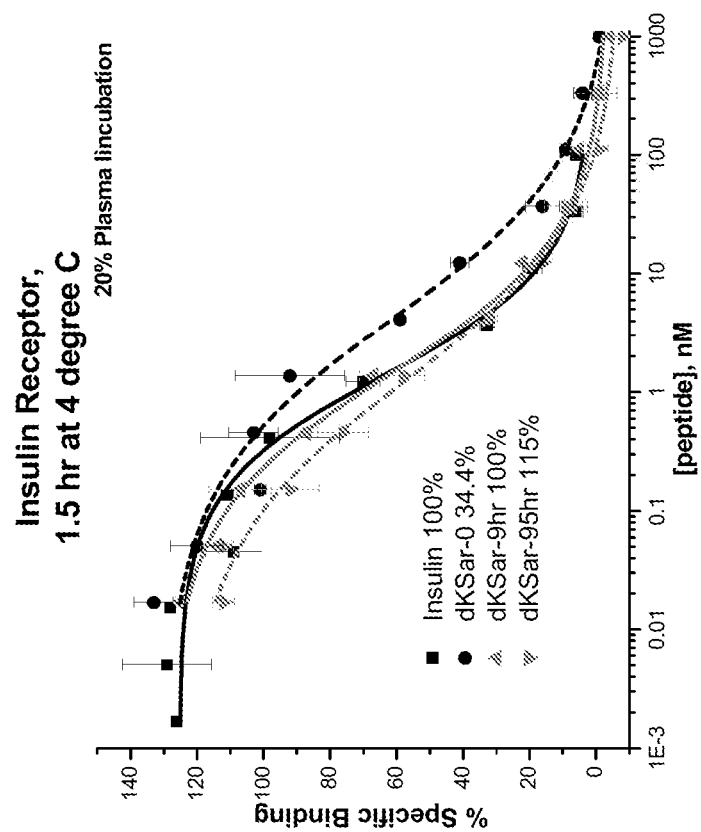
Figure 13:
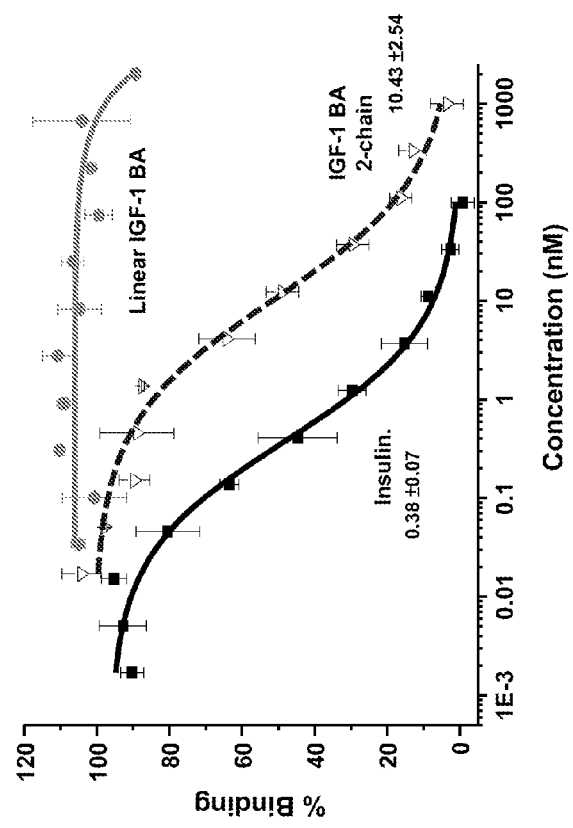
FIG. 13 is a graph comparing relative insulin receptor binding of native insulin heteroduplex and the IGF-1 A and B chain heteroduplex and a single chain IGF-1 analog wherein the carboxy terminus of the B chain is directly linked to the N-terminus of the IGF-1 A chain.
Figure 14:
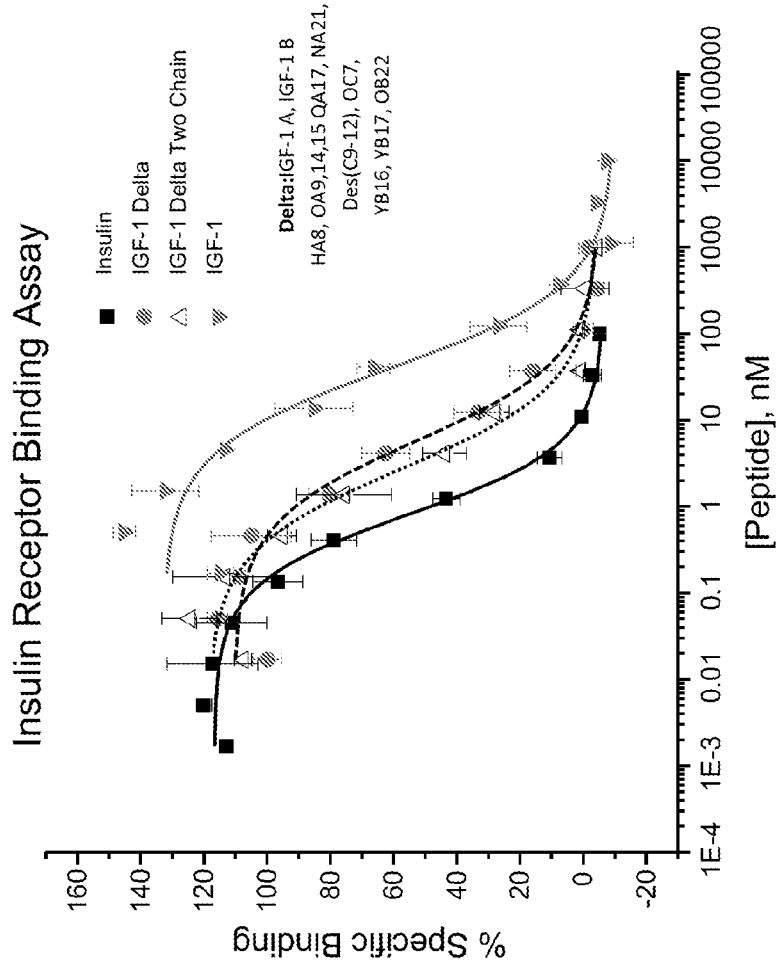
FIG. 14 is a graph comparing relative insulin receptor binding of native insulin heteroduplex, IGF-1, the IGF-1 delta heteroduplex and a single chain IGF-1 delta single chain analog wherein the carboxy terminus of the B chain is linked to the N-terminus of the IGF-1 A chain through a peptide linker consisting of the sequence GYGSSSOR (SEQ ID NO: 65), wherein the IGF-1 delta analog comprises the native IGF-1 sequence with the following amino acid substitutions: HA8, OA9, OA14, OA15, QA17, NA21, YB16, LB17, OB22.

FIGS. 12A & 12B are graphs depicting the in vitro activity of the prodrug dK(e-acetyl), Sar)-IGF1YL (dipeptide linked through the A19 4-aminoPhe). FIG. 12A is a graph comparing relative insulin receptor binding of native insulin (measured at 1 hour at 4° C.) and the A19 IGF prodrug derivative (IGF1YL: dK(e-acetyl), Sar) over time (0 hours, 7.2 hours and 91.6 hours) incubated in PBS. FIG. 12B is a graph comparing relative insulin receptor binding of native insulin and the A19 IGF prodrug derivative (IGF1YL: dK(e-acetyl), Sar) over time (0 hours, 9 hours and 95 hours) incubated in 20% plasma/PBS at 37° C. As indicated by the data presented in the graph, increased activity is recovered form the A19 IGF prodrug derivative sample as the prodrug form is converted to the active IGF1YL peptide.

EXAMPLE 14

Biosynthesis and Purification of Single Chain Insulin Analogs

An insulin-IGF-1 minigene comprising a native insulin B and A chain linked via the IGF-I C chain)(B$^0$-C$^1$-A$^0$) was cloned into expression vector pGAPZα A (purchased from Invitrogen) under GAP promoter (promoter of the glyceraldehyde-3-phosphate dehydrogenase (GAPDH)) for constitutive expression and purification of recombinant protein in yeast *Pichia pastoris*. The minigene was fused to an N-terminal peptide encoding *Saccharomyces cerevisiae* α-mating factor leader signal for secretion of the recombinant protein into the medium. A Kex2 cleavage site between the minigene and the leading α-mating factor sequence was used to cleave the leader sequence for secretion of the minigene with native amino termini. Single-site alanine mutations were introduced into C peptide at positions 1 (G1A), 2 (Y2A), 3 (G3A), 4 (S4A), 5 (S5A), 6 (S6A), 7 (R7A), 8 (R8A), 10 (P10A), 11 (Q11A), and 12 (T12A) of the B$^0$C$^1$A$^0$ minigene.

The minigenes including B$^0$C$^1$A$^0$, eleven alanine mutants, and other select derivatives were transformed into yeast *Pichia pastoris* by electroporation. Positive transformants were selected on minimal methanol plates and a genomic preparation of each *Pichia* isolate was performed and integration of the constructs into the yeast genome was confirmed by PCR. An 833 base pair PCR product was visualized on an agarose DNA gel. The insulin analogs were produced by fermentation of a corresponding yeast line. The yeast cells were pelleted by centrifugation at 5 K for 20 minutes in 500 ml Beckman centrifuge tubes and the media was kept for subsequent protein purification.

Growth media supernatants were filtered through 0.2 μm Millipore filter. Acetonitrile (ACN) was added to the supernatant to a final volume of 20%. The supernatant was purified over a Amberlite XAD7HP resin from Sigma, pre-equilibrated with 20% aqueous ACN. The resin was then rinsed twice with 30 ml of 20% aqueous ACN and contaminants were removed with 30% aqueous ACN containing 0.1% TFA. Partially purified insulin analogs were eluted from the column with 54% aqueous ACN containing 0.1% TFA and lyophilized. Lyophilized samples were re-suspended in 0.025M NH$_3$HCO$_3$ pH 8 and purified on a Luna C18 column (10 μm particle size, 300A° pore size). Protein was eluted from the column using a linear gradient of 20-60% aqueous ACN. MALDI-MS positive fractions were pooled and transferred to a disposable scintillation vial for subsequent lyophilization. Lyophilized samples were then resuspended in 20% aqueous ACN containing 0.1% TFA, and purified on a Luna C18 column (10 μm particle size, 300A° pore size). The protein was eluted from the column using a linear gradient of 18-54% aqueous ACN with 0.1% TFA. Protein elution was monitored at an absorbance 280 nm. MALDI-TOF MS positive fractions were analyzed via a C8 analytical column to insure purity.

Figure 15:
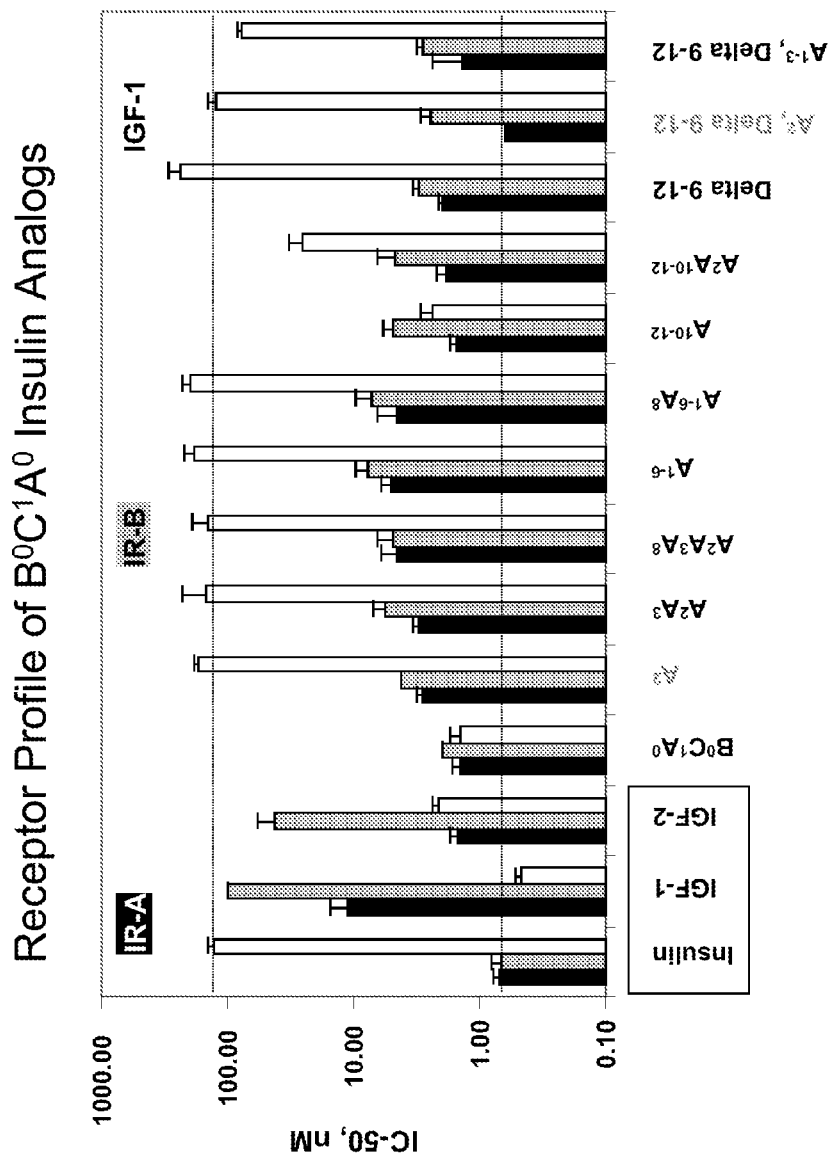
FIG. 15 is a bar graph depicting the relative in vitro binding activity of single chain insulin analogs at the IGF-1 receptor or the A or B subtype insulin receptors wherein the carboxy terminus of the native insulin B chain is linked to the amino terminus of the native insulin A chain via the IGF-1 C peptide or various derivative of the IGF-1 C peptide. In the $B^0C^1A^0$ insulin analog nomenclature, the $B^0$ and $A^0$ designations refer to the insulin sequences of the A and B chain, while $C^1$ designates the IGF-1 C peptide. As shown by the data a single chain insulin analog that links the B chain to the A chain via the IGF-1 C peptide is a potent insulin agonist. Furthermore, modifications of position 2 (e.g., substituting alanine for native tyrosine), or alternatively deleting the last four amino acids of the IGF-1 C linking peptide, generates a high potency, insulin selective single chain insulin analog.

FIG. 15 illustrates the potency of the single-chain insulin analogs. The B$^0$-C$^1$-A$^0$ analog demonstrated potency that was equally effective at both insulin receptor isoforms and the IGF-1 receptor. Mutation of the tyrosine at position 2 to alanine or the shortening of the C-peptide to eight amino acids through deletion of C9-12 provided a selective enhancement in the specificity of insulin action by significant reduction in the IGF-1 receptor activity. See also the data provided in Tables 15A and 15B:

TABLE 15A

Insulin Binding & Phosphorylation Analysis (B$^0$C$^1$A$^0$)

| Peptide | Insulin Binding | | Insulin Phosphorylation | |
|---|---|---|---|---|
| | IC$_{50}$, nM | n | EC$_{50}$, nM | n |
| Insulin | 0.54 ± 0.02 | 4 | 1.67 ± 0.13 | 1 |
| IGF-1 | 18.81 ± 1.77 | 3 | 29.20 ± 8.41 | 1 |
| 010 (B$^0$C$^1$A$^0$) | 2.83 ± 0.52 | 2 | 1.93 ± 0.43 | 1 |
| G1A | 1.21 ± 0.15 | 1 | 2.4 ± 0.24 | 1 |
| Y2A | 1.95 ± 0.28 | 3 | 1.86 ± 0.42 | 1 |
| G3A | 1.41 ± 0.05 | 2 | 2.13 ± 0.02 | 1 |
| S4A | 0.84 ± 0.47 | 2 | 0.76 ± 0.35 | 1 |
| S5A | 0.93 ± 0.44 | 1 | 2.23 ± 1.27 | 1 |
| S6A | 1.15 ± 0.24 | 1 | 2.33 ± 1.65 | 2 |
| R7A | 6.04 ± 0.82 | 1 | 5.21 ± 4.14 | 1 |
| R8A | 0.63 ± 0.09 | 1 | 2.03 ± 0.06 | 2 |
| P10A | 2.86 ± 0.93 | 1 | 2.59 ± 1.2 | 1 |
| Q11A | 1.79 ± 0.47 | 1 | 2.58 ± 0.83 | 1 |
| T12A | 1.2 ± 0.18 | 1 | 2.83 ± 1.31 | 1 |

TABLE 15B

IGF-1 Binding & Phosphorylation Analysis (B$^0$C$^1$A$^0$)

| Peptide | IGF-1 Binding | | IGF-1 Phosphorylation | |
|---|---|---|---|---|
| | IC$_{50}$, nM | n | EC$_{50}$, nM | n |
| Insulin | 60.63 ± 4.43 | 1 | 48.66 ± 1.59 | 1 |
| IGF-1 | 0.38 ± 0.07 | 1 | 0.88 ± 0.41 | 1 |
| 010 (B$^0$C$^1$A$^0$) | 4.49 ± 1.04 | 1 | 1.29 ± 2.28 | 1 |
| G1A | 42.36 ± 16.24 | 1 | 1.4 ± 0.62 | 1 |

TABLE 15B-continued

IGF-1 Binding & Phosphorylation Analysis (B⁰C¹A⁰)

| Peptide | IGF-1 Binding IC$_{50}$, nM | n | IGF-1 Phosphorylation EC$_{50}$, nM | n |
|---|---|---|---|---|
| Y2A | 257.9 ± 29.59 | 1 | 35.6 ± 14.55 | 1 |
| G3A | 34.02 ± 16.09 | 1 | 7.85 ± 0.78 | 1 |
| S4A | 15.30 ± 3.10 | 1 | 1.64 ± 1.65 | 1 |
| S5A | 13.06 ± 3.01 | 1 | 2.63 ± 1.88 | 1 |
| S6A | 2.44 ± 0.79 | 1 | 1.54 ± 0.62 | 2 |
| R7 | 43.86 ± 8.72 | 1 | 1.26 ± 1.55 | 1 |
| R8 | 10.85 ± 1.47 | 1 | 0.50 ± 0.23 | 2 |
| P10A | 6.42 ± 0.47 | 1 | 2.79 ± 1.12 | 1 |
| Q11A | 4.23 ± 0.43 | 1 | 0.41 ± 0.69 | 1 |
| T12A | 9.15 ± 0.83 | 1 | 1.44 ± 1.36 | 1 |

Figure 16:
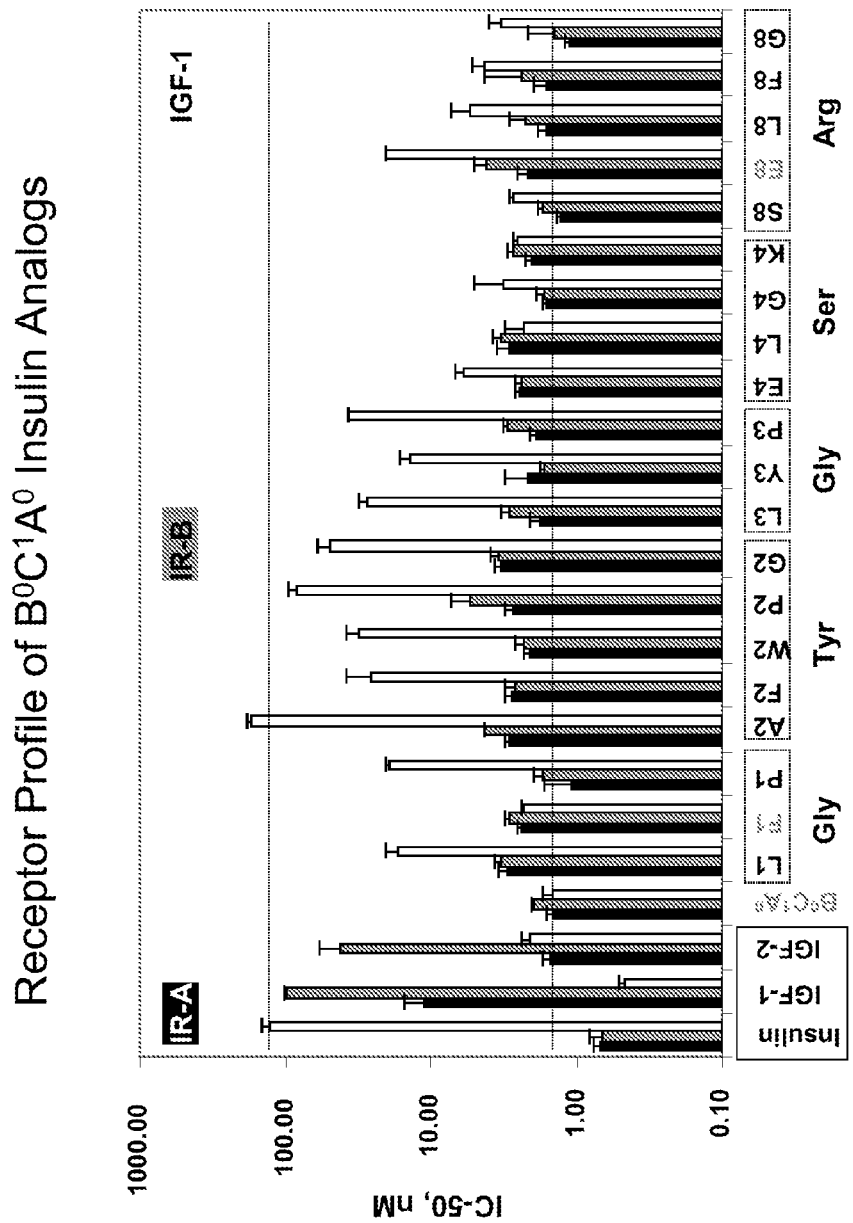
FIG. 16 is a bar graph depicting the relative in vitro binding activity of single chain insulin analogs of the formula $B^0C^1A^0$ at the IGF-1 receptor or the A or B subtype insulin receptors wherein the native sequence of the linking IGF-1 C peptide has been modified by the indicated amino acid substitutions at position 1, 2, 3, 4 or 8. In the $B^0C^1A^0$ insulin analog nomenclature, the $B^0$ and $A^0$ designations refer to the insulin sequences of the A and B chain, while $C^1$ designates the IGF-1 C peptide
Figure 17:
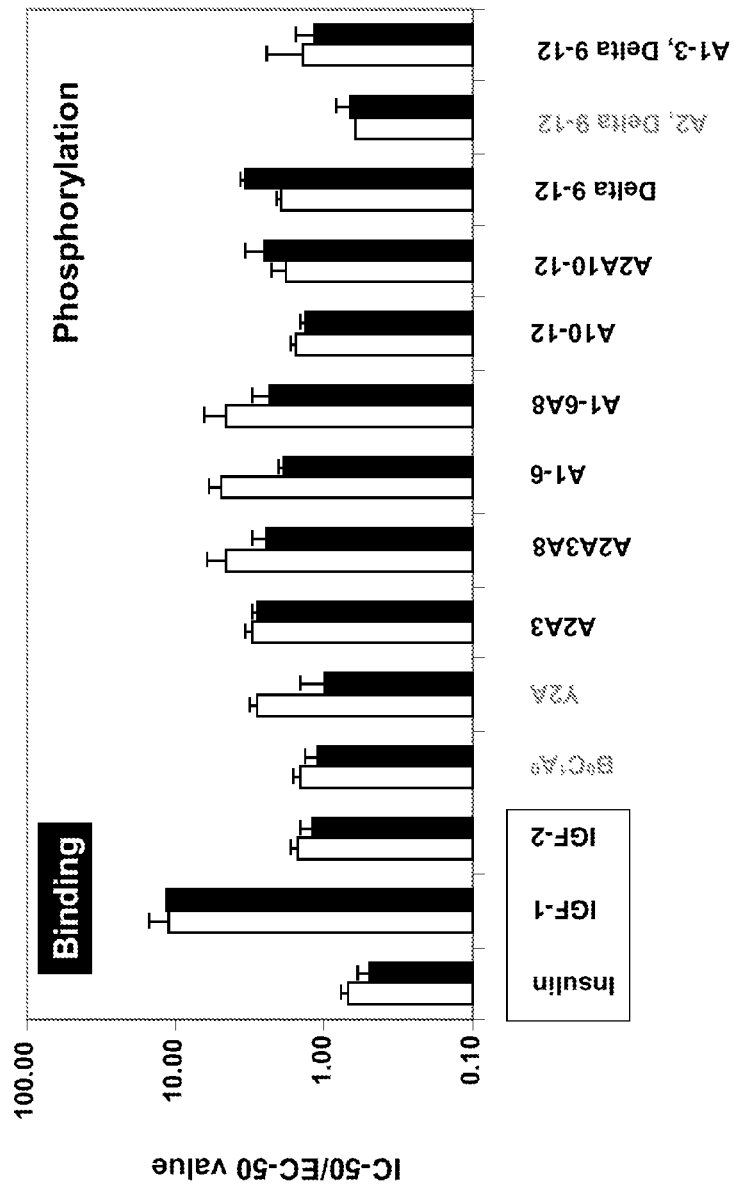
FIG. 17 is a bar graph depicting the relative in vitro binding activity and phosphorylation activity of single chain $B^0C^1A^0$ insulin analogs at the A subtype insulin. The activity of the native IGF-1 C peptide (010) relative to various amino acid substitutions or deletions was compared. In the $B^0C^1A^0$ insulin analog nomenclature, the $B^0$ and $A^0$ designations refer to the insulin sequences of the A and B chain, while $C^1$ designates the IGF-1 C peptide
Figure 18:
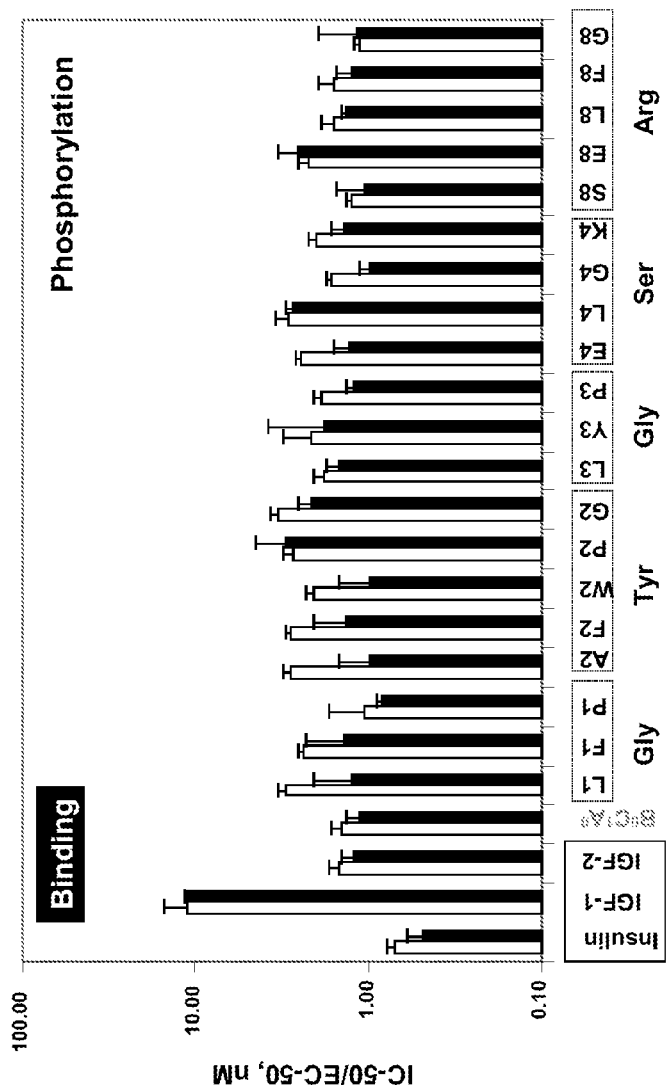
FIG. 18 is a bar graph depicting the relative in vitro binding activity and phosphorylation activity of single chain $B^0C^1A^0$ insulin analogs at the A subtype insulin wherein the native sequence of the linking IGF-1 C peptide has been modified by the indicated amino acid substitutions at position 1, 2, 3, 4 or 8. This data in conjunction with the data provided in FIG. 17 demonstrate the consistency between the binding and phosphorylation activity of the insulin analogs.

FIG. 16 demonstrates that position 2 and 3 in the C-peptide are most sensitive to modification at the IGF-1 receptor with the insulin receptor proving to be relatively immune to modification. Finally, FIGS. 17 and 18 present the in vitro analysis of the single-chain insulin mutants as a ratio of binding affinity (IC50) and biochemical signaling through tyrosine phosphorylation (EC50). The two independent measurements demonstrate great consistency thereby validating this in vitro approach to structure-function analysis. All of the analogs maintained single unit nanomolar activity with certain specific analogs proving to be slightly enhanced in potency (low single unit nanomolar). The most insulin selective analogs were those that we missing the last four residues of the C-peptide, had an alanine mutation at position two of the C-peptide, or a combination of the two changes.

EXAMPLE 15

Synthesis and Characterization of Single Chain Insulin Analogs linked by Mini-Peg A series of single chain insulin analogs were prepared by solid-phase synthesis using a two-step native chain ligation approach. The initial peptide was a linear construct where the N-terminus started at CysB 19 and continued through to AsnA21 with a short linear polymer of ethylene glycol serving as a connection from the C-terminus of the last B-chain amino acid to the N-terminus of the first amino acid of the A-chain, typically glycine. The N-terminal end of the B-chain (which typically starts with the first N-terminal amino acid of the final insulin analog and ends with amino acid 18 of the B-chain, typically valine) was fragment-coupled to the single linear peptide. Once coupled by thiol-assisted native chain ligation, the peptide was purified chromatographically, converted to the correct disulfide isomer and purified once more by high performance chromatography. All insulin analogs were analyzed for purity by HPLC and MS analysis.

Figure 19:
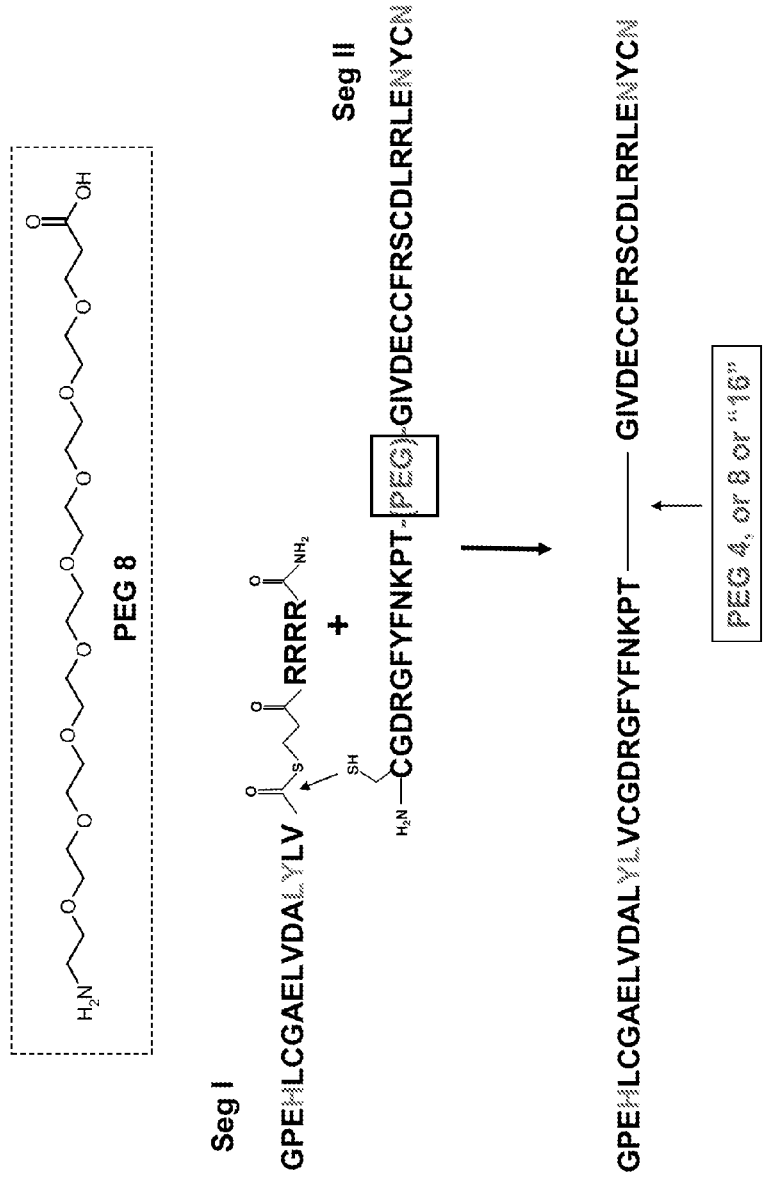
FIG. 19 is a schematic drawing showing the preparation of an IGF-1 YL single chain insulin analog that uses a PEG polymer as the linking moiety.

FIG. 19 provides a schematic overview of the synthetic design with a single example of using PEG8 as a linker. The same approach was employed to synthesize analogs of shorter and longer length as well as those of variable length obtained by the use of more than one mini-peg covalently linked in linear fashion as an amide.

FIGS. 20-24 provide in vitro experimental results obtained through the study of the single chain insulin analogs linked by a mini-peg of defined length at a specific location. FIG. 20 illustrates that the use of the minipeg of 4, 8, or 16 ethylene glycol units yielded poor potency insulin analogs of less than 5% activity relative to the native hormone as measured by binding or biochemical signaling. These results are less impressive than the potency we had previously observed for single insulin analogs where peptides varying in length of 8-12 amino acids were used to linearly couple the C-terminus of the B-chain with the N-terminus of the A-chain (see FIGS. 14-18).

Figure 21:
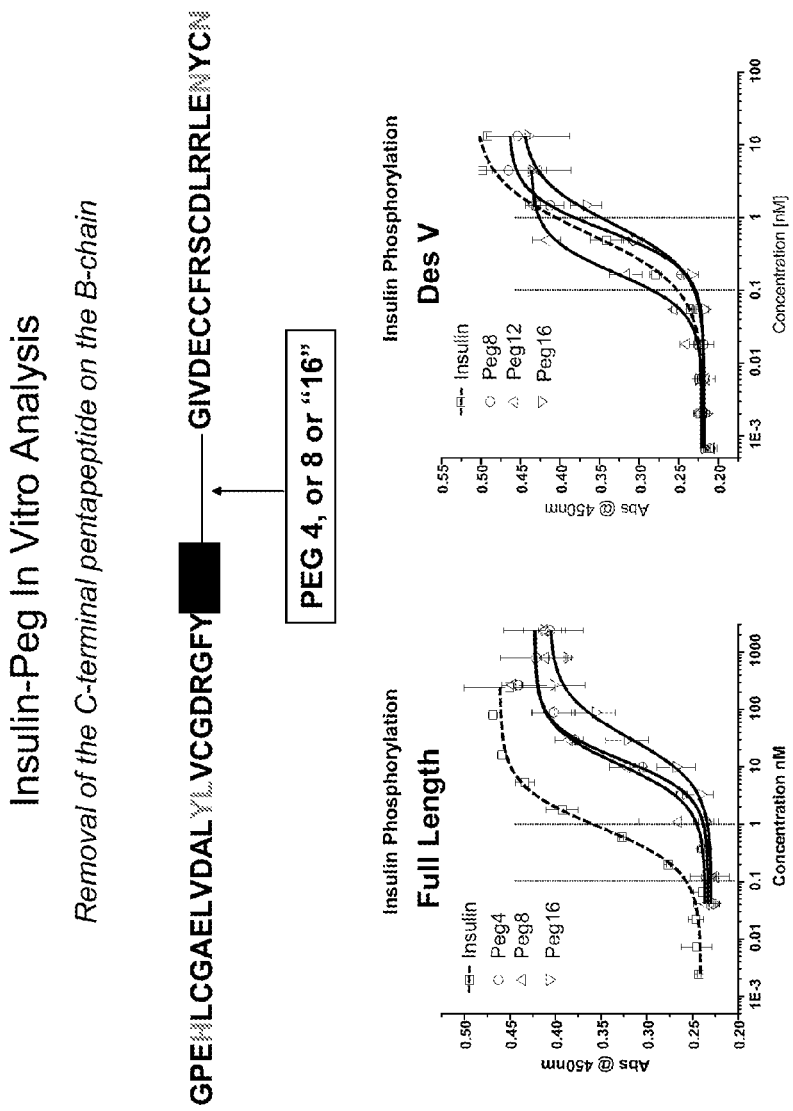
FIGS. 21A & B are graphs demonstrating the phosphorylation activity of single chain insulin analogs at the insulin and IGF-1 receptors. Single chain insulin analogs comprise the full length native insulin B and A chains linked together by either a 4, 8 or 16 monomeric PEG linking moiety have relatively low insulin potency as compared to native insulin heteroduplex (FIG. 21A), although they exhibit 10 to 100 fold greater activity relative to a single chain insulin analog without a PEG or other linking moiety (see Table 16). However, when the last 5 carboxy amino acids of the insulin B chain ($B^{26-30}$) are deleted (DesV) and the carboxy terminus of the remaining B chain is linked to the native insulin A chain by either an 8, 12 or 16 monomeric PEG linking moiety, the single chain analogs exhibit at least equivalent or higher potency relative to the native insulin heteroduplex.

Table 16 and FIG. 21 demonstrate a dramatic increase in potency when the same size mini-peg linkers were used to couple the C-terminus of a shortened B-chain to the N-terminus of the A-chain. The des-V (missing amino acids B26-30) insulin analog once coupled with the mini-pegs were competitively potent with native hormone, more than a tenfold increase relative to the full length B-chain analogs.

TABLE 16

Phosphorylation Activity of mini-PEG linked Single Chain Insulin Analogs at Insulin and IGF-1 receptors

| | Insulin | | IGF-1 | |
|---|---|---|---|---|
| | % Insulin | n | % Insulin | n |
| PEG 4 | 5.69 | 3 | 0.44 | 2 |
| PEG 8 | 7.44 | 5 | 1.21 | 4 |
| PEG 16 | 5.17 | 3 | 0.16 | 2 |
| No PEG DesV | 0.04 | 1 | 0 | 1 |
| k-PEG 4 DesV | 2.37 | 2 | 0.16 | 2 |
| PEG 8 DesV | 91.2 | 5 | 2.43 | 5 |
| PEG 12 DesV | 179 | 3 | 4.51 | 3 |
| PEG 16 DesV | 83.3 | 3 | 1.39 | 3 |

Figure 22A:
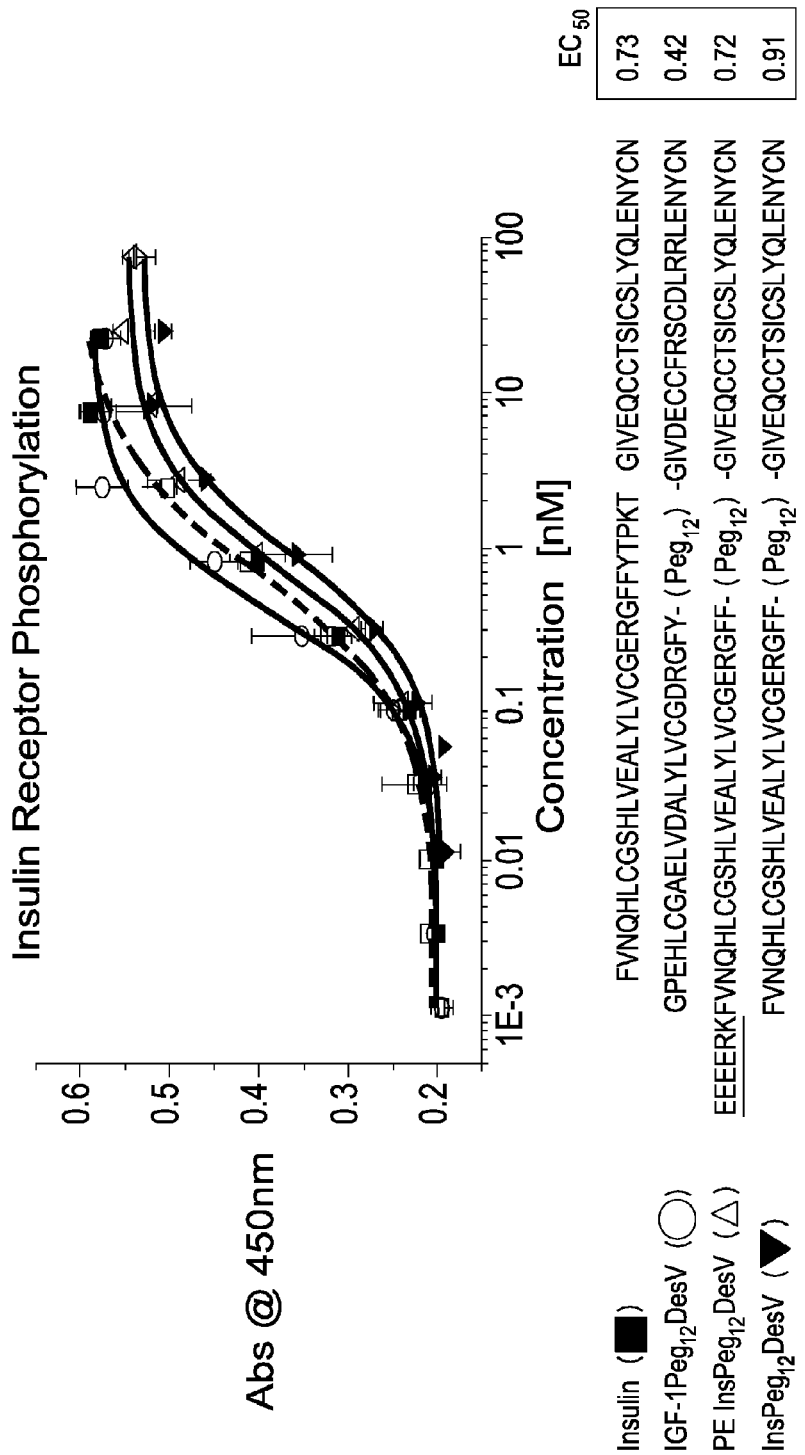
FIG. 22A-C are graphs demonstrating the near equivalency of single chain insulin analogs at the insulin receptor.
Figure 22:
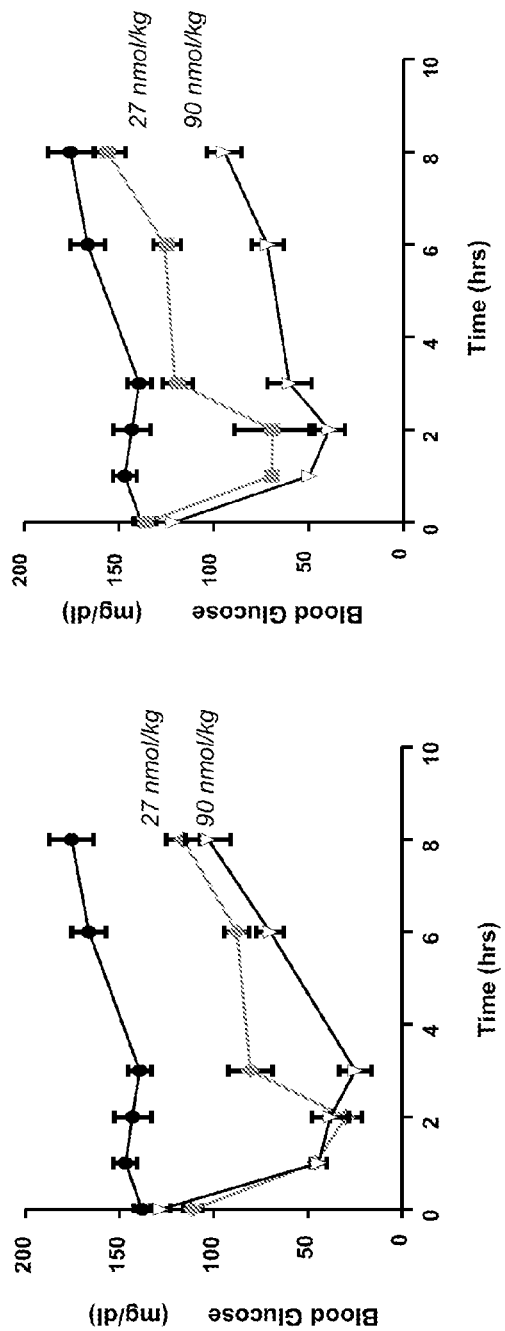
Figure 23:
FIG. 23 is a table demonstrating various histidine substitutions to single chain insulin/IGF-1 based analogs. The substitution of histidine at position 8 of the IGF-1 A chain can enhance the potency of IGF based single chain insulin analog agonists.
Figure 24:
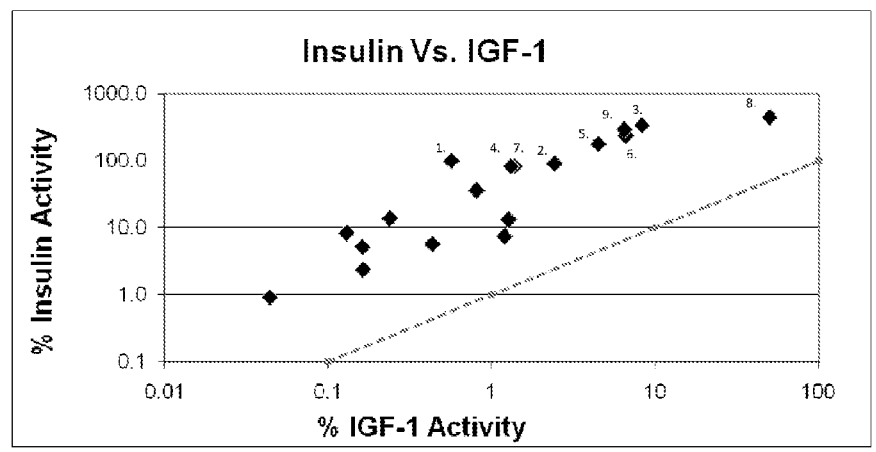
FIG. 24 is a comparative analysis of the single chain peg-linked analogs activities at the insulin and IGF-1 receptors as measured by receptor signaling through phosphorylation.

FIG. 22 demonstrates the competitive performance of two-chain heteroduplex native insulin with single chain insulin analogs where the A and B chains were either largely derived from insulin or IGF-1. The peptides were found to be of comparable bioactivity. FIG. 23 is a further analysis using a peg-12 linker in the des-V format of the B-chain with largely IGF-1 based sequence, but including the B16,17 YL change to enhance insulin receptor activity. The results clearly demonstrate that very high potency insulin analogs can be obtained through the use of histidine at position A8. Residual IGF-1 receptor activity is slightly greater than native insulin. FIG. 24 shows that there is a linear correlation of insulin receptor activity to IGF-1 receptor activity which is consistent with the type of relationship known for structure-function analysis performed with the two-chain native insulin structure.

Figure 25:
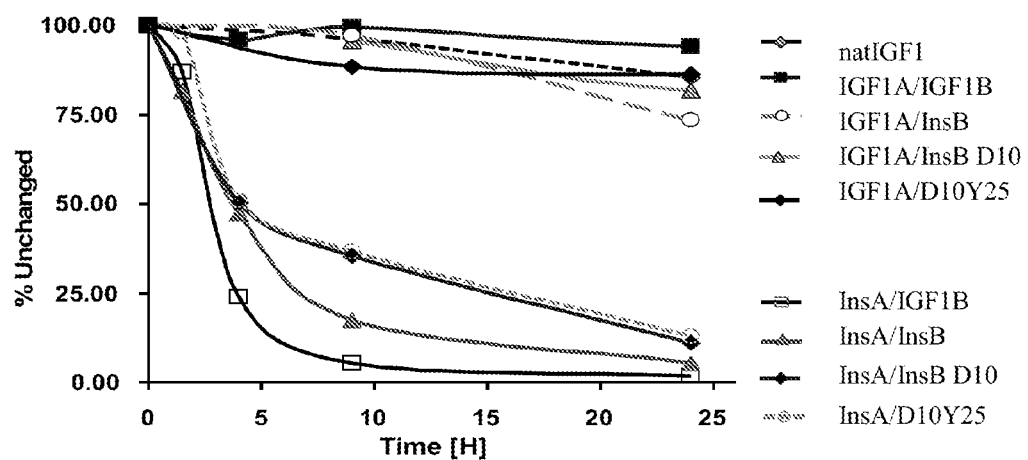
FIG. 25 is a graph demonstrating that single chain analogs comprising an IGF-1 A chain have enhanced resistance to degradation by the specific insulin degrading enzyme (IDE) relative to single chain analogs comprising an insulin A chain.
Figure 26:
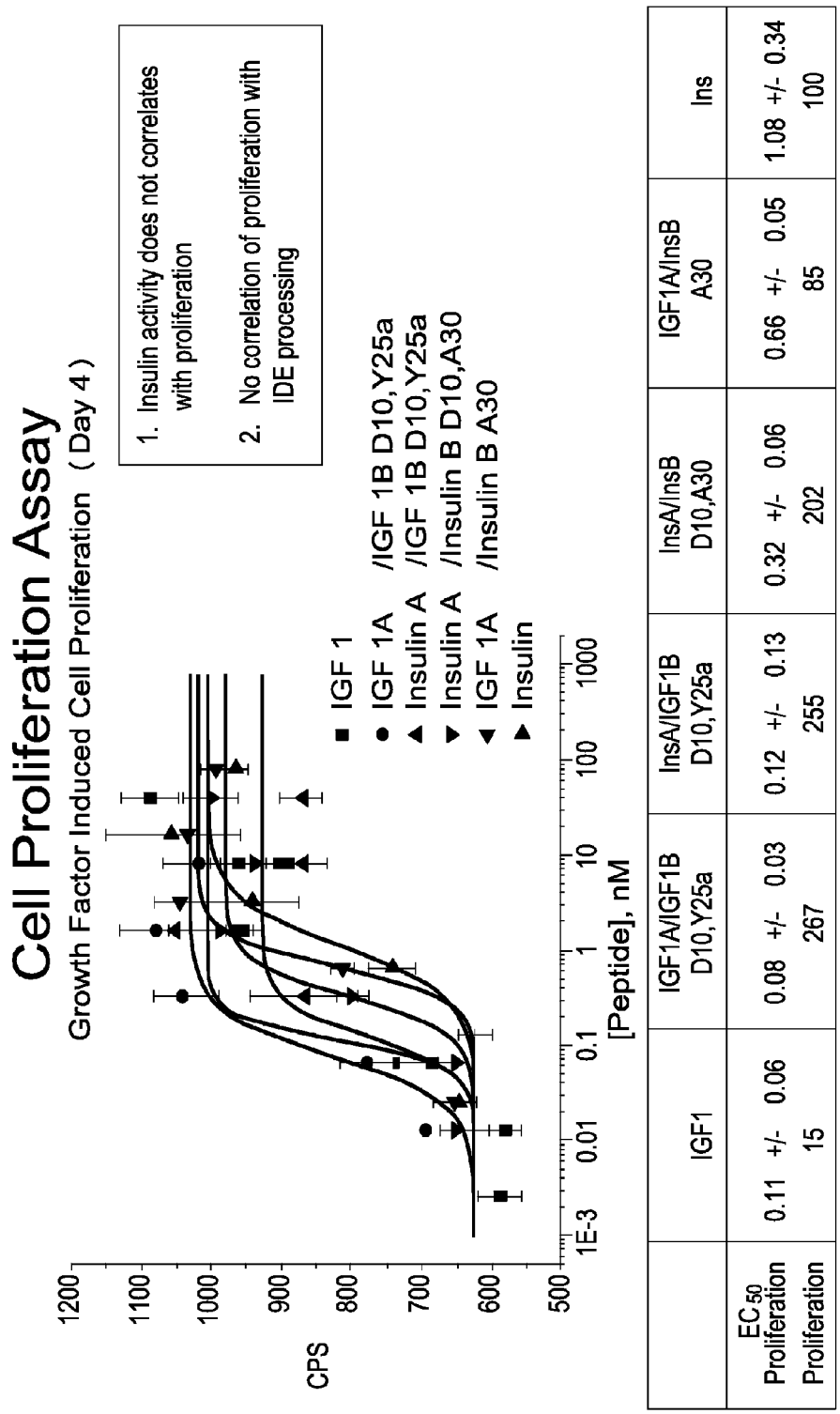
FIG. 26 is a graph demonstrating the relative activity of IGF-1, insulin and insulin/IGF chimera to induce in vitro cellular proliferation. The results indicate that the insulin activity associated with the IGF-1 single chain insulin analogs does not correlate with the proliferation activity associated with native IGF-1.

FIG. 25 demonstrates that the cleavage of insulin analogs by the insulin-specific degrading enzyme (IDE) is extremely robust and easily detected in those insulin analogs where the A-chain is derived from the native insulin sequence. In contrast those analogs where the A-chain is derived from the sequence of IGF-1 appear to be extremely resistant to proteolysis. The prospect that the increased stability might engender increased mitogenicity was explored and the results are reported in FIG. 26. There did not appear to be a correlation of the higher insulin potency analogs with increased proliferation. Furthermore, and of specific importance to proteolytic stability the analogs that were more resistant to IDE did not appear to be of any greater mitogenic potential.

Figure 27:
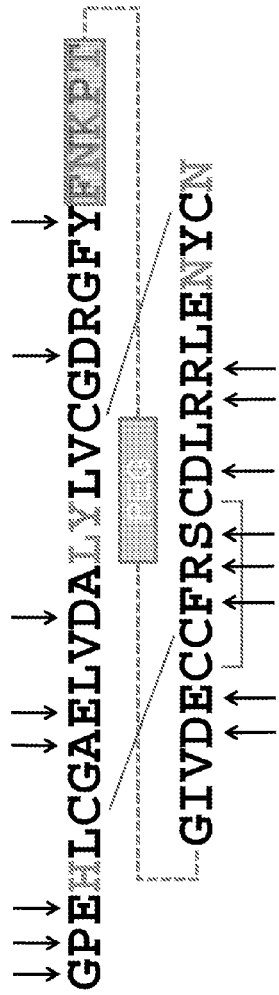
FIG. 27 is a comparative analysis of single chain peg-linked analogs activities at the insulin and IGF-1 receptors as measured by receptor signaling through phosphorylation. Single chain analogs using PEG chain linkers of different lengths were analyzed to measure how different sized PEG linking moieties impact in vitro activities at the insulin and IGF-1 receptors. The data presented in FIG. 27 reveals that a $PEG_{12}DesV$ construct (wherein the 5 carboxy terminal amino acid of the B chain have been deleted) provides the most potent compound.

A comparative analysis was conducted on single chain analogs using PEG chain linkers to measure how different sized PEG linking moieties impact in vitro activities at the at the insulin and IGF-1 receptors as measured by receptor signaling through phosphorylation. The data presented in FIG. 27 reveals that a PEG$_{12}$DesV construct (wherein the 5 carboxy terminal amino acid of the B chain have been deleted) provides the most potent compounds.

Figure 28A:
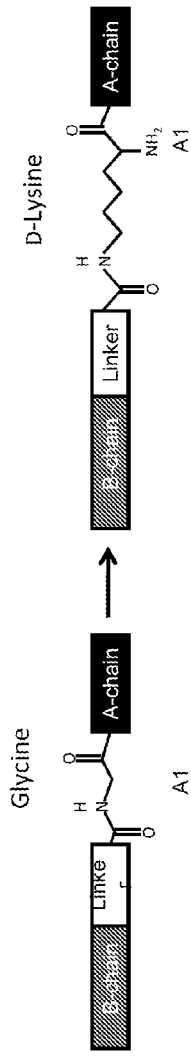

A single chain analog was constructed comprising a $PEG_{12}$ and a single amino acid (glycine or lysine) as the linking moiety, linking a DesV B chain to the native insulin A chain. Comparative analysis of single chain peg/amino acid-linked analogs in vitro activities at the insulin and IGF-1 receptors as measured by receptor binding and receptor signaling through phosphorylation revealed the peg/amino acid-linked analogs were potent insulin receptor agonists (see FIG. 28A). Similarly the addition of two lysine residues to the linking moiety (single chain peg/(lysine)$_2$-linked analog) produced a potent single chain peg/amino acid-linked insulin receptor agonist (see FIG. 28B) as measured by receptor binding and receptor signaling through phosphorylation.

Figure 29B:
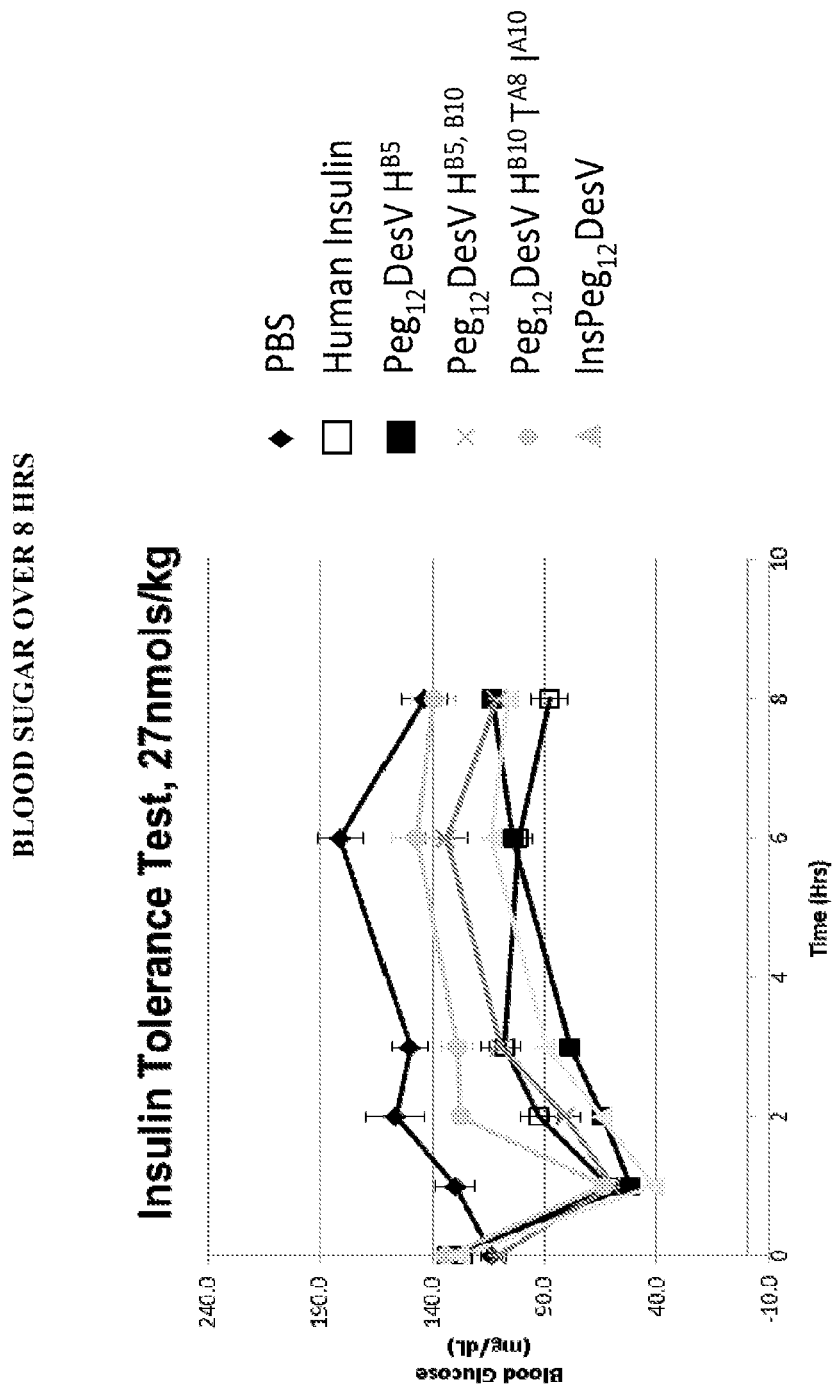
Figure 29C:
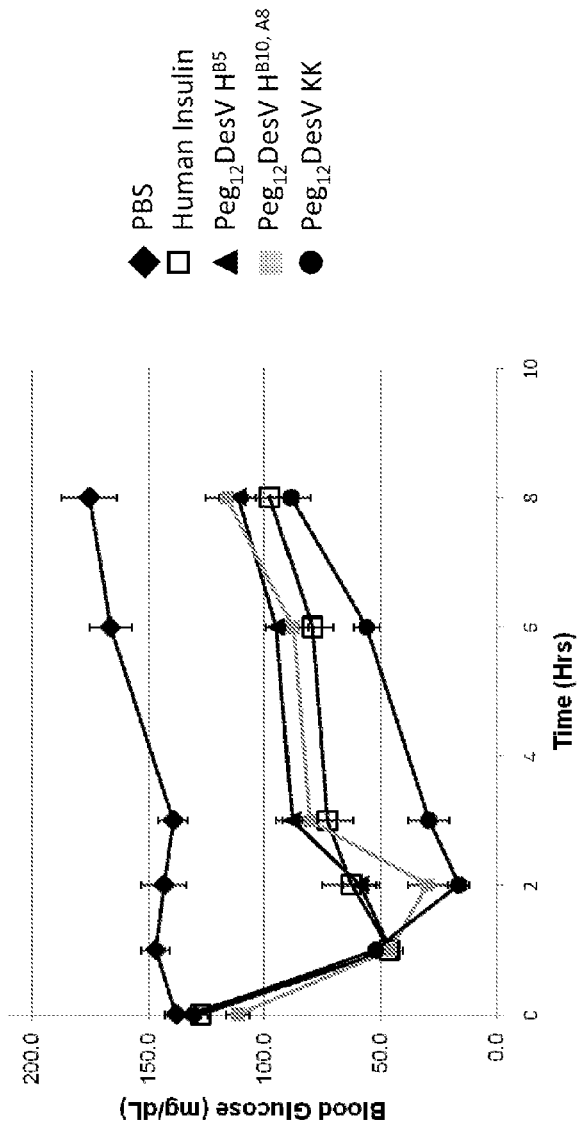
Figure 29D:
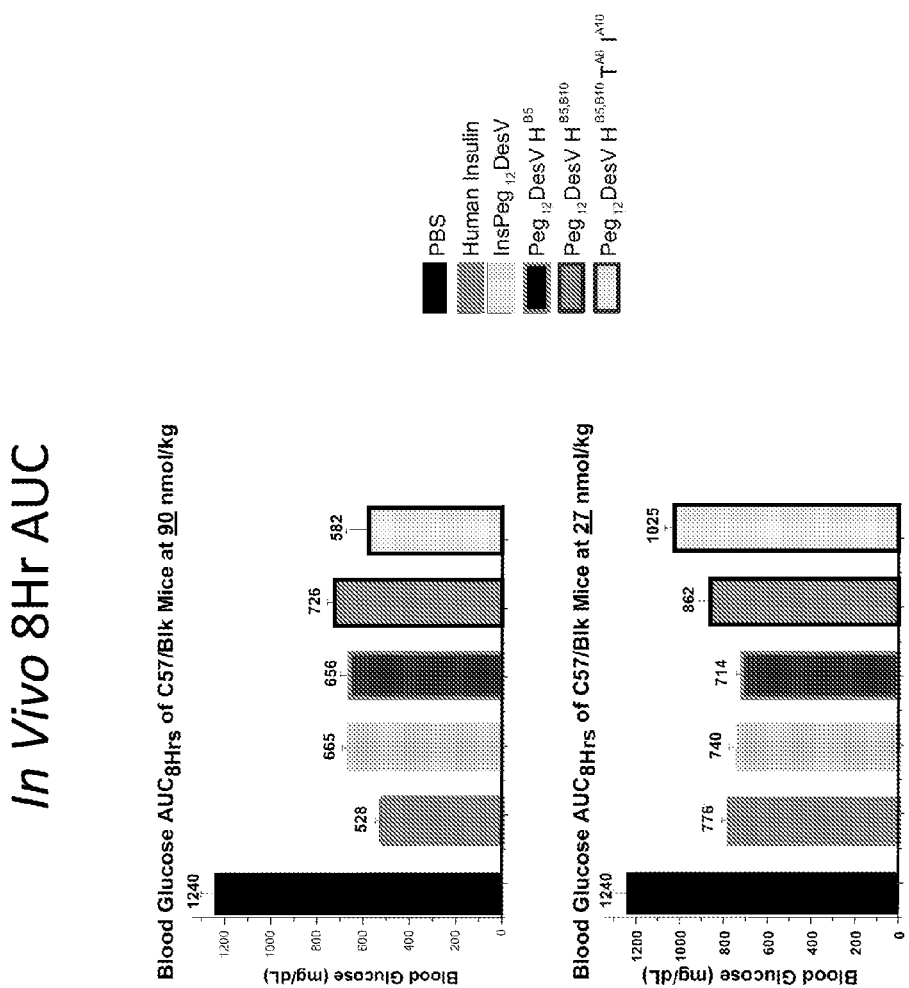
Figure 29E:
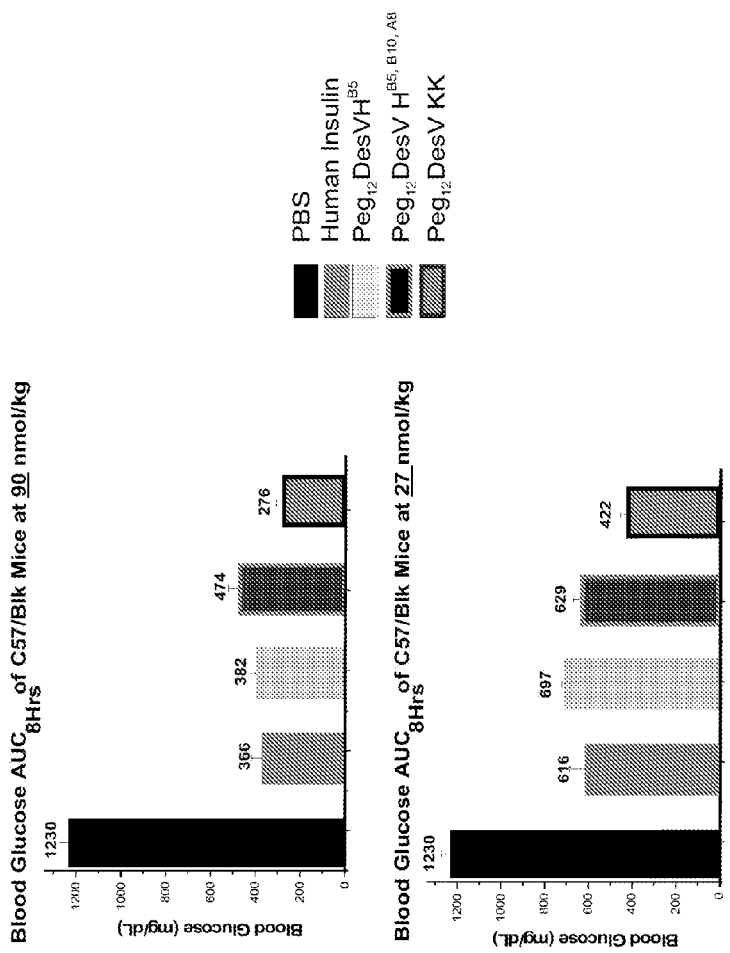
Figure 30A:
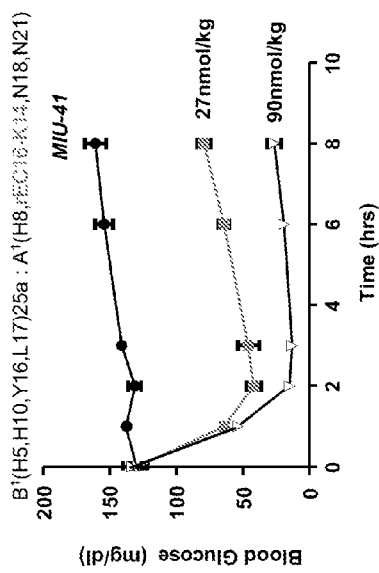
FIGS. 30A-30D are graphs showing the results of comparative insulin tolerance tests conducted on mice comparing the ability of human insulin to reduce and sustain low blood glucose concentration relative to three different acylated insulin analogs. The compounds were tested at two different concentrations (27 nmol/kg and 90 nmol/kg). The acylated insulins included MIU-41, MIU-36 and MIU-37. MIU-41 [$B^1$(H5, H10, Y16, L17)25a:$A^1$(H8, rEC16-K14, N18, N21)], is a two chain insulin analog having a C16 acylation via a gamma glutamic acid linker attached to a lysine residue located at position A14. MIU-36 [$B^1$(C16-K0, H5, H10, Y16, L17)25a:$A^1$(N18, N21)], is a two chain insulin analog having a C16 acylation linked to the N-terminus of the B chain). MIU-37 [$B^1$(H5, H10, Y16, L17, C16rE-K22)25a:$A^1$(N18, N21)], is a two chain insulin analog having a C16 acylation via a gamma glutamic acid linker attached to a lysine residue located at position B22.
Figure 30B:
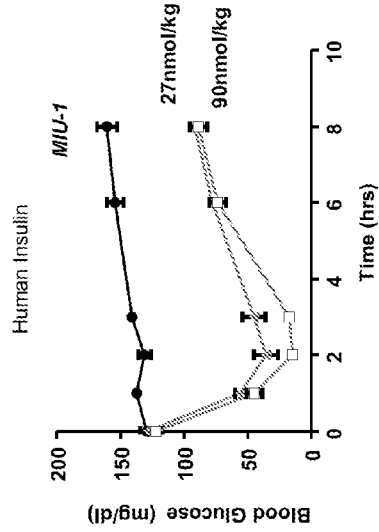
Figure 30C:
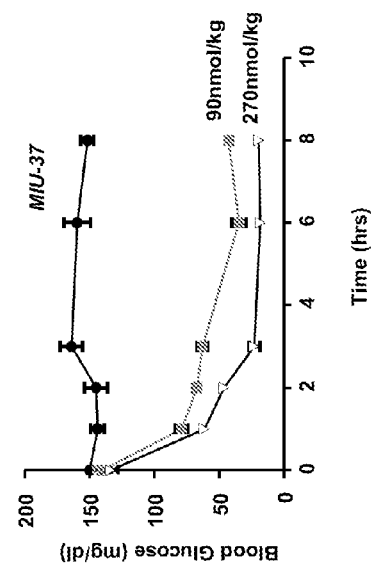
Figure 30D:
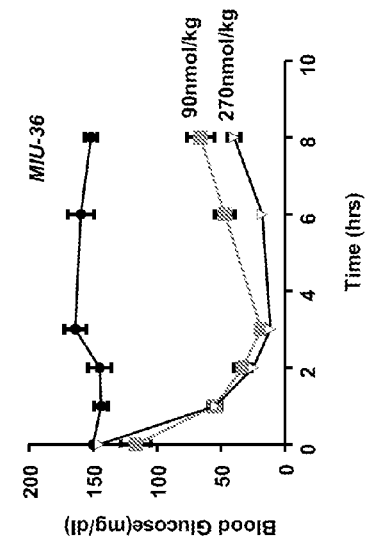

FIG. 29A-E provides data of mice administered various single chain insulin analogs. FIG. 29A provides in vitro comparative analysis of single chain peg-linked analogs activities at the insulin receptor as measured by receptor binding and receptor signaling through phosphorylation. The activity of the compounds in vivo was also tested by administering the compounds to mice. Food was removed four hours prior to administering peptide to normal mice and withheld for the duration of the study. Glucose was measured just prior to administration of test compounds and at 1, 2, 3, 6 and 8, 12, 16, 20 and 24 hours after administration. All insulin analogs were administered subcutaneously in a volume of 10 ul/gm of body weight. FIGS. 29B and 29C provide data on blood glucose concentrations over 8 hours after administration of the listed analogs. FIGS. 29D and 29E provide data on blood glucose AUC values after administration of the listed analogs.

Analysis of blood glucose during an Insulin Tolerance Test (ITT) in mice revealed that a peg-12 linker in the des-V format of the B-chain with either an insulin sequence or a largely IGF-1 based sequence, but including the B16,17 YL produced equivalent results as human insulin. See FIG. 27. Accordingly the single chain insulins linked with a PEG linking moiety function in vivo.

EXAMPLE 16

Acylated Insulin analogs

Comparative insulin tolerance tests were conducted on mice comparing the ability of human insulin relative to three different acylated insulin analogs to reduce and sustain low blood glucose concentration. The compounds were tested at two different concentrations (27 nmol/kg and 90 nmol/kg). The acylated insulins included MIU-41 (a two chain insulin analog having a $C_{16}$ acylation via a gamma glutamic acid linker attached to a lysine residue located at position A14), MIU-36 (a two chain insulin analog having a $C_{16}$ acylation linked to the N-terminus of the B chain) and MIU-37 (a two chain insulin analog having a $C_{16}$ acylation via a gamma glutamic acid linker attached to a lysine residue located at position B22). All three acylated insulin analogs provided a more basal and sustained lowered glucose levels relative to native insulin, even after 8 hours (See FIG. 30A-30D).

Figure 32A:
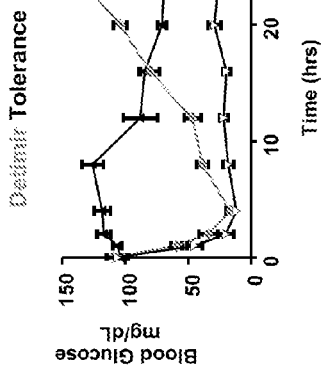
FIGS. 32A-32D show the results of comparative insulin tolerance tests conducted on mice comparing the activity of the commercially available acylated insulin analog (Detemir) relative to the acylated two chain insulin analog MIU-49. MIU-49 [$B^1$(C16-rE, H5, Aib9, H10, E13-K17, Y16)25a:$A^1$(N18, N21)] is a two chain insulin agonist having the C-terminal 5 amino acids of the B chain deleted and acylated with a C16 fatty acid through a gamma Glu linker at the α-amino group of Gly B2). The results indicate that MIU-49 is about one third as potent as Detemir (see FIGS. 32A and 32B. The data also indicate that the acylated forms of insulin are longer acting than the non-acylated forms and that MIU-49 while less potent than Detemir, exhibits a similar profile as Detemir.
Figure 32B:
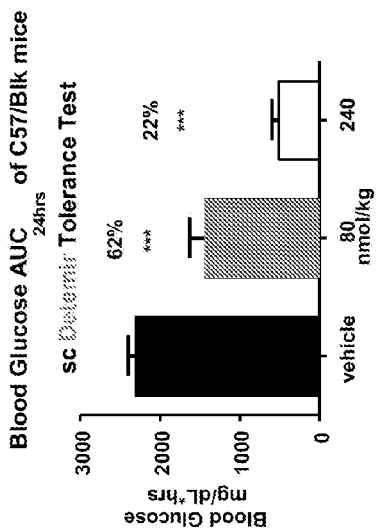
Figure 32C:
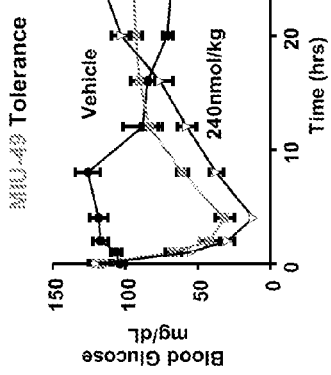
Figure 32D:
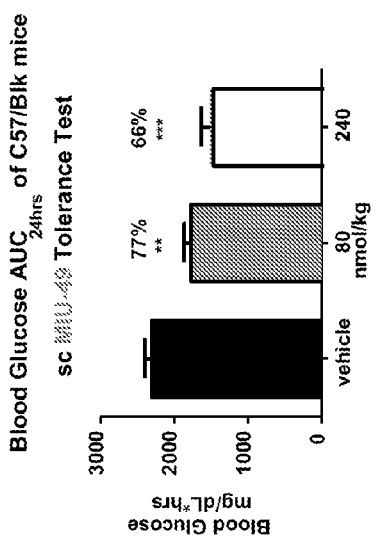

FIGS. 31A-31D show the results of comparative insulin tolerance tests conducted on mice comparing the ability of the commercially available acylated insulin analog (Detemir) to the acylated two chain insulin agonist MIU-55. MIU-55 [$B^1$(H5, 10, Y16, L17, C16rE-K22)25a:$A^1$(N18, N21)] has the C-terminal 5 amino acids of the B chain deleted and is acylated with a C14 fatty acid (myristoylic acid) through a gamma Glu linker at the e-amino group of Lys B29. The results indicate that MIU-55 is about one third as potent as Detemir (See FIGS. 31A and 31B). The data indicate that the acylated forms of insulin are longer acting than the non-acylated forms and that MIU-55 while less potent than Detemir, exhibits a similar profile as Detemir. FIGS. 31C and 31D provide data on blood glucose AUC values after administration of the listed analogs. A comparison of Detemir and MIU-49 in insulin tolerance tests revealed similar results (see FIGS. 32A-32D). MIU-49 [$B^1$(C16-rE0, H5, Aib9, H10, E13-K17, Y16)25a:$A^1$(N18, N21)] is a two chain insulin agonist having the C-terminal 5 amino acids of the B chain deleted and acylated with a C16 fatty acid at the through a gamma Glu linker at the α-amino group of Gly B2. Again, the data shows that MIU-49 is about one third as potent as Detemir (See FIGS. 32A and 32B that MIU-49 while less potent than Detemir, exhibits a similar profile as Detemir.

EXAMPLE 17

Pegylated Insulin Analogs

Various pegylated insulin analogs were prepared and tested in vitro. Table 17 shows the percent activity of each analog relative to native insulin.

TABLE 17

Pegylated IGF-1 and Insulin Analogs

| MIU # | Name | | % Insulin Activity | | |
|---|---|---|---|---|---|
| | | | IR-B | IR-A | IGF-1 R |
| MIU-35 | $B^1$(H5,H10,Y16,L17)25-$C^1$-$A^1$ (H8,N18,N21) | | 17.4 | 61.4 | 3.2 |
| MIU-56 | C8-PEG20K $B^1$(H5,Y16,L17)25-PEG8-K-PEG4-$A^1$ (N18,N21) | | | | 14.8 |
| MIU-57 | B1-PEG20K | MIU-35 | 1.1 | 3.1 | 1.2 |
| MIU-58 | B2-PEG20K-B2-Dimer | MIU-35 | 5.8 | 19.7 | 2.6 |
| MIU-59 | B1-PEG20K | insulin | 11.7 | 17.3 | 0.3 |
| MIU-60 | B29-PEG20K, B1,A1-$NH_2$CO | insulin | 2.7 | 2.4 | <<0.3 |
| MIU-61 | B1,B29,A1-tri-PEG5K | insulin | <0.1 | 0.2 | <<<0.3 |
| MIU-66 | B1-PEG20K, A1-$NH_2$CO | insulin | 2.9 | 3.0 | <0.3 |
| MIU-67 | B2, C8-PEG10K di-PEGylated | MIU-35 | 0.1 | 0.2 | <0.1 |
| MIU-68 | B2, B22-PEG10K di-PEGylated | MIU-35 | 0.1 | 0.4 | <0.1 |
| MIU-69 | B2, A14-PEG10K di-PEGylated | MIU-35 | 0.5 | 1.0 | <0.1 |
| MIU-1 | Insulin Standard | | 100 | 100 | 1.77 |

Figure 33A:
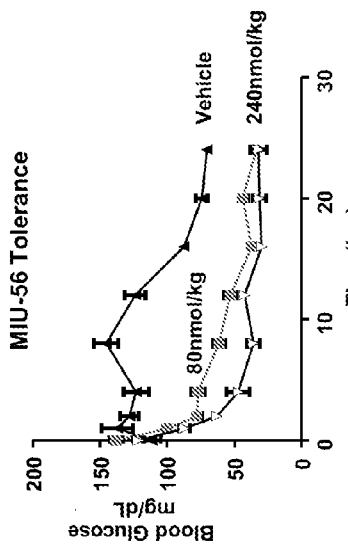
FIGS. 33A-33D represents the results obtained from a comparative insulin tolerance test for Detemir and MIU-56 using C57/Blk mice. MIU-56 is an insulin single chain analog $B^1$(H5, Y16, L17)25α-PEG8-K-PEG4-$A^1$(N18, 21) comprising a 20 kDa PEG linked to the side chain of the single lysine residue in the linking moiety (PEG8-K-PEG4) that joins the A chain and the B chain.
Figure 33C:
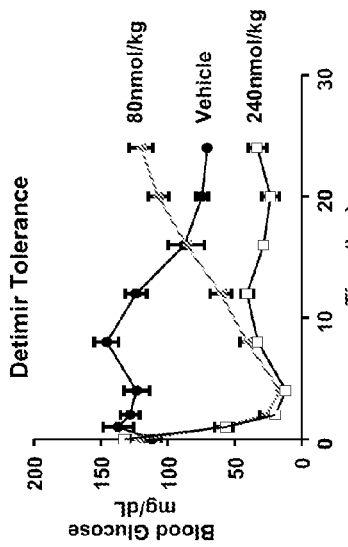
Figure 33B:
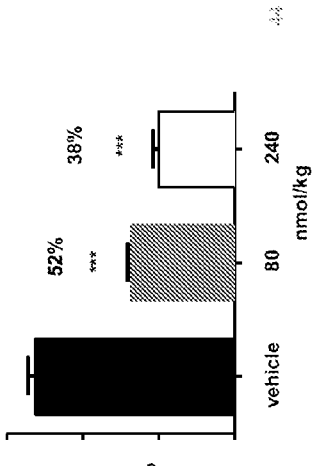
Figure 33D:
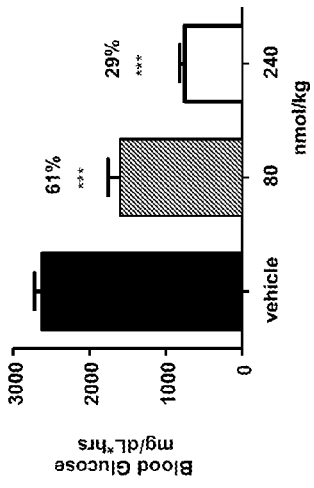
Figure 34E:
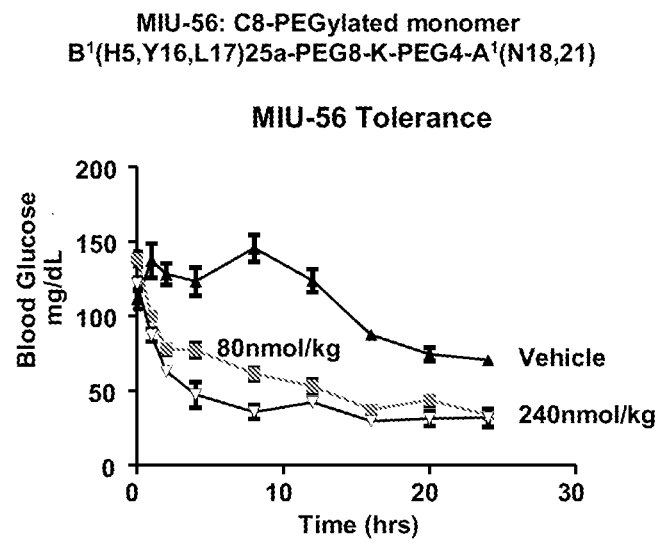
Figure 34F:
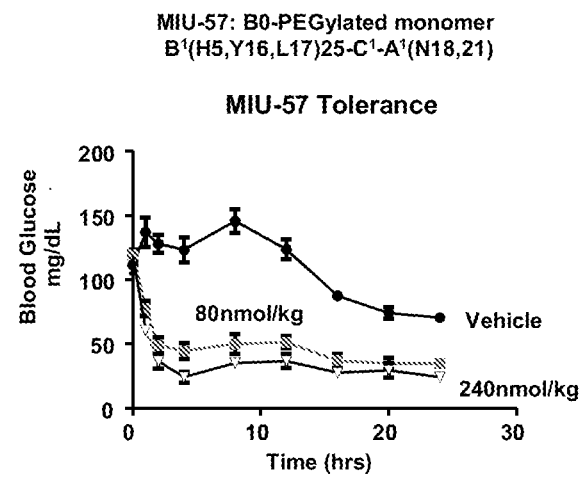

Comparative insulin tolerance tests were conducted on mice comparing the ability of the acylated insulin analog Detemir relative to the pegylated single chain insulin analog MIU-56: $B^1$(H5, Y16, L17)25-PEG8-K-PEG4-$A^1$(N18, 21). This single chain analog comprises a 20 kDa PEG linked to the side chain of the single lysine residue in the linking moiety (PEG8-K-PEG4) that joins the A chain and the B chain. As shown in FIG. 33A-33D, the pegylated analog has a sustained duration of action for 24 hours and its onset is gradual enough to avoid sedation of animals at the dosage required for sustained action through 24 hours. FIGS. 33C and 33D show the blood glucose $AUC_{24\ hrs}$ in mice administered Detemir and MIU-56, respectively. Similar results were obtained for another pegylated single chain insulin analog MIU-57 (see FIGS. 34A-34D). MIU-57 is an insulin single chain analog ($B^1$(H5, Y16, L17)25-$C^1$-$A^1$(N18, 21) comprising a 20 kDa PEG linked to the N-terminal amine of the B chain. FIGS. 34A and 34B show the results of a comparative insulin dose titration of single chain insulin analogs pegylated at the linking moiety (MIU-56) or pegylated at the N-terminal amine of the B chain (MIU-57), respectively. FIGS. 34C and 34D show the blood glucose $AUC_{24\ hrs}$ in mice administered MIU-56 and MIU-57, respectively. The data shows these analogs remain potent and have an improved therapeutic index relative to native insulin. Results from comparative insulin dose titrations of MIU-56 and MIU-57 reveal that a similar profile is obtained in mice for dosages ranging from 20 nmol/kg through 80 nmol/kg (see FIGS. 34E and 34F)

Figure 34G:
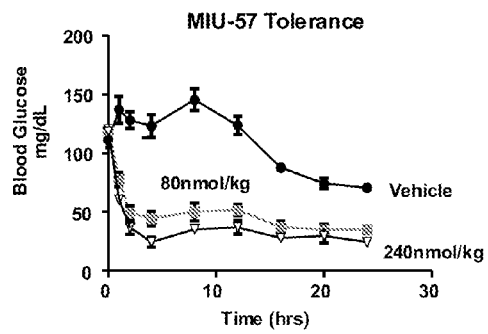
FIGS. 34G-34J represents the results obtained from a comparative insulin tolerance test for MIU-57 and MIU-58 using C57/Blk mice.
Figure 34H:
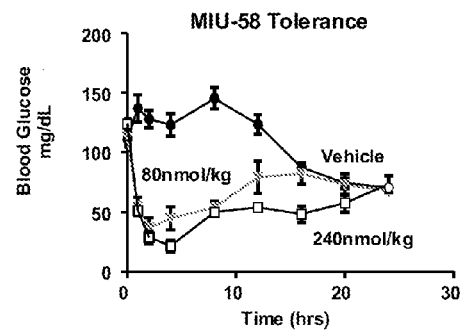
Figure 34I:
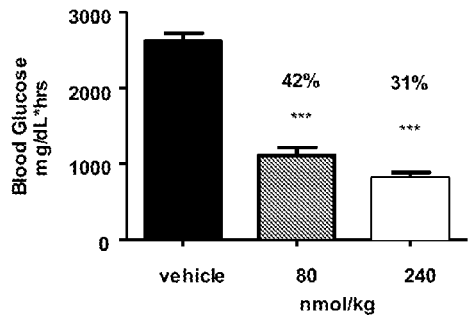
Figure 34J:
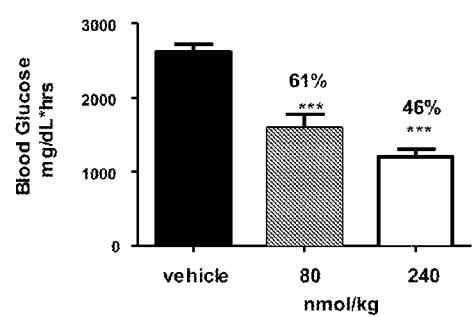

A dimer (MIU 58) was prepared comprising two insulin single chain analogs (B$^1$(H5, Y16, L17)25-C$^1$-A$^1$(N18, 21) linked head to head via a 20 kDa PEG chain. FIGS. 34G-34J represents the results obtained from a comparative insulin tolerance test for MIU-57 and MIU-58 using C57/Blk mice. FIGS. 34G and 34H are graphs showing the results of insulin tolerance tests comparing MIU-57 and MIU-58. FIGS. 34I and 34J show the blood glucose AUC$_{24\,hrs}$ in mice administered MIU-57 and MIU-58, respectively. The dimer is less potent than the parent compound, but is still active.

Figure 35:
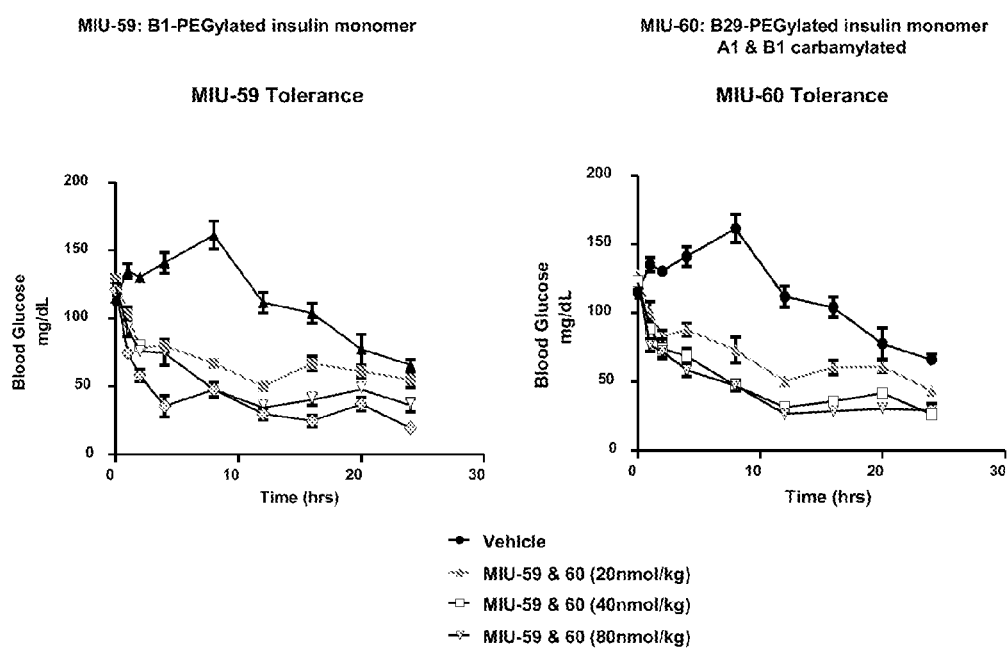
FIGS. 35A - 35B provide data from a comparative insulin dose titration of two pegylated insulin derivatives. The insulin derivatives differ based on the placement of a 20 kDa PEG which is linked to the N-terminus (FIG. 35A) of MIU-59, or to the side chain of amino acid B29, of an insulin analog MIU-60, wherein the A1 and B1 amino acids have been carbamylated (FIG. 35B).
Figure 36A:
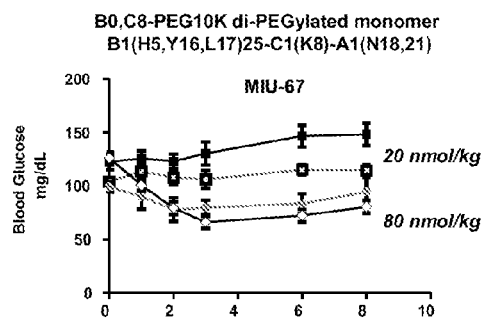
FIGS. 36A-36D provide data from a comparative insulin dose titration of the three single chain insulin analogs MIU-67, MIU-68 and MIU-69, each comprising two PEG chains of 10 kDa each relative to the single pegylated (20K PEG) native insulin derivative (MIU-59). More particularly, the activities of single chain insulin analogs MIU-67 ($B^1$(H5, Y16, L17) 25-$C^1$(K8)-$A^1$(N18, 21)) having two PEG chains (10K each) one linked at the N-terminus and the other at amino acid 8 of the linking moiety (position C8), MIU-68 ($B^1$(H5, Y16, L17, K22)25-$C^1$(K8)-$A^1$(N18, 21)) having two PEG chains (10K each) one linked at the N-terminus and the other at amino acid B22 and MIU-69 (B$^1$(H5, Y16, L17)25-C$^1$(K8)-A$^1$(K14, N18, 21)) having two PEG chains (10K each) one linked at the N-terminus and the other at amino acid A14 were compared. Each compound was administered at two dosages (20 and 80 nmol/kg).
Figure 36B:
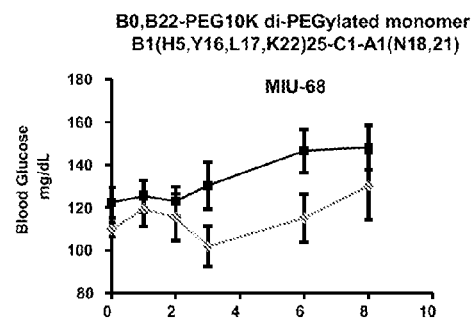
Figure 36C:
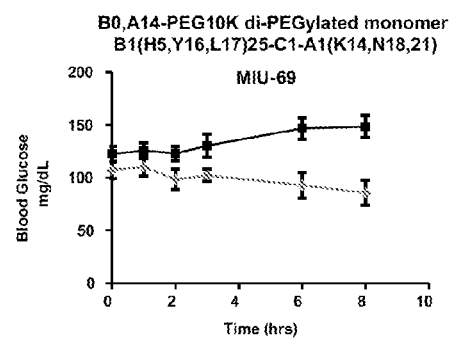
Figure 36D:
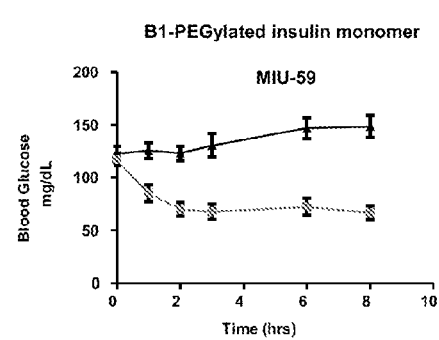

FIGS. 35A and 35B provide data from a comparative insulin dose titration of two pegylated native insulin heterodimers. The analogs comprise two native insulin A and B chain sequences linked via the native disulfide linkages, and modified to have either a 20 kDa PEG linked at the N-terminus of the B chain or at position B29 (with the amino terminus of the A and B chain carbamylated). The data shows that while these compounds differ slightly in their in vitro activities (See Table 17), they behave similarly in vivo in mice. Both compounds remain potent and have an improved therapeutic index relative to non-pegylated native insulin (slow onset, sustained activity for 24 hours and relative flatness of the response).

Insulin analogs were also constructed having two or more covalently linked polyethylene glycol chains and compared to a native insulin analog having a single 20 kDa PEG linked to its N-terminus. More particularly, the activities of a single chain insulin analog (B$^1$(H5, Y16, L17)25-C$^1$(K8)-A$^1$(N18, 21)) having two PEG chains (10K each) linked at the N-terminal alpha amine and at amino acid 8 of the linking moiety (position C8), a single chain insulin analog (B$^1$(H5, Y16, L17, K22)25-C$^1$(K8)-A$^1$(N18, 21)) having two PEG chains (10K each) linked at the N-terminal alpha amine and at amino acid B22, and a single chain insulin analog (B$^1$(H5, Y16, L17)25-C$^1$(K8)-A$^1$(K14, N18, 21)) having two PEG chains (10K each) linked at the N-terminal alpha amine and at amino acid A14 were compared. FIGS. 36A-36D provide data from a comparative insulin dose titration of the three pegylated insulin analogs relative to the single pegylated native insulin derivative. The activity in vitro is dramatically reduced by at least 10×. However, while the in vivo data shows that some potency is lost, the double pegylated insulin analogs are still effective (particularly for the analog pegylated at the linking moiety). More particularly, MIU-67 at 80 nmol/kg is roughly equivalent to MIU-59 administered at 40 nmol/kg in reducing blood glucose levels at least up to 8 hours after administration. Accordingly, insulin analogs can be prepared having two PEG chains of 10 kDa in length that will provide an improved therapeutic index relative to non-pegylated insulin analogs. In addition pegylation at the linking moiety of single chain analogs appears to be a preferred site of pegylation.

Figure 37A:
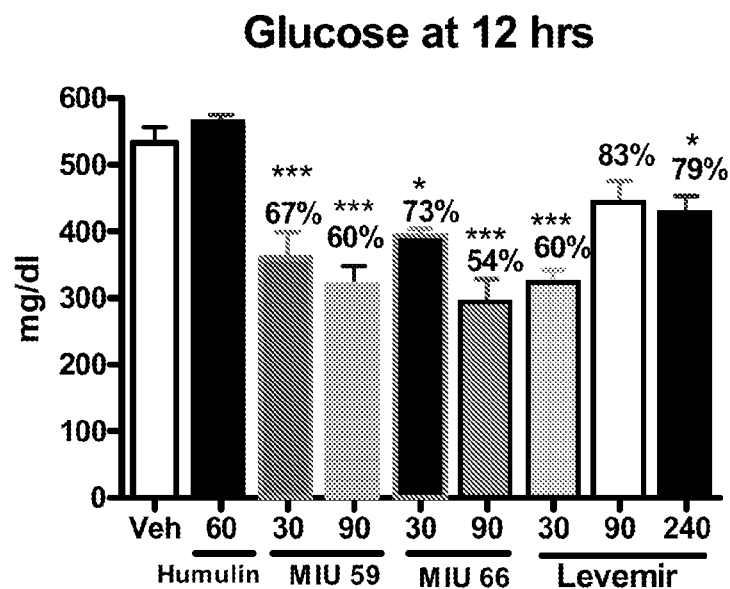
FIGS. 37A & 37B Diabetic mice (db/db mice) were administered pegylated insulin analogs to compare their relative activity in relation to commercially available insulin analogs. The x-axis indicates the concentration of the administered compound (i.e., vehicle control, 30 or 90 nmol/kg or 60 nmol/kg for Humulin and 30, 90 and 240 for Levemir). In particular, insulin analogs Levemir and Humulin were compared to the pegylated insulin analogs MIU-59 (native insulin analog having a single 20 kDa PEG linked to its N-terminus) and MIU-66 (native insulin analog having a single 20 kDa PEG linked to its N-terminus and the amino terminus of the A and B chain carbamylated. Both MIU-59 and MIU-66 have improved activity relative to Levemir and Humulin (see FIGS. 37A at 12 hrs and 37B at 24 hours).
Figure 37B:
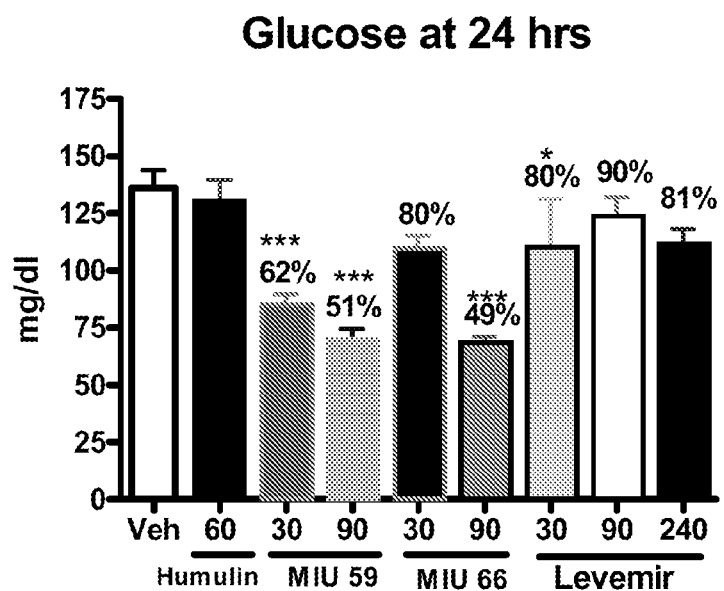

Diabetic mice (db/db mice) were administered pegylated insulin analogs to compare their efficacy to commercially available insulin analogs. In particular, insulin analogs Levemir and Humulin were compared to the pegylated insulin analogs MIU-59 (native insulin analog having a single 20 kDa PEG linked to its N-terminus) and MIU-66 (native insulin analog having a single 20 kDa PEG linked to its B chain N-terminus, and having the amino terminus of the A chain carbamylated). Although the in vitro data (see Table 17) indicated that MIU-66 was far less potent than MIU-59, MIU-59 and MIU-66 behave similarly in vivo, and both have improved activity relative to Levemir and Humulin (see FIGS. 37A and 37B).

In summary, pegylation of insulin analogs, whether using an insulin based or IGF based peptide backbone, in vivo, provides for a more extended duration of action and a basal profile in the absence of hypoglycemia.

EXAMPLE 18

Comparative Insulin Tolerance for Insulin Prodrug Analogs

Figure 38:
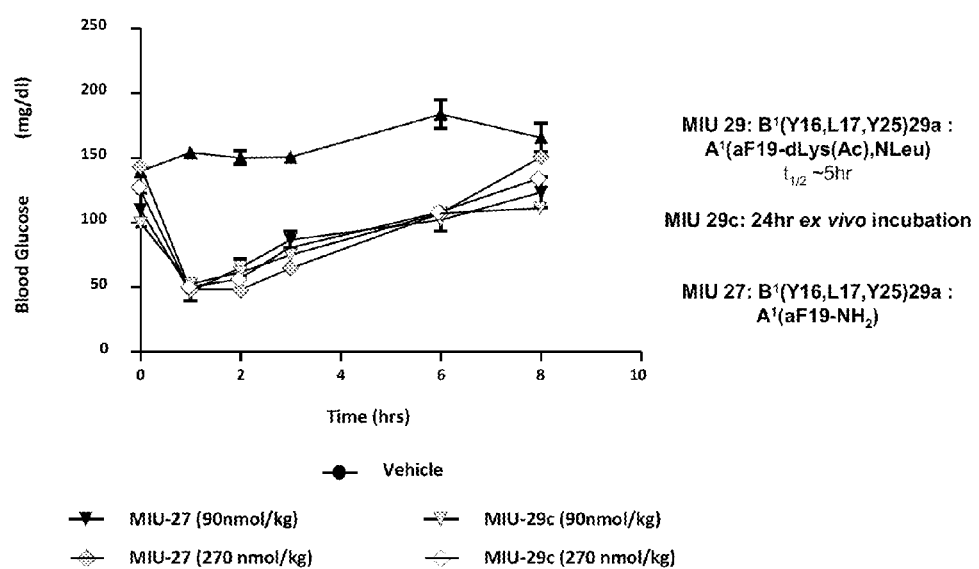
FIG. 38 is a graph showing the results of a comparative insulin tolerance test conducted in normal mice for a prodrug two chain insulin analog acylated at the dipeptide prodrug element (MIU-29: [B$^1$(Y16, L17, Y25)29a:A$^1$(aF19-dLys (Ac), NLeu)] relative to it parent insulin analog (MIU-27: [B$^1$(Y16, L17, Y25)29a:A$^1$(aF19-)]. The prodrug derivative MIU-29 comprises a 4-amino-phenylalanine substitution at position A19 wherein a dipeptide dLys(Ac), NLeu has been covalently linked at the 4-amino position of the A19 residue and the side chain of the lysine of the dipeptide element has been acylated with a C14 fatty acid. This dipeptide will auto-cleave under physiological conditions with a half life of approximately 5 hours. After incubating MIU-29 for 24 hours ex vivo, the resultant compound (designated "MIU-29c") was administered to mice and its ability to lower blood glucose was compared to parent compound.

Normal mice were administered either an insulin heterodimer analog [B$^1$(Y16, L17, Y25)29a:A$^1$(aF19-NH2)], or a prodrug derivative thereof. The prodrug derivative [B$^1$(Y16, L17, Y25)29a:A$^1$(aF19-dLys(Ac), NLeu)] comprises a 4-amino-phenylalnine substitution at position A19 wherein a dipeptide dLys(Ac), NLeu have been covalently linked at the 4-amino position of the A19 residue. This dipeptide will autocleave under physiological conditions with a half life of approximately 5 hours. After incubating the prodrug derivative [B$^1$(Y16, L17, Y25)29a:A$^1$(aF19-dLys(Ac), NLeu)] for 24 hours ex vivo, the resultant compound was administered to mice and it ability to lower blood glucose was compared to parent compound. As shown in FIG. 38 the two compounds performed almost identically.

EXAMPLE 19

Pegylated Low Potency Alanine Analogs

The duration of action of the various insulin analogs disclosed herein can be increased by decreasing their activity at the insulin receptor. Accordingly, in one embodiment the insulin analogs disclosed herein can be modified to decrease their potency at the insulin receptor, including modification by 1 to 8, 1 to 5, 1 to 3, 1 to 2 or 1 amino acid substitution. In one embodiment the amino acid substitution is an alanine substitution at a position selected from the group consisting of B5, B10, B24, A1 or A8. Alanine substitutions at one or more of these positions substantially reduces potency, thus extending the duration of action at the insulin receptors. In one embodiment an insulin analog as disclosed herein is further modified by a single alanine amino acid substitution at position B5, B24, A1 or A8. These compounds can be further modified by pegylation as indicated in Table 18 (GE$_5$W=GEEEEEW, a peptide added to the N-terminus of the insulin analog to increase solubility).

TABLE 18

| Name | Sequence | IR-B | IR-A | IGF-1 R |
|---|---|---|---|---|
| MIU-35 | B$^1$(H5,10Y16L17)25-C$^1$-A$^1$(H8N18,21) | 17.4% | 61.4% | 3.2% |
| GE$_5$W-Ala,B5 | GE$_5$W-B$^1$(A5H10Y16L17)25-C$^1$-A$^1$(H8N18N21) | 2.3% | 8.6% | 0.3% |
| Ala,B5 | B$^1$(A5H10Y16L17)25-C$^1$-A$^1$(H8N18N21) | 5.7% |  | 2.5% |
| Ala,B24 | B$^1$(H5,10Y16L17A24)25-C$^1$-A$^1$(H8N18N21) | 0.4% | 0.1% | 0.3% |
| GE$_5$W-Ala,A1 | GE$_5$W-B$^1$(H5,10Y16L17)25-C$^1$-A$^1$(A1H8N18,21) | 0.7% | 2.1% | 0.5% |
| Thr,A8 | B$^1$(H5,10Y16L17)25-C$^1$-A$^1$(T8N18,21) | 8.4% | 20.4% | 3.7% |
| PEGylated Analogs | | | | |
| MIU-57 | B1-PEG20K MIU-35 | 1.1% | 4.5% | 1.2% |
|  | B$^1$-PEG20K (GE$_5$W)- MIU-35 Ala,A1 | 0.1% | 0.3% |  |

As shown in Table 19, single chain and two chain insulin analogs have been prepared and tested in vitro for activity at the insulin and IGF-1 receptors and compared to their pegylated derivatives. Non-pegylated forms have higher activity relative to the pegylated derivatives. Furthermore, dipegylating two chain insulin analogs using two 10 kDa PEG chains produces compounds of approximately similar activity relative to the same analog comprising a single 20 kDa PEG chain (see the relative activities of B'(H5, 10Y16L17K29)29:A$^1$ (H8, N18, 21) relative to B1, A14-10K B$^1$(H5, 10Y16L17R29)29:A$^1$(H8K14N18, 21) and B$^1$(H5, 10Y16L17K29)29: A$^1$(H$_8$N18, 21). For the single chain analog B$^1$(H5, 10Y16L17K29)29-A$^1$(H8, N18, 21) the addition of a 20 kDa produces a compound (B$^1$(H5, 10Y16L17K29) 29-A$^1$(H$_8$N18, 21) having almost 100 fold activity at the insulin type-A receptor. Accordingly, by preparing insulin analogs as two chain or single chain analogs and by selecting the size, number and site of attachment of a PEG chain, the in vivo potency of the insulin analog can be modified, and presumably the in vivo duration of action.

TABLE 19

PEGylation of Two-chain IGF-1 Analogs

| | Analog Name | | Sequence | IR-A | IR-B | IGF-1R |
|---|---|---|---|---|---|---|
| | | | Parent Peptide Backbones | | | |
| MIU-43 | DP8Mut3 | | B$^1$(H5,10Y16L17R29)30-C$^1$des9-12-A$^1$(H8,N18,21) | 97.5% | 16.7% | 14.2% |
| | DP8Mut3KA14 | | B$^1$(H5,10Y16L17R29)30-C$^1$des9-12-A$^1$(H8,K14,N18,21) | 132.2% | 12.6% | |
| | DP3(SC) | | B$^1$(H5,10Y16L17K29)29-A$^1$(H8,N18,21) | 0.03% | | |
| | DP3(TC) | | B$^1$(H5,10Y16L17K29)29: A$^1$(H8,N18,21) | 159.8% | 33.1% | |
| | | | PEGylated Analogs | | | |
| MIU-79 | di-10K-SC | B1,A14-10K | B$^1$(H5,10Y16L17R29)30-C$^1$des9-12-A$^1$(H8,K14,N18,21) | 1.7% | 0.2% | |
| | di-10K-TC | B1,A14-10K | B$^1$(H5,10Y16L17K29)29: A$^1$(H8K14N18,21) | 6.4% | 2.1% | |
| MIU-77 | mono-20K-SC | B1-20K | B$^1$(H5,10Y16L17K29)29-A$^1$(H8N18,21) | 0.1% | | |
| MIU-78 | mono-20K-TC | B1-20K | B$^1$(H5,10Y16L17K29)29: A$^1$(H8N18,21) | 8.2% | 3.2% | |

The invention claimed is:

1. A single chain insulin agonist analog comprising the general structure B-LM-A wherein B represents an insulin B chain comprising the sequence $R_{22}$-$X_{25}$LCGX$_{29}$X$_{30}$LVX$_{33}$X$_{34}$LX$_{36}$LVCGX$_{41}$X$_{42}$GFX$_{45}$ (SEQ ID NO: 20);

A represents an insulin A chain comprising the sequence GIVX$_4$X$_5$CCX$_8$X$_9$X$_{10}$CX$_{12}$LX$_{14}$X$_{15}$LX$_{17}$X$_{18}$X$_{19}$CX$_{21}$-R$_{13}$ (SEQ ID NO: 22); and LM represents a linking moiety linking the carboxy terminus of the B chain to the amino terminus of the A chain;

further wherein said linking moiety consists of the amino acid sequence of GAGSSSRR (SEQ ID NO: 32), wherein $R_{13}$ is COOH or CONH$_2$;

$R_{22}$ is selected from the group consisting of AYRPSE (SEQ ID NO: 14), FVNQ (SEQ ID NO: 12), PGPE (SEQ ID NO: 11), a tripeptide glycine-proline-glutamic acid, a tripeptide valine-asparagine-glutamine, a dipeptide proline-glutamic acid, a dipeptide asparagine-glutamine, glutamine, glutamic acid and an N-terminal amine $X_4$ is glutamic acid or aspartic acid;

$X_5$ is glutamine or glutamic acid;

$X_8$ is histidine, threonine or phenylalanine;

$X_9$ is serine, arginine, lysine, ornithine or alanine;

$X_{10}$ is isoleucine or serine;

$X_{12}$ is serine or aspartic acid;

$X_{14}$ is tyrosine, arginine, lysine, ornithine or alanine;

$X_{15}$ is glutamine, glutamic acid, arginine, alanine, lysine, ornithine or leucine;

$X_{17}$ is glutamine, glutamic acid, arginine, aspartic acid or lysine, ornithine;

$X_{18}$ is methionine, asparagine, glutamine, aspartic acid, glutamic acid or threonine;

$X_{19}$ is tyrosine, 4-methoxy-phenylalanine or 4-amino phenylalanine;

$X_{21}$ is selected from the group consisting of alanine, glycine, serine, valine, threonine, isoleucine, leucine, glutamine, glutamic acid, asparagine, aspartic acid, histidine, tryptophan, tyrosine, and methionine;

$X_{25}$ is selected from the group consisting of histidine and threonine;

$X_{29}$ is selected from the group consisting of alanine, glycine and serine;

$X_{30}$ is selected from the group consisting of histidine, aspartic acid, glutamic acid, homocysteic acid and cysteic acid;

$X_{33}$ is selected from the group consisting of aspartic acid and glutamic acid;

$X_{34}$ is selected from the group consisting of alanine and threonine;

$X_{36}$ is tyrosine;

$X_{41}$ is selected from the group consisting of glutamic acid, aspartic acid or asparagine;

$X_{42}$ is selected from the group consisting of alanine, ornithine, lysine and arginine;

$X_{45}$ is selected from the group consisting of tyrosine, histidine, asparagine and phenylalanine.

2. A dimer or multimer comprising two or more single chain insulin agonists of claim 1 linked to one another via a linker.

3. A pharmaceutical composition comprising a single chain insulin agonist of claim 1, and a pharmaceutically acceptable carrier.

4. A method of treating diabetes, said method comprising administering an effective amount of a pharmaceutical composition of claim 3.

* * * * *

SEQUENCE LISTING

<160> NUMBER OF SEQ ID NOS: 197

<210> SEQ ID NO 1
<211> LENGTH: 21
<212> TYPE: PRT
<213> ORGANISM: Homo sapiens

<400> SEQUENCE: 1

Gly Ile Val Glu Gln Cys Cys Thr Ser Ile Cys Ser Leu Tyr Gln Leu
1               5                   10                  15

Glu Asn Tyr Cys Asn
            20

<210> SEQ ID NO 2
<211> LENGTH: 30
<212> TYPE: PRT
<213> ORGANISM: Homo sapiens

<400> SEQUENCE: 2

Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys Thr
            20                  25                  30

<210> SEQ ID NO 3
<211> LENGTH: 70
<212> TYPE: PRT
<213> ORGANISM: Homo sapiens

<400> SEQUENCE: 3

Gly Pro Glu Thr Leu Cys Gly Ala Glu Leu Val Asp Ala Leu Gln Phe
1               5                   10                  15

Val Cys Gly Asp Arg Gly Phe Tyr Phe Asn Lys Pro Thr Gly Tyr Gly
            20                  25                  30

Ser Ser Ser Arg Arg Ala Pro Gln Thr Gly Ile Val Asp Glu Cys Cys
        35                  40                  45

```
Phe Arg Ser Cys Asp Leu Arg Arg Leu Glu Met Tyr Cys Ala Pro Leu
    50                  55                  60

Lys Pro Ala Lys Ser Ala
 65                  70

<210> SEQ ID NO 4
<211> LENGTH: 67
<212> TYPE: PRT
<213> ORGANISM: Homo sapiens

<400> SEQUENCE: 4

Ala Tyr Arg Pro Ser Glu Thr Leu Cys Gly Gly Glu Leu Val Asp Thr
 1               5                  10                  15

Leu Gln Phe Val Cys Gly Asp Arg Gly Phe Tyr Phe Ser Arg Pro Ala
                20                  25                  30

Ser Arg Val Ser Arg Arg Ser Arg Gly Ile Val Glu Glu Cys Cys Phe
            35                  40                  45

Arg Ser Cys Asp Leu Ala Leu Leu Glu Thr Tyr Cys Ala Thr Pro Ala
    50                  55                  60

Lys Ser Glu
 65

<210> SEQ ID NO 5
<211> LENGTH: 21
<212> TYPE: PRT
<213> ORGANISM: Homo sapiens

<400> SEQUENCE: 5

Gly Ile Val Asp Glu Cys Cys Phe Arg Ser Cys Asp Leu Arg Arg Leu
 1               5                  10                  15

Glu Met Tyr Cys Ala
                20

<210> SEQ ID NO 6
<211> LENGTH: 29
<212> TYPE: PRT
<213> ORGANISM: Homo sapiens

<400> SEQUENCE: 6

Gly Pro Glu Thr Leu Cys Gly Ala Glu Leu Val Asp Ala Leu Gln Phe
 1               5                  10                  15

Val Cys Gly Asp Arg Gly Phe Tyr Phe Asn Lys Pro Thr
                20                  25

<210> SEQ ID NO 7
<211> LENGTH: 21
<212> TYPE: PRT
<213> ORGANISM: Homo sapiens

<400> SEQUENCE: 7

Gly Ile Val Glu Glu Cys Cys Phe Arg Ser Cys Asp Leu Ala Leu Leu
 1               5                  10                  15

Glu Thr Tyr Cys Ala
                20

<210> SEQ ID NO 8
<211> LENGTH: 32
<212> TYPE: PRT
<213> ORGANISM: Homo sapiens

<400> SEQUENCE: 8
```

```
Ala Tyr Arg Pro Ser Glu Thr Leu Cys Gly Gly Glu Leu Val Asp Thr
1               5                   10                  15

Leu Gln Phe Val Cys Gly Asp Arg Gly Phe Tyr Phe Ser Arg Pro Ala
                20                  25                  30

<210> SEQ ID NO 9
<211> LENGTH: 8
<212> TYPE: PRT
<213> ORGANISM: Artificial Sequence
<220> FEATURE:
<223> OTHER INFORMATION: spacer sequence
<220> FEATURE:
<221> NAME/KEY: MISC_FEATURE
<222> LOCATION: (1)..(1)
<223> OTHER INFORMATION: The Xaa at position 1 represents an amino acid
      selected from glycine, alanine, valine, leucine, isoleucine,
      proline, phenylalanine and methionine
<220> FEATURE:
<221> NAME/KEY: MISC_FEATURE
<222> LOCATION: (2)..(2)
<223> OTHER INFORMATION: The Xaa at position 2 represents any amino acid
      other than tyrosine
<220> FEATURE:
<221> NAME/KEY: MISC_FEATURE
<222> LOCATION: (3)..(6)
<223> OTHER INFORMATION: The Xaas at positions 3-6 are independently any
      amino acid
<220> FEATURE:
<221> NAME/KEY: MISC_FEATURE
<222> LOCATION: (7)..(8)
<223> OTHER INFORMATION: The Xaas at positions 7 and 8 are independently
      selected from arginine, lysine or ornithine

<400> SEQUENCE: 9

Xaa Xaa Xaa Xaa Xaa Xaa Xaa Xaa
1               5

<210> SEQ ID NO 10
<211> LENGTH: 8
<212> TYPE: PRT
<213> ORGANISM: Artificial Sequence
<220> FEATURE:
<223> OTHER INFORMATION: spacer sequence
<220> FEATURE:
<221> NAME/KEY: MISC_FEATURE
<222> LOCATION: (1)..(1)
<223> OTHER INFORMATION: The Xaa at position 1 represents an amino acid
      selected from glycine, alanine, valine, leucine, isoleucine,
      proline, phenylalanine and methionine
<220> FEATURE:
<221> NAME/KEY: MISC_FEATURE
<222> LOCATION: (2)..(2)
<223> OTHER INFORMATION: The Xaa at position 2 represents any amino acid
      other than tyrosine
<220> FEATURE:
<221> NAME/KEY: MISC_FEATURE
<222> LOCATION: (3)..(6)
<223> OTHER INFORMATION: The Xaas at positions 3-6 are independently any
      amino acid

<400> SEQUENCE: 10

Xaa Xaa Xaa Xaa Xaa Xaa Arg Arg
1               5

<210> SEQ ID NO 11
<211> LENGTH: 4
<212> TYPE: PRT
<213> ORGANISM: Artificial Sequence
<220> FEATURE:
<223> OTHER INFORMATION: spacer sequence

<400> SEQUENCE: 11
```

```
Pro Gly Pro Glu
1

<210> SEQ ID NO 12
<211> LENGTH: 4
<212> TYPE: PRT
<213> ORGANISM: Artificial Sequence
<220> FEATURE:
<223> OTHER INFORMATION: spacer sequence

<400> SEQUENCE: 12

Phe Val Asn Gln
1

<210> SEQ ID NO 13
<211> LENGTH: 5
<212> TYPE: PRT
<213> ORGANISM: Artificial Sequence
<220> FEATURE:
<223> OTHER INFORMATION: spacer sequence
<220> FEATURE:
<221> NAME/KEY: MISC_FEATURE
<222> LOCATION: (1)..(5)
<223> OTHER INFORMATION: The Xaas at positions 1-5 are independently any
      amino acid

<400> SEQUENCE: 13

Xaa Xaa Xaa Xaa Xaa
1               5

<210> SEQ ID NO 14
<211> LENGTH: 6
<212> TYPE: PRT
<213> ORGANISM: Artificial Sequence
<220> FEATURE:
<223> OTHER INFORMATION: spacer sequence

<400> SEQUENCE: 14

Ala Tyr Arg Pro Ser Glu
1               5

<210> SEQ ID NO 15
<211> LENGTH: 4
<212> TYPE: PRT
<213> ORGANISM: Artificial Sequence
<220> FEATURE:
<223> OTHER INFORMATION: spacer sequence
<220> FEATURE:
<221> NAME/KEY: MISC_FEATURE
<222> LOCATION: (1)..(4)
<223> OTHER INFORMATION: The Xaas at positions 1-4 are independently any
      amino acid

<400> SEQUENCE: 15

Xaa Xaa Xaa Xaa
1

<210> SEQ ID NO 16
<211> LENGTH: 5
<212> TYPE: PRT
<213> ORGANISM: Artificial Sequence
<220> FEATURE:
<223> OTHER INFORMATION: spacer sequence

<400> SEQUENCE: 16

Tyr Thr Pro Lys Thr
1               5
```

-continued

<210> SEQ ID NO 17
<211> LENGTH: 12
<212> TYPE: PRT
<213> ORGANISM: Homo sapiens

<400> SEQUENCE: 17

Gly Tyr Gly Ser Ser Ser Arg Arg Ala Pro Gln Thr
1               5                   10

<210> SEQ ID NO 18
<211> LENGTH: 8
<212> TYPE: PRT
<213> ORGANISM: Homo sapiens

<400> SEQUENCE: 18

Gly Tyr Gly Ser Ser Ser Arg Arg
1               5

<210> SEQ ID NO 19
<211> LENGTH: 21
<212> TYPE: PRT
<213> ORGANISM: Artificial Sequence
<220> FEATURE:
<223> OTHER INFORMATION: Analog of the insulin A chain
<220> FEATURE:
<221> NAME/KEY: MISC_FEATURE
<222> LOCATION: (4)..(4)
<223> OTHER INFORMATION: Xaa at position 4 is aspartic acid or glutamic
      acid
<220> FEATURE:
<221> NAME/KEY: MISC_FEATURE
<222> LOCATION: (8)..(8)
<223> OTHER INFORMATION: Xaa at position 8 is histidine, threonine or
      phenylalanine
<220> FEATURE:
<221> NAME/KEY: MISC_FEATURE
<222> LOCATION: (9)..(9)
<223> OTHER INFORMATION: Xaa at position 9 is serine, arginine,
      ornithine, lysine or alanine
<220> FEATURE:
<221> NAME/KEY: MISC_FEATURE
<222> LOCATION: (14)..(14)
<223> OTHER INFORMATION: Xaa at position 14 is tyrosine, arginine,
      ornithine, lysine or alanine
<220> FEATURE:
<221> NAME/KEY: MISC_FEATURE
<222> LOCATION: (15)..(15)
<223> OTHER INFORMATION: Xaa at position 15 is glutamine, glutamic acid,
      arginine, ornithine, alanine, lysine or leucine
<220> FEATURE:
<221> NAME/KEY: MISC_FEATURE
<222> LOCATION: (17)..(17)
<223> OTHER INFORMATION: Xaa at position 17 is glutamine or glutamic
      acid
<220> FEATURE:
<221> NAME/KEY: MISC_FEATURE
<222> LOCATION: (18)..(18)
<223> OTHER INFORMATION: Xaa at position 18 is methionine, asparagine,
      glutamine, glutamic acid, aspartic acid or threonine
<220> FEATURE:
<221> NAME/KEY: MISC_FEATURE
<222> LOCATION: (19)..(19)
<223> OTHER INFORMATION: Xaa at position 19 is tyrosine, 4-methoxy
      phenylalanine or 4-amino-phenylalanine
<220> FEATURE:
<221> NAME/KEY: MISC_FEATURE
<222> LOCATION: (21)..(21)
<223> OTHER INFORMATION: Xaa at position 21 is alanine, glycine, serine,
      valine, threonine, isoleucine, leucine, glutamine, glutamic acid,
      asparagine, aspartic acid, histidine, tryptophan, tyrosine, or
      methionine

<400> SEQUENCE: 19

```
Gly Ile Val Xaa Glu Cys Cys Xaa Xaa Ser Cys Asp Leu Xaa Xaa Leu
1               5                   10                  15

Xaa Xaa Xaa Cys Xaa
            20

<210> SEQ ID NO 20
<211> LENGTH: 21
<212> TYPE: PRT
<213> ORGANISM: Artificial Sequence
<220> FEATURE:
<223> OTHER INFORMATION: Analog of the insulin B chain
<220> FEATURE:
<221> NAME/KEY: MISC_FEATURE
<222> LOCATION: (1)..(1)
<223> OTHER INFORMATION: Xaa at position 1 is histidine or threonine
<220> FEATURE:
<221> NAME/KEY: MISC_FEATURE
<222> LOCATION: (5)..(5)
<223> OTHER INFORMATION: Xaa at position 5 is alanine, glycine or serine
<220> FEATURE:
<221> NAME/KEY: MISC_FEATURE
<222> LOCATION: (6)..(6)
<223> OTHER INFORMATION: Xaa at position 6 is histidine, aspartic acid,
      glutamic acid, homocysteic acid or cysteic acid
<220> FEATURE:
<221> NAME/KEY: MISC_FEATURE
<222> LOCATION: (9)..(9)
<223> OTHER INFORMATION: Xaa at position 9 is aspartic acid, glutamine
      or glutamic acid
<220> FEATURE:
<221> NAME/KEY: MISC_FEATURE
<222> LOCATION: (10)..(10)
<223> OTHER INFORMATION: Xaa at position 10 is alanine or threonine
<220> FEATURE:
<221> NAME/KEY: MISC_FEATURE
<222> LOCATION: (12)..(12)
<223> OTHER INFORMATION: Xaa at position 12 is tyrosine or 4-amino-
      phenylalanine
<220> FEATURE:
<221> NAME/KEY: MISC_FEATURE
<222> LOCATION: (17)..(17)
<223> OTHER INFORMATION: Xaa at position 12 is glutamic acid, aspartic
      acid or asparagine
<220> FEATURE:
<221> NAME/KEY: MISC_FEATURE
<222> LOCATION: (18)..(18)
<223> OTHER INFORMATION: Xaa at position 18 is alanine, ornithine,
      lysine or arginine
<220> FEATURE:
<221> NAME/KEY: MISC_FEATURE
<222> LOCATION: (21)..(21)
<223> OTHER INFORMATION: Xaa at position 21 is tyrosine, phenylalanine
      or 4-amino-phenylalanine

<400> SEQUENCE: 20

Xaa Leu Cys Gly Xaa Xaa Leu Val Xaa Xaa Leu Xaa Leu Val Cys Gly
1               5                   10                  15

Xaa Xaa Gly Phe Xaa
            20

<210> SEQ ID NO 21
<211> LENGTH: 21
<212> TYPE: PRT
<213> ORGANISM: Artificial Sequence
<220> FEATURE:
<223> OTHER INFORMATION: Analog of the insulin B chain
<220> FEATURE:
<221> NAME/KEY: MISC_FEATURE
<222> LOCATION: (1)..(1)
<223> OTHER INFORMATION: Xaa at position 1 is histidine or threonine
<220> FEATURE:
<221> NAME/KEY: MISC_FEATURE
<222> LOCATION: (5)..(5)
<223> OTHER INFORMATION: Xaa at position 5 is alanine, glycine or serine
```

```
<220> FEATURE:
<221> NAME/KEY: MISC_FEATURE
<222> LOCATION: (6)..(6)
<223> OTHER INFORMATION: Xaa at position 6 is histidine, aspartic acid,
      glutamic acid, homocysteic acid or cysteic acid
<220> FEATURE:
<221> NAME/KEY: MISC_FEATURE
<222> LOCATION: (9)..(9)
<223> OTHER INFORMATION: Xaa at position 9 is aspartic acid, glutamine
      or glutamic acid
<220> FEATURE:
<221> NAME/KEY: MISC_FEATURE
<222> LOCATION: (10)..(10)
<223> OTHER INFORMATION: Xaa at position 10 is alanine or threonine
<220> FEATURE:
<221> NAME/KEY: MISC_FEATURE
<222> LOCATION: (17)..(17)
<223> OTHER INFORMATION: Xaa at position 17 is glutamic acid, aspartic
      acid or asparagine
<220> FEATURE:
<221> NAME/KEY: MISC_FEATURE
<222> LOCATION: (18)..(18)
<223> OTHER INFORMATION: Xaa at position 18 is alanine, ornithine,
      lysine or arginine
<220> FEATURE:
<221> NAME/KEY: MISC_FEATURE
<222> LOCATION: (21)..(21)
<223> OTHER INFORMATION: Xaa at position 21 is tyrosine, histidine,
      asparagine or 4-amino-phenylalanine

<400> SEQUENCE: 21

Xaa Leu Cys Gly Xaa Xaa Leu Val Xaa Xaa Leu Tyr Leu Val Cys Gly
1               5                   10                  15

Xaa Xaa Gly Phe Xaa
            20

<210> SEQ ID NO 22
<211> LENGTH: 21
<212> TYPE: PRT
<213> ORGANISM: Artificial Sequence
<220> FEATURE:
<223> OTHER INFORMATION: Analog of the insulin A chain
<220> FEATURE:
<221> NAME/KEY: MISC_FEATURE
<222> LOCATION: (4)..(4)
<223> OTHER INFORMATION: Xaa at position 4 is aspartic acid or glutamic
      acid
<220> FEATURE:
<221> NAME/KEY: MISC_FEATURE
<222> LOCATION: (5)..(5)
<223> OTHER INFORMATION: Xaa at position 5 is glutamine or glutamic acid
<220> FEATURE:
<221> NAME/KEY: MISC_FEATURE
<222> LOCATION: (8)..(8)
<223> OTHER INFORMATION: Xaa at position 8 is histidine, threonine or
      phenylalanine
<220> FEATURE:
<221> NAME/KEY: MISC_FEATURE
<222> LOCATION: (9)..(9)
<223> OTHER INFORMATION: Xaa at position 9 is serine, arginine,
      ornithine, lysine or alanine
<220> FEATURE:
<221> NAME/KEY: MISC_FEATURE
<222> LOCATION: (10)..(10)
<223> OTHER INFORMATION: Xaa at position 10 is isoleucine or serine
<220> FEATURE:
<221> NAME/KEY: MISC_FEATURE
<222> LOCATION: (12)..(12)
<223> OTHER INFORMATION: Xaa at position 12 is aspartic acid or serine
<220> FEATURE:
<221> NAME/KEY: MISC_FEATURE
<222> LOCATION: (14)..(14)
<223> OTHER INFORMATION: Xaa at position 14 is tyrosine, arginine,
      ornithine, lysine or alanine
<220> FEATURE:
<221> NAME/KEY: MISC_FEATURE
```

```
<222> LOCATION: (15)..(15)
<223> OTHER INFORMATION: Xaa at position 15 is glutamine, glutamic acid,
      arginine, ornithine, alanine, lysine or leucine
<220> FEATURE:
<221> NAME/KEY: MISC_FEATURE
<222> LOCATION: (17)..(17)
<223> OTHER INFORMATION: Xaa at position 17 is glutamine or glutamic
      acid
<220> FEATURE:
<221> NAME/KEY: MISC_FEATURE
<222> LOCATION: (18)..(18)
<223> OTHER INFORMATION: Xaa at position 18 is methionine, asparagine,
      glutamine, glutamic acid, aspartic acid or threonine
<220> FEATURE:
<221> NAME/KEY: MISC_FEATURE
<222> LOCATION: (19)..(19)
<223> OTHER INFORMATION: Xaa at position 19 is tyrosine, 4-methoxy
      phenylalanine or 4-amino-phenylalanine
<220> FEATURE:
<221> NAME/KEY: MISC_FEATURE
<222> LOCATION: (21)..(21)
<223> OTHER INFORMATION: Xaa at position 21 is alanine, glycine, serine,
      valine, threonine, isoleucine, leucine, glutamine, glutamic acid,
      asparagine, aspartic acid, histidine, tryptophan, tyrosine, or
      methionine

<400> SEQUENCE: 22

Gly Ile Val Xaa Xaa Cys Cys Xaa Xaa Xaa Cys Xaa Leu Xaa Xaa Leu
1               5                   10                  15

Xaa Xaa Xaa Cys Xaa
            20

<210> SEQ ID NO 23
<211> LENGTH: 8
<212> TYPE: PRT
<213> ORGANISM: Artificial Sequence
<220> FEATURE:
<223> OTHER INFORMATION: linker sequence
<220> FEATURE:
<221> NAME/KEY: MISC_FEATURE
<222> LOCATION: (1)..(1)
<223> OTHER INFORMATION: The Xaa at position 1 represents an amino acid
      selected from glycine, alanine, valine, leucine, isoleucine,
      proline, phenylalanine and methionine
<220> FEATURE:
<221> NAME/KEY: MISC_FEATURE
<222> LOCATION: (3)..(6)
<223> OTHER INFORMATION: The Xaas at positions 3-6 are independently any
      amino acid

<400> SEQUENCE: 23

Xaa Ala Xaa Xaa Xaa Xaa Arg Arg
1               5

<210> SEQ ID NO 24
<211> LENGTH: 4
<212> TYPE: PRT
<213> ORGANISM: Artificial Sequence
<220> FEATURE:
<223> OTHER INFORMATION: linker sequence
<220> FEATURE:
<221> NAME/KEY: MISC_FEATURE
<222> LOCATION: (1)..(4)
<223> OTHER INFORMATION: The Xaas at positions 1-4 are independently any
      amino acid

<400> SEQUENCE: 24

Xaa Xaa Xaa Xaa
1

<210> SEQ ID NO 25
<211> LENGTH: 8
```

```
<212> TYPE: PRT
<213> ORGANISM: Artificial Sequence
<220> FEATURE:
<223> OTHER INFORMATION: linker sequence
<220> FEATURE:
<221> NAME/KEY: MISC_FEATURE
<222> LOCATION: (1)..(7)
<223> OTHER INFORMATION: The Xaas at positions 1-7 are independently any
      amino acid

<400> SEQUENCE: 25

Xaa Xaa Xaa Xaa Xaa Xaa Xaa Arg
1               5

<210> SEQ ID NO 26
<211> LENGTH: 8
<212> TYPE: PRT
<213> ORGANISM: Artificial Sequence
<220> FEATURE:
<223> OTHER INFORMATION: linker sequence
<220> FEATURE:
<221> NAME/KEY: MISC_FEATURE
<222> LOCATION: (1)..(5)
<223> OTHER INFORMATION: The Xaas at positions 1-5 are independently any
      amino acid

<400> SEQUENCE: 26

Xaa Xaa Xaa Xaa Xaa Ser Arg Arg
1               5

<210> SEQ ID NO 27
<211> LENGTH: 8
<212> TYPE: PRT
<213> ORGANISM: Artificial Sequence
<220> FEATURE:
<223> OTHER INFORMATION: linker sequence
<220> FEATURE:
<221> NAME/KEY: MISC_FEATURE
<222> LOCATION: (1)..(1)
<223> OTHER INFORMATION: The Xaa at positions 1 is glycine, alanine,
      valine, leucine, isoleucine, proline or methionine
<220> FEATURE:
<221> NAME/KEY: MISC_FEATURE
<222> LOCATION: (2)..(2)
<223> OTHER INFORMATION: The Xaa at positions 2 is any non-aromatic
      amino acid

<400> SEQUENCE: 27

Xaa Xaa Gly Ser Ser Ser Arg Arg
1               5

<210> SEQ ID NO 28
<211> LENGTH: 8
<212> TYPE: PRT
<213> ORGANISM: Artificial Sequence
<220> FEATURE:
<223> OTHER INFORMATION: linker sequence
<220> FEATURE:
<221> NAME/KEY: MISC_FEATURE
<222> LOCATION: (1)..(1)
<223> OTHER INFORMATION: Xaa at position 1 is any amino acid
<220> FEATURE:
<221> NAME/KEY: MISC_FEATURE
<222> LOCATION: (3)..(7)
<223> OTHER INFORMATION: Xaas at positions 3-7 are independently any
      amino acid

<400> SEQUENCE: 28

Xaa Ala Xaa Xaa Xaa Xaa Xaa Arg
1               5
```

-continued

```
<210> SEQ ID NO 29
<211> LENGTH: 8
<212> TYPE: PRT
<213> ORGANISM: Artificial Sequence
<220> FEATURE:
<223> OTHER INFORMATION: linker sequence
<220> FEATURE:
<221> NAME/KEY: MISC_FEATURE
<222> LOCATION: (1)..(1)
<223> OTHER INFORMATION: Xaa at position 1 is glycine, alanine, valine,
      leucine, isoleucine, proline, phenylalanine and methionine
<220> FEATURE:
<221> NAME/KEY: MISC_FEATURE
<222> LOCATION: (2)..(2)
<223> OTHER INFORMATION: Xaa at position 2 is any non-aromatic amino
      acid
<220> FEATURE:
<221> NAME/KEY: MISC_FEATURE
<222> LOCATION: (7)..(8)
<223> OTHER INFORMATION: Xaas at positions 7 and 8 are independently
      arginine, lysine or ornithine

<400> SEQUENCE: 29

Xaa Xaa Gly Ser Ser Ser Xaa Xaa
1               5

<210> SEQ ID NO 30
<211> LENGTH: 12
<212> TYPE: PRT
<213> ORGANISM: Artificial Sequence
<220> FEATURE:
<223> OTHER INFORMATION: linker sequence
<220> FEATURE:
<221> NAME/KEY: MISC_FEATURE
<222> LOCATION: (1)..(1)
<223> OTHER INFORMATION: Xaa at position 1 is glycine, alanine, valine,
      leucine, isoleucine, proline, phenylalanine and methionine

<400> SEQUENCE: 30

Xaa Ala Gly Ser Ser Ser Arg Arg Ala Pro Gln Thr
1               5                   10

<210> SEQ ID NO 31
<211> LENGTH: 8
<212> TYPE: PRT
<213> ORGANISM: Artificial Sequence
<220> FEATURE:
<223> OTHER INFORMATION: peptide linker
<220> FEATURE:
<221> NAME/KEY: MISC_FEATURE
<222> LOCATION: (2)..(2)
<223> OTHER INFORMATION: Xaa at position 2 is any amino acid

<400> SEQUENCE: 31

Gly Xaa Gly Ser Ser Ser Arg Arg
1               5

<210> SEQ ID NO 32
<211> LENGTH: 8
<212> TYPE: PRT
<213> ORGANISM: Artificial Sequence
<220> FEATURE:
<223> OTHER INFORMATION: peptide linker

<400> SEQUENCE: 32

Gly Ala Gly Ser Ser Ser Arg Arg
1               5

<210> SEQ ID NO 33
<211> LENGTH: 9
<212> TYPE: PRT
```

```
<213> ORGANISM: Artificial Sequence
<220> FEATURE:
<223> OTHER INFORMATION: linker sequence

<400> SEQUENCE: 33

Gly Ala Gly Ser Ser Ser Arg Arg Ala
1               5

<210> SEQ ID NO 34
<211> LENGTH: 10
<212> TYPE: PRT
<213> ORGANISM: Artificial Sequence
<220> FEATURE:
<223> OTHER INFORMATION: linker sequence

<400> SEQUENCE: 34

Gly Ala Gly Ser Ser Ser Arg Arg Ala Pro
1               5                   10

<210> SEQ ID NO 35
<211> LENGTH: 11
<212> TYPE: PRT
<213> ORGANISM: Artificial Sequence
<220> FEATURE:
<223> OTHER INFORMATION: peptide linker

<400> SEQUENCE: 35

Gly Ala Gly Ser Ser Ser Arg Arg Ala Pro Gln
1               5                   10

<210> SEQ ID NO 36
<211> LENGTH: 12
<212> TYPE: PRT
<213> ORGANISM: Artificial Sequence
<220> FEATURE:
<223> OTHER INFORMATION: linker sequence

<400> SEQUENCE: 36

Gly Ala Gly Ser Ser Ser Arg Arg Ala Pro Gln Thr
1               5                   10

<210> SEQ ID NO 37
<211> LENGTH: 12
<212> TYPE: PRT
<213> ORGANISM: Homo sapiens
<220> FEATURE:
<221> NAME/KEY: MISC_FEATURE
<222> LOCATION: (7)..(8)
<223> OTHER INFORMATION: The Xaas at positions 7 and 8 are independently
      arginine, lysine or ornithine

<400> SEQUENCE: 37

Gly Tyr Gly Ser Ser Ser Xaa Xaa Ala Pro Gln Thr
1               5                   10

<210> SEQ ID NO 38
<211> LENGTH: 12
<212> TYPE: PRT
<213> ORGANISM: Homo sapiens
<220> FEATURE:
<221> NAME/KEY: MISC_FEATURE
<222> LOCATION: (2)..(2)
<223> OTHER INFORMATION: The Xaas at position 2 is alanine, valine,
      leucine, isoleucine or proline
<220> FEATURE:
<221> NAME/KEY: MISC_FEATURE
<222> LOCATION: (8)..(8)
<223> OTHER INFORMATION: The Xaas at position 8 is arginine, lysine or
      ornithine
```

<400> SEQUENCE: 38

Gly Xaa Gly Ser Ser Ser Arg Xaa Ala Pro Gln Thr
1               5                   10

<210> SEQ ID NO 39
<211> LENGTH: 8
<212> TYPE: PRT
<213> ORGANISM: Artificial Sequence
<220> FEATURE:
<223> OTHER INFORMATION: linker sequence

<400> SEQUENCE: 39

Pro Tyr Gly Ser Ser Ser Arg Arg
1               5

<210> SEQ ID NO 40
<211> LENGTH: 8
<212> TYPE: PRT
<213> ORGANISM: Artificial Sequence
<220> FEATURE:
<223> OTHER INFORMATION: linker sequence

<400> SEQUENCE: 40

Pro Ala Gly Ser Ser Ser Arg Arg
1               5

<210> SEQ ID NO 41
<211> LENGTH: 9
<212> TYPE: PRT
<213> ORGANISM: Artificial Sequence
<220> FEATURE:
<223> OTHER INFORMATION: linker sequence

<400> SEQUENCE: 41

Pro Ala Gly Ser Ser Ser Arg Arg Ala
1               5

<210> SEQ ID NO 42
<211> LENGTH: 10
<212> TYPE: PRT
<213> ORGANISM: Artificial Sequence
<220> FEATURE:
<223> OTHER INFORMATION: linker sequence

<400> SEQUENCE: 42

Pro Ala Gly Ser Ser Ser Arg Arg Ala Pro
1               5                   10

<210> SEQ ID NO 43
<211> LENGTH: 11
<212> TYPE: PRT
<213> ORGANISM: Artificial Sequence
<220> FEATURE:
<223> OTHER INFORMATION: linker sequence

<400> SEQUENCE: 43

Pro Ala Gly Ser Ser Ser Arg Arg Ala Pro Gln
1               5                   10

<210> SEQ ID NO 44
<211> LENGTH: 12
<212> TYPE: PRT
<213> ORGANISM: Artificial Sequence
<220> FEATURE:
<223> OTHER INFORMATION: linker sequence

```
<400> SEQUENCE: 44

Pro Ala Gly Ser Ser Ser Arg Arg Ala Pro Gln Thr
1               5                   10

<210> SEQ ID NO 45
<211> LENGTH: 8
<212> TYPE: PRT
<213> ORGANISM: Artificial Sequence
<220> FEATURE:
<223> OTHER INFORMATION: peptide linker
<220> FEATURE:
<221> NAME/KEY: MISC_FEATURE
<222> LOCATION: (8)..(8)
<223> OTHER INFORMATION: The Xaa at position 8 is arginine, lysine or
      ornithine

<400> SEQUENCE: 45

Gly Tyr Gly Ser Ser Ser Arg Xaa
1               5

<210> SEQ ID NO 46
<211> LENGTH: 12
<212> TYPE: PRT
<213> ORGANISM: Artificial Sequence
<220> FEATURE:
<223> OTHER INFORMATION: linker sequence
<220> FEATURE:
<221> NAME/KEY: MISC_FEATURE
<222> LOCATION: (1)..(1)
<223> OTHER INFORMATION: Xaa at position 1 is glycine, alanine, valine,
      leucine, isoleucine, proline, phenylalanine and methionine
<220> FEATURE:
<221> NAME/KEY: MISC_FEATURE
<222> LOCATION: (2)..(2)
<223> OTHER INFORMATION: Xaa at position 2 is any non-aromatic amino
      acid
<220> FEATURE:
<221> NAME/KEY: MISC_FEATURE
<222> LOCATION: (7)..(8)
<223> OTHER INFORMATION: Xaas at positions 7 and 8 are independently
      arginine, lysine or ornithine

<400> SEQUENCE: 46

Xaa Xaa Gly Ser Ser Ser Xaa Xaa Ala Pro Gln Thr
1               5                   10

<210> SEQ ID NO 47
<211> LENGTH: 7
<212> TYPE: PRT
<213> ORGANISM: Artificial Sequence
<220> FEATURE:
<223> OTHER INFORMATION: peptide linker
<220> FEATURE:
<221> NAME/KEY: MISC_FEATURE
<222> LOCATION: (1)..(1)
<223> OTHER INFORMATION: the Xaa at position 1 is glycine, glutamic acid
      or aspartic acid
<220> FEATURE:
<221> NAME/KEY: MISC_FEATURE
<222> LOCATION: (2)..(6)
<223> OTHER INFORMATION: the Xaas at positions 2-6 are independently
      glutamic acid or aspartic acid

<400> SEQUENCE: 47

Xaa Xaa Xaa Xaa Xaa Xaa Lys
1               5

<210> SEQ ID NO 48
<211> LENGTH: 7
<212> TYPE: PRT
<213> ORGANISM: Artificial Sequence
```

```
<220> FEATURE:
<223> OTHER INFORMATION: peptide linker
<220> FEATURE:
<221> NAME/KEY: MISC_FEATURE
<222> LOCATION: (2)..(6)
<223> OTHER INFORMATION: the Xaas at positions 2-6 are independently
      glutamic acid or aspartic acid

<400> SEQUENCE: 48

Gly Xaa Xaa Xaa Xaa Xaa Lys
1               5

<210> SEQ ID NO 49
<211> LENGTH: 7
<212> TYPE: PRT
<213> ORGANISM: Artificial Sequence
<220> FEATURE:
<223> OTHER INFORMATION: peptide linker
<220> FEATURE:
<221> NAME/KEY: MISC_FEATURE
<222> LOCATION: (1)..(5)
<223> OTHER INFORMATION: the Xaas at positions 1-5 are independently
      glutamic acid or aspartic acid

<400> SEQUENCE: 49

Xaa Xaa Xaa Xaa Xaa Arg Lys
1               5

<210> SEQ ID NO 50
<211> LENGTH: 31
<212> TYPE: PRT
<213> ORGANISM: Artificial Sequence
<220> FEATURE:
<223> OTHER INFORMATION: insulin analog
<220> FEATURE:
<221> NAME/KEY: MISC_FEATURE
<222> LOCATION: (28)..(28)
<223> OTHER INFORMATION: The Xaa at position 28 is alanine, lysine,
      ornithine or arginine

<400> SEQUENCE: 50

Gly Glu Glu Glu Glu Lys Gly Pro Glu His Leu Cys Gly Ala His
1               5                   10                  15

Leu Val Asp Ala Leu Tyr Leu Val Cys Gly Asp Xaa Gly Phe Tyr
            20                  25                  30

<210> SEQ ID NO 51
<211> LENGTH: 8
<212> TYPE: PRT
<213> ORGANISM: Artificial Sequence
<220> FEATURE:
<223> OTHER INFORMATION: peptide linker
<220> FEATURE:
<221> NAME/KEY: MISC_FEATURE
<222> LOCATION: (7)..(7)
<223> OTHER INFORMATION: The Xaa at position 7 is arginine, lysine or
      ornithine

<400> SEQUENCE: 51

Gly Tyr Gly Ser Ser Ser Xaa Arg
1               5

<210> SEQ ID NO 52
<211> LENGTH: 21
<212> TYPE: PRT
<213> ORGANISM: Artificial Sequence
<220> FEATURE:
<223> OTHER INFORMATION: Analog of the insulin A chain
<220> FEATURE:
<221> NAME/KEY: MISC_FEATURE
```

```
<222> LOCATION: (8)..(8)
<223> OTHER INFORMATION: Xaa at position 8 is histidine or threonine
<220> FEATURE:
<221> NAME/KEY: MISC_FEATURE
<222> LOCATION: (17)..(17)
<223> OTHER INFORMATION: Xaa at position 17 is glutamine or glutamic
      acid
<220> FEATURE:
<221> NAME/KEY: MISC_FEATURE
<222> LOCATION: (19)..(19)
<223> OTHER INFORMATION: Xaa at position 19 is tyrosine, 4-methoxy
      phenylalanine or 4-amino-phenylalanine
<220> FEATURE:
<221> NAME/KEY: MISC_FEATURE
<222> LOCATION: (21)..(21)
<223> OTHER INFORMATION: Xaa at position 21 is asparagine or glycine

<400> SEQUENCE: 52

Gly Ile Val Glu Gln Cys Cys Xaa Ser Ile Cys Ser Leu Tyr Gln Leu
1               5                   10                  15

Xaa Asn Xaa Cys Xaa
            20

<210> SEQ ID NO 53
<211> LENGTH: 21
<212> TYPE: PRT
<213> ORGANISM: Artificial Sequence
<220> FEATURE:
<223> OTHER INFORMATION: Analog of the insulin B chain
<220> FEATURE:
<221> NAME/KEY: MISC_FEATURE
<222> LOCATION: (1)..(1)
<223> OTHER INFORMATION: Xaa at position 1 is histidine or threonine
<220> FEATURE:
<221> NAME/KEY: MISC_FEATURE
<222> LOCATION: (5)..(5)
<223> OTHER INFORMATION: Xaa at position 5 is alanine, glycine or serine
<220> FEATURE:
<221> NAME/KEY: MISC_FEATURE
<222> LOCATION: (6)..(6)
<223> OTHER INFORMATION: Xaa at position 6 is histidine, aspartic acid,
      glutamic acid, homocysteic acid or cysteic acid

<400> SEQUENCE: 53

Xaa Leu Cys Gly Xaa Xaa Leu Val Glu Ala Leu Tyr Leu Val Cys Gly
1               5                   10                  15

Glu Arg Gly Phe Phe
            20

<210> SEQ ID NO 54
<211> LENGTH: 27
<212> TYPE: PRT
<213> ORGANISM: Artificial Sequence
<220> FEATURE:
<223> OTHER INFORMATION: Analog of the insulin B chain
<220> FEATURE:
<221> NAME/KEY: MISC_FEATURE
<222> LOCATION: (1)..(1)
<223> OTHER INFORMATION: Xaa at position 1 is phenylalanine and
      desamino-phenylalanine
<220> FEATURE:
<221> NAME/KEY: MISC_FEATURE
<222> LOCATION: (5)..(5)
<223> OTHER INFORMATION: Xaa at position 5 is histidine and threonine
<220> FEATURE:
<221> NAME/KEY: MISC_FEATURE
<222> LOCATION: (9)..(9)
<223> OTHER INFORMATION: Xaa at position 9 is alanine, glycine or serine
<220> FEATURE:
<221> NAME/KEY: MISC_FEATURE
<222> LOCATION: (10)..(10)
<223> OTHER INFORMATION: Xaa at position 10 is histidine, aspartic acid,
      glutamic acid, homocysteic acid or cysteic acid
```

<400> SEQUENCE: 54

Xaa Val Asn Gln Xaa Leu Cys Gly Xaa Xaa Leu Val Glu Ala Leu Tyr
1               5                   10                  15

Leu Val Cys Gly Glu Arg Gly Phe Phe Tyr Thr
            20                  25

<210> SEQ ID NO 55
<211> LENGTH: 21
<212> TYPE: PRT
<213> ORGANISM: Artificial Sequence
<220> FEATURE:
<223> OTHER INFORMATION: Analog of the insulin A chain
<220> FEATURE:
<221> NAME/KEY: MISC_FEATURE
<222> LOCATION: (8)..(8)
<223> OTHER INFORMATION: Xaa at position 8 is histidine or phenylalanine
<220> FEATURE:
<221> NAME/KEY: MISC_FEATURE
<222> LOCATION: (19)..(19)
<223> OTHER INFORMATION: Xaa at position 19 is tyrosine or 4-amino-
      phenylalanine
<220> FEATURE:
<221> NAME/KEY: MISC_FEATURE
<222> LOCATION: (21)..(21)
<223> OTHER INFORMATION: Xaa at position 21 is alanine, glycine or
      asparagine

<400> SEQUENCE: 55

Gly Ile Val Glu Gln Cys Cys Xaa Ser Ile Cys Ser Leu Tyr Gln Leu
1               5                   10                  15

Glu Asn Xaa Cys Xaa
            20

<210> SEQ ID NO 56
<211> LENGTH: 21
<212> TYPE: PRT
<213> ORGANISM: Artificial Sequence
<220> FEATURE:
<223> OTHER INFORMATION: Analog of the insulin A chain
<220> FEATURE:
<221> NAME/KEY: MISC_FEATURE
<222> LOCATION: (8)..(8)
<223> OTHER INFORMATION: Xaa at position 8 is histidine or phenylalnine
<220> FEATURE:
<221> NAME/KEY: MISC_FEATURE
<222> LOCATION: (9)..(9)
<223> OTHER INFORMATION: Xaa at position 9 is arginine, lysine,
      ornithine or alanine
<220> FEATURE:
<221> NAME/KEY: MISC_FEATURE
<222> LOCATION: (14)..(14)
<223> OTHER INFORMATION: Xaa at position 14 is arginine, lysine,
      ornithine or alanine
<220> FEATURE:
<221> NAME/KEY: MISC_FEATURE
<222> LOCATION: (15)..(15)
<223> OTHER INFORMATION: Xaa at position 15 is arginine, lysine,
      ornithine or leucine
<220> FEATURE:
<221> NAME/KEY: MISC_FEATURE
<222> LOCATION: (17)..(17)
<223> OTHER INFORMATION: Xaa at position 17 is glutamine or glutamic
      acid
<220> FEATURE:
<221> NAME/KEY: MISC_FEATURE
<222> LOCATION: (18)..(18)
<223> OTHER INFORMATION: Xaa at position 18 is methionine, asparagine or
      threonine
<220> FEATURE:
<221> NAME/KEY: MISC_FEATURE
<222> LOCATION: (19)..(19)
<223> OTHER INFORMATION: Xaa at position 19 is tyrosine, 4-methoxy

```
          phenylalanine or 4-amino-phenylalanine
<220> FEATURE:
<221> NAME/KEY: MISC_FEATURE

```
<222> LOCATION: (5)..(5)
<223> OTHER INFORMATION: Xaa at position 5 is alanine, glycine or serine
<220> FEATURE:
<221> NAME/KEY: MISC_FEATURE
<222> LOCATION: (6)..(6)
<223> OTHER INFORMATION: Xaa at position 6 is histidine, aspartic acid,
      glutamic acid, homocysteic acid or cysteic acid
<220> FEATURE:
<221> NAME/KEY: MISC_FEATURE
<222> LOCATION: (9)..(9)
<223> OTHER INFORMATION: Xaa at position 9 is aspartic acid or glutamic
      acid
<220> FEATURE:
<221> NAME/KEY: MISC_FEATURE
<222> LOCATION: (10)..(10)
<223> OTHER INFORMATION: Xaa at position 10 is alanine or threonine
<220> FEATURE:
<221> NAME/KEY: MISC_FEATURE
<222> LOCATION: (18)..(18)
<223> OTHER INFORMATION: Xaa at position 18 is alanine, ornithine,
      lysine or arginine
<220> FEATURE:
<221> NAME/KEY: MISC_FEATURE
<222> LOCATION: (21)..(21)
<223> OTHER INFORMATION: Xaa at position 21 is tyrosine, histidine,
      asparagine or phenylalanine

<400> SEQUENCE: 58

Xaa Leu Cys Gly Xaa Xaa Leu Val Xaa Xaa Leu Tyr Leu Val Cys Gly
1               5                   10                  15

Asp Xaa Gly Phe Xaa
            20

<210> SEQ ID NO 59
<211> LENGTH: 21
<212> TYPE: PRT
<213> ORGANISM: Artificial Sequence
<220> FEATURE:
<223> OTHER INFORMATION: Analog of the insulin A chain
<220> FEATURE:
<221> NAME/KEY: MISC_FEATURE
<222> LOCATION: (9)..(9)
<223> OTHER INFORMATION: Xaa at position 9 is arginine, ornithine, or
      lysine
<220> FEATURE:
<221> NAME/KEY: MISC_FEATURE
<222> LOCATION: (14)..(14)
<223> OTHER INFORMATION: Xaa at position 14 is arginine, ornithine, or
      lysine
<220> FEATURE:
<221> NAME/KEY: MISC_FEATURE
<222> LOCATION: (15)..(15)
<223> OTHER INFORMATION: Xaa at position 15 is arginine, ornithine, or
      lysine
<220> FEATURE:
<221> NAME/KEY: MISC_FEATURE
<222> LOCATION: (17)..(17)
<223> OTHER INFORMATION: Xaa at position 17 is glutamine or glutamic
      acid
<220> FEATURE:
<221> NAME/KEY: MISC_FEATURE
<222> LOCATION: (19)..(19)
<223> OTHER INFORMATION: Xaa at position 19 is tyrosine, 4-methoxy
      phenylalanine or 4-amino-phenylalanine
<220> FEATURE:
<221> NAME/KEY: MISC_FEATURE
<222> LOCATION: (21)..(21)
<223> OTHER INFORMATION: Xaa at position 21 is alanine, glycine or
      asparagine

<400> SEQUENCE: 59

Gly Ile Val Asp Glu Cys Cys His Xaa Ser Cys Asp Leu Xaa Xaa Leu
1               5                   10                  15

Xaa Met Xaa Cys Xaa
```

```
                20

<210> SEQ ID NO 60
<211> LENGTH: 21
<212> TYPE: PRT
<213> ORGANISM: Artificial Sequence
<220> FEATURE:
<223> OTHER INFORMATION: Analog of the insulin B chain
<220> FEATURE:
<221> NAME/KEY: MISC_FEATURE
<222> LOCATION: (1)..(1)
<223> OTHER INFORMATION: Xaa at position 1 is histidine or threonine
<220> FEATURE:
<221> NAME/KEY: MISC_FEATURE
<222> LOCATION: (6)..(6)
<223> OTHER INFORMATION: Xaa at position 6 is histidine, aspartic acid,
      or glutamic acid
<220> FEATURE:
<221> NAME/KEY: MISC_FEATURE
<222> LOCATION: (18)..(18)
<223> OTHER INFORMATION: Xaa at position 18 is alanine, ornithine,
      lysine or arginine
<220> FEATURE:
<221> NAME/KEY: MISC_FEATURE
<222> LOCATION: (21)..(21)
<223> OTHER INFORMATION: Xaa at position 21 is tyrosine or phenylalanine

<400> SEQUENCE: 60

Xaa Leu Cys Gly Ala Xaa Leu Val Asp Ala Leu Tyr Leu Val Cys Gly
1               5                   10                  15

Asp Xaa Gly Phe Xaa
            20

<210> SEQ ID NO 61
<211> LENGTH: 21
<212> TYPE: PRT
<213> ORGANISM: Artificial Sequence
<220> FEATURE:
<223> OTHER INFORMATION: analog of IGF B chain
<220> FEATURE:
<221> NAME/KEY: MISC_FEATURE
<222> LOCATION: (18)..(18)
<223> OTHER INFORMATION: The Xaa at position 18 is ornithine, lysine or
      arginine

<400> SEQUENCE: 61

His Leu Cys Gly Ala Glu Leu Val Asp Ala Leu Tyr Leu Val Cys Gly
1               5                   10                  15

Asp Xaa Gly Phe Tyr
            20

<210> SEQ ID NO 62
<211> LENGTH: 24
<212> TYPE: PRT
<213> ORGANISM: Artificial Sequence
<220> FEATURE:
<223> OTHER INFORMATION: analog of IGF B chain
<220> FEATURE:
<221> NAME/KEY: MISC_FEATURE
<222> LOCATION: (21)..(21)
<223> OTHER INFORMATION: The Xaa at position 21 is ornithine, lysine or
      arginine

<400> SEQUENCE: 62

Gly Pro Glu His Leu Cys Gly Ala Glu Leu Val Asp Ala Leu Tyr Leu
1               5                   10                  15

Val Cys Gly Asp Xaa Gly Phe Tyr
            20
```

```
<210> SEQ ID NO 63
<211> LENGTH: 29
<212> TYPE: PRT
<213> ORGANISM: Artificial Sequence
<220> FEATURE:
<223> OTHER INFORMATION: analog of IGF B chain
<220> FEATURE:
<221> NAME/KEY: MISC_FEATURE
<222> LOCATION: (21)..(21)
<223> OTHER INFORMATION: The Xaa at position 21 is ornithine, lysine or
      arginine

<400> SEQUENCE: 63

Gly Pro Glu His Leu Cys Gly Ala Glu Leu Val Asp Ala Leu Tyr Leu
1               5                   10                  15

Val Cys Gly Asp Xaa Gly Phe Tyr Phe Asn Pro Lys Thr
            20                  25

<210> SEQ ID NO 64
<211> LENGTH: 29
<212> TYPE: PRT
<213> ORGANISM: Artificial Sequence
<220> FEATURE:
<223> OTHER INFORMATION: analog of IGF B chain
<220> FEATURE:
<221> NAME/KEY: MISC_FEATURE
<222> LOCATION: (21)..(21)
<223> OTHER INFORMATION: The Xaa at position 21 is ornithine, lysine or
      arginine

<400> SEQUENCE: 64

Gly Pro Glu His Leu Cys Gly Ala Glu Leu Val Asp Ala Leu Tyr Leu
1               5                   10                  15

Val Cys Gly Asp Xaa Gly Phe Tyr Phe Asn Lys Pro Thr
            20                  25

<210> SEQ ID NO 65
<211> LENGTH: 8
<212> TYPE: PRT
<213> ORGANISM: Homo sapiens
<220> FEATURE:
<221> NAME/KEY: MISC_FEATURE
<222> LOCATION: (7)..(7)
<223> OTHER INFORMATION: Xaa at position 7 is ornithine

<400> SEQUENCE: 65

Gly Tyr Gly Ser Ser Ser Xaa Arg
1               5

<210> SEQ ID NO 66
<211> LENGTH: 21
<212> TYPE: PRT
<213> ORGANISM: Artificial Sequence
<220> FEATURE:
<223> OTHER INFORMATION: Analog of the insulin A chain
<220> FEATURE:
<221> NAME/KEY: MISC_FEATURE
<222> LOCATION: (9)..(9)
<223> OTHER INFORMATION: Xaa at position 9 is arginine, ornithine, or
      lysine
<220> FEATURE:
<221> NAME/KEY: MISC_FEATURE
<222> LOCATION: (14)..(14)
<223> OTHER INFORMATION: Xaa at position 14 is arginine, ornithine, or
      lysine
<220> FEATURE:
<221> NAME/KEY: MISC_FEATURE
<222> LOCATION: (15)..(15)
<223> OTHER INFORMATION: Xaa at position 15 is arginine, ornithine, or
      lysine
```

```
<400> SEQUENCE: 66

Gly Ile Val Asp Glu Cys Cys His Xaa Ser Cys Asp Leu Xaa Xaa Leu
1               5                   10                  15

Gln Met Tyr Cys Asn
            20

<210> SEQ ID NO 67
<211> LENGTH: 12
<212> TYPE: PRT
<213> ORGANISM: Homo sapiens
<220> FEATURE:
<221> NAME/KEY: MISC_FEATURE
<222> LOCATION: (7)..(7)
<223> OTHER INFORMATION: Xaa at position 7 is ornithine, lysine or
      arginine

<400> SEQUENCE: 67

Gly Ala Gly Ser Ser Ser Xaa Arg Ala Pro Gln Thr
1               5                   10

<210> SEQ ID NO 68
<211> LENGTH: 21
<212> TYPE: PRT
<213> ORGANISM: Artificial Sequence
<220> FEATURE:
<223> OTHER INFORMATION: Analog of the insulin A chain
<220> FEATURE:
<221> NAME/KEY: MISC_FEATURE
<222> LOCATION: (19)..(19)
<223> OTHER INFORMATION: Xaa at position 19 is tyrosine, 4-methoxy
      phenylalanine or 4-amino-phenylalanine
<220> FEATURE:
<221> NAME/KEY: MISC_FEATURE
<222> LOCATION: (21)..(21)
<223> OTHER INFORMATION: Xaa at position 21 is alanine, glycine or
      asparagine

<400> SEQUENCE: 68

Gly Ile Val Glu Gln Cys Cys His Ser Ile Cys Ser Leu Tyr Gln Leu
1               5                   10                  15

Glu Asn Xaa Cys Xaa
            20

<210> SEQ ID NO 69
<211> LENGTH: 21
<212> TYPE: PRT
<213> ORGANISM: Artificial Sequence
<220> FEATURE:
<223> OTHER INFORMATION: Analog of the insulin A chain
<220> FEATURE:
<221> NAME/KEY: MISC_FEATURE
<222> LOCATION: (8)..(8)
<223> OTHER INFORMATION: Xaa at position 8 is histidine or phenylalnine
<220> FEATURE:
<221> NAME/KEY: MISC_FEATURE
<222> LOCATION: (9)..(9)
<223> OTHER INFORMATION: Xaa at position 9 is arginine, lysine,
      ornithine or alanine
<220> FEATURE:
<221> NAME/KEY: MISC_FEATURE
<222> LOCATION: (14)..(14)
<223> OTHER INFORMATION: Xaa at position 14 is arginine, lysine,
      ornithine or alanine
<220> FEATURE:
<221> NAME/KEY: MISC_FEATURE
<222> LOCATION: (15)..(15)
<223> OTHER INFORMATION: Xaa at position 15 is arginine, lysine,
      ornithine or leucine
<220> FEATURE:
<221> NAME/KEY: MISC_FEATURE
<222> LOCATION: (17)..(17)
```

```
<223> OTHER INFORMATION: Xaa at position 17 is glutamine or glutamic
      acid
<220> FEATURE:
<221> NAME/KEY: MISC_FEATURE
<222> LOCATION: (18)..(18)
<223> OTHER INFORMATION: Xaa at position 18 is methionine, asparagine or
      threonine
<220> FEATURE:
<221> NAME/KEY: MISC_FEATURE
<222> LOCATION: (19)..(19)
<223> OTHER INFORMATION: Xaa at position 19 is tyrosine, 4-methoxy
      phenylalanine or 4-amino-phenylalanine
<220> FEATURE:
<221> NAME/KEY: MISC_FEATURE
<222> LOCATION: (21)..(21)
<223> OTHER INFORMATION: Xaa at position 21 is alanine, glycine or
      asparagine

<400> SEQUENCE: 69

Gly Ile Val Asp Glu Cys Cys Xaa Xaa Ser Cys Asp Leu Xaa Xaa Leu
1               5                   10                  15

Xaa Xaa Xaa Cys Xaa
            20

<210> SEQ ID NO 70
<211> LENGTH: 8
<212> TYPE: PRT
<213> ORGANISM: Artificial Sequence
<220> FEATURE:
<223> OTHER INFORMATION: peptide linker
<220> FEATURE:
<221> NAME/KEY: MISC_FEATURE
<222> LOCATION: (1)..(1)
<223> OTHER INFORMATION: Xaa at position 1 is any amino acid
<220> FEATURE:
<221> NAME/KEY: MISC_FEATURE
<222> LOCATION: (3)..(6)
<223> OTHER INFORMATION: Xaas at positions 3-6 are independently any
      amino acid
<220> FEATURE:
<221> NAME/KEY: MISC_FEATURE
<222> LOCATION: (7)..(8)
<223> OTHER INFORMATION: Xaas at positions 7-8 are independently
      arginine, lysine or ornithine

<400> SEQUENCE: 70

Xaa Ala Xaa Xaa Xaa Xaa Xaa Xaa
1               5

<210> SEQ ID NO 71
<211> LENGTH: 21
<212> TYPE: PRT
<213> ORGANISM: Homo sapiens
<220> FEATURE:
<221> NAME/KEY: MISC_FEATURE
<222> LOCATION: (18)..(18)
<223> OTHER INFORMATION: The Xaa at position 18 is ornithine

<400> SEQUENCE: 71

His Leu Cys Gly Ala Glu Leu Val Asp Ala Leu Tyr Leu Val Cys Gly
1               5                   10                  15

Asp Xaa Gly Phe Tyr
            20

<210> SEQ ID NO 72
<211> LENGTH: 24
<212> TYPE: PRT
<213> ORGANISM: Homo sapiens
<220> FEATURE:
<221> NAME/KEY: MISC_FEATURE
<222> LOCATION: (21)..(21)
```

```
<223> OTHER INFORMATION: The Xaa at position 21 is ornithine

<400> SEQUENCE: 72

Gly Pro Glu His Leu Cys Gly Ala Glu Leu Val Asp Ala Leu Tyr Leu
1               5                   10                  15

Val Cys Gly Asp Xaa Gly Phe Tyr
            20

<210> SEQ ID NO 73
<211> LENGTH: 29
<212> TYPE: PRT
<213> ORGANISM: Homo sapiens
<220> FEATURE:
<221> NAME/KEY: MISC_FEATURE
<222> LOCATION: (21)..(21)
<223> OTHER INFORMATION: The Xaa at position 21 is ornithine

<400> SEQUENCE: 73

Gly Pro Glu His Leu Cys Gly Ala Glu Leu Val Asp Ala Leu Tyr Leu
1               5                   10                  15

Val Cys Gly Asp Xaa Gly Phe Tyr Phe Asn Pro Lys Thr
            20                  25

<210> SEQ ID NO 74
<211> LENGTH: 29
<212> TYPE: PRT
<213> ORGANISM: Homo sapiens
<220> FEATURE:
<221> NAME/KEY: misc_feature
<222> LOCATION: (21)..(21)
<223> OTHER INFORMATION: Xaa at position 21 is ornithine

<400> SEQUENCE: 74

Gly Pro Glu His Leu Cys Gly Ala Glu Leu Val Asp Ala Leu Tyr Leu
1               5                   10                  15

Val Cys Gly Asp Xaa Gly Phe Tyr Phe Asn Lys Pro Thr
            20                  25

<210> SEQ ID NO 75
<211> LENGTH: 21
<212> TYPE: PRT
<213> ORGANISM: Homo sapiens
<220> FEATURE:
<221> NAME/KEY: MISC_FEATURE
<222> LOCATION: (9)..(9)
<223> OTHER INFORMATION: The Xaa at position 9 is ornithine
<220> FEATURE:
<221> NAME/KEY: MISC_FEATURE
<222> LOCATION: (14)..(15)
<223> OTHER INFORMATION: The Xaas at positions 14 and 15 are both
      ornithine
<220> FEATURE:
<221> NAME/KEY: MISC_FEATURE
<222> LOCATION: (19)..(19)
<223> OTHER INFORMATION: The Xaa at position 19 is tyrosine, 4-methoxy-
      phenylalanine or 4-amino phenylalanine

<400> SEQUENCE: 75

Gly Ile Val Asp Glu Cys Cys His Xaa Ser Cys Asp Leu Xaa Xaa Leu
1               5                   10                  15

Gln Met Xaa Cys Asn
            20

<210> SEQ ID NO 76
<211> LENGTH: 5
<212> TYPE: PRT
<213> ORGANISM: Homo sapiens
```

```
<400> SEQUENCE: 76

Phe Asn Lys Pro Thr
1               5

<210> SEQ ID NO 77
<211> LENGTH: 4
<212> TYPE: PRT
<213> ORGANISM: Homo sapiens

<400> SEQUENCE: 77

Phe Asn Lys Pro
1

<210> SEQ ID NO 78
<211> LENGTH: 4
<212> TYPE: PRT
<213> ORGANISM: Homo sapiens

<400> SEQUENCE: 78

Tyr Thr Pro Lys
1

<210> SEQ ID NO 79
<211> LENGTH: 4
<212> TYPE: PRT
<213> ORGANISM: Artificial Sequence
<220> FEATURE:
<223> OTHER INFORMATION: insulin B chain derivative sequence

<400> SEQUENCE: 79

Phe Asn Pro Lys
1

<210> SEQ ID NO 80
<211> LENGTH: 5
<212> TYPE: PRT
<213> ORGANISM: Artificial Sequence
<220> FEATURE:
<223> OTHER INFORMATION: insulin B chain derivative sequence

<400> SEQUENCE: 80

Tyr Thr Lys Pro Thr
1               5

<210> SEQ ID NO 81
<211> LENGTH: 5
<212> TYPE: PRT
<213> ORGANISM: Artificial Sequence
<220> FEATURE:
<223> OTHER INFORMATION: insulin B chain derivative sequence

<400> SEQUENCE: 81

Phe Asn Pro Lys Thr
1               5

<210> SEQ ID NO 82
<211> LENGTH: 4
<212> TYPE: PRT
<213> ORGANISM: Homo sapiens

<400> SEQUENCE: 82

Ala Pro Gln Thr
1
```

```
<210> SEQ ID NO 83
<211> LENGTH: 12
<212> TYPE: PRT
<213> ORGANISM: Homo sapiens
<220> FEATURE:
<221> NAME/KEY: MISC_FEATURE
<222> LOCATION: (2)..(2)
<223> OTHER INFORMATION: The Xaa at position 2 is any non-aromatic amino
      acid

<400> SEQUENCE: 83

Gly Xaa Gly Ser Ser Ser Arg Arg Ala Pro Gln Thr
1               5                   10

<210> SEQ ID NO 84
<211> LENGTH: 4
<212> TYPE: PRT
<213> ORGANISM: Homo sapiens
<220> FEATURE:
<221> NAME/KEY: MISC_FEATURE
<222> LOCATION: (1)..(1)
<223> OTHER INFORMATION: The Xaa at position 1 is phenylalanine or
      desamino-phenylalanine

<400> SEQUENCE: 84

Xaa Val Asn Gln
1

<210> SEQ ID NO 85
<211> LENGTH: 8
<212> TYPE: PRT
<213> ORGANISM: Homo sapiens
<220> FEATURE:
<221> NAME/KEY: MISC_FEATURE
<222> LOCATION: (7)..(8)
<223> OTHER INFORMATION: The Xaas at positions 7 and 8 are independently
      arginine, lysine or ornithine

<400> SEQUENCE: 85

Gly Tyr Gly Ser Ser Ser Xaa Xaa
1               5

<210> SEQ ID NO 86
<211> LENGTH: 13
<212> TYPE: PRT
<213> ORGANISM: Artificial Sequence
<220> FEATURE:
<223> OTHER INFORMATION: linking peptide
<220> FEATURE:
<221> NAME/KEY: MISC_FEATURE
<222> LOCATION: (1)..(7)
<223> OTHER INFORMATION: The Xaas at positions 1-7 are independently any
      amino acid

<400> SEQUENCE: 86

Xaa Xaa Xaa Xaa Xaa Xaa Xaa Gly Ser Ser Ser Arg Arg
1               5                   10

<210> SEQ ID NO 87
<211> LENGTH: 17
<212> TYPE: PRT
<213> ORGANISM: Artificial Sequence
<220> FEATURE:
<223> OTHER INFORMATION: linking peptide
<220> FEATURE:
<221> NAME/KEY: MISC_FEATURE
<222> LOCATION: (1)..(7)
<223> OTHER INFORMATION: The Xaas at positions 1-7 are independently any
      amino acid
<220> FEATURE:
<221> NAME/KEY: MISC_FEATURE
```

```
<222> LOCATION: (13)..(13)
<223> OTHER INFORMATION: The Xaa at positions 13 is arginine, lysine or
      ornithine

<400> SEQUENCE: 87

Xaa Xaa Xaa Xaa Xaa Xaa Xaa Gly Ser Ser Ser Arg Xaa Ala Pro Gln
1               5                   10                  15

Thr

<210> SEQ ID NO 88
<211> LENGTH: 21
<212> TYPE: PRT
<213> ORGANISM: Homo sapiens
<220> FEATURE:
<221> NAME/KEY: MISC_FEATURE
<222> LOCATION: (19)..(19)
<223> OTHER INFORMATION: The Xaa at position 19 is tyrosine, 4-methoxy-
      phenylalanine or 4-amino phenylalanine
<220> FEATURE:
<221> NAME/KEY: MISC_FEATURE
<222> LOCATION: (21)..(21)
<223> OTHER INFORMATION: The Xaa at position 21 is alanine, glycine or
      asparagine

<400> SEQUENCE: 88

Gly Ile Val Asp Glu Cys Cys His Arg Ser Cys Asp Leu Arg Arg Leu
1               5                   10                  15

Glu Met Xaa Cys Xaa
            20

<210> SEQ ID NO 89
<211> LENGTH: 29
<212> TYPE: PRT
<213> ORGANISM: Homo sapiens

<400> SEQUENCE: 89

Gly Pro Glu Thr Leu Cys Gly Ala Glu Leu Val Asp Ala Leu Tyr Leu
1               5                   10                  15

Val Cys Gly Asp Arg Gly Phe Tyr Phe Asn Pro Lys Thr
            20                  25

<210> SEQ ID NO 90
<211> LENGTH: 8
<212> TYPE: PRT
<213> ORGANISM: Homo sapiens
<220> FEATURE:
<221> NAME/KEY: MISC_FEATURE
<222> LOCATION: (2)..(2)
<223> OTHER INFORMATION: The Xaa at position 2 is any amino acid other
      than tyrosine
<220> FEATURE:
<221> NAME/KEY: misc_feature
<222> LOCATION: (7)..(7)
<223> OTHER INFORMATION: Xaa can be any naturally occurring amino acid

<400> SEQUENCE: 90

Gly Xaa Gly Ser Ser Ser Xaa Arg
1               5

<210> SEQ ID NO 91
<211> LENGTH: 8
<212> TYPE: PRT
<213> ORGANISM: Homo sapiens
<220> FEATURE:
<221> NAME/KEY: MISC_FEATURE
<222> LOCATION: (7)..(7)
<223> OTHER INFORMATION: The Xaa at position 7 is arginine, lysine or
      ornithine
```

```
<400> SEQUENCE: 91

Gly Tyr Gly Ser Ser Ser Xaa Arg
1               5

<210> SEQ ID NO 92
<211> LENGTH: 35
<212> TYPE: PRT
<213> ORGANISM: Homo sapiens

<400> SEQUENCE: 92

Arg Arg Glu Ala Glu Asp Leu Gln Val Gly Gln Val Glu Leu Gly Gly
1               5                   10                  15

Gly Pro Gly Ala Gly Ser Leu Gln Pro Leu Ala Leu Glu Gly Ser Leu
            20                  25                  30

Gln Lys Arg
        35

<210> SEQ ID NO 93
<211> LENGTH: 51
<212> TYPE: PRT
<213> ORGANISM: Homo sapiens
<220> FEATURE:
<221> NAME/KEY: MISC_FEATURE
<222> LOCATION: (22)..(22)
<223> OTHER INFORMATION: The Xaa at position 22 is ornithine
<220> FEATURE:
<221> NAME/KEY: MISC_FEATURE
<222> LOCATION: (39)..(39)
<223> OTHER INFORMATION: The Xaa at position 39 is ornithine
<220> FEATURE:
<221> NAME/KEY: MISC_FEATURE
<222> LOCATION: (44)..(45)
<223> OTHER INFORMATION: The Xaa at positions 44-45 are ornithine

<400> SEQUENCE: 93

Cys Gly Pro Glu His Leu Cys Gly Ala Glu Leu Val Asp Ala Leu Tyr
1               5                   10                  15

Leu Val Cys Gly Asp Xaa Gly Phe Tyr Phe Asn Lys Pro Thr Gly Ile
            20                  25                  30

Val Asp Glu Cys Cys Phe Xaa Ser Cys Asp Leu Xaa Xaa Leu Glu Asn
        35                  40                  45

Tyr Cys Asn
    50

<210> SEQ ID NO 94
<211> LENGTH: 9
<212> TYPE: PRT
<213> ORGANISM: Artificial Sequence
<220> FEATURE:
<223> OTHER INFORMATION: linking peptide
<220> FEATURE:
<221> NAME/KEY: MISC_FEATURE
<222> LOCATION: (2)..(2)
<223> OTHER INFORMATION: The Xaa at position 2 is glycine, alanine,
      valine, leucine, isoleucine, proline, phenylalanine or methionine
<220> FEATURE:
<221> NAME/KEY: MISC_FEATURE
<222> LOCATION: (4)..(7)
<223> OTHER INFORMATION: The Xaas at positions 4-7 are independently any
      amino acid

<400> SEQUENCE: 94

Phe Xaa Ala Xaa Xaa Xaa Xaa Arg Arg
1               5
```

```
<210> SEQ ID NO 95
<211> LENGTH: 10
<212> TYPE: PRT
<213> ORGANISM: Artificial Sequence
<220> FEATURE:
<223> OTHER INFORMATION: linking peptide
<220> FEATURE:
<221> NAME/KEY: MISC_FEATURE
<222> LOCATION: (2)..(2)
<223> OTHER INFORMATION: The Xaa at position 2 is glycine, alanine,
      valine, leucine, isoleucine, proline, phenylalanine or methionine
<220> FEATURE:
<221> NAME/KEY: MISC_FEATURE
<222> LOCATION: (4)..(7)
<223> OTHER INFORMATION: The Xaas at positions 4-7 are independently any
      amino acid

<400> SEQUENCE: 95

Phe Xaa Ala Xaa Xaa Xaa Xaa Arg Arg Ala
1               5                   10

<210> SEQ ID NO 96
<211> LENGTH: 11
<212> TYPE: PRT
<213> ORGANISM: Artificial Sequence
<220> FEATURE:
<223> OTHER INFORMATION: linking peptide
<220> FEATURE:
<221> NAME/KEY: MISC_FEATURE
<222> LOCATION: (2)..(2)
<223> OTHER INFORMATION: The Xaa at position 2 is glycine, alanine,
      valine, leucine, isoleucine, proline, phenylalanine or methionine
<220> FEATURE:
<221> NAME/KEY: MISC_FEATURE
<222> LOCATION: (4)..(7)
<223> OTHER INFORMATION: The Xaas at positions 4-7 are independently any
      amino acid

<400> SEQUENCE: 96

Phe Xaa Ala Xaa Xaa Xaa Xaa Arg Arg Ala Pro
1               5                   10

<210> SEQ ID NO 97
<211> LENGTH: 12
<212> TYPE: PRT
<213> ORGANISM: Artificial Sequence
<220> FEATURE:
<223> OTHER INFORMATION: linking peptide
<220> FEATURE:
<221> NAME/KEY: MISC_FEATURE
<222> LOCATION: (2)..(2)
<223> OTHER INFORMATION: The Xaa at position 2 is glycine, alanine,
      valine, leucine, isoleucine, proline, phenylalanine or methionine
<220> FEATURE:
<221> NAME/KEY: MISC_FEATURE
<222> LOCATION: (4)..(7)
<223> OTHER INFORMATION: The Xaas at positions 4-7 are independently any
      amino acid

<400> SEQUENCE: 97

Phe Xaa Ala Xaa Xaa Xaa Xaa Arg Arg Ala Pro Gln
1               5                   10

<210> SEQ ID NO 98
<211> LENGTH: 13
<212> TYPE: PRT
<213> ORGANISM: Artificial Sequence
<220> FEATURE:
<223> OTHER INFORMATION: linking peptide
<220> FEATURE:
<221> NAME/KEY: MISC_FEATURE
<222> LOCATION: (2)..(2)
<223> OTHER INFORMATION: The Xaa at position 2 is glycine, alanine,
```

```
      valine, leucine, isoleucine, proline, phenylalanine or methionine
<220> FEATURE:
<221> NAME/KEY: MISC_FEATURE
<222> LOCATION: (4)..(7)
<223> OTHER INFORMATION: The Xaas at positions 4-7 are independently any
      amino acid

<400> SEQUENCE: 98

Phe Xaa Ala Xaa Xaa Xaa Xaa Arg Arg Ala Pro Gln Thr
1               5                   10

<210> SEQ ID NO 99
<211> LENGTH: 10
<212> TYPE: PRT
<213> ORGANISM: Artificial Sequence
<220> FEATURE:
<223> OTHER INFORMATION: linking peptide
<220> FEATURE:
<221> NAME/KEY: MISC_FEATURE
<222> LOCATION: (3)..(3)
<223> OTHER INFORMATION: The Xaa at position 3 is glycine, alanine,
      valine, leucine, isoleucine, proline, phenylalanine or methionine
<220> FEATURE:
<221> NAME/KEY: MISC_FEATURE
<222> LOCATION: (5)..(8)
<223> OTHER INFORMATION: The Xaas at positions 5-8 are independently any
      amino acid

<400> SEQUENCE: 99

Phe Asn Xaa Ala Xaa Xaa Xaa Xaa Arg Arg
1               5                   10

<210> SEQ ID NO 100
<211> LENGTH: 11
<212> TYPE: PRT
<213> ORGANISM: Artificial Sequence
<220> FEATURE:
<223> OTHER INFORMATION: linking peptide
<220> FEATURE:
<221> NAME/KEY: MISC_FEATURE
<222> LOCATION: (3)..(3)
<223> OTHER INFORMATION: The Xaa at position 3 is glycine, alanine,
      valine, leucine, isoleucine, proline, phenylalanine or methionine
<220> FEATURE:
<221> NAME/KEY: MISC_FEATURE
<222> LOCATION: (5)..(8)
<223> OTHER INFORMATION: The Xaas at positions 5-8 are independently any
      amino acid

<400> SEQUENCE: 100

Phe Asn Xaa Ala Xaa Xaa Xaa Xaa Arg Arg Ala
1               5                   10

<210> SEQ ID NO 101
<211> LENGTH: 12
<212> TYPE: PRT
<213> ORGANISM: Artificial Sequence
<220> FEATURE:
<223> OTHER INFORMATION: linking peptide
<220> FEATURE:
<221> NAME/KEY: MISC_FEATURE
<222> LOCATION: (3)..(3)
<223> OTHER INFORMATION: The Xaa at position 3 is glycine, alanine,
      valine, leucine, isoleucine, proline, phenylalanine or methionine
<220> FEATURE:
<221> NAME/KEY: MISC_FEATURE
<222> LOCATION: (5)..(8)
<223> OTHER INFORMATION: The Xaas at positions 5-8 are independently any
      amino acid

<400> SEQUENCE: 101

Phe Asn Xaa Ala Xaa Xaa Xaa Xaa Arg Arg Ala Pro
```

```
1               5                   10
```

<210> SEQ ID NO 102
<211> LENGTH: 13
<212> TYPE: PRT
<213> ORGANISM: Artificial Sequence
<220> FEATURE:
<223> OTHER INFORMATION: linking peptide
<220> FEATURE:
<221> NAME/KEY: MISC_FEATURE
<222> LOCATION: (3)..(3)
<223> OTHER INFORMATION: The Xaa at position 3 is glycine, alanine,
      valine, leucine, isoleucine, proline, phenylalanine or methionine
<220> FEATURE:
<221> NAME/KEY: MISC_FEATURE
<222> LOCATION: (5)..(8)
<223> OTHER INFORMATION: The Xaas at positions 5-8 are independently any
      amino acid

<400> SEQUENCE: 102

Phe Asn Xaa Ala Xaa Xaa Xaa Xaa Arg Arg Ala Pro Gln
1               5                   10

<210> SEQ ID NO 103
<211> LENGTH: 14
<212> TYPE: PRT
<213> ORGANISM: Artificial Sequence
<220> FEATURE:
<223> OTHER INFORMATION: linking peptide
<220> FEATURE:
<221> NAME/KEY: MISC_FEATURE
<222> LOCATION: (3)..(3)
<223> OTHER INFORMATION: The Xaa at position 3 is glycine, alanine,
      valine, leucine, isoleucine, proline, phenylalanine or methionine
<220> FEATURE:
<221> NAME/KEY: MISC_FEATURE
<222> LOCATION: (5)..(8)
<223> OTHER INFORMATION: The Xaas at positions 5-8 are independently any
      amino acid

<400> SEQUENCE: 103

Phe Asn Xaa Ala Xaa Xaa Xaa Xaa Arg Arg Ala Pro Gln Thr
1               5                   10

<210> SEQ ID NO 104
<211> LENGTH: 11
<212> TYPE: PRT
<213> ORGANISM: Artificial Sequence
<220> FEATURE:
<223> OTHER INFORMATION: peptide linker
<220> FEATURE:
<221> NAME/KEY: MISC_FEATURE
<222> LOCATION: (4)..(4)
<223> OTHER INFORMATION: The Xaa at position 4 is glycine, alanine,
      valine, leucine, isoleucine, proline, phenylalanine or methionine
<220> FEATURE:
<221> NAME/KEY: MISC_FEATURE
<222> LOCATION: (6)..(9)
<223> OTHER INFORMATION: The Xaas at positions 6-9 are independently any
      amino acid

<400> SEQUENCE: 104

Phe Asn Lys Xaa Ala Xaa Xaa Xaa Xaa Arg Arg
1               5                   10

<210> SEQ ID NO 105
<211> LENGTH: 12
<212> TYPE: PRT
<213> ORGANISM: Artificial Sequence
<220> FEATURE:
<223> OTHER INFORMATION: peptide linker
<220> FEATURE:

```
<221> NAME/KEY: MISC_FEATURE
<222> LOCATION: (4)..(4)
<223> OTHER INFORMATION: The Xaa at position 4 is glycine, alanine,
      valine, leucine, isoleucine, proline, phenylalanine or methionine
<220> FEATURE:
<221> NAME/KEY: MISC_FEATURE
<222> LOCATION: (6)..(9)
<223> OTHER INFORMATION: The Xaas at positions 6-9 are independently any
      amino acid

<400> SEQUENCE: 105

Phe Asn Lys Xaa Ala Xaa Xaa Xaa Xaa Arg Arg Ala
1               5                   10

<210> SEQ ID NO 106
<211> LENGTH: 13
<212> TYPE: PRT
<213> ORGANISM: Artificial Sequence
<220> FEATURE:
<223> OTHER INFORMATION: peptide linker
<220> FEATURE:
<221> NAME/KEY: MISC_FEATURE
<222> LOCATION: (4)..(4)
<223> OTHER INFORMATION: The Xaa at position 4 is glycine, alanine,
      valine, leucine, isoleucine, proline, phenylalanine or methionine
<220> FEATURE:
<221> NAME/KEY: MISC_FEATURE
<222> LOCATION: (6)..(9)
<223> OTHER INFORMATION: The Xaas at positions 6-9 are independently any
      amino acid

<400> SEQUENCE: 106

Phe Asn Lys Xaa Ala Xaa Xaa Xaa Xaa Arg Arg Ala Pro
1               5                   10

<210> SEQ ID NO 107
<211> LENGTH: 14
<212> TYPE: PRT
<213> ORGANISM: Artificial Sequence
<220> FEATURE:
<223> OTHER INFORMATION: peptide linker
<220> FEATURE:
<221> NAME/KEY: MISC_FEATURE
<222> LOCATION: (4)..(4)
<223> OTHER INFORMATION: The Xaa at position 4 is glycine, alanine,
      valine, leucine, isoleucine, proline, phenylalanine or methionine
<220> FEATURE:
<221> NAME/KEY: MISC_FEATURE
<222> LOCATION: (6)..(9)
<223> OTHER INFORMATION: The Xaas at positions 6-9 are independently any
      amino acid

<400> SEQUENCE: 107

Phe Asn Lys Xaa Ala Xaa Xaa Xaa Xaa Arg Arg Ala Pro Gln
1               5                   10

<210> SEQ ID NO 108
<211> LENGTH: 15
<212> TYPE: PRT
<213> ORGANISM: Artificial Sequence
<220> FEATURE:
<223> OTHER INFORMATION: peptide linker
<220> FEATURE:
<221> NAME/KEY: MISC_FEATURE
<222> LOCATION: (4)..(4)
<223> OTHER INFORMATION: The Xaa at position 4 is glycine, alanine,
      valine, leucine, isoleucine, proline, phenylalanine or methionine
<220> FEATURE:
<221> NAME/KEY: MISC_FEATURE
<222> LOCATION: (6)..(9)
<223> OTHER INFORMATION: The Xaas at positions 6-9 are independently any
      amino acid
```

```
<400> SEQUENCE: 108

Phe Asn Lys Xaa Ala Xaa Xaa Xaa Xaa Arg Arg Ala Pro Gln Thr
1               5                   10                  15

<210> SEQ ID NO 109
<211> LENGTH: 12
<212> TYPE: PRT
<213> ORGANISM: Artificial Sequence
<220> FEATURE:
<223> OTHER INFORMATION: peptide linker
<220> FEATURE:
<221> NAME/KEY: MISC_FEATURE
<222> LOCATION: (5)..(5)
<223> OTHER INFORMATION: The Xaa at position 5 is glycine, alanine,
      valine, leucine, isoleucine, proline, phenylalanine or methionine
<220> FEATURE:
<221> NAME/KEY: MISC_FEATURE
<222> LOCATION: (7)..(10)
<223> OTHER INFORMATION: The Xaas at positions 7-10 are independently
      any amino acid

<400> SEQUENCE: 109

Phe Asn Lys Pro Xaa Ala Xaa Xaa Xaa Xaa Arg Arg
1               5                   10

<210> SEQ ID NO 110
<211> LENGTH: 13
<212> TYPE: PRT
<213> ORGANISM: Artificial Sequence
<220> FEATURE:
<223> OTHER INFORMATION: peptide linker
<220> FEATURE:
<221> NAME/KEY: MISC_FEATURE
<222> LOCATION: (5)..(5)
<223> OTHER INFORMATION: The Xaa at position 5 is glycine, alanine,
      valine, leucine, isoleucine, proline, phenylalanine or methionine
<220> FEATURE:
<221> NAME/KEY: MISC_FEATURE
<222> LOCATION: (7)..(10)
<223> OTHER INFORMATION: The Xaas at positions 7-10 are independently
      any amino acid

<400> SEQUENCE: 110

Phe Asn Lys Pro Xaa Ala Xaa Xaa Xaa Xaa Arg Arg Ala
1               5                   10

<210> SEQ ID NO 111
<211> LENGTH: 14
<212> TYPE: PRT
<213> ORGANISM: Artificial Sequence
<220> FEATURE:
<223> OTHER INFORMATION: peptide linker
<220> FEATURE:
<221> NAME/KEY: MISC_FEATURE
<222> LOCATION: (5)..(5)
<223> OTHER INFORMATION: The Xaa at position 5 is glycine, alanine,
      valine, leucine, isoleucine, proline, phenylalanine or methionine
<220> FEATURE:
<221> NAME/KEY: MISC_FEATURE
<222> LOCATION: (7)..(10)
<223> OTHER INFORMATION: The Xaas at positions 7-10 are independently
      any amino acid

<400> SEQUENCE: 111

Phe Asn Lys Pro Xaa Ala Xaa Xaa Xaa Xaa Arg Arg Ala Pro
1               5                   10

<210> SEQ ID NO 112
<211> LENGTH: 15
<212> TYPE: PRT
<213> ORGANISM: Artificial Sequence
```

```
<220> FEATURE:
<223> OTHER INFORMATION: peptide linker
<220> FEATURE:
<221> NAME/KEY: MISC_FEATURE
<222> LOCATION: (5)..(5)
<223> OTHER INFORMATION: The Xaa at position 5 is glycine, alanine,
      valine, leucine, isoleucine, proline, phenylalanine or methionine
<220> FEATURE:
<221> NAME/KEY: MISC_FEATURE
<222> LOCATION: (7)..(10)
<223> OTHER INFORMATION: The Xaas at positions 7-10 are independently
      any amino acid

<400> SEQUENCE: 112

Phe Asn Lys Pro Xaa Ala Xaa Xaa Xaa Xaa Arg Arg Ala Pro Gln
1               5                   10                  15

<210> SEQ ID NO 113
<211> LENGTH: 16
<212> TYPE: PRT
<213> ORGANISM: Artificial Sequence
<220> FEATURE:
<223> OTHER INFORMATION: peptide linker
<220> FEATURE:
<221> NAME/KEY: MISC_FEATURE
<222> LOCATION: (5)..(5)
<223> OTHER INFORMATION: The Xaa at position 5 is glycine, alanine,
      valine, leucine, isoleucine, proline, phenylalanine or methionine
<220> FEATURE:
<221> NAME/KEY: MISC_FEATURE
<222> LOCATION: (7)..(10)
<223> OTHER INFORMATION: The Xaas at positions 7-10 are independently
      any amino acid

<400> SEQUENCE: 113

Phe Asn Lys Pro Xaa Ala Xaa Xaa Xaa Xaa Arg Arg Ala Pro Gln Thr
1               5                   10                  15

<210> SEQ ID NO 114
<211> LENGTH: 13
<212> TYPE: PRT
<213> ORGANISM: Artificial Sequence
<220> FEATURE:
<223> OTHER INFORMATION: peptide linker
<220> FEATURE:
<221> NAME/KEY: MISC_FEATURE
<222> LOCATION: (6)..(6)
<223> OTHER INFORMATION: The Xaa at position 6 is glycine, alanine,
      valine, leucine, isoleucine, proline, phenylalanine or methionine
<220> FEATURE:
<221> NAME/KEY: MISC_FEATURE
<222> LOCATION: (8)..(11)
<223> OTHER INFORMATION: The Xaas at positions 8-11 are independently
      any amino acid

<400> SEQUENCE: 114

Phe Asn Lys Pro Thr Xaa Ala Xaa Xaa Xaa Xaa Arg Arg
1               5                   10

<210> SEQ ID NO 115
<211> LENGTH: 14
<212> TYPE: PRT
<213> ORGANISM: Artificial Sequence
<220> FEATURE:
<223> OTHER INFORMATION: peptide linker
<220> FEATURE:
<221> NAME/KEY: MISC_FEATURE
<222> LOCATION: (6)..(6)
<223> OTHER INFORMATION: The Xaa at position 6 is glycine, alanine,
      valine, leucine, isoleucine, proline, phenylalanine or methionine
<220> FEATURE:
<221> NAME/KEY: MISC_FEATURE
<222> LOCATION: (8)..(11)
```

```
<223> OTHER INFORMATION: The Xaas at positions 8-11 are independently
      any amino acid

<400> SEQUENCE: 115

Phe Asn Lys Pro Thr Xaa Ala Xaa Xaa Xaa Xaa Arg Arg Ala
1               5                   10

<210> SEQ ID NO 116
<211> LENGTH: 15
<212> TYPE: PRT
<213> ORGANISM: Artificial Sequence
<220> FEATURE:
<223> OTHER INFORMATION: peptide linker
<220> FEATURE:
<221> NAME/KEY: MISC_FEATURE
<222> LOCATION: (6)..(6)
<223> OTHER INFORMATION: The Xaa at position 6 is glycine, alanine,
      valine, leucine, isoleucine, proline, phenylalanine or methionine
<220> FEATURE:
<221> NAME/KEY: MISC_FEATURE
<222> LOCATION: (8)..(11)
<223> OTHER INFORMATION: The Xaas at positions 8-11 are independently
      any amino acid

<400> SEQUENCE: 116

Phe Asn Lys Pro Thr Xaa Ala Xaa Xaa Xaa Xaa Arg Arg Ala Pro
1               5                   10                  15

<210> SEQ ID NO 117
<211> LENGTH: 16
<212> TYPE: PRT
<213> ORGANISM: Artificial Sequence
<220> FEATURE:
<223> OTHER INFORMATION: peptide linker
<220> FEATURE:
<221> NAME/KEY: MISC_FEATURE
<222> LOCATION: (6)..(6)
<223> OTHER INFORMATION: The Xaa at position 6 is glycine, alanine,
      valine, leucine, isoleucine, proline, phenylalanine or methionine
<220> FEATURE:
<221> NAME/KEY: MISC_FEATURE
<222> LOCATION: (8)..(11)
<223> OTHER INFORMATION: The Xaas at positions 8-11 are independently
      any amino acid

<400> SEQUENCE: 117

Phe Asn Lys Pro Thr Xaa Ala Xaa Xaa Xaa Xaa Arg Arg Ala Pro Gln
1               5                   10                  15

<210> SEQ ID NO 118
<211> LENGTH: 17
<212> TYPE: PRT
<213> ORGANISM: Artificial Sequence
<220> FEATURE:
<223> OTHER INFORMATION: peptide linker
<220> FEATURE:
<221> NAME/KEY: MISC_FEATURE
<222> LOCATION: (6)..(6)
<223> OTHER INFORMATION: The Xaa at position 6 is glycine, alanine,
      valine, leucine, isoleucine, proline, phenylalanine or methionine
<220> FEATURE:
<221> NAME/KEY: MISC_FEATURE
<222> LOCATION: (8)..(11)
<223> OTHER INFORMATION: The Xaas at positions 8-11 are independently
      any amino acid

<400> SEQUENCE: 118

Phe Asn Lys Pro Thr Xaa Ala Xaa Xaa Xaa Xaa Arg Arg Ala Pro Gln
1               5                   10                  15

Thr
```

```
<210> SEQ ID NO 119
<211> LENGTH: 9
<212> TYPE: PRT
<213> ORGANISM: Artificial Sequence
<220> FEATURE:
<223> OTHER INFORMATION: peptide linker
<220> FEATURE:
<221> NAME/KEY: MISC_FEATURE
<222> LOCATION: (2)..(2)
<223> OTHER INFORMATION: The Xaa at position 2 is glycine, alanine,
      valine, leucine, isoleucine, proline, phenylalanine or methionine
<220> FEATURE:
<221> NAME/KEY: MISC_FEATURE
<222> LOCATION: (3)..(3)
<223> OTHER INFORMATION: The Xaa at position 3 is any amino acid other
      than tyrosine

<400> SEQUENCE: 119

Phe Xaa Xaa Gly Ser Ser Ser Arg Arg
1               5

<210> SEQ ID NO 120
<211> LENGTH: 10
<212> TYPE: PRT
<213> ORGANISM: Artificial Sequence
<220> FEATURE:
<223> OTHER INFORMATION: peptide linker
<220> FEATURE:
<221> NAME/KEY: MISC_FEATURE
<222> LOCATION: (2)..(2)
<223> OTHER INFORMATION: The Xaa at position 2 is glycine, alanine,
      valine, leucine, isoleucine, proline, phenylalanine or methionine
<220> FEATURE:
<221> NAME/KEY: MISC_FEATURE
<222> LOCATION: (3)..(3)
<223> OTHER INFORMATION: The Xaa at position 3 is any amino acid other
      than tyrosine

<400> SEQUENCE: 120

Phe Xaa Xaa Gly Ser Ser Ser Arg Arg Ala
1               5                   10

<210> SEQ ID NO 121
<211> LENGTH: 11
<212> TYPE: PRT
<213> ORGANISM: Artificial Sequence
<220> FEATURE:
<223> OTHER INFORMATION: peptide linker
<220> FEATURE:
<221> NAME/KEY: MISC_FEATURE
<222> LOCATION: (2)..(2)
<223> OTHER INFORMATION: The Xaa at position 2 is glycine, alanine,
      valine, leucine, isoleucine, proline, phenylalanine or methionine
<220> FEATURE:
<221> NAME/KEY: MISC_FEATURE
<222> LOCATION: (3)..(3)
<223> OTHER INFORMATION: The Xaa at position 3 is any amino acid other
      than tyrosine

<400> SEQUENCE: 121

Phe Xaa Xaa Gly Ser Ser Ser Arg Arg Ala Pro
1               5                   10

<210> SEQ ID NO 122
<211> LENGTH: 12
<212> TYPE: PRT
<213> ORGANISM: Artificial Sequence
<220> FEATURE:
<223> OTHER INFORMATION: peptide linker
<220> FEATURE:
<221> NAME/KEY: MISC_FEATURE
<222> LOCATION: (2)..(2)
```

```
<223> OTHER INFORMATION: The Xaa at position 2 is glycine, alanine,
      valine, leucine, isoleucine, proline, phenylalanine or methionine
<220> FEATURE:
<221> NAME/KEY: MISC_FEATURE
<222> LOCATION: (3)..(3)
<223> OTHER INFORMATION: The Xaa at position 3 is any amino acid other
      than tyrosine

<400> SEQUENCE: 122

Phe Xaa Xaa Gly Ser Ser Ser Arg Arg Ala Pro Gln
1               5                   10

<210> SEQ ID NO 123
<211> LENGTH: 13
<212> TYPE: PRT
<213> ORGANISM: Artificial Sequence
<220> FEATURE:
<223> OTHER INFORMATION: peptide linker
<220> FEATURE:
<221> NAME/KEY: MISC_FEATURE
<222> LOCATION: (2)..(2)
<223> OTHER INFORMATION: The Xaa at position 2 is glycine, alanine,
      valine, leucine, isoleucine, proline, phenylalanine or methionine
<220> FEATURE:
<221> NAME/KEY: MISC_FEATURE
<222> LOCATION: (3)..(3)
<223> OTHER INFORMATION: The Xaa at position 3 is any amino acid other
      than tyrosine

<400> SEQUENCE: 123

Phe Xaa Xaa Gly Ser Ser Ser Arg Arg Ala Pro Gln Thr
1               5                   10

<210> SEQ ID NO 124
<211> LENGTH: 10
<212> TYPE: PRT
<213> ORGANISM: Artificial Sequence
<220> FEATURE:
<223> OTHER INFORMATION: peptide linker
<220> FEATURE:
<221> NAME/KEY: MISC_FEATURE
<222> LOCATION: (3)..(3)
<223> OTHER INFORMATION: The Xaa at position 3 is glycine, alanine,
      valine, leucine, isoleucine, proline, phenylalanine or methionine
<220> FEATURE:
<221> NAME/KEY: MISC_FEATURE
<222> LOCATION: (4)..(4)
<223> OTHER INFORMATION: The Xaa at position 4 is any amino acid other
      than tyrosine

<400> SEQUENCE: 124

Phe Asn Xaa Xaa Gly Ser Ser Ser Arg Arg
1               5                   10

<210> SEQ ID NO 125
<211> LENGTH: 11
<212> TYPE: PRT
<213> ORGANISM: Artificial Sequence
<220> FEATURE:
<223> OTHER INFORMATION: peptide linker
<220> FEATURE:
<221> NAME/KEY: MISC_FEATURE
<222> LOCATION: (3)..(3)
<223> OTHER INFORMATION: The Xaa at position 3 is glycine, alanine,
      valine, leucine, isoleucine, proline, phenylalanine or methionine
<220> FEATURE:
<221> NAME/KEY: MISC_FEATURE
<222> LOCATION: (4)..(4)
<223> OTHER INFORMATION: The Xaa at position 4 is any amino acid other
      than tyrosine

<400> SEQUENCE: 125
```

```
Phe Asn Xaa Xaa Gly Ser Ser Ser Arg Arg Ala
1               5                   10

<210> SEQ ID NO 126
<211> LENGTH: 12
<212> TYPE: PRT
<213> ORGANISM: Artificial Sequence
<220> FEATURE:
<223> OTHER INFORMATION: peptide linker
<220> FEATURE:
<221> NAME/KEY: MISC_FEATURE
<222> LOCATION: (3)..(3)
<223> OTHER INFORMATION: The Xaa at position 3 is glycine, alanine,
      valine, leucine, isoleucine, proline, phenylalanine or methionine
<220> FEATURE:
<221> NAME/KEY: MISC_FEATURE
<222> LOCATION: (4)..(4)
<223> OTHER INFORMATION: The Xaa at position 4 is any amino acid other
      than tyrosine

<400> SEQUENCE: 126

Phe Asn Xaa Xaa Gly Ser Ser Ser Arg Arg Ala Pro
1               5                   10

<210> SEQ ID NO 127
<211> LENGTH: 13
<212> TYPE: PRT
<213> ORGANISM: Artificial Sequence
<220> FEATURE:
<223> OTHER INFORMATION: peptide linker
<220> FEATURE:
<221> NAME/KEY: MISC_FEATURE
<222> LOCATION: (3)..(3)
<223> OTHER INFORMATION: The Xaa at position 3 is glycine, alanine,
      valine, leucine, isoleucine, proline, phenylalanine or methionine
<220> FEATURE:
<221> NAME/KEY: MISC_FEATURE
<222> LOCATION: (4)..(4)
<223> OTHER INFORMATION: The Xaa at position 4 is any amino acid other
      than tyrosine

<400> SEQUENCE: 127

Phe Asn Xaa Xaa Gly Ser Ser Ser Arg Arg Ala Pro Gln
1               5                   10

<210> SEQ ID NO 128
<211> LENGTH: 14
<212> TYPE: PRT
<213> ORGANISM: Artificial Sequence
<220> FEATURE:
<223> OTHER INFORMATION: peptide linker
<220> FEATURE:
<221> NAME/KEY: MISC_FEATURE
<222> LOCATION: (3)..(3)
<223> OTHER INFORMATION: The Xaa at position 3 is glycine, alanine,
      valine, leucine, isoleucine, proline, phenylalanine or methionine
<220> FEATURE:
<221> NAME/KEY: MISC_FEATURE
<222> LOCATION: (4)..(4)
<223> OTHER INFORMATION: The Xaa at position 4 is any amino acid other
      than tyrosine

<400> SEQUENCE: 128

Phe Asn Xaa Xaa Gly Ser Ser Ser Arg Arg Ala Pro Gln Thr
1               5                   10

<210> SEQ ID NO 129
<211> LENGTH: 11
<212> TYPE: PRT
<213> ORGANISM: Artificial Sequence
<220> FEATURE:
<223> OTHER INFORMATION: peptide linker
```

```
<220> FEATURE:
<221> NAME/KEY: MISC_FEATURE
<222> LOCATION: (4)..(4)
<223> OTHER INFORMATION: The Xaa at position 4 is glycine, alanine,
      valine, leucine, isoleucine, proline, phenylalanine or methionine
<220> FEATURE:
<221> NAME/KEY: MISC_FEATURE
<222> LOCATION: (5)..(5)
<223> OTHER INFORMATION: The Xaa at position 5 is any amino acid other
      than tyrosine

<400> SEQUENCE: 129

Phe Asn Lys Xaa Xaa Gly Ser Ser Ser Arg Arg
1               5                   10

<210> SEQ ID NO 130
<211> LENGTH: 12
<212> TYPE: PRT
<213> ORGANISM: Artificial Sequence
<220> FEATURE:
<223> OTHER INFORMATION: peptide linker
<220> FEATURE:
<221> NAME/KEY: MISC_FEATURE
<222> LOCATION: (4)..(4)
<223> OTHER INFORMATION: The Xaa at position 4 is glycine, alanine,
      valine, leucine, isoleucine, proline, phenylalanine or methionine
<220> FEATURE:
<221> NAME/KEY: MISC_FEATURE
<222> LOCATION: (5)..(5)
<223> OTHER INFORMATION: The Xaa at position 5 is any amino acid other
      than tyrosine

<400> SEQUENCE: 130

Phe Asn Lys Xaa Xaa Gly Ser Ser Ser Arg Arg Ala
1               5                   10

<210> SEQ ID NO 131
<211> LENGTH: 13
<212> TYPE: PRT
<213> ORGANISM: Artificial Sequence
<220> FEATURE:
<223> OTHER INFORMATION: peptide linker
<220> FEATURE:
<221> NAME/KEY: MISC_FEATURE
<222> LOCATION: (4)..(4)
<223> OTHER INFORMATION: The Xaa at position 4 is glycine, alanine,
      valine, leucine, isoleucine, proline, phenylalanine or methionine
<220> FEATURE:
<221> NAME/KEY: MISC_FEATURE
<222> LOCATION: (5)..(5)
<223> OTHER INFORMATION: The Xaa at position 5 is any amino acid other
      than tyrosine

<400> SEQUENCE: 131

Phe Asn Lys Xaa Xaa Gly Ser Ser Ser Arg Arg Ala Pro
1               5                   10

<210> SEQ ID NO 132
<211> LENGTH: 14
<212> TYPE: PRT
<213> ORGANISM: Artificial Sequence
<220> FEATURE:
<223> OTHER INFORMATION: peptide linker
<220> FEATURE:
<221> NAME/KEY: MISC_FEATURE
<222> LOCATION: (4)..(4)
<223> OTHER INFORMATION: The Xaa at position 4 is glycine, alanine,
      valine, leucine, isoleucine, proline, phenylalanine or methionine
<220> FEATURE:
<221> NAME/KEY: MISC_FEATURE
<222> LOCATION: (5)..(5)
<223> OTHER INFORMATION: The Xaa at position 5 is any amino acid other
      than tyrosine
```

<400> SEQUENCE: 132

Phe Asn Lys Xaa Xaa Gly Ser Ser Ser Arg Arg Ala Pro Gln
1               5                   10

<210> SEQ ID NO 133
<211> LENGTH: 15
<212> TYPE: PRT
<213> ORGANISM: Artificial Sequence
<220> FEATURE:
<223> OTHER INFORMATION: peptide linker
<220> FEATURE:
<221> NAME/KEY: MISC_FEATURE
<222> LOCATION: (4)..(4)
<223> OTHER INFORMATION: The Xaa at position 4 is glycine, alanine,
      valine, leucine, isoleucine, proline, phenylalanine or methionine
<220> FEATURE:
<221> NAME/KEY: MISC_FEATURE
<222> LOCATION: (5)..(5)
<223> OTHER INFORMATION: The Xaa at position 5 is any amino acid other
      than tyrosine

<400> SEQUENCE: 133

Phe Asn Lys Xaa Xaa Gly Ser Ser Ser Arg Arg Ala Pro Gln Thr
1               5                   10                  15

<210> SEQ ID NO 134
<211> LENGTH: 12
<212> TYPE: PRT
<213> ORGANISM: Artificial Sequence
<220> FEATURE:
<223> OTHER INFORMATION: peptide linker
<220> FEATURE:
<221> NAME/KEY: MISC_FEATURE
<222> LOCATION: (5)..(5)
<223> OTHER INFORMATION: The Xaa at position 5 is glycine, alanine,
      valine, leucine, isoleucine, proline, phenylalanine or methionine
<220> FEATURE:
<221> NAME/KEY: MISC_FEATURE
<222> LOCATION: (6)..(6)
<223> OTHER INFORMATION: The Xaa at position 6 is any amino acid other
      than tyrosine

<400> SEQUENCE: 134

Phe Asn Lys Pro Xaa Xaa Gly Ser Ser Ser Arg Arg
1               5                   10

<210> SEQ ID NO 135
<211> LENGTH: 13
<212> TYPE: PRT
<213> ORGANISM: Artificial Sequence
<220> FEATURE:
<223> OTHER INFORMATION: peptide linker
<220> FEATURE:
<221> NAME/KEY: MISC_FEATURE
<222> LOCATION: (5)..(5)
<223> OTHER INFORMATION: The Xaa at position 5 is glycine, alanine,
      valine, leucine, isoleucine, proline, phenylalanine or methionine
<220> FEATURE:
<221> NAME/KEY: MISC_FEATURE
<222> LOCATION: (6)..(6)
<223> OTHER INFORMATION: The Xaa at position 6 is any amino acid other
      than tyrosine

<400> SEQUENCE: 135

Phe Asn Lys Pro Xaa Xaa Gly Ser Ser Ser Arg Arg Ala
1               5                   10

<210> SEQ ID NO 136
<211> LENGTH: 14
<212> TYPE: PRT

```
<213> ORGANISM: Artificial Sequence
<220> FEATURE:
<223> OTHER INFORMATION: peptide linker
<220> FEATURE:
<221> NAME/KEY: MISC_FEATURE
<222> LOCATION: (5)..(5)
<223> OTHER INFORMATION: The Xaa at position 5 is glycine, alanine,
      valine, leucine, isoleucine, proline, phenylalanine or methionine
<220> FEATURE:
<221> NAME/KEY: MISC_FEATURE
<222> LOCATION: (6)..(6)
<223> OTHER INFORMATION: The Xaa at position 6 is any amino acid other
      than tyrosine

<400> SEQUENCE: 136

Phe Asn Lys Pro Xaa Xaa Gly Ser Ser Ser Arg Arg Ala Pro
1               5                   10

<210> SEQ ID NO 137
<211> LENGTH: 15
<212> TYPE: PRT
<213> ORGANISM: Artificial Sequence
<220> FEATURE:
<223> OTHER INFORMATION: peptide linker
<220> FEATURE:
<221> NAME/KEY: MISC_FEATURE
<222> LOCATION: (5)..(5)
<223> OTHER INFORMATION: The Xaa at position 5 is glycine, alanine,
      valine, leucine, isoleucine, proline, phenylalanine or methionine
<220> FEATURE:
<221> NAME/KEY: MISC_FEATURE
<222> LOCATION: (6)..(6)
<223> OTHER INFORMATION: The Xaa at position 6 is any amino acid other
      than tyrosine

<400> SEQUENCE: 137

Phe Asn Lys Pro Xaa Xaa Gly Ser Ser Ser Arg Arg Ala Pro Gln
1               5                   10                  15

<210> SEQ ID NO 138
<211> LENGTH: 16
<212> TYPE: PRT
<213> ORGANISM: Artificial Sequence
<220> FEATURE:
<223> OTHER INFORMATION: peptide linker
<220> FEATURE:
<221> NAME/KEY: MISC_FEATURE
<222> LOCATION: (5)..(5)
<223> OTHER INFORMATION: The Xaa at position 5 is glycine, alanine,
      valine, leucine, isoleucine, proline, phenylalanine or methionine
<220> FEATURE:
<221> NAME/KEY: MISC_FEATURE
<222> LOCATION: (6)..(6)
<223> OTHER INFORMATION: The Xaa at position 6 is any amino acid other
      than tyrosine

<400> SEQUENCE: 138

Phe Asn Lys Pro Xaa Xaa Gly Ser Ser Ser Arg Arg Ala Pro Gln Thr
1               5                   10                  15

<210> SEQ ID NO 139
<211> LENGTH: 12
<212> TYPE: PRT
<213> ORGANISM: Artificial Sequence
<220> FEATURE:
<223> OTHER INFORMATION: peptide linker
<220> FEATURE:
<221> NAME/KEY: MISC_FEATURE
<222> LOCATION: (5)..(5)
<223> OTHER INFORMATION: The Xaa at position 5 is glycine, alanine,
      valine, leucine, isoleucine, proline, phenylalanine or methionine
<220> FEATURE:
<221> NAME/KEY: MISC_FEATURE
```

```
<222> LOCATION: (6)..(6)
<223> OTHER INFORMATION: The Xaa at position 6 is any amino acid other
      than tyrosine

<400> SEQUENCE: 139

Phe Asn Lys Pro Xaa Xaa Gly Ser Ser Ser Arg Arg
1               5                   10

<210> SEQ ID NO 140
<211> LENGTH: 13
<212> TYPE: PRT
<213> ORGANISM: Artificial Sequence
<220> FEATURE:
<223> OTHER INFORMATION: peptide linker
<220> FEATURE:
<221> NAME/KEY: MISC_FEATURE
<222> LOCATION: (5)..(5)
<223> OTHER INFORMATION: The Xaa at position 5 is glycine, alanine,
      valine, leucine, isoleucine, proline, phenylalanine or methionine
<220> FEATURE:
<221> NAME/KEY: MISC_FEATURE
<222> LOCATION: (6)..(6)
<223> OTHER INFORMATION: The Xaa at position 6 is any amino acid other
      than tyrosine

<400> SEQUENCE: 140

Phe Asn Lys Pro Xaa Xaa Gly Ser Ser Ser Arg Arg Ala
1               5                   10

<210> SEQ ID NO 141
<211> LENGTH: 14
<212> TYPE: PRT
<213> ORGANISM: Artificial Sequence
<220> FEATURE:
<223> OTHER INFORMATION: peptide linker
<220> FEATURE:
<221> NAME/KEY: MISC_FEATURE
<222> LOCATION: (5)..(5)
<223> OTHER INFORMATION: The Xaa at position 5 is glycine, alanine,
      valine, leucine, isoleucine, proline, phenylalanine or methionine
<220> FEATURE:
<221> NAME/KEY: MISC_FEATURE
<222> LOCATION: (6)..(6)
<223> OTHER INFORMATION: The Xaa at position 6 is any amino acid other
      than tyrosine

<400> SEQUENCE: 141

Phe Asn Lys Pro Xaa Xaa Gly Ser Ser Ser Arg Arg Ala Pro
1               5                   10

<210> SEQ ID NO 142
<211> LENGTH: 15
<212> TYPE: PRT
<213> ORGANISM: Artificial Sequence
<220> FEATURE:
<223> OTHER INFORMATION: peptide linker
<220> FEATURE:
<221> NAME/KEY: MISC_FEATURE
<222> LOCATION: (5)..(5)
<223> OTHER INFORMATION: The Xaa at position 5 is glycine, alanine,
      valine, leucine, isoleucine, proline, phenylalanine or methionine
<220> FEATURE:
<221> NAME/KEY: MISC_FEATURE
<222> LOCATION: (6)..(6)
<223> OTHER INFORMATION: The Xaa at position 6 is any amino acid other
      than tyrosine

<400> SEQUENCE: 142

Phe Asn Lys Pro Xaa Xaa Gly Ser Ser Ser Arg Arg Ala Pro Gln
1               5                   10                  15
```

```
<210> SEQ ID NO 143
<211> LENGTH: 16
<212> TYPE: PRT
<213> ORGANISM: Artificial Sequence
<220> FEATURE:
<223> OTHER INFORMATION: peptide linker
<220> FEATURE:
<221> NAME/KEY: MISC_FEATURE
<222> LOCATION: (5)..(5)
<223> OTHER INFORMATION: The Xaa at position 5 is glycine, alanine,
      valine, leucine, isoleucine, proline, phenylalanine or methionine
<220> FEATURE:
<221> NAME/KEY: MISC_FEATURE
<222> LOCATION: (6)..(6)
<223> OTHER INFORMATION: The Xaa at position 6 is any amino acid other
      than tyrosine

<400> SEQUENCE: 143

Phe Asn Lys Pro Xaa Xaa Gly Ser Ser Ser Arg Arg Ala Pro Gln Thr
1               5                   10                  15

<210> SEQ ID NO 144
<211> LENGTH: 9
<212> TYPE: PRT
<213> ORGANISM: Artificial Sequence
<220> FEATURE:
<223> OTHER INFORMATION: peptide linker

<400> SEQUENCE: 144

Thr Gly Tyr Gly Ser Ser Ser Arg Arg
1               5

<210> SEQ ID NO 145
<211> LENGTH: 10
<212> TYPE: PRT
<213> ORGANISM: Artificial Sequence
<220> FEATURE:
<223> OTHER INFORMATION: linking peptide

<400> SEQUENCE: 145

Lys Thr Gly Tyr Gly Ser Ser Ser Arg Arg
1               5                   10

<210> SEQ ID NO 146
<211> LENGTH: 11
<212> TYPE: PRT
<213> ORGANISM: Artificial Sequence
<220> FEATURE:
<223> OTHER INFORMATION: linking peptide

<400> SEQUENCE: 146

Pro Lys Thr Gly Tyr Gly Ser Ser Ser Arg Arg
1               5                   10

<210> SEQ ID NO 147
<211> LENGTH: 12
<212> TYPE: PRT
<213> ORGANISM: Artificial Sequence
<220> FEATURE:
<223> OTHER INFORMATION: linking peptide

<400> SEQUENCE: 147

Thr Pro Lys Thr Gly Tyr Gly Ser Ser Ser Arg Arg
1               5                   10

<210> SEQ ID NO 148
<211> LENGTH: 12
<212> TYPE: PRT
<213> ORGANISM: Artificial Sequence
```

```
<220> FEATURE:
<223> OTHER INFORMATION: linking peptide

<400> SEQUENCE: 148

Thr Lys Pro Thr Gly Tyr Gly Ser Ser Ser Arg Arg
1               5                   10

<210> SEQ ID NO 149
<211> LENGTH: 12
<212> TYPE: PRT
<213> ORGANISM: Artificial Sequence
<220> FEATURE:
<223> OTHER INFORMATION: linking peptide

<400> SEQUENCE: 149

Ser Arg Pro Ala Gly Tyr Gly Ser Ser Ser Arg Arg
1               5                   10

<210> SEQ ID NO 150
<211> LENGTH: 21
<212> TYPE: PRT
<213> ORGANISM: Artificial Sequence
<220> FEATURE:
<223> OTHER INFORMATION: Analog of the insulin B chain
<220> FEATURE:
<221> NAME/KEY: MISC_FEATURE
<222> LOCATION: (1)..(1)
<223> OTHER INFORMATION: Xaa at position 1 is histidine or threonine
<220> FEATURE:
<221> NAME/KEY: MISC_FEATURE
<222> LOCATION: (5)..(5)
<223> OTHER INFORMATION: Xaa at position 5 is alanine, glycine or serine
<220> FEATURE:
<221> NAME/KEY: MISC_FEATURE
<222> LOCATION: (6)..(6)
<223> OTHER INFORMATION: Xaa at position 6 is histidine, aspartic acid,
      glutamic acid, homocysteic acid or cysteic acid

<400> SEQUENCE: 150

Xaa Leu Cys Gly Xaa Xaa Leu Val Glu Ala Leu Tyr Leu Val Cys Gly
1               5                   10                  15

Glu Arg Gly Phe Phe
            20

<210> SEQ ID NO 151
<211> LENGTH: 21
<212> TYPE: PRT
<213> ORGANISM: Artificial Sequence
<220> FEATURE:
<223> OTHER INFORMATION: Analog of the insulin A chain
<220> FEATURE:
<221> NAME/KEY: MISC_FEATURE
<222> LOCATION: (4)..(4)
<223> OTHER INFORMATION: Xaa at position 4 is aspartic acid or glutamic
      acid
<220> FEATURE:
<221> NAME/KEY: MISC_FEATURE
<222> LOCATION: (8)..(8)
<223> OTHER INFORMATION: Xaa at position 8 is histidine, threonine or
      phenylalanine
<220> FEATURE:
<221> NAME/KEY: MISC_FEATURE
<222> LOCATION: (9)..(9)
<223> OTHER INFORMATION: Xaa at position 9 is serine, arginine,
      ornithine, lysine or alanine
<220> FEATURE:
<221> NAME/KEY: MISC_FEATURE
<222> LOCATION: (14)..(14)
<223> OTHER INFORMATION: Xaa at position 14 is tyrosine, arginine,
      ornithine, lysine or alanine
<220> FEATURE:
<221> NAME/KEY: MISC_FEATURE
```

```
<222> LOCATION: (15)..(15)
<223> OTHER INFORMATION: Xaa at position 15 is glutamine, glutamic acid,
      arginine, ornithine, alanine, lysine or leucine
<220> FEATURE:
<221> NAME/KEY: MISC_FEATURE
<222> LOCATION: (19)..(19)
<223> OTHER INFORMATION: Xaa at position 19 is tyrosine, 4-methoxy
      phenylalanine or 4-amino-phenylalanine

<400> SEQUENCE: 151

Gly Ile Val Xaa Glu Cys Cys Xaa Xaa Ser Cys Asp Leu Xaa Xaa Leu
1               5                   10                  15

Glu Asn Xaa Cys Asn
            20

<210> SEQ ID NO 152
<211> LENGTH: 21
<212> TYPE: PRT
<213> ORGANISM: Artificial Sequence
<220> FEATURE:
<223> OTHER INFORMATION: Analog of the insulin A chain
<220> FEATURE:
<221> NAME/KEY: MISC_FEATURE
<222> LOCATION: (4)..(4)
<223> OTHER INFORMATION: Xaa at position 4 is aspartic acid or glutamic
      acid
<220> FEATURE:
<221> NAME/KEY: MISC_FEATURE
<222> LOCATION: (5)..(5)
<223> OTHER INFORMATION: Xaa at position 5 is glutamine or glutamic acid
<220> FEATURE:
<221> NAME/KEY: MISC_FEATURE
<222> LOCATION: (8)..(8)
<223> OTHER INFORMATION: Xaa at position 8 is histidine, threonine or
      phenylalanine
<220> FEATURE:
<221> NAME/KEY: MISC_FEATURE
<222> LOCATION: (9)..(9)
<223> OTHER INFORMATION: Xaa at position 9 is serine, arginine,
      ornithine, lysine or alanine
<220> FEATURE:
<221> NAME/KEY: MISC_FEATURE
<222> LOCATION: (10)..(10)
<223> OTHER INFORMATION: Xaa at position 10 is isoleucine or serine
<220> FEATURE:
<221> NAME/KEY: MISC_FEATURE
<222> LOCATION: (12)..(12)
<223> OTHER INFORMATION: Xaa at position 12 is aspartic acid or serine
<220> FEATURE:
<221> NAME/KEY: MISC_FEATURE
<222> LOCATION: (14)..(14)
<223> OTHER INFORMATION: Xaa at position 14 is tyrosine, arginine,
      ornithine, lysine or alanine
<220> FEATURE:
<221> NAME/KEY: MISC_FEATURE
<222> LOCATION: (15)..(15)
<223> OTHER INFORMATION: Xaa at position 15 is glutamine, glutamic acid,
      arginine, ornithine, alanine, lysine or leucine
<220> FEATURE:
<221> NAME/KEY: MISC_FEATURE
<222> LOCATION: (18)..(18)
<223> OTHER INFORMATION: Xaa at position 18 is methionine, asparagine,
      glutamine, glutamic acid, aspartic acid or threonine
<220> FEATURE:
<221> NAME/KEY: MISC_FEATURE
<222> LOCATION: (19)..(19)
<223> OTHER INFORMATION: Xaa at position 19 is tyrosine, 4-methoxy
      phenylalanine or 4-amino-phenylalanine
<220> FEATURE:
<221> NAME/KEY: MISC_FEATURE
<222> LOCATION: (21)..(21)
<223> OTHER INFORMATION: Xaa at position 21 is alanine, glycine, serine,
      valine, threonine, isoleucine, leucine, glutamine, glutamic acid,
      asparagine, aspartic acid, histidine, tryptophan, tyrosine, or
      methionine
```

```
<400> SEQUENCE: 152

Gly Ile Val Xaa Xaa Cys Cys Xaa Xaa Xaa Cys Xaa Leu Xaa Xaa Leu
1               5                   10                  15

Glu Xaa Xaa Cys Xaa
            20

<210> SEQ ID NO 153
<211> LENGTH: 7
<212> TYPE: PRT
<213> ORGANISM: Artificial Sequence
<220> FEATURE:
<223> OTHER INFORMATION: linking pepetide
<220> FEATURE:
<221> NAME/KEY: MISC_FEATURE
<222> LOCATION: (2)..(6)
<223> OTHER INFORMATION: the Xaas at positions 2-6 are independently
      glutamic acid or aspartic acid

<400> SEQUENCE: 153

Gly Xaa Xaa Xaa Xaa Xaa Lys
1               5

<210> SEQ ID NO 154
<211> LENGTH: 21
<212> TYPE: PRT
<213> ORGANISM: Homo sapiens
<220> FEATURE:
<221> NAME/KEY: MISC_FEATURE
<222> LOCATION: (6)..(6)
<223> OTHER INFORMATION: The Xaa at position 6 is histidine, aspartic
      acid, glutamic acid, homocysteic acid or cysteic acid

<400> SEQUENCE: 154

His Leu Cys Gly Ser Xaa Leu Val Glu Ala Leu Tyr Leu Val Cys Gly
1               5                   10                  15

Glu Arg Gly Phe Phe
            20

<210> SEQ ID NO 155
<211> LENGTH: 21
<212> TYPE: PRT
<213> ORGANISM: Artificial Sequence
<220> FEATURE:
<223> OTHER INFORMATION: Analog of the insulin B chain
<220> FEATURE:
<221> NAME/KEY: MISC_FEATURE
<222> LOCATION: (19)..(19)
<223> OTHER INFORMATION: Xaa at position 19 is tyrosine or 4-amino
      phenylanaline

<400> SEQUENCE: 155

Gly Ile Val Asp Glu Cys Cys His Arg Ser Cys Asp Leu Arg Arg Leu
1               5                   10                  15

Glu Met Xaa Cys Ala
            20

<210> SEQ ID NO 156
<211> LENGTH: 6
<212> TYPE: PRT
<213> ORGANISM: Artificial Sequence
<220> FEATURE:
<223> OTHER INFORMATION: synthetic peptide for testing cleavage of
      dipeptide prodrug element

<400> SEQUENCE: 156

His Ser Arg Gly Thr Phe
1               5
```

<210> SEQ ID NO 157
<211> LENGTH: 8
<212> TYPE: PRT
<213> ORGANISM: Artificial Sequence
<220> FEATURE:
<223> OTHER INFORMATION: synthetic peptide for testing cleavage of
      dipeptide prodrug element
<220> FEATURE:
<221> NAME/KEY: MISC_FEATURE
<222> LOCATION: (2)..(2)
<223> OTHER INFORMATION: Xaa at position 2 is Sarcosine

<400> SEQUENCE: 157

Lys Xaa His Ser Thr Gly Thr Phe
1               5

<210> SEQ ID NO 158
<211> LENGTH: 6
<212> TYPE: PRT
<213> ORGANISM: Artificial Sequence
<220> FEATURE:
<223> OTHER INFORMATION: glucagon analogue
<220> FEATURE:
<221> NAME/KEY: MOD_RES
<222> LOCATION: (1)..(1)
<223> OTHER INFORMATION: Xaa at position 1 is d-histidine
<220> FEATURE:
<221> NAME/KEY: MOD_RES
<222> LOCATION: (2)..(2)
<223> OTHER INFORMATION: Xaa at position 2 is d-threonine
<220> FEATURE:
<221> NAME/KEY: MOD_RES
<222> LOCATION: (3)..(3)
<223> OTHER INFORMATION: Xaa at position 3 is d-arginine
<220> FEATURE:
<221> NAME/KEY: MOD_RES
<222> LOCATION: (5)..(5)
<223> OTHER INFORMATION: Xaa at position 5 is d-threonine
<220> FEATURE:
<221> NAME/KEY: MOD_RES
<222> LOCATION: (6)..(6)
<223> OTHER INFORMATION: Xaa at position 6 is d-phenylalanine

<400> SEQUENCE: 158

Xaa Xaa Xaa Gly Xaa Xaa
1               5

<210> SEQ ID NO 159
<211> LENGTH: 8
<212> TYPE: PRT
<213> ORGANISM: Artificial Sequence
<220> FEATURE:
<223> OTHER INFORMATION: glucagon analogue
<220> FEATURE:
<221> NAME/KEY: MOD_RES
<222> LOCATION: (1)..(1)
<223> OTHER INFORMATION: Xaa at position 1 is d-lysine
<220> FEATURE:
<221> NAME/KEY: MOD_RES
<222> LOCATION: (2)..(2)
<223> OTHER INFORMATION: Xaa at position 2 is d-sarcosine
<220> FEATURE:
<221> NAME/KEY: MOD_RES
<222> LOCATION: (3)..(3)
<223> OTHER INFORMATION: Xaa at position 3 is d-histidine
<220> FEATURE:
<221> NAME/KEY: MOD_RES
<222> LOCATION: (4)..(4)
<223> OTHER INFORMATION: Xaa at position 4 is d-threonine
<220> FEATURE:
<221> NAME/KEY: MOD_RES
<222> LOCATION: (5)..(5)
<223> OTHER INFORMATION: Xaa at position 5 is d-arginine

```
<220> FEATURE:
<221> NAME/KEY: MOD_RES
<222> LOCATION: (7)..(7)
<223> OTHER INFORMATION: Xaa at position 7 is d-threonine
<220> FEATURE:
<221> NAME/KEY: MOD_RES
<222> LOCATION: (8)..(8)
<223> OTHER INFORMATION: Xaa at position 8 is d-phenylalanine

<400> SEQUENCE: 159

Xaa Xaa Xaa Xaa Xaa Gly Xaa Xaa
1               5

<210> SEQ ID NO 160
<211> LENGTH: 6
<212> TYPE: PRT
<213> ORGANISM: Artificial Sequence
<220> FEATURE:
<223> OTHER INFORMATION: synthetic peptide for testing cleavage of
      dipeptide prodrug element
<220> FEATURE:
<221> NAME/KEY: MISC_FEATURE
<222> LOCATION: (1)..(1)
<223> OTHER INFORMATION: The Xaa at position 1 is histidine, d-histidine
      or N-methyl-histdine

<400> SEQUENCE: 160

Xaa Ser Arg Gly Thr Phe
1               5

<210> SEQ ID NO 161
<211> LENGTH: 4
<212> TYPE: PRT
<213> ORGANISM: Artificial Sequence
<220> FEATURE:
<223> OTHER INFORMATION: linker sequence
<220> FEATURE:
<221> NAME/KEY: MISC_FEATURE
<222> LOCATION: (1)..(3)
<223> OTHER INFORMATION: The Xaas at positions 1-3 are independently any
      amino acid

<400> SEQUENCE: 161

Xaa Xaa Xaa Thr
1

<210> SEQ ID NO 162
<211> LENGTH: 24
<212> TYPE: PRT
<213> ORGANISM: Artificial Sequence
<220> FEATURE:
<223> OTHER INFORMATION: analog of IGF B chain sequence
<220> FEATURE:
<221> NAME/KEY: MISC_FEATURE
<222> LOCATION: (12)..(12)
<223> OTHER INFORMATION: The Xaa at position 12 is aspartic acid or
      glutamic acid
<220> FEATURE:
<221> NAME/KEY: MISC_FEATURE
<222> LOCATION: (21)..(21)
<223> OTHER INFORMATION: The Xaa at position 21 is ornithine, lysine or
      arginine

<400> SEQUENCE: 162

Gly Pro Glu His Leu Cys Gly Ser His Leu Val Xaa Ala Leu Tyr Leu
1               5                   10                  15

Val Cys Gly Asp Xaa Gly Phe Tyr
            20

<210> SEQ ID NO 163
```

```
<211> LENGTH: 8
<212> TYPE: PRT
<213> ORGANISM: Artificial Sequence
<220> FEATURE:
<223> OTHER INFORMATION: linking peptide
<220> FEATURE:
<221> NAME/KEY: MISC_FEATURE
<222> LOCATION: (7)..(8)
<223> OTHER INFORMATION: The Xaas at positions 7 and 8 are independently
      arginine, lysine or ornithine

<400> SEQUENCE: 163

Gly Ala Gly Ser Ser Ser Xaa Xaa
1               5

<210> SEQ ID NO 164
<211> LENGTH: 21
<212> TYPE: PRT
<213> ORGANISM: Artificial Sequence
<220> FEATURE:
<223> OTHER INFORMATION: Analog of the insulin A chain
<220> FEATURE:
<221> NAME/KEY: MISC_FEATURE
<222> LOCATION: (8)..(8)
<223> OTHER INFORMATION: Xaa at position 8 is histidine, threonine or
      phenylalanine
<220> FEATURE:
<221> NAME/KEY: MISC_FEATURE
<222> LOCATION: (19)..(19)
<223> OTHER INFORMATION: Xaa at position 19 is tyrosine, 4-methoxy
      phenylalanine or 4-amino-phenylalanine
<220> FEATURE:
<221> NAME/KEY: MISC_FEATURE
<222> LOCATION: (21)..(21)
<223> OTHER INFORMATION: Xaa at position 21 is alanine, glycine, serine,
      valine, threonine, isoleucine, leucine, glutamine, glutamic acid,
      asparagine, aspartic acid, histidine, tryptophan, tyrosine, or
      methionine

<400> SEQUENCE: 164

Gly Ile Val Glu Gln Cys Cys Xaa Ser Ile Cys Ser Leu Tyr Gln Leu
1               5                   10                  15

Glu Asn Xaa Cys Xaa
            20

<210> SEQ ID NO 165
<211> LENGTH: 23
<212> TYPE: PRT
<213> ORGANISM: Artificial Sequence
<220> FEATURE:
<223> OTHER INFORMATION: Analog of the insulin B chain
<220> FEATURE:
<221> NAME/KEY: MISC_FEATURE
<222> LOCATION: (1)..(1)
<223> OTHER INFORMATION: Xaa at position 1 is histidine or threonine
<220> FEATURE:
<221> NAME/KEY: MISC_FEATURE
<222> LOCATION: (6)..(6)
<223> OTHER INFORMATION: Xaa at position 6 is histidine, aspartic acid,
      glutamic acid, homocysteic acid or cysteic acid
<220> FEATURE:
<221> NAME/KEY: MISC_FEATURE
<222> LOCATION: (18)..(18)
<223> OTHER INFORMATION: Xaa at position 18 is alanine, ornithine,
      lysine or arginine

<400> SEQUENCE: 165

Xaa Leu Cys Gly Ala Xaa Leu Val Asp Ala Leu Tyr Leu Val Cys Gly
1               5                   10                  15

Asp Xaa Gly Phe Tyr Phe Asn
            20
```

```
<210> SEQ ID NO 166
<211> LENGTH: 21
<212> TYPE: PRT
<213> ORGANISM: Artificial Sequence
<220> FEATURE:
<223> OTHER INFORMATION: Analog of the insulin A chain
<220> FEATURE:
<221> NAME/KEY: MISC_FEATURE
<222> LOCATION: (8)..(8)
<223> OTHER INFORMATION: Xaa at position 8 is histidine, threonine or
      phenylalanine
<220> FEATURE:
<221> NAME/KEY: MISC_FEATURE
<222> LOCATION: (9)..(9)
<223> OTHER INFORMATION: Xaa at position 9 is serine, arginine,
      ornithine, lysine or alanine
<220> FEATURE:
<221> NAME/KEY: MISC_FEATURE
<222> LOCATION: (19)..(19)
<223> OTHER INFORMATION: Xaa at position 19 is tyrosine, 4-methoxy
      phenylalanine or 4-amino-phenylalanine
<220> FEATURE:
<221> NAME/KEY: MISC_FEATURE
<222> LOCATION: (21)..(21)
<223> OTHER INFORMATION: Xaa at position 21 is alanine, glycine, serine,
      valine, threonine, isoleucine, leucine, glutamine, glutamic acid,
      asparagine, aspartic acid, histidine, tryptophan, tyrosine, or
      methionine

<400> SEQUENCE: 166

Gly Ile Val Asp Glu Cys Cys Xaa Xaa Ser Cys Asp Leu Arg Arg Leu
1               5                   10                  15

Glu Met Xaa Cys Xaa
            20

<210> SEQ ID NO 167
<211> LENGTH: 13
<212> TYPE: PRT
<213> ORGANISM: Homo sapiens
<220> FEATURE:
<221> NAME/KEY: MISC_FEATURE
<222> LOCATION: (8)..(8)
<223> OTHER INFORMATION: Xaa at position 8 is ornithine, lysine or
      arginine

<400> SEQUENCE: 167

Gly Ala Gly Ser Ser Ser Arg Xaa Arg Ala Pro Gln Thr
1               5                   10

<210> SEQ ID NO 168
<211> LENGTH: 29
<212> TYPE: PRT
<213> ORGANISM: Homo sapiens

<400> SEQUENCE: 168

Gly Pro Glu Thr Leu Cys Gly Ala Glu Leu Val Asp Ala Leu Tyr Leu
1               5                   10                  15

Val Cys Gly Asp Arg Gly Phe Tyr Phe Asn Lys Pro Thr
            20                  25

<210> SEQ ID NO 169
<211> LENGTH: 9
<212> TYPE: PRT
<213> ORGANISM: Artificial Sequence
<220> FEATURE:
<223> OTHER INFORMATION: peptide linker

<400> SEQUENCE: 169

Gly Glu Glu Glu Glu Glu Glu Arg Lys
```

```
<210> SEQ ID NO 170
<211> LENGTH: 8
<212> TYPE: PRT
<213> ORGANISM: Artificial Sequence
<220> FEATURE:
<223> OTHER INFORMATION: peptide linker

<400> SEQUENCE: 170

Gly Glu Glu Glu Glu Glu Arg Lys
1               5

<210> SEQ ID NO 171
<211> LENGTH: 7
<212> TYPE: PRT
<213> ORGANISM: Artificial Sequence
<220> FEATURE:
<223> OTHER INFORMATION: peptide linker

<400> SEQUENCE: 171

Gly Glu Glu Glu Glu Arg Lys
1               5

<210> SEQ ID NO 172
<211> LENGTH: 6
<212> TYPE: PRT
<213> ORGANISM: Artificial Sequence
<220> FEATURE:
<223> OTHER INFORMATION: peptide linker

<400> SEQUENCE: 172

Gly Glu Glu Glu Arg Lys
1               5

<210> SEQ ID NO 173
<211> LENGTH: 5
<212> TYPE: PRT
<213> ORGANISM: Artificial Sequence
<220> FEATURE:
<223> OTHER INFORMATION: peptide linker

<400> SEQUENCE: 173

Gly Glu Glu Arg Lys
1               5

<210> SEQ ID NO 174
<211> LENGTH: 4
<212> TYPE: PRT
<213> ORGANISM: Artificial Sequence
<220> FEATURE:
<223> OTHER INFORMATION: peptide linker

<400> SEQUENCE: 174

Gly Glu Arg Lys
1

<210> SEQ ID NO 175
<211> LENGTH: 9
<212> TYPE: PRT
<213> ORGANISM: Artificial Sequence
<220> FEATURE:
<223> OTHER INFORMATION: peptide linker

<400> SEQUENCE: 175

Gly Glu Glu Glu Glu Glu Glu Arg Lys
1               5
```

```
<210> SEQ ID NO 176
<211> LENGTH: 8
<212> TYPE: PRT
<213> ORGANISM: Artificial Sequence
<220> FEATURE:
<223> OTHER INFORMATION: peptide linker

<400> SEQUENCE: 176

Gly Glu Glu Glu Glu Glu Glu Lys
1               5

<210> SEQ ID NO 177
<211> LENGTH: 7
<212> TYPE: PRT
<213> ORGANISM: Artificial Sequence
<220> FEATURE:
<223> OTHER INFORMATION: peptide linker

<400> SEQUENCE: 177

Gly Glu Glu Glu Glu Glu Lys
1               5

<210> SEQ ID NO 178
<211> LENGTH: 6
<212> TYPE: PRT
<213> ORGANISM: Artificial Sequence
<220> FEATURE:
<223> OTHER INFORMATION: peptide linker

<400> SEQUENCE: 178

Gly Glu Glu Glu Glu Lys
1               5

<210> SEQ ID NO 179
<211> LENGTH: 4
<212> TYPE: PRT
<213> ORGANISM: Artificial Sequence
<220> FEATURE:
<223> OTHER INFORMATION: peptide linker

<400> SEQUENCE: 179

Gly Glu Glu Lys
1

<210> SEQ ID NO 180
<211> LENGTH: 9
<212> TYPE: PRT
<213> ORGANISM: Artificial Sequence
<220> FEATURE:
<223> OTHER INFORMATION: peptide linker

<400> SEQUENCE: 180

Gly Asp Asp Asp Asp Asp Asp Arg Lys
1               5

<210> SEQ ID NO 181
<211> LENGTH: 8
<212> TYPE: PRT
<213> ORGANISM: Artificial Sequence
<220> FEATURE:
<223> OTHER INFORMATION: peptide linker

<400> SEQUENCE: 181

Gly Asp Asp Asp Asp Asp Arg Lys
1               5
```

<210> SEQ ID NO 182
<211> LENGTH: 7
<212> TYPE: PRT
<213> ORGANISM: Artificial Sequence
<220> FEATURE:
<223> OTHER INFORMATION: peptide linker

<400> SEQUENCE: 182

Gly Asp Asp Asp Asp Arg Lys
1               5

<210> SEQ ID NO 183
<211> LENGTH: 6
<212> TYPE: PRT
<213> ORGANISM: Artificial Sequence
<220> FEATURE:
<223> OTHER INFORMATION: peptide linker

<400> SEQUENCE: 183

Gly Asp Asp Asp Arg Lys
1               5

<210> SEQ ID NO 184
<211> LENGTH: 5
<212> TYPE: PRT
<213> ORGANISM: Artificial Sequence
<220> FEATURE:
<223> OTHER INFORMATION: peptide linker

<400> SEQUENCE: 184

Gly Asp Asp Arg Lys
1               5

<210> SEQ ID NO 185
<211> LENGTH: 4
<212> TYPE: PRT
<213> ORGANISM: Artificial Sequence
<220> FEATURE:
<223> OTHER INFORMATION: peptide linker

<400> SEQUENCE: 185

Gly Asp Arg Lys
1

<210> SEQ ID NO 186
<211> LENGTH: 8
<212> TYPE: PRT
<213> ORGANISM: Artificial Sequence
<220> FEATURE:
<223> OTHER INFORMATION: peptide linker

<400> SEQUENCE: 186

Gly Asp Asp Asp Asp Asp Asp Lys
1               5

<210> SEQ ID NO 187
<211> LENGTH: 7
<212> TYPE: PRT
<213> ORGANISM: Artificial Sequence
<220> FEATURE:
<223> OTHER INFORMATION: peptide linker

<400> SEQUENCE: 187

Gly Asp Asp Asp Asp Asp Lys
1               5

```
<210> SEQ ID NO 188
<211> LENGTH: 6
<212> TYPE: PRT
<213> ORGANISM: Artificial Sequence
<220> FEATURE:
<223> OTHER INFORMATION: peptide linker

<400> SEQUENCE: 188

Gly Asp Asp Asp Asp Lys
1               5

<210> SEQ ID NO 189
<211> LENGTH: 5
<212> TYPE: PRT
<213> ORGANISM: Artificial Sequence
<220> FEATURE:
<223> OTHER INFORMATION: peptide linker

<400> SEQUENCE: 189

Gly Asp Asp Asp Lys
1               5

<210> SEQ ID NO 190
<211> LENGTH: 4
<212> TYPE: PRT
<213> ORGANISM: Artificial Sequence
<220> FEATURE:
<223> OTHER INFORMATION: peptide linker

<400> SEQUENCE: 190

Gly Asp Asp Lys
1

<210> SEQ ID NO 191
<211> LENGTH: 8
<212> TYPE: PRT
<213> ORGANISM: Artificial Sequence
<220> FEATURE:
<223> OTHER INFORMATION: N-terminal extension peptide
<220> FEATURE:
<221> NAME/KEY: MISC_FEATURE
<222> LOCATION: (2)..(7)
<223> OTHER INFORMATION: Xaa at positions 2-7 are independently glutamic
      acid or aspartic acid
<220> FEATURE:
<221> NAME/KEY: MISC_FEATURE
<222> LOCATION: (3)..(7)
<223> OTHER INFORMATION: any or all of amino acids at positions 3-7 are
      present or absent

<400> SEQUENCE: 191

Gly Xaa Xaa Xaa Xaa Xaa Xaa Lys
1               5

<210> SEQ ID NO 192
<211> LENGTH: 9
<212> TYPE: PRT
<213> ORGANISM: Artificial Sequence
<220> FEATURE:
<223> OTHER INFORMATION: N-terminal extension peptide
<220> FEATURE:
<221> NAME/KEY: MISC_FEATURE
<222> LOCATION: (1)..(1)
<223> OTHER INFORMATION: Xaa at position 1 is glycine, glutamic acid or
      aspartic acid
<220> FEATURE:
<221> NAME/KEY: MISC_FEATURE
<222> LOCATION: (2)..(7)
<223> OTHER INFORMATION: Xaa at positions 2-7 are independently glutamic
      acid or aspartic acid
<220> FEATURE:
```

```
<221> NAME/KEY: MISC_FEATURE
<222> LOCATION: (4)..(7)
<223> OTHER INFORMATION: any or all of amino acids at positions 4-7 are
      present or absent
<220> FEATURE:
<221> NAME/KEY: MISC_FEATURE
<222> LOCATION: (8)..(8)
<223> OTHER INFORMATION: Xaa at position 8 is arginine, glutamic acid or
      aspartic acid

<400> SEQUENCE: 192

Xaa Xaa Xaa Xaa Xaa Xaa Xaa Xaa Lys
1               5

<210> SEQ ID NO 193
<211> LENGTH: 8
<212> TYPE: PRT
<213> ORGANISM: Artificial Sequence
<220> FEATURE:
<223> OTHER INFORMATION: N-terminal extension peptide
<220> FEATURE:
<221> NAME/KEY: MISC_FEATURE
<222> LOCATION: (2)..(7)
<223> OTHER INFORMATION: Xaa at positions 2-7 are independently glutamic
      acid or aspartic acid

<400> SEQUENCE: 193

Gly Xaa Xaa Xaa Xaa Xaa Xaa Lys
1               5

<210> SEQ ID NO 194
<211> LENGTH: 21
<212> TYPE: PRT
<213> ORGANISM: Artificial Sequence
<220> FEATURE:
<223> OTHER INFORMATION: Analog of the insulin B chain
<220> FEATURE:
<221> NAME/KEY: MISC_FEATURE
<222> LOCATION: (19)..(19)
<223> OTHER INFORMATION: Xaa at position 19 is tyrosine or 4-amino
      phenylanaline

<400> SEQUENCE: 194

Gly Ile Val Glu Gln Cys Cys Thr Ser Ile Cys Ser Leu Tyr Gln Leu
1               5                   10                  15

Glu Asn Xaa Cys Asn
            20

<210> SEQ ID NO 195
<211> LENGTH: 21
<212> TYPE: PRT
<213> ORGANISM: Artificial Sequence
<220> FEATURE:
<223> OTHER INFORMATION: Analog of the insulin A chain
<220> FEATURE:
<221> NAME/KEY: MISC_FEATURE
<222> LOCATION: (8)..(8)
<223> OTHER INFORMATION: Xaa at position 8 is histidine or phenylalanine
<220> FEATURE:
<221> NAME/KEY: MISC_FEATURE
<222> LOCATION: (19)..(19)
<223> OTHER INFORMATION: Xaa at position 19 is tyrosine or 4-amino-
      phenylalanine

<400> SEQUENCE: 195

Gly Ile Val Asp Glu Cys Cys Xaa Arg Ser Cys Asp Leu Tyr Gln Leu
1               5                   10                  15

Glu Asn Xaa Cys Asn
            20
```

```
<210> SEQ ID NO 196
<211> LENGTH: 24
<212> TYPE: PRT
<213> ORGANISM: Artificial Sequence
<220> FEATURE:
<223> OTHER INFORMATION: Analog of the insulin B chain
<220> FEATURE:
<221> NAME/KEY: MISC_FEATURE
<222> LOCATION: (4)..(4)
<223> OTHER INFORMATION: Xaa at position 4 is histidine or threonine
<220> FEATURE:
<221> NAME/KEY: MISC_FEATURE
<222> LOCATION: (21)..(21)
<223> OTHER INFORMATION: Xaa at position 21 is alanine, ornithine,
      lysine or arginine
<220> FEATURE:
<221> NAME/KEY: MISC_FEATURE
<222> LOCATION: (24)..(24)
<223> OTHER INFORMATION: Xaa at position 24 is tyrosine, histidine,
      asparagine or phenylalanine

<400> SEQUENCE: 196

Gly Pro Glu Xaa Leu Cys Gly Ser His Leu Val Asp Ala Leu Tyr Leu
1               5                   10                  15

Val Cys Gly Asp Xaa Gly Phe Xaa
            20

<210> SEQ ID NO 197
<211> LENGTH: 29
<212> TYPE: PRT
<213> ORGANISM: Artificial Sequence
<220> FEATURE:
<223> OTHER INFORMATION: Analog of the insulin B chain
<220> FEATURE:
<221> NAME/KEY: MISC_FEATURE
<222> LOCATION: (8)..(8)
<223> OTHER INFORMATION: Xaa at position 8 is alanine or an alpha, alpha
      disubstituted amino acid
<220> FEATURE:
<221> NAME/KEY: MISC_FEATURE
<222> LOCATION: (13)..(13)
<223> OTHER INFORMATION: Xaa at position 13 is alanine or an alpha,
      alpha disubsituted amino acid
<220> FEATURE:
<221> NAME/KEY: MISC_FEATURE
<222> LOCATION: (21)..(21)
<223> OTHER INFORMATION: Xaa at position 21 is alanine, lysine,
      ornithine and arginine

<400> SEQUENCE: 197

Gly Pro Glu Thr Leu Cys Gly Xaa Glu Leu Val Asp Xaa Leu Tyr Leu
1               5                   10                  15

Val Cys Gly Asp Xaa Gly Phe Tyr Phe Asn Lys Pro Thr
            20                  25
```